(12) United States Patent
Driver et al.

(10) Patent No.: US 11,584,766 B2
(45) Date of Patent: Feb. 21, 2023

(54) NICOTINAMIDE PHOSPHORIBOSYLTRANSFERASE INHIBITORS AND METHODS FOR USE OF THE SAME

(71) Applicants: THE TRUSTEES OF INDIANA UNIVERSITY, Indianapolis, IN (US); THE BOARD OF TRUSTEES OF THE UNIVERSITY OF ILLINOIS, Urbana, IL (US)

(72) Inventors: Tom G. Driver, Chicago, IL (US); Roberto F. Machado, Carmel, IN (US); Najing Su, Newark, DE (US); Xinyu Guan, Chicago, IL (US); Wrickban Mazumdar, Chicago, IL (US); Kira Ratia, Chicago, IL (US); Jason Ralph Hickok, Chicago, IL (US); Angelia Denise Lockett, Indianapolis, IN (US)

(73) Assignees: THE TRUSTEES OF INDIANA UNIVERSITY, Indianapolis, IN (US); THE BOARD OF TRUSTEES OF THE UNIVERSITY OF ILLINOIS, Urbana, IN (US)

( * ) Notice: Subject to any disclaimer, the term of this patent is extended or adjusted under 35 U.S.C. 154(b) by 94 days.

(21) Appl. No.: 16/967,279

(22) PCT Filed: Feb. 5, 2019

(86) PCT No.: PCT/US2019/016684
§ 371 (c)(1),
(2) Date: Aug. 4, 2020

(87) PCT Pub. No.: WO2019/153007
PCT Pub. Date: Aug. 8, 2019

(65) Prior Publication Data
US 2021/0070784 A1 Mar. 11, 2021

Related U.S. Application Data

(60) Provisional application No. 62/626,188, filed on Feb. 5, 2018.

(51) Int. Cl.
*C07F 7/00* (2006.01)
*C07F 7/08* (2006.01)
*C07D 401/12* (2006.01)
*C07D 491/056* (2006.01)

(52) U.S. Cl.
CPC .......... *C07F 7/0816* (2013.01); *C07D 401/12* (2013.01); *C07D 491/056* (2013.01)

(58) Field of Classification Search
CPC .................................................. C07F 7/0816
See application file for complete search history.

(56) References Cited

U.S. PATENT DOCUMENTS

| 6,506,572 | B2 | 1/2003 | Biedermann et al. |
| 7,320,993 | B1 | 1/2008 | Biedermann et al. |
| 11,078,195 | B2 * | 8/2021 | Kim ..................... C07D 417/12 |
| 2010/0227896 | A1 | 9/2010 | Biedermann et al. |
| 2014/0275057 | A1 | 9/2014 | Bair et al. |

FOREIGN PATENT DOCUMENTS

| EP | 3431472 | 1/2019 | |
| WO | 1999/031064 | 6/1999 | |
| WO | 2017/160116 | 9/2017 | |
| WO | 20170160116 A2 | 9/2017 | |
| WO | WO-2018191747 A1 * | 10/2018 | ........... A61K 31/403 |

OTHER PUBLICATIONS

Wislicenus, J. "Adolph Strecker's Short Textbook of Organic Chemistry" 1881, Spottiswoode: London, pp. 38-39.*
PCT Search Report and Written Opinion completed by the ISA/US dated Mar. 19, 2019 and issued in connection with PCT/US2019/016684.
Supplemental EP Search Report for EP application No. 19746569.3, dated Sept. 9, 2021.

* cited by examiner

*Primary Examiner* — David K O'Dell
(74) *Attorney, Agent, or Firm* — Barnes & Thornburg LLC

(57) ABSTRACT

Disclosed herein are compounds that can act as inhibitors of nicotinamide phosphoribosyltransferase ("NAMPT"), and methods for their use in treating or preventing diseases, such as pulmonary arterial hypertension ("PAH"). The compounds described herein can include compounds of Formula (II) and pharmaceutically acceptable salts thereof: wherein the substituents are as described.

15 Claims, 17 Drawing Sheets

NICOTINAMIDE PHOSPHORIBOSYLTRANSFERASE INHIBITORS AND METHODS FOR USE OF THE SAME

CROSS REFERENCE TO RELATED APPLICATIONS

This application is a U.S. national stage entry of PCT Application No. PCT/US2019/016684, filed Feb. 5, 2019, which claims the benefit of U.S. Provisional Patent Application No. 62/626,188, filed 5 Feb. 2018, the disclosure of each of which is hereby incorporated by reference in its entirety.

STATEMENT OF GOVERNMENT SUPPORT

This invention was made with government support under, HHSN268291700006C awarded by the National Institutes of Health. The Government has certain rights in the invention.

BACKGROUND

Technical Field

The present disclosure relates to compounds that can act as inhibitors of nicotinamide phosphoribosyltransferase ("NAMPT"), and methods of using the compounds to inhibit NAMPT and to treat diseases and disorders wherein inhibition of NAMPT would provide a benefit, such as pulmonary arterial hypertension ("PAH") and cancer.

Description of Related Technology

Pulmonary arterial hypertension ("PAH") is a debilitating disease caused by the vascular remodeling of pulmonary cells, which results in increased pressure in the right ventricle of the heart, and culminates in heart failure and death (FIG. 1). With PAH, pulmonary arteries are progressively narrowed, leading to an increase in pulmonary vascular resistance and pulmonary artery pressure. PAH occurs twice as frequently in females as in males, and tends to most affect females between the ages of 30 and 60. In the United States alone, approximately 500 to 1000 new cases of PAH are diagnosed each year. Symptoms of PAH include dyspnea, especially during exercise, chest pain, and fainting episodes. There is no cure for PAH, and once diagnosed, the median survival is three years.

Current treatment of PAH, such as with phosphodiesterase-5 inhibitors (e.g., tadalafil, sildednafil citrate, and bosentan), endothelin ETA receptor antagonists (e.g., ambrisentan), prostaglandin I2 receptor agonists (e.g., epoprostenol sodium, treprostinil sodium, and treprostinil sodium), and guanylate cyclase stimulators (e.g., riociguat) addresses only the side effect of the disease, pulmonary hypertension, rather than its underlying cause of pulmonary vascular remodeling. Further, these molecules can have debilitating toxicity, solubility issues, and stability issues. Treatment with tradition PAH therapeutics can result in side effects, such as flushing, jaw pain, and nausea. Moreover, a proportion of patients will continue to worsen despite treatment with the best drugs, and will require lung transplantation, or very rarely, atrial septostomy, which creates a connection from the right side of the heart to the left side, to allow blood to bypass the lungs. Thus, there is a significant need to develop safe and effective therapeutics to treat PAH.

Nicotinamide phosphoribosyltransferase ("NAMPT"), also known as pre-B-cell colony-enhancing factor, is the rate-limiting enzyme that converts nicotinamide to nicotinamide mononucleotide ("NMN") in the salvage pathway of $NAD^+$ biosynthesis in animals. The expression of NAMPT is upregulated in patients that suffer from PAH and is a significant contributor to pulmonary vascular remodeling. Thus, molecules that act at NAMPT may help to treat PAH. For example, FK866 (APO866) and CHS-828, each shown below, are inhibitors of NAMPT that were found to both prevent and reverse the vascular remodeling caused by PAH in rat models. FK866, for example, has $IC_{50}$ values ranging between 0.09 nm and 27.2 nm in different cell lines with dose limiting toxicity. See, e.g., Bai et al., J. Med. Chem. 59:5766 (2016); Nahimana et al., Blood 113:3276 (2009); Zabka et al., Toxicol. Sci. 144:163 (2015); and Holen et al., Investigational New Drugs 25:45 (2008). These compounds, however, do not possess characteristics that would allow for entereal or airway administration required for the chronic treatment of PAH. Further, these compounds exhibit renal toxicity, which has prevented them from moving forward. Id.

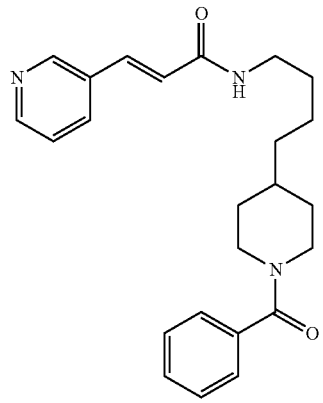

FK866 (APO866)

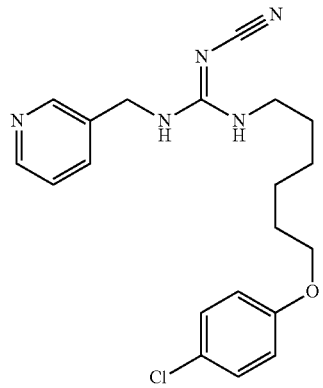

CHS-828

Accordingly, the development of safe and effective therapeutics that inhibit NAMPT would be of advantageous in the treatment of PAH.

SUMMARY OF THE INVENTION

Disclosed herein are compounds of Formula (II), and pharmaceutically acceptable salts thereof:

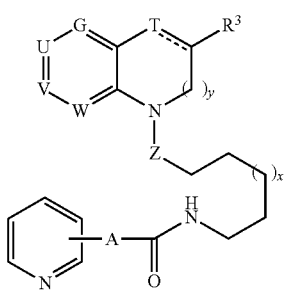
(II)

wherein:

═══ is a single bond or a double bond;

each of x and y independently is 0, 1, or 2;

A is

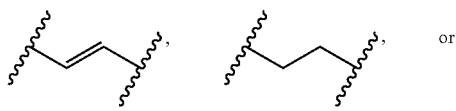

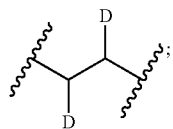

T is $CR^aR^b$ or $SiR^1R^2$, provided that when T is $SiR^1R^2$, then ═══ is a single bond;

each of G, U, V, and W independently is $CR^4$ or N, provided that at least three of G, U, V, and W are $CR^4$;

Z is $CH_2$ or C═O;

$R^a$ is H, $C_{1-4}$alkyl, or $CH_2CO_2R^5$;

$R^b$, when present, is H or $C_{1-4}$alkyl;

each of $R^1$ and $R^2$ independently is $C_{1-4}$alkyl or phenyl;

$R^3$ is H, $C_{1-4}$alkyl, or aryl;

each $R^4$ independently is H, halo, $C_{1-4}$alkyl, OH, $OC_{1-4}$alkyl, OBn, $O(C═O)(CH_2)_n(C═O)(CH_2CH_2O)_mC_{1-4}$alkyl, or $O(C═O)(CH_2)_n(C═O)(CH_2CH_2O)_mH$, or two adjacent $R^4$ groups are each $OC_{1-4}$ alkyl, and together with the carbon atoms to which they are attached, form a five- or six-membered ring;

$R^5$ is H, $C_{1-4}$alkyl, $(CH_2CH_2O)_mC_{1-4}$alkyl, or $(CH_2CH_2O)_mH$;

n is 1-4; and m is 1-10;

with the proviso that when y is 2, then the two carbon atoms adjacent to N can optionally be fused to a phenyl group, and the compound or salt thereof is not

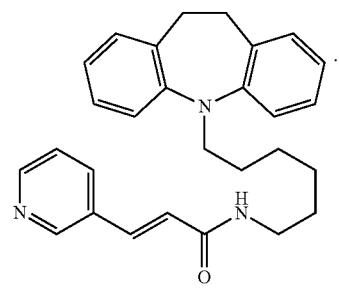 [SMILES: O=C(/C=C/c1cccnc1)NCCCCCCN1c2ccccc2CCc2ccccc21]

In some embodiments, x is 1 and y is 0. In various embodiments, A is

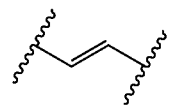

In some cases, Z is $CH_2$. In various cases, Z is C═O. In some embodiments, each of G, U, V, and W is $CR^4$. In various embodiments, each $R^4$ group is H. In some cases, $R^3$ is Me or Ph.

In various cases, T is $SiR^1R^2$ and ═══ is a single bond. In some embodiments, the compound has a structure of Formula (III):

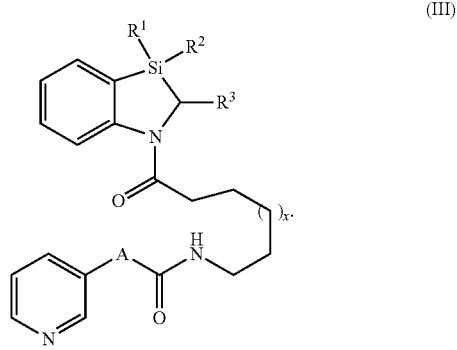
(III)

In various embodiments, x is 1; A is

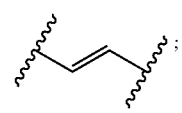 [SMILES: */C=C/*]

each of $R^1$ and $R^2$ independently is Me or each of $R^1$ and $R^2$ independently is Et; and $R^3$ is H, Me, or Ph. In some cases, the compound or salt is selected from the group consisting of:

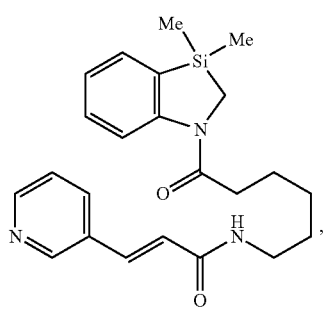
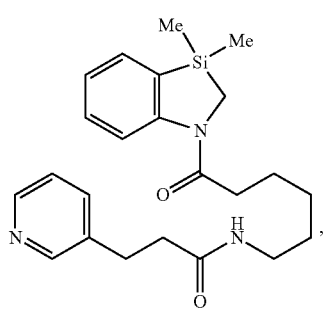
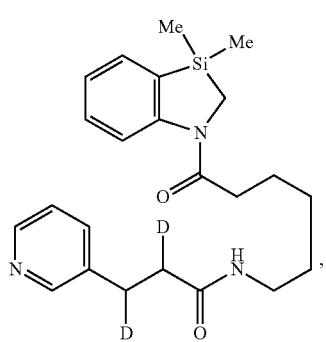
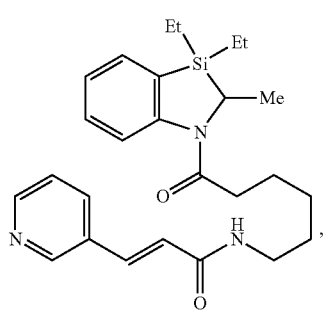
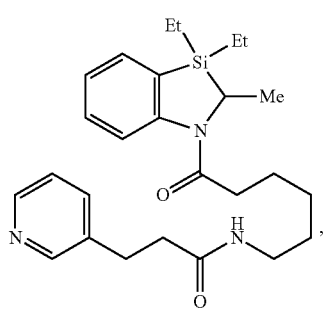
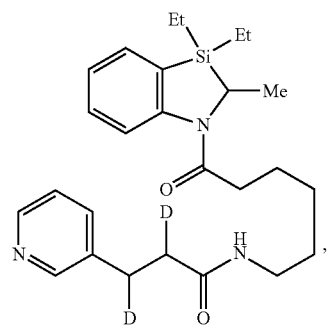
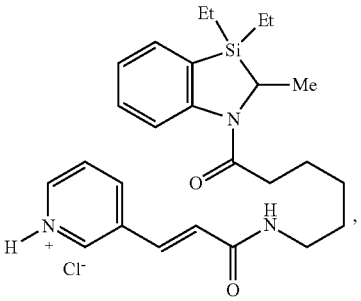
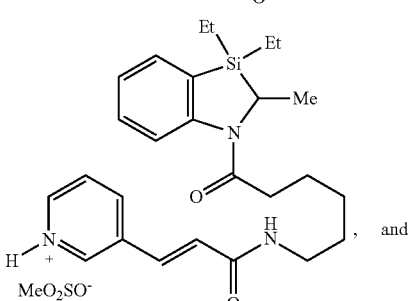
, and
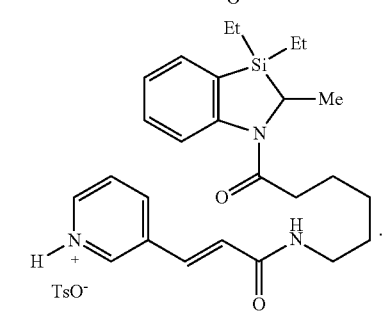
.
In various cases, the compound of Formula (I) is selected from
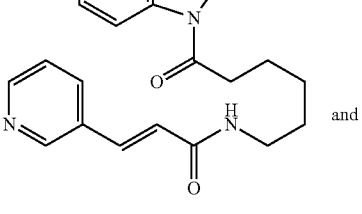
and
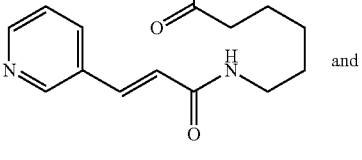

-continued
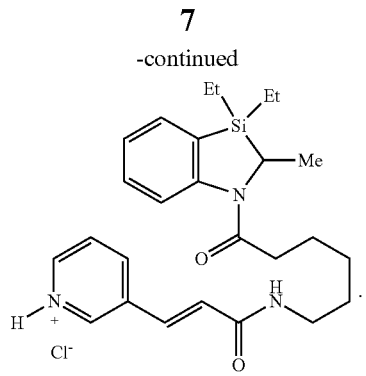
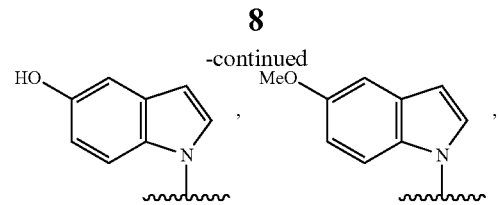
In some embodiments, T is $CR^aR^b$. In various embodiments, ═ is a single bond and each of $R^a$ and $R^b$ is H. In some cases, ═ is a double bond; $R^a$ is H or $CH_2CO_2R^5$; and $R^5$ is H, OMe, OEt, or $(CH_2CH_2O)_4Me$. In various cases, the compound or salt has a structure of Formula (IV):
(IV)
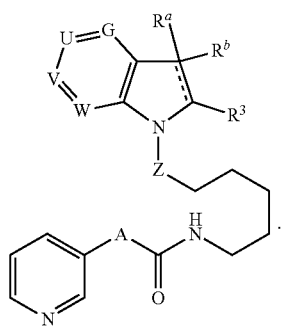
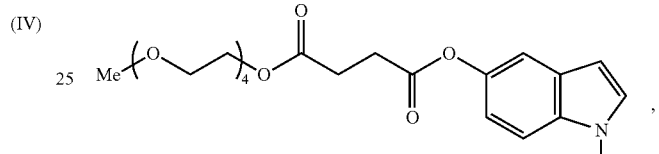
In some embodiments,
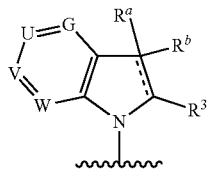
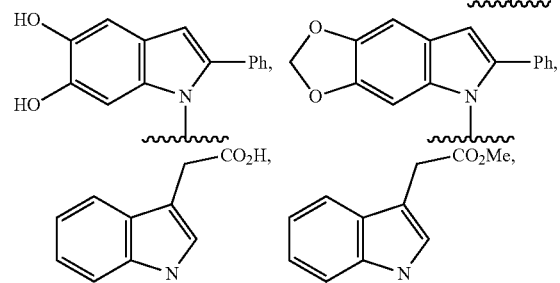
is selected from the group consisting of
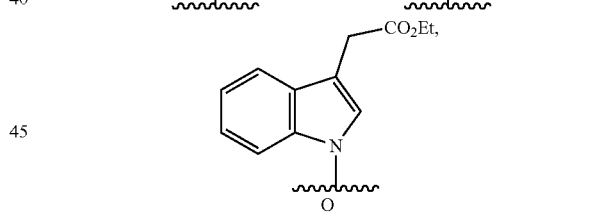
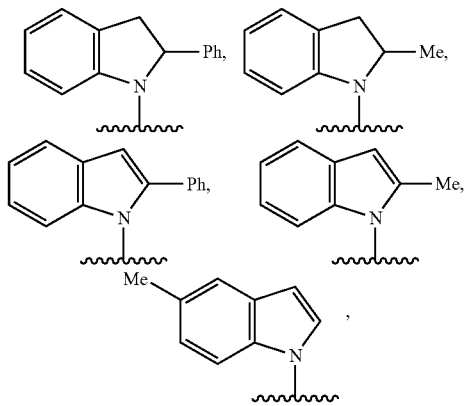
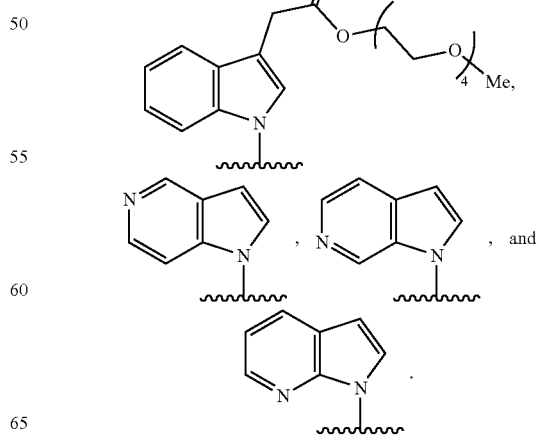
, and In various embodiments,
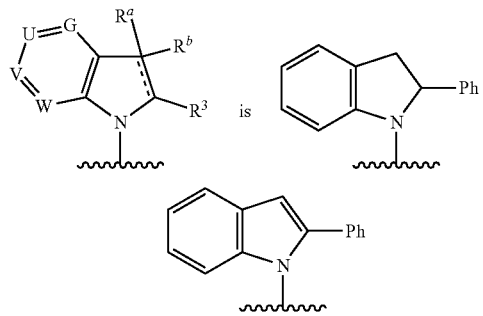
is
and A is
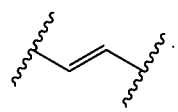 [SMILES: */C=C/*]
In some cases, the compound or salt of Formula (I) has a structure selected from the group consisting of:
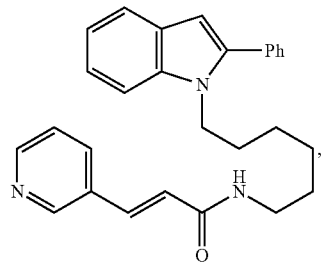
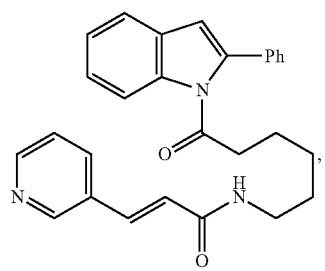
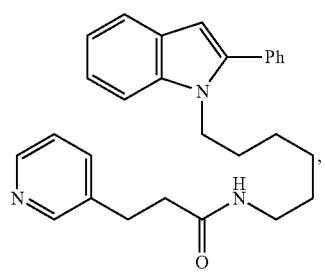
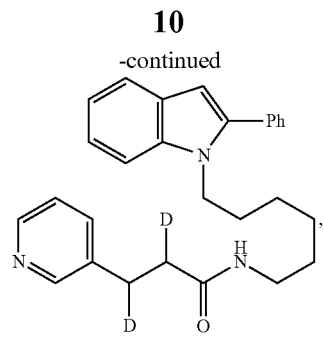

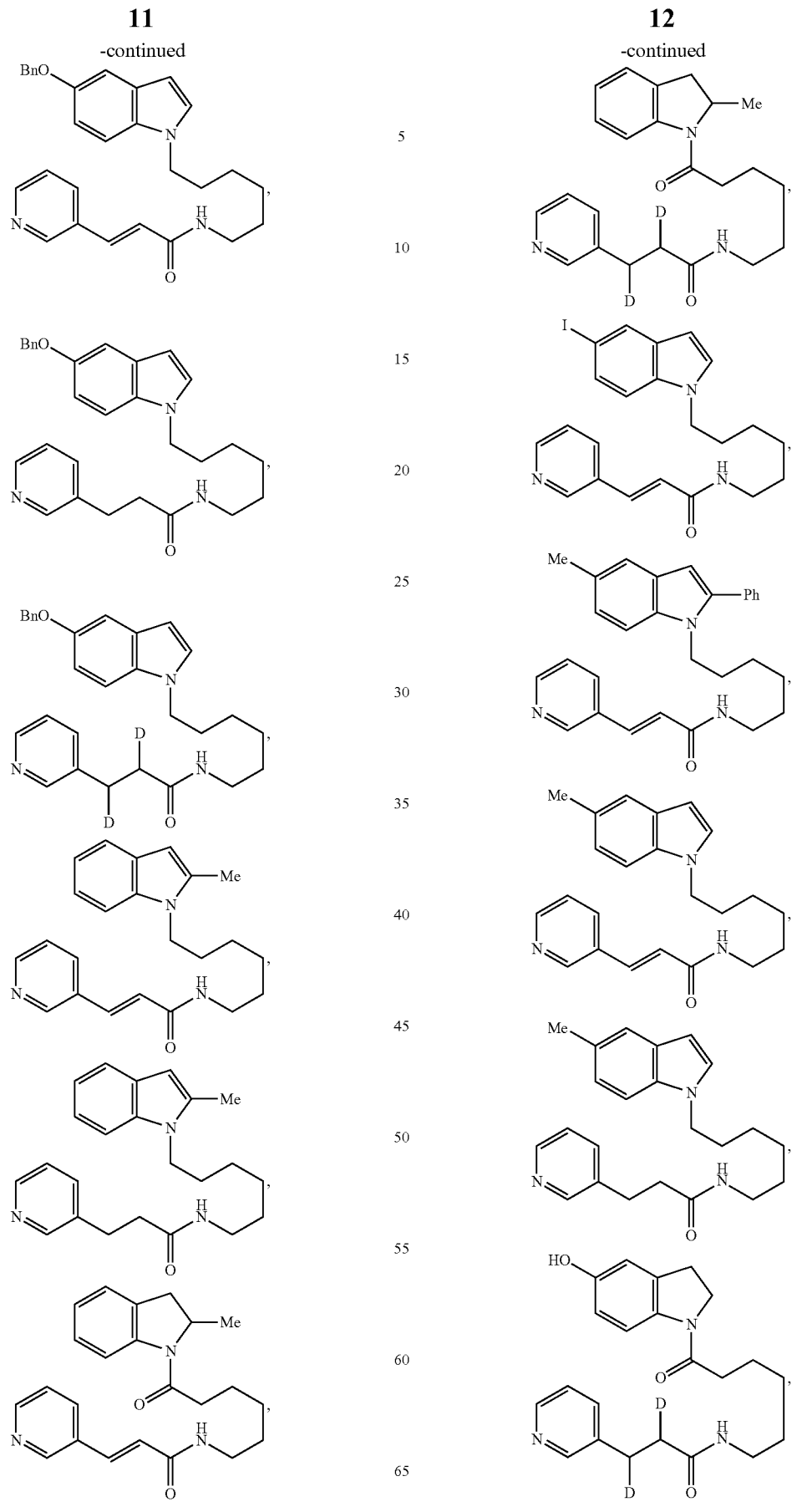

-continued

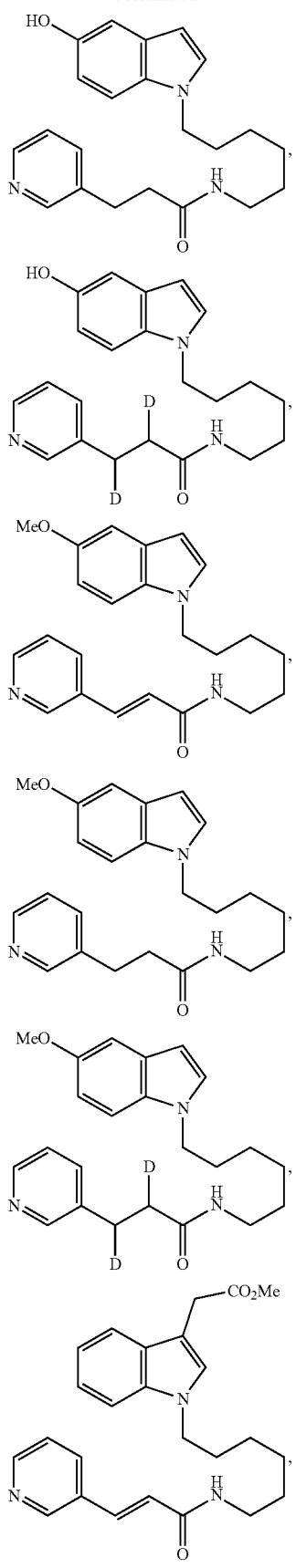
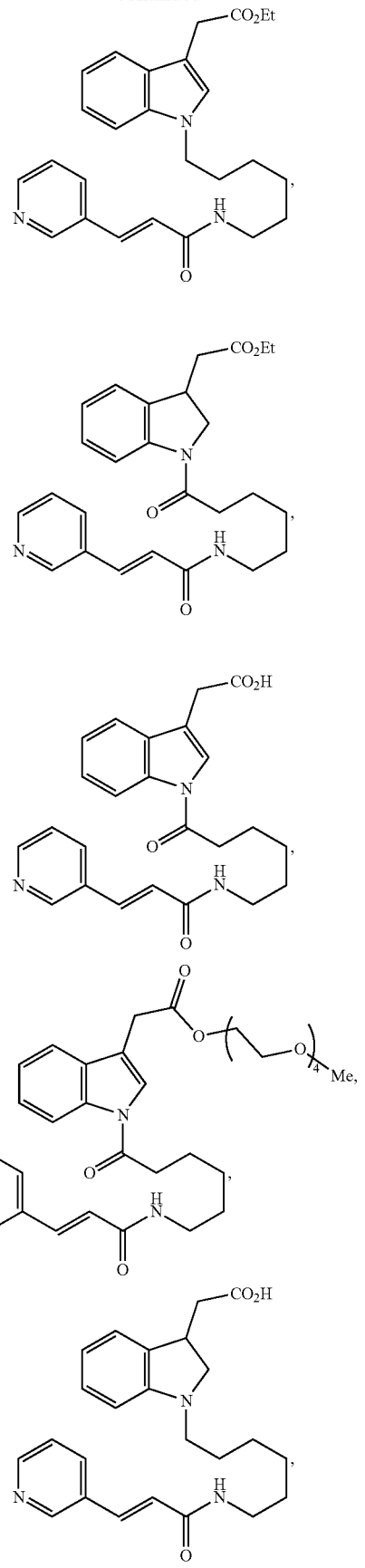

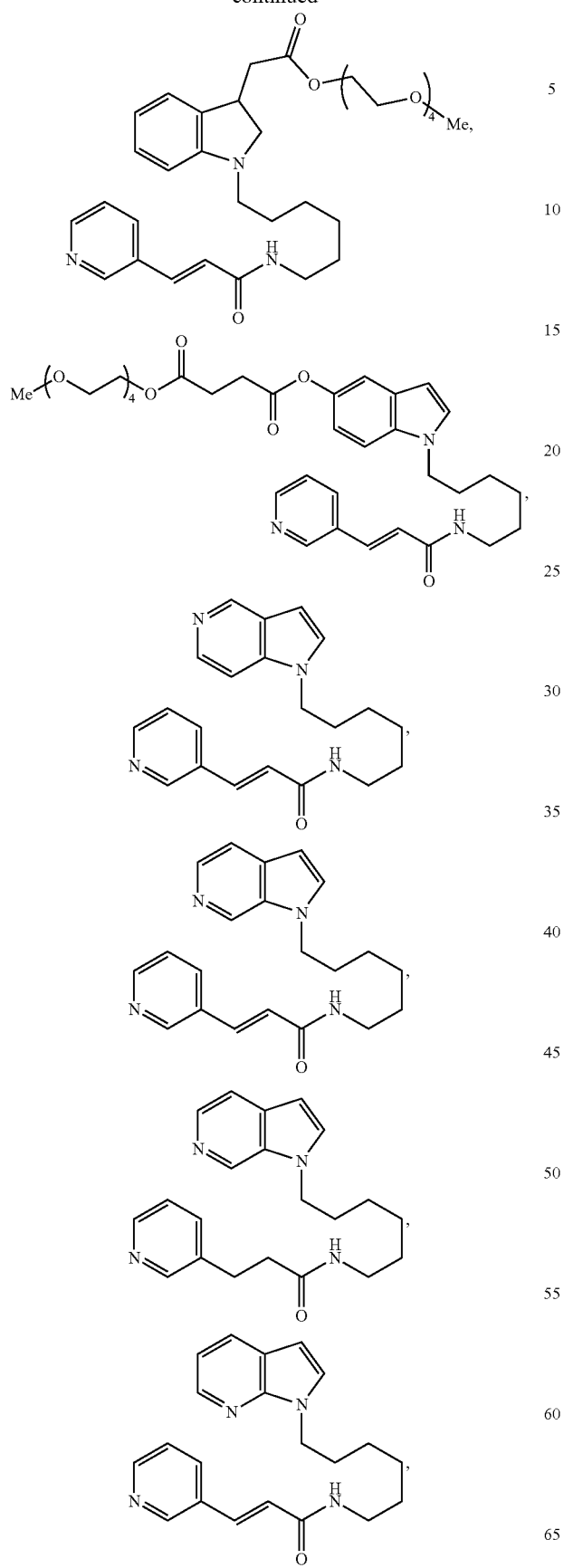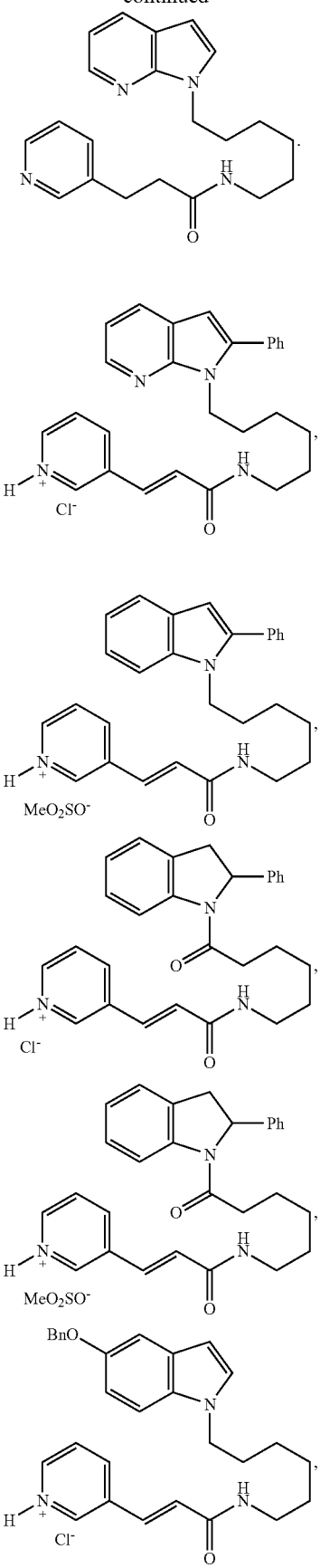

-continued
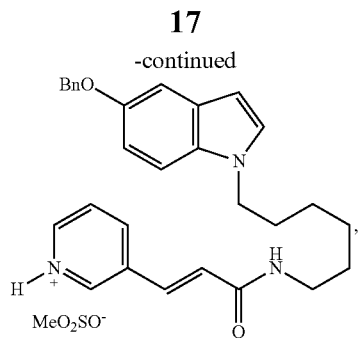
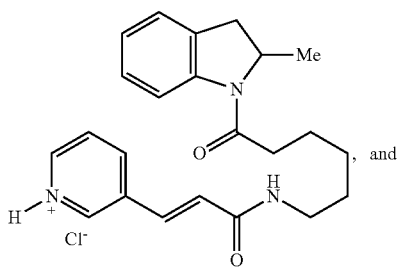
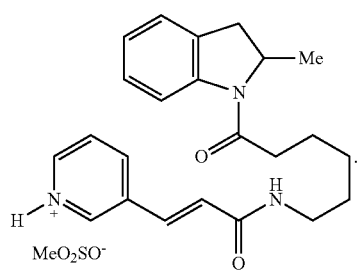
In some cases, the compound or salt of Formula (I) has a structure selected from:
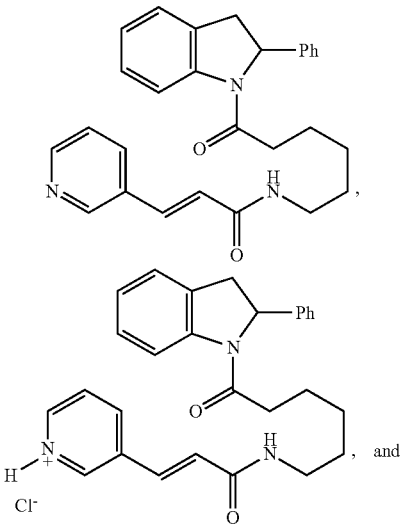
-continued
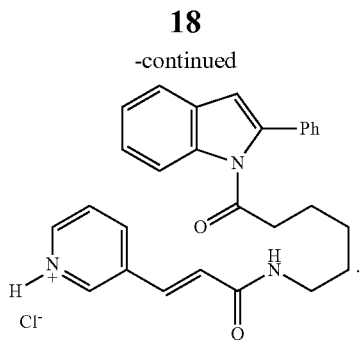
In various cases, the compound or salt of Formula (I) has a structure of Formula (V):
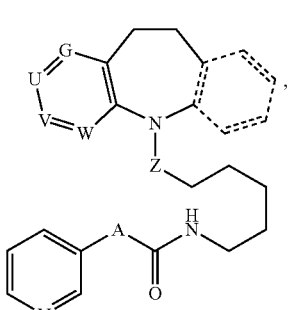
(V)
wherein
is present or absent. In some cases, the compound or salt of Formula (I) has a structure selected from the group consisting of
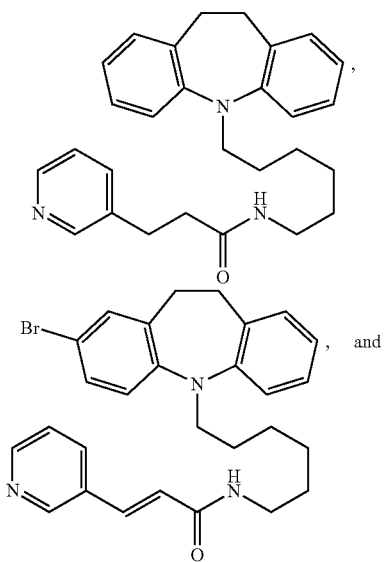

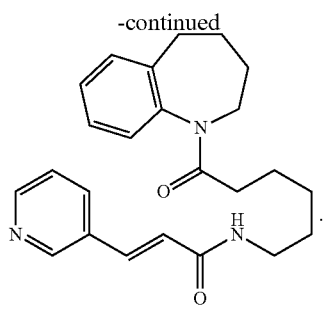

Further provided herein are pharmaceutical compositions comprising the compound or salt disclosed herein and a pharmaceutically acceptable excipient.

Also provided herein is a method of inhibiting nicotinamide phosphoribosyltransferase in a cell comprising contacting the cell with a compound or salt of described herein

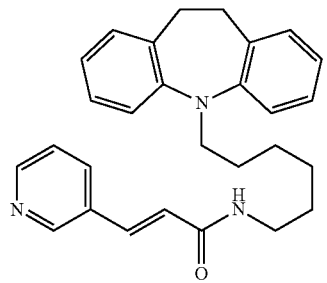 [SMILES: O=C(/C=C/c1cccnc1)NCCCCCCN1c2ccccc2CCc2ccccc21]

or a salt thereof, or the pharmaceutical composition described herein, in an amount effective to inhibit nicotinamide phosphoribosyltransferase. In some cases, the contacting comprises administering the compound or composition to a subject. In some embodiments, the subject suffers from pulmonary arterial hypertension.

Further provided herein is a method of treating a subject having a disease or disorder wherein inhibition of nicotinamide phosphoribosyltransferase would provide a benefit comprising administering to the subject a therapeutically effective amount of a compound or salt described herein,

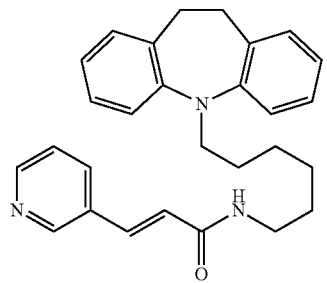

or a salt thereof, or the pharmaceutical composition described herein. In some cases, the disease or disorder is pulmonary arterial hypertension. In various cases, the disease or disorder is selected from the group consisting of cancer, lung disorders, and metabolic disease.

Further aspects and advantages will be apparent to those of ordinary skill in the art from a review of the following detailed description, taken in conjunction with the drawings.

While the compounds and methods disclosed herein are susceptible of embodiments in various forms, the description hereafter includes specific embodiments with the understanding that the disclosure is illustrative, and is not intended to limit the invention to the specific embodiments described herein.

DETAILED DESCRIPTION OF THE INVENTION

Figure 1:
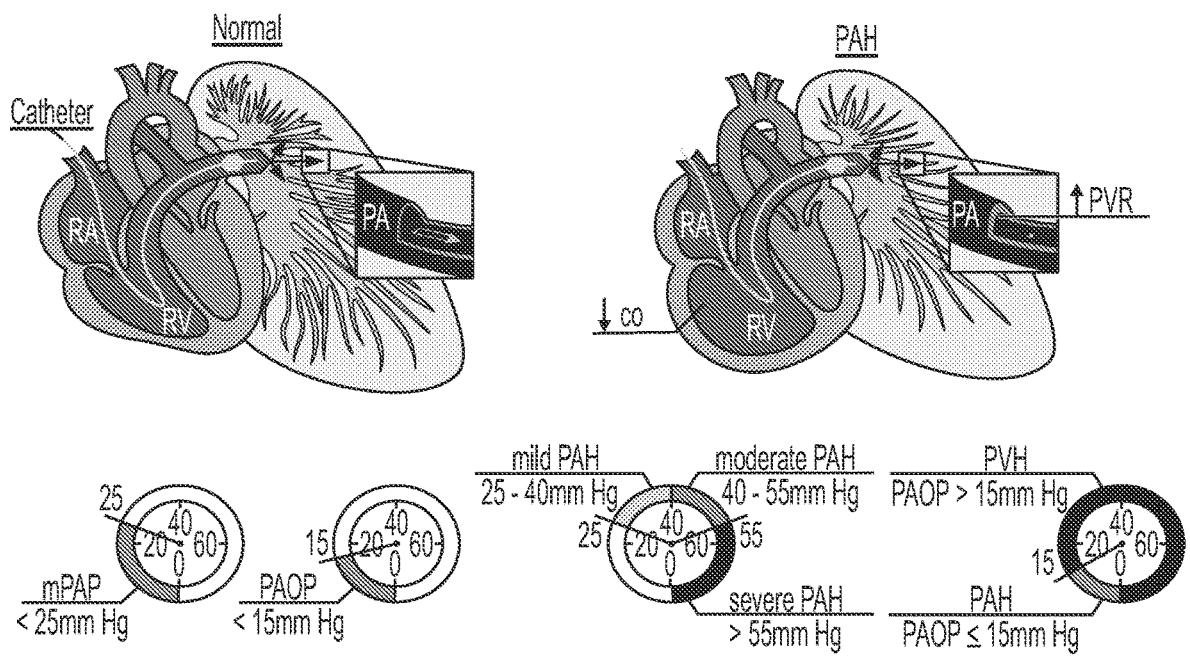
FIG. 1 depicts the effect of pulmonary arterial hypertension on right ventricular function. See, Lai et al., Circulation Research. 115:115 (2014).
Figure 2:
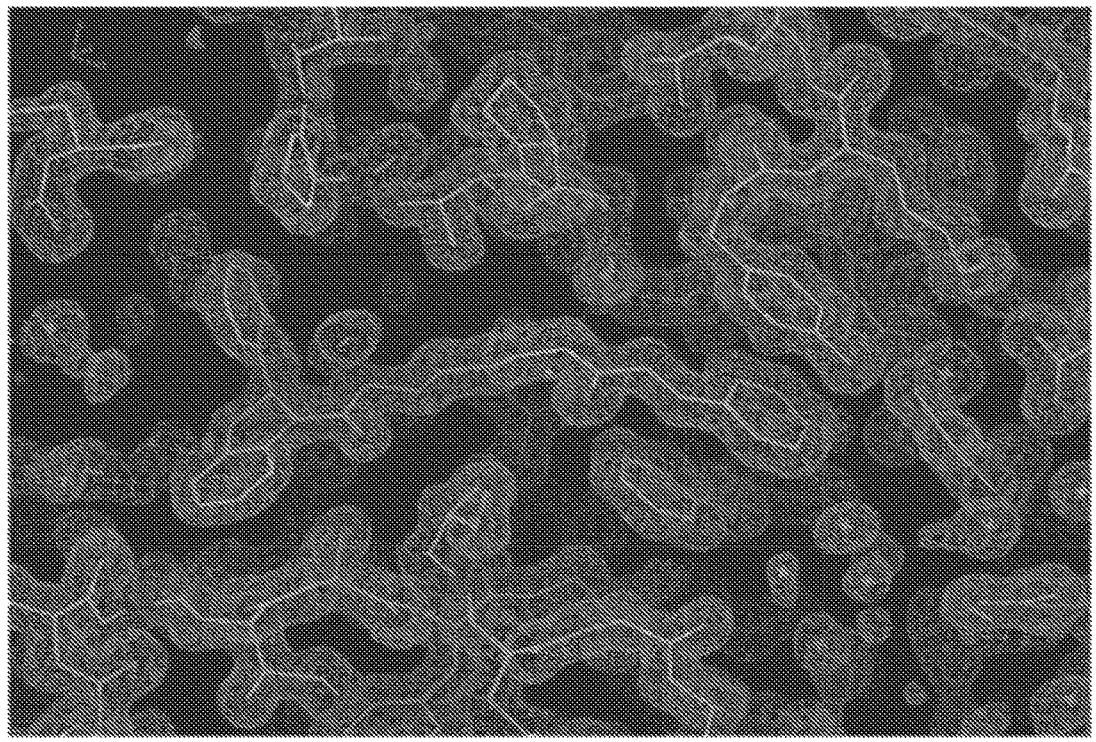
FIG. 2 depicts DGMS-RAR-7 bound to the binding pocket of NAMPT.

Provided herein are compounds that can act as inhibitors of nicotinamide phosphoribosyltransferase ("NAMPT"), and methods of using the compounds to treat and prevent diseases and disorders associated with deregulation of NAMPT, or diseases and disorders in which inhibition of NAMPT would provide a benefit, such as pulmonary arterial hypertension ("PAH"). The compounds disclosed herein have been found to inhibit NAMPT with nanomolar potency. Further, the disclosed compounds can suppress cell growth and promote apoptosis in pulmonary smooth muscle cells and pulmonary arterial endothelial cells in a dose-dependent manner. The compounds also were shown to decrease right ventricle hypertrophy ("RVH") and reduce right ventricular systolic pressure ("RSVP"), both of which are elevated in PAH, attenuating the severity of pulmonary arterial hypertension.

The compounds were further shown to prevent and reverse the vascular remodeling that occurs due to PAH. The compounds of the disclosure have good solubility, especially when coupled to polyethylene glycol or in the form of a salt. The compounds of the disclosure are advantageous over traditional molecules that treat pulmonary arterial hypertension because they directly address the disease by inhibiting NAMPT and then reversing the pulmonary vascular remodeling, which is the cause of pulmonary hypertension.

The compounds of the disclosure can inhibit NAMPT by more than about 50%, 55%, 60%, 65%, 70%, 75%, 80%, 85%, 90%, 95%, 97%, or 99% of the positive control. In some embodiments, the compounds of the disclosure can inhibit NAMPT by more than about 75%, 80%, 85%, 90%, 95%, 97%, or 99% of the positive control. For example, the compounds disclosed herein can inhibit NAMPT by more than about 85%, 86%, 87%, 88%, 89%, 90%, 91%, 92%, 93%, 94%, 95%, 96%, 97%, 98%, or 99% of the positive control. Furthermore, the compounds disclosed herein can act at NAMPT with an $IC_{50}$ of less than about 3 µM, or less than about 2 µM, or less than about 1 µM, or less than about 0.5 µM, or less than about 0.4 µM, or less than about 0.3 µM, or less than about 0.2 µM, or less than about 0.1 µM, or less than about 90 nM, or less than about 80 nM, or less than about 70 nM, or less than about 60 nM, or less than about 50 nM, or less than about 40 nM, or less than about 30 nM, or less than about 20 nM, or less than about 10 nM. In some cases, the compounds of the disclosure can act at NAMPT with an $IC_{50}$ of less than about 0.1 µM, or less than about 90 nM, or less than about 80 nM, or less than about 70 nM, or less than about 60 nM, or less than about 50 nM, or less than about 40 nM, or less than about 30 nM, or less than about 20 nM, or less than about 10 nM. In some cases, the compounds of the disclosure can act at NAMPT with an $IC_{50}$ of less than about 50 nM, or less than about 45 nM, or less than about 40 nM, or less than about 35 nM, or less than about 30 nM, or less than about 25 nM, or less than about 20 nM, or less than about 15 nM, or less than about 10 nM. In some embodiments, the compounds of the disclosure can act at NAMPT with an $IC_{50}$ of less than about 10 nM, or less than about 9 nM, or less than about 8 nM, or less than about 7 nM, or less than about 6 nM, or less than about 5 nM, or less than about 4 nM, or less than about 3 nM, or less than about 2 nM, or less than about 1 nM. In various embodiments, the compounds of the disclosure can act at NAMPT with an $IC_{50}$ of less than about 1 nM, or less than about 0.9 nM, or less than about 0.8 nM, or less than about 0.7 nM, or less than about 0.6 nM, or less than about 0.5 nM, or less than about 0.4 nM, or less than about 0.3 nM, or less than about 0.2 nM, or less than about 0.1 nM

Nicotinamide Phosphoribosyltransferase ("NAMPT") Inhibitors

Disclosed herein are compounds that can inhibit NAMPT with nanomolar potency and excellent solubility.

As used herein, the term "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_{1-7}$ alkyl refers to an alkyl group having a number of carbon atoms encompassing the entire range (e.g., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group. For example, an alkyl group can be substituted with one or more fluorine atoms to form a fluoroalkyl group (e.g., a methyl group can be substituted with 1 to 3 fluorine atoms to form $CH_2F$, $CHF_2$, or $CF_3$).

As used herein, the term "aryl" refers to a cyclic aromatic group, such as a monocyclic aromatic group, e.g., phenyl. Unless otherwise indicated, an aryl group can be unsubstituted or substituted with one or more, and in particular one to four groups independently selected from, for example, halo, alkyl, alkenyl, $OCF_3$, $NO_2$, CN, NC, OH, alkoxy, amino, $CO_2H$, $CO_2$alkyl, aryl, and heteroaryl. Aryl groups can be isolated (e.g., phenyl) or fused to another aryl group (e.g., naphthyl, anthracenyl), a cycloalkyl group (e.g. tetraydronaphthyl), a heterocycloalkyl group, and/or a heteroaryl group. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "halo" refers to a fluoro, chloro, bromo, or iodo group.

A used herein, the term "substituted," when used to modify a chemical functional group, refers to the replacement of at least one hydrogen radical on the functional group with a substituent. Substituents can include, but are not limited to, alkyl, cycloalkyl, alkenyl, cycloalkenyl, alkynyl, heterocycloalkyl, thioether, polythioether, aryl, heteroaryl, hydroxyl, oxy, alkoxy, heteroalkoxy, aryloxy, heteroaryloxy, ester, thioester, carboxy, cyano, nitro, amino, amido, acetamide, and halo (e.g., fluoro, chloro, bromo, or iodo). When a chemical functional group includes more than one substituent, the substituents can be bound to the same carbon atom or to two or more different carbon atoms. A substituted chemical functional group can itself include one or more substituents.

The chemical structures having one or more stereocenters depicted with dashed and bold bonds (i.e., ⋯ and ➝) are meant to indicate absolute stereochemistry of the stereocenter(s) present in the chemical structure. Bonds symbolized by a simple line do not indicate a stereo-preference. Unless otherwise indicated to the contrary, chemical structures that include one or more stereocenters which are illustrated herein without indicating absolute or relative stereochemistry, encompass all possible stereoisomeric forms of the compound (e.g., diastereomers, enantiomers) and mixtures thereof. Structures with a single bold or dashed line, and at least one additional simple line, encompass a single enantiomeric series of all possible diastereomers.

In some embodiments the compounds include a compound of Formula (II), or a pharmaceutically acceptable salt thereof:

(II)

wherein:
=== is a single bond or a double bond;
each of x and y independently is 0, 1, or 2;
A is T is CR$^a$R$^b$ or SiR$^1$R$^2$, provided that when T is SiR$^1$R$^2$, then === is a single bond;
each of G, U, V, and W independently is CR$^4$ or N, provided that at least three of G, U, V, and W are CR$^4$;
Z is CH$_2$ or C=O;
R$^a$ is H, C$_{1-4}$alkyl, or CH$_2$CO$_2$R$^5$;
R$^b$, when present, is H or C$_{1-4}$alkyl;
each of R$^1$ and R$^2$ independently is C$_{1-4}$alkyl or phenyl;
R$^3$ is H, C$_{1-4}$alkyl, or aryl;
each R$^4$ independently is H, halo, C$_{1-4}$alkyl, OH, OC$_{1-4}$alkyl, OBn, O(C=O)(CH$_2$)$_n$(C=O)(CH$_2$CH$_2$O)$_m$C$_{1-4}$alkyl, or O(C=O)(CH$_2$)$_n$(C=O)(CH$_2$CH$_2$O)$_m$H, or two adjacent R$^4$ groups are each OC$_{1-4}$alkyl, and together with the carbon atoms to which they are attached, form a five- or six-membered ring;
R$^5$ is H, C$_{1-4}$alkyl, (CH$_2$CH$_2$O)$_m$C$_{1-4}$alkyl, or (CH$_2$CH$_2$O)$_m$H;
n is 1-4; and
m is 1-10;
with the proviso that when y is 2, then the two carbon atoms adjacent to N can optionally be fused to a phenyl group, and the compound or salt thereof is not In various cases, the compound or salt of Formula (II) has a structure of Formula (II)':

(II')

wherein the substituents are as described above and Q is a counterion. In some embodiments, Q is chloride, mesylate, or tosylate.

In some embodiments, x is 0. In various embodiments, x is 1. In some cases, x is 2.

In various cases, y is 0. In some embodiments, y is 1. In various embodiments, y is 2.

In some cases, A is

In various cases, A is

In some embodiments, A is

In some cases, Z is CH$_2$. In various cases, Z is C=O.
In some embodiments, each of G, U, V, and W is CR$^4$. In some cases, G is N. In various embodiments, U is N. In some cases, V is N. In various cases, W is N. In some cases, each R⁴ group is H. In various cases, each of G, U, V, and W is CH. In some cases, G in N and each of U, V, and W is CH. In some embodiments, U is N and each of G, V, and W is CH. In various embodiments, V is N and each of G, U, and W is CH. In some cases, W is N and each of G, U, and V is CH. In various cases, one R⁴ group is halo, $C_{1-4}$alkyl, OH, $OC_{1-4}$alkyl, OBn, $O(C=O)(CH_2)_n(C=O)(CH_2CH_2O)_m$ $C_{1-4}$alkyl, or $O(C=O)(CH_2)_n(C=O)(CH_2CH_2O)_mH$, and the other three R⁴ groups are each H. In some embodiments, one R⁴ group is I, Br, Cl, F, Me, OH, OMe, OCF₃, OBn, or $O(C=O)(CH_2)_2(C=O)(CH_2CH_2O)_4Me$. In some cases, U is C(I), C(Br), C(Me), C(OMe), C(OBn), or $C(O(C=O)(CH_2)_n(C=O)(CH_2CH_2O)_mC_{1-4}$alkyl) and each of G, V, and W is CH. In various embodiments, two R⁴ groups are H and each of the other two R⁴ groups is independently OH or $OC_{1-4}$alkyl. In some cases, the two R⁴ groups are each OH. In various cases U is C(OH), V is C(OH), G is CH, and W is CH. In some embodiments, the two R⁴ groups are $OC_{1-4}$alkyl attached to adjacent carbon atoms, and together with the carbon atoms to which they are attached, form a five- or six-membered ring. In various embodiments, G is CH, W is CH, and each of U and V is $OC_{1-4}$alkyl that, together with the carbon atoms to which they are attached, form a five-membered ring.

In some embodiments, R³ is H. In various embodiments, R³ is Me. In some cases, R³ is aryl. In various cases, R³ is Ph.

In some cases, T is $SiR^1R^2$ and ═ is a single bond. In some embodiments, each of R¹ and R² is $C_{1-4}$alkyl. In various embodiments, one of R¹ and R² is $C_{1-4}$alkyl and the other is Ph. In various cases, each of R¹ and R² independently is Me or Et. In some embodiments, each of R¹ and R² is Me. In various embodiments, each of R¹ and R² is Et.

In some embodiments, T is $CR^aR^b$. In various embodiments, ═ is a single bond. In some cases, R^a and R^b are each H. In some embodiments, one of R^a and R^b is H and the other is $C_{1-4}$alkyl, or $CH_2CO_2R^5$. In various embodiments, one of R^a and R^b is H and the other is Me or Et. In some cases, each of R^a and R^b is Me or Et. In various cases, ═ is a double bond. In some embodiments, R^a is H. In some cases, R^a is $C_{1-4}$alkyl. In various cases, R^a is Me or Et. In various embodiments, R^a is $CH_2CO_2R^5$ and R⁵ is H, $C_{1-4}$alkyl, or $(CH_2CH_2O)_mC_{1-4}$alkyl or $(CH_2CH_2O)_mH$. In some cases, R⁵ is H, OMe, OEt, or $(CH_2CH_2O)_4Me$.

In various cases, the compound or salt of Formula (II) is a silylindoline compound having a silicon atom at the 3-position of the N-heterocycle. Without intending to be bound by any particular theory, the silicon atom increases binding of the compound to NAMPT by enhancing van der Waal effects and increasing lipophilicity. The silicon atom also improves metabolic stability of the compounds.

In some embodiments, the compound or salt of Formula (II) has a structure of Formula (III) or Formula (III′):

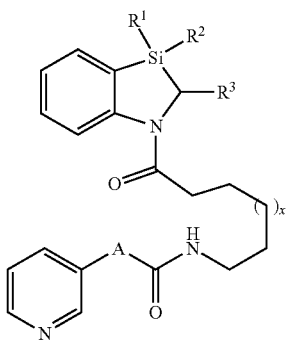

(III)

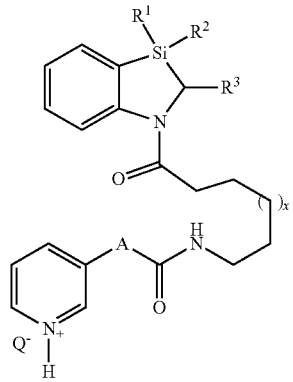

(III′)

wherein the substituents are as described above. In some embodiments, x is 1; each of R¹ and R² is Me or each of R¹ and R² is Et; and R³ is H, Me, or phenyl. In some cases, A is

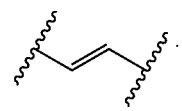 [SMILES: */C=C/*]

In various embodiments, each of R¹ and R² is Et. In some cases, R³ is Me. In various embodiments, x is 1, A is

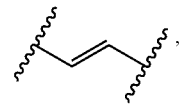

each of R¹ and R² is Et, and R³ is Me. In some cases, x is 1, A is

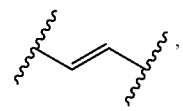

each of R¹ and R² is Et, and R³ is Me; and Q is Cl.

Accordingly, contemplated compounds of the disclosure include the compounds listed in Table A, below, and pharmaceutically acceptable salts thereof.

TABLE A

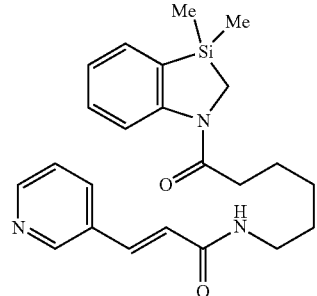

TABLE A-continued
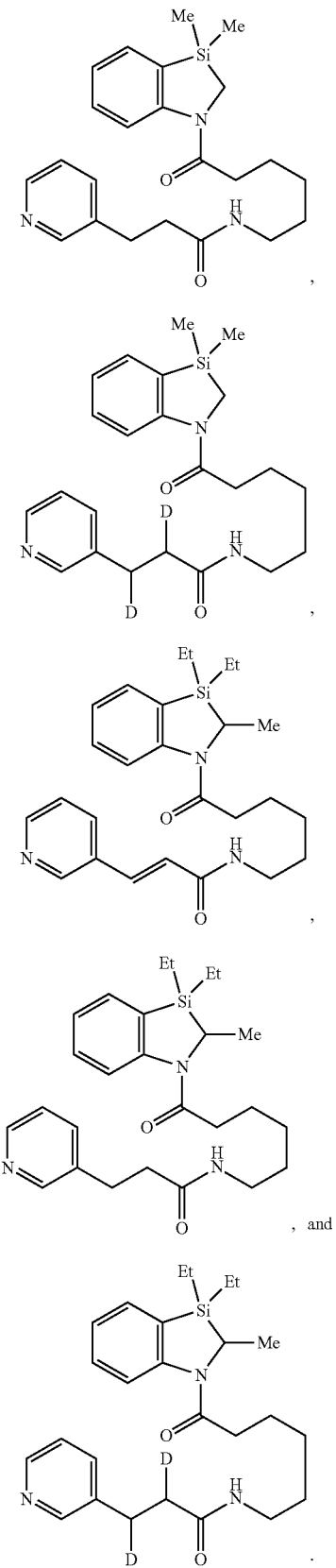
In some embodiments, the compound Formula (II) is a salt. Contemplated salts of the compound of Formula (II) include:
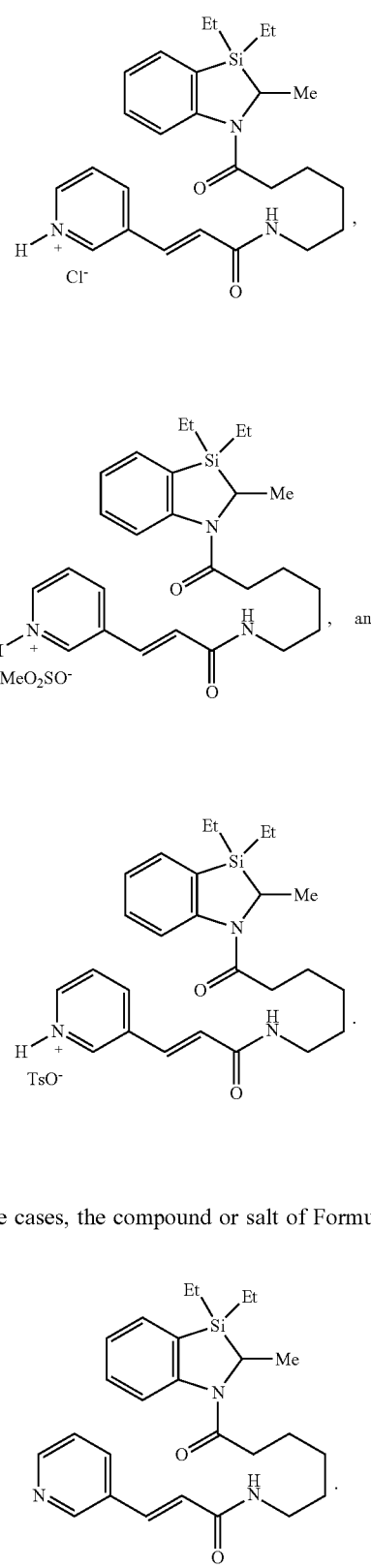
In some cases, the compound or salt of Formula (II) is In some embodiments, the compound or salt of Formula (II) is
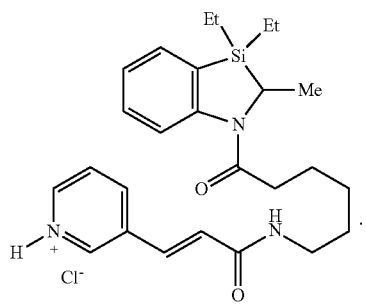
In various cases, the compound or salt of Formula (II) has a structure of Formula (IV) or (IV'):
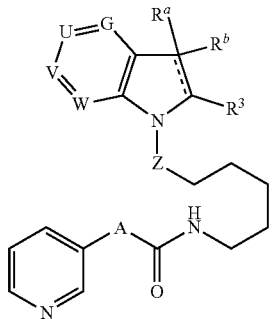
(IV)
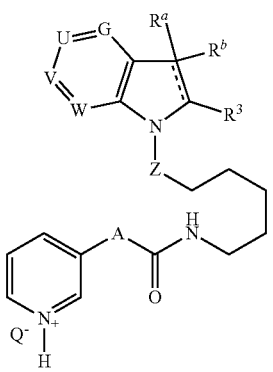
(IV')
wherein each variable is as described above and Q is a counterion (e.g., Cl, OMs, OTs). In some embodiments,
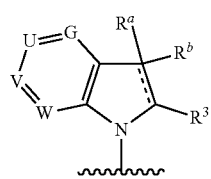
is selected from the group consisting of
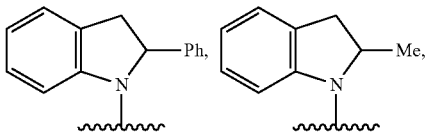
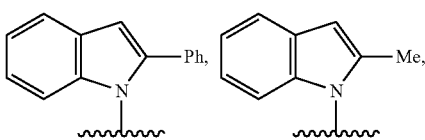
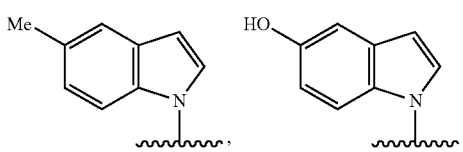
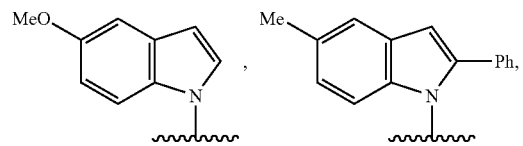
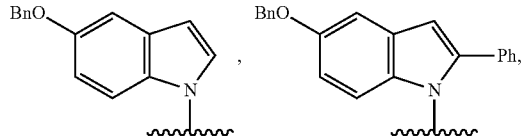
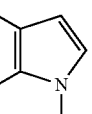
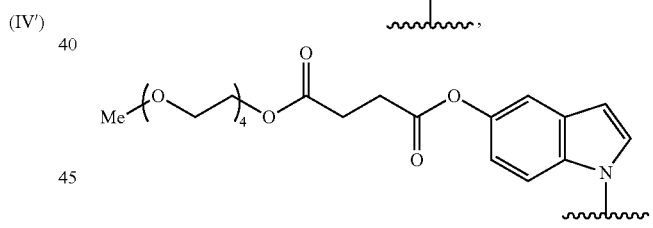
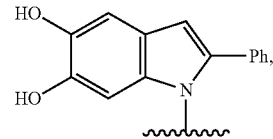
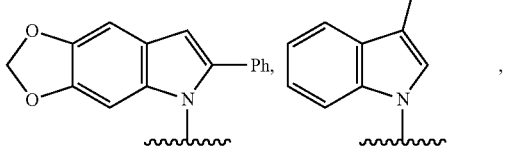
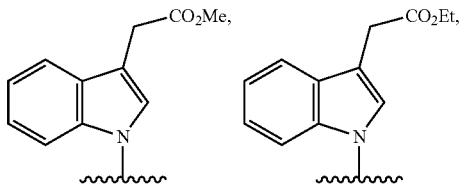

-continued
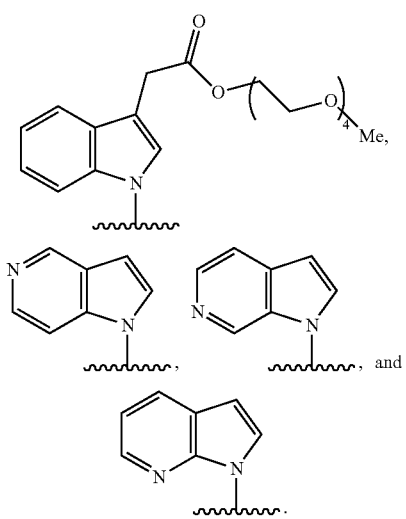, and
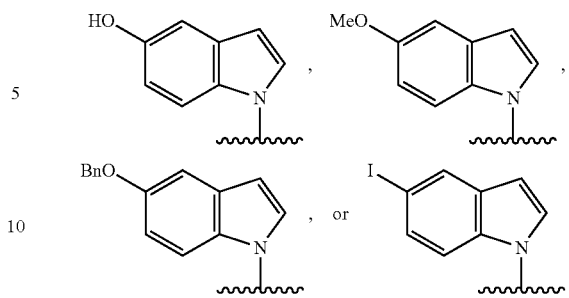
In some embodiments,
In various embodiments,
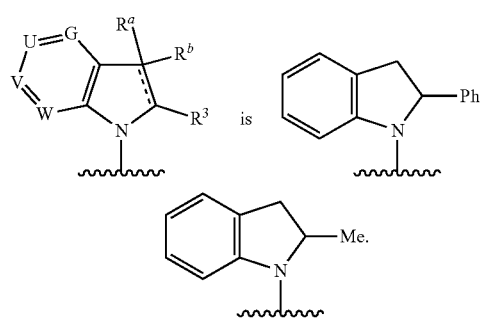 is
In some embodiments, 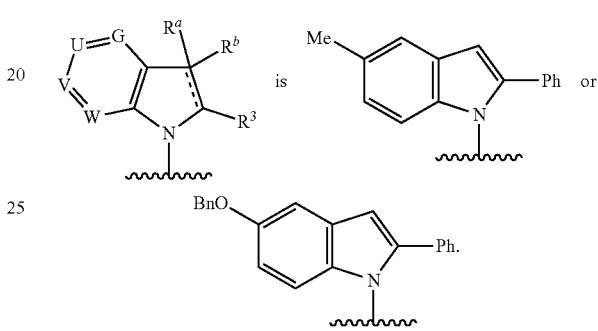 is
In various embodiments,
In some cases,
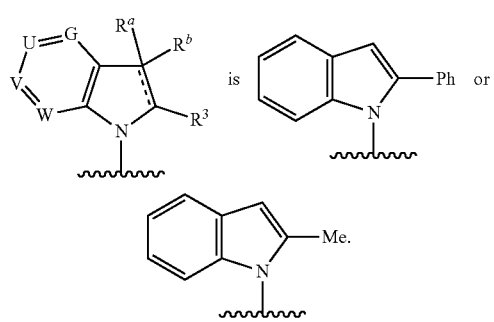 is
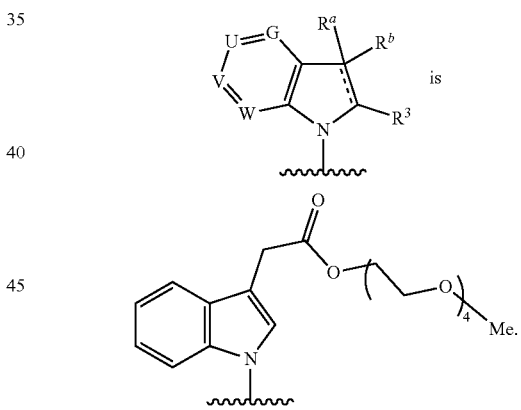 is
In various cases,
In some cases,
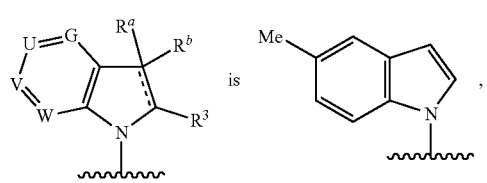 is
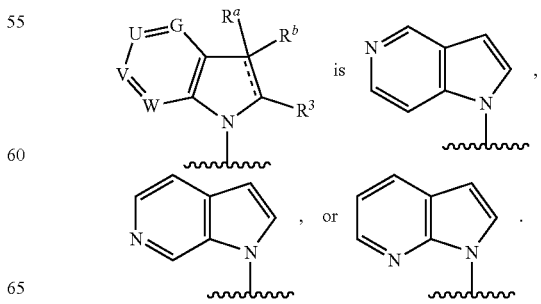 is In various cases,
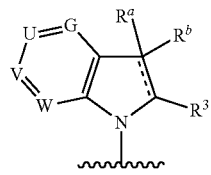
is not
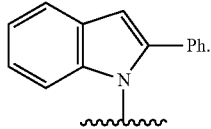
In some cases,
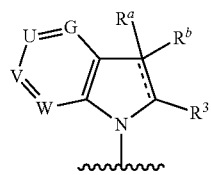
is not
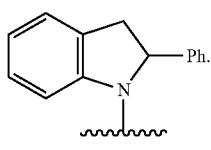
In some embodiments,
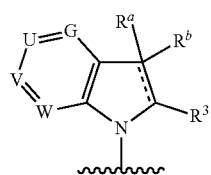
is not
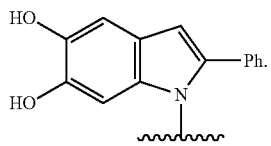
In various embodiments,
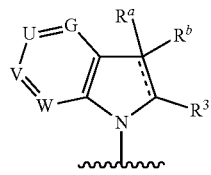
is not
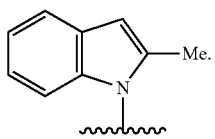 [SMILES: *n1c(C)cc2ccccc21]
In some cases,
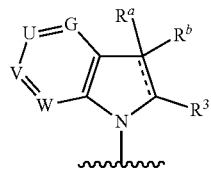
is not
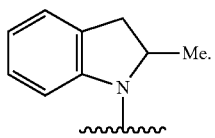 [SMILES: *N1c2ccccc2CC1C]
In various cases,
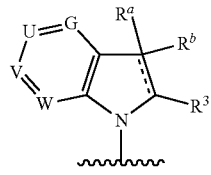
is not
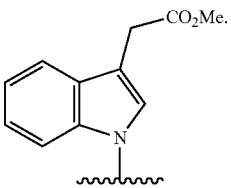 [SMILES: *n1cc(CC(=O)OC)c2ccccc21]

In some embodiments,

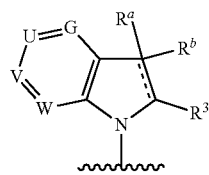

is not

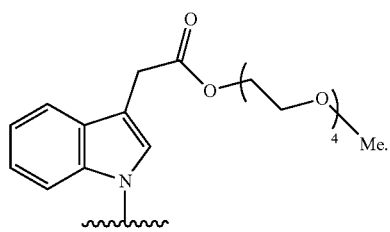

In various embodiments,

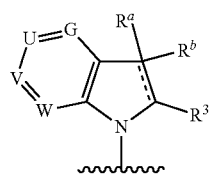

is not

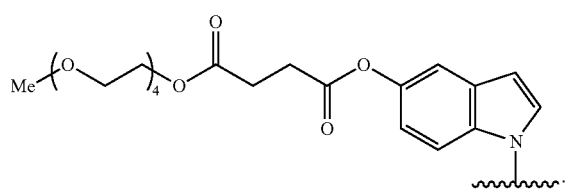

In some cases,

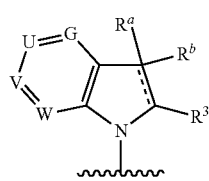

is not

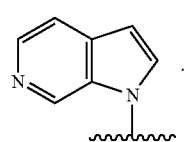

In some embodiments, A is

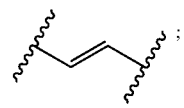 [SMILES: */C=C/*]

each of G, U, V, and W is CH; ⚌ is a single bond; each of $R^a$ and $R^b$ is H, and Z is C═O. In various embodiments, A is

each of G, U, V, and W is CH; ⚌ is a single bond; each of $R^a$ and $R^b$ is H; and Z is $CH_2$. In some cases, A is

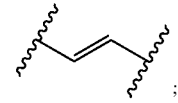 [SMILES: */C=C/*]

each of G, U, V, and W is CH; ⚌ is a double bond; $R^a$ is H; and Z is C═O. In various cases, A is

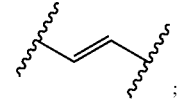 [SMILES: */C=C/*]

each of G, U, V, and W is CH; ⚌ is a double bond; $R^a$ is H; and Z is $CH_2$. In some embodiments $R^3$ is Ph. In various embodiments, A is

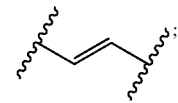 [SMILES: */C=C/*]

each of G, U, V, and W is CH; ⚌ is a single bond; each of $R^a$ and $R^b$ is H, and Z is C═O.

Accordingly, contemplated compounds of the disclosure include the compounds listed in Table B, below, and pharmaceutically acceptable salts thereof.

TABLE B

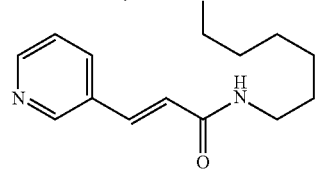

TABLE B-continued
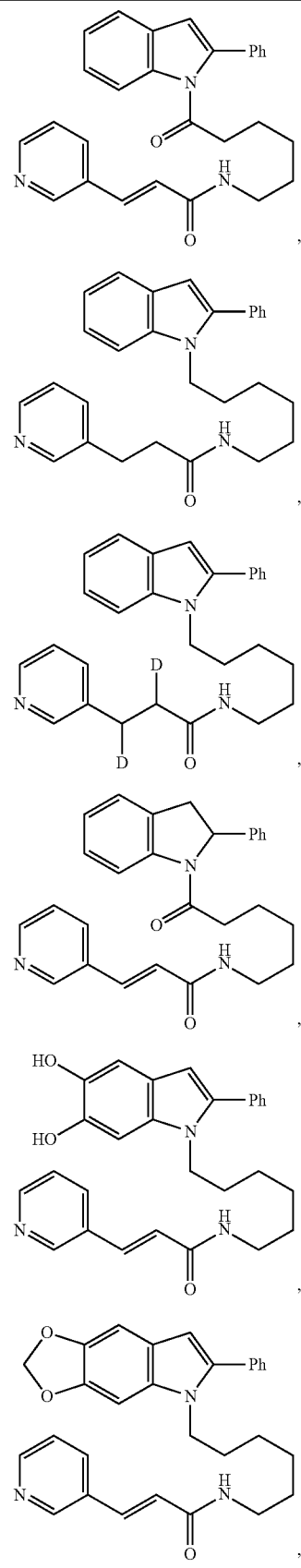
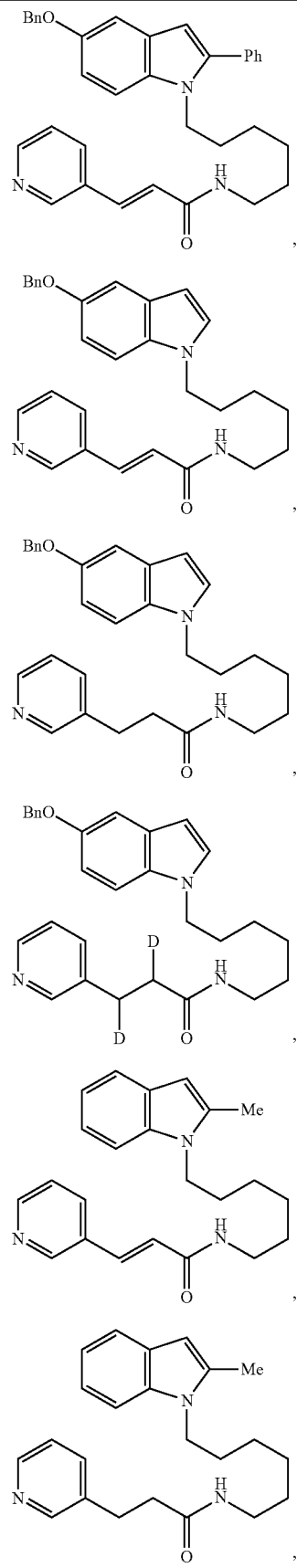

TABLE B-continued
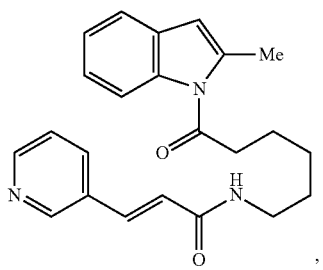
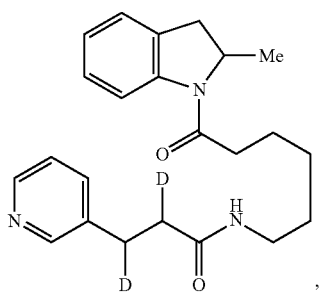 [SMILES: [2H]C(C(=O)NCCCCCC(=O)N1c2ccccc2CC1C)C([2H])c1cccnc1]
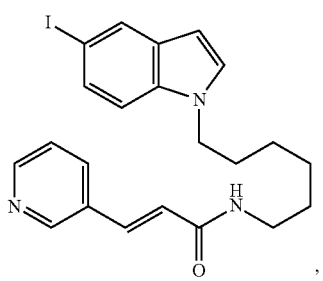 [SMILES: O=C(/C=C/c1cccnc1)NCCCCCCn1ccc2cc(I)ccc21]
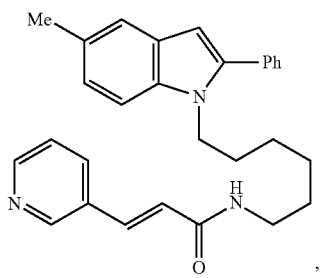 [SMILES: Cc1ccc2c(c1)cc(-c1ccccc1)n2CCCCCCNC(=O)/C=C/c1cccnc1]
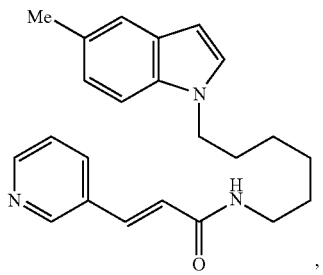
TABLE B-continued
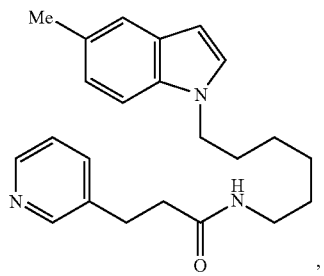 [SMILES: Cc1ccc2c(ccn2CCCCCCNC(=O)CCc2cccnc2)c1]
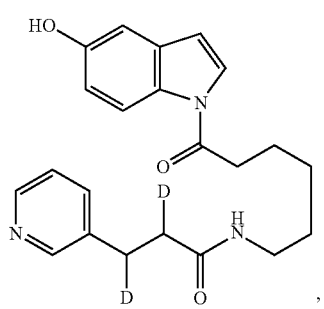 [SMILES: [2H]C(C(=O)NCCCCCC(=O)n1ccc2cc(O)ccc21)C([2H])c1cccnc1]
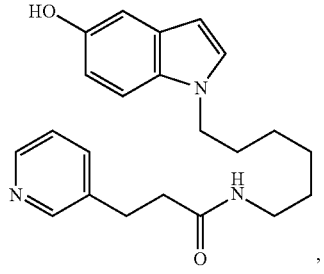 [SMILES: O=C(CCc1cccnc1)NCCCCCCn1ccc2cc(O)ccc21]
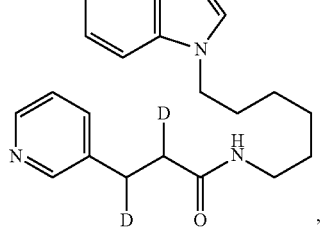

TABLE B-continued

TABLE B-continued
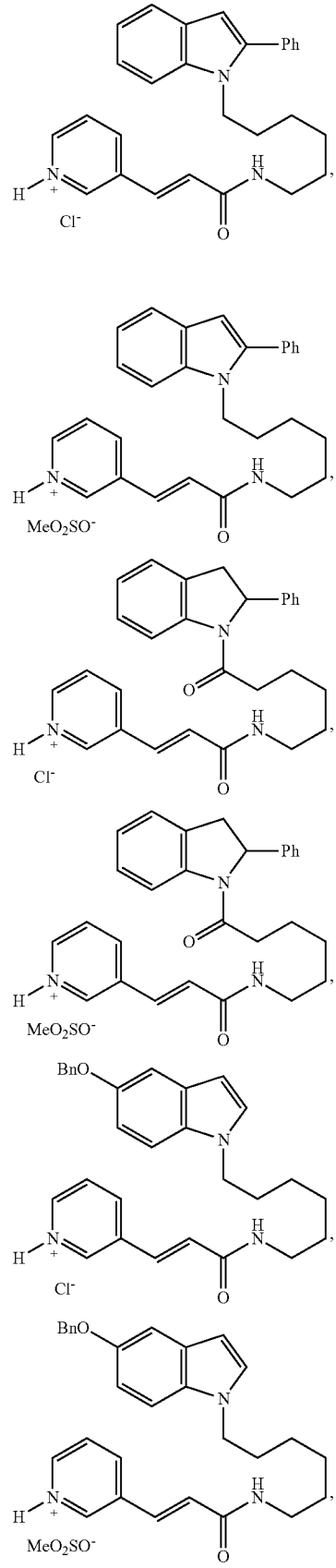
In some embodiments, the compound or salt of Formula (II) is a salt. In various embodiments, the salt is selected from the group consisting of:

-continued
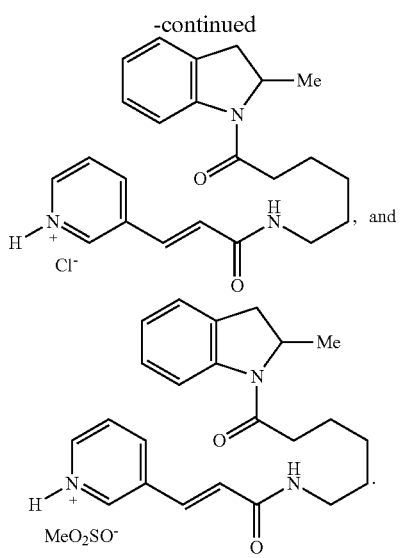
In various embodiments, the compound of Formula (II) is selected from the group consisting of:
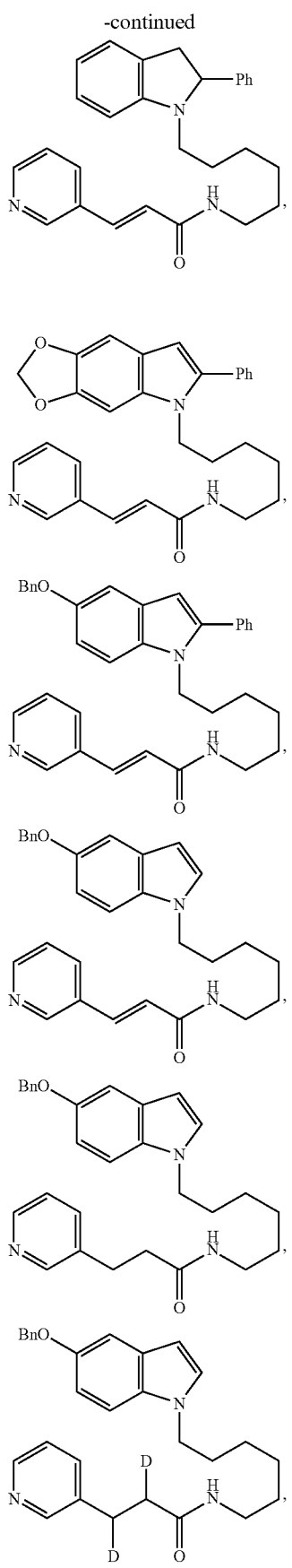

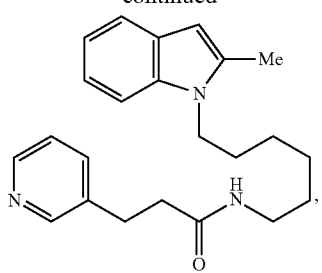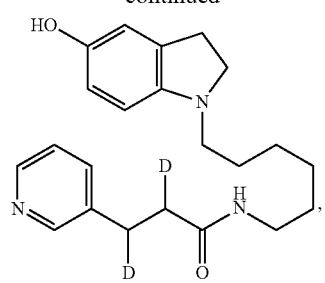

and pharmaceutically acceptable salts thereof. In some cases, the compound of Formula (II) is selected from the group consisting of

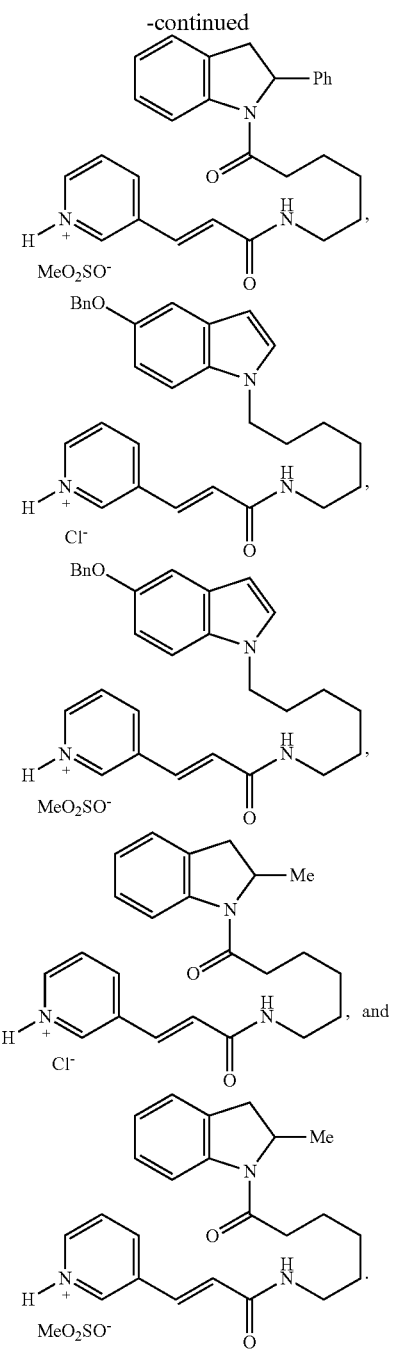
In various embodiments, the compound or salt of Formula (II) is not:
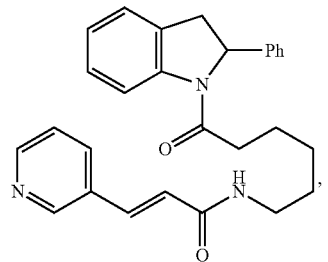
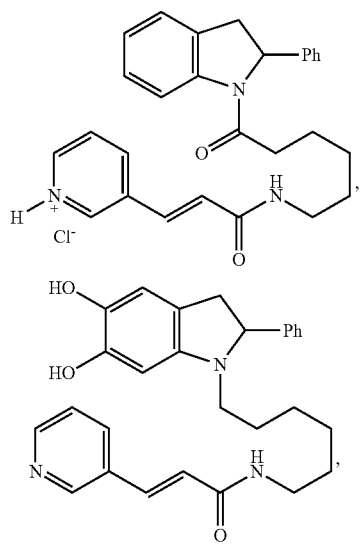
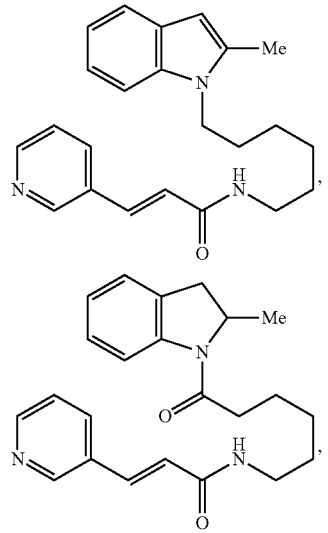
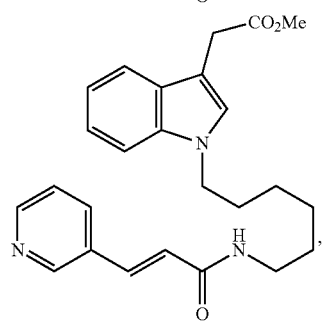

-continued

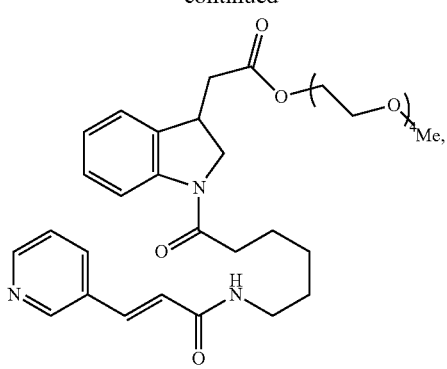

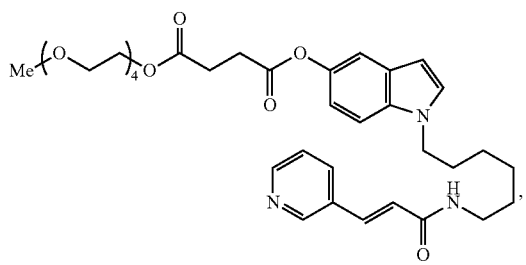

In various embodiments, the compound or salt of Formula (II) is selected from

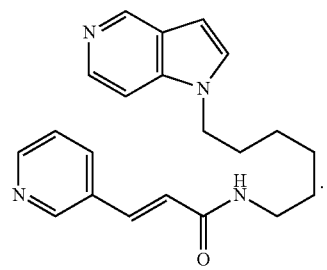 [SMILES: O=C(/C=C/c1cccnc1)NCCCCCCn1ccc2cnccc21]

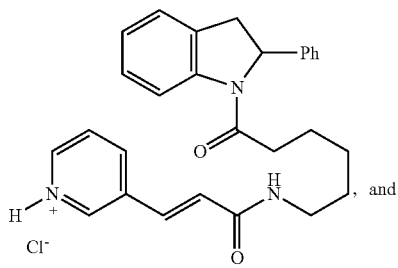

-continued

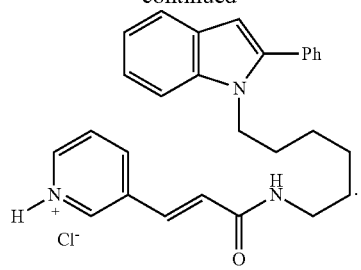

In some cases, the disclosure provides compounds or salts of Formula (II) wherein y is 2, and the two carbon atoms adjacent to the nitrogen atom are fused to a phenyl group. In various cases, the compound or salt of Formula (II) has a structure of Formula (V) or (V'):

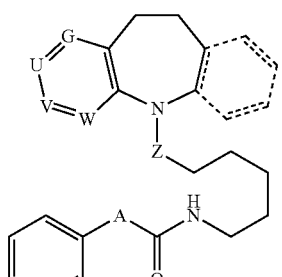
(V)

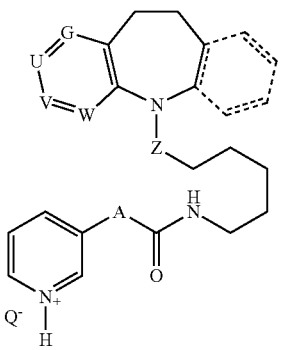
(V')

wherein

is present or absent, Q is a counterion (e.g., Cl, OMs, OTs), and the remaining substituents are as described above. In some cases, the compound or salt is not

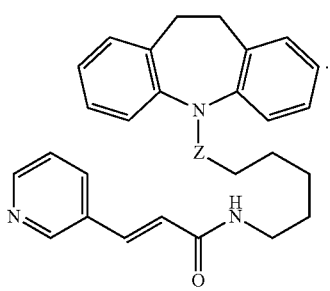
In some cases,
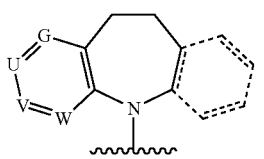
is selected from the group consisting of
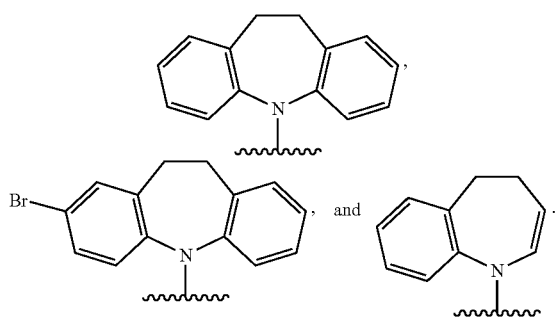
In some embodiments,
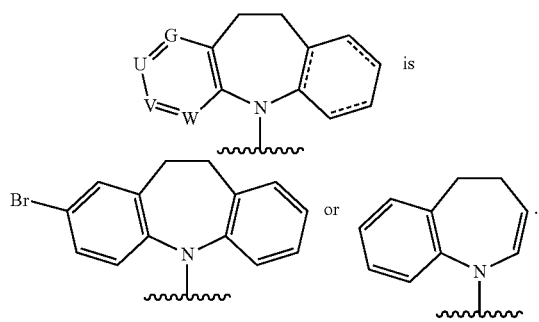
In various embodiments,
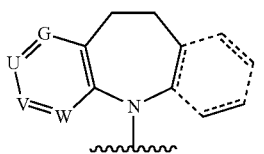
is not
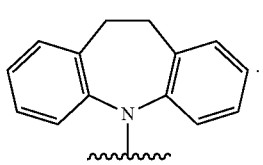
Accordingly, contemplated compounds of the disclosure include the compounds listed in Table C, below, and pharmaceutically acceptable salts thereof.
TABLE C
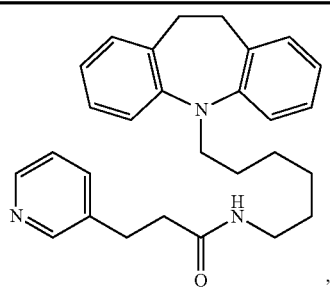
,
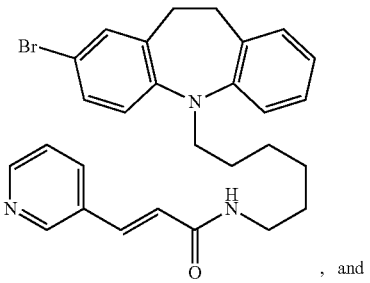 [SMILES: O=C(/C=C/c1cccnc1)NCCCCCCN1c2ccccc2CCc2cc(Br)ccc21]
, and
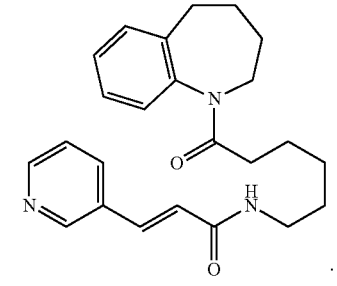 [SMILES: O=C(/C=C/c1cccnc1)NCCCCCC(=O)N1CCCCc2ccccc21]
.
In some embodiments, the compound or salt of Formula II is
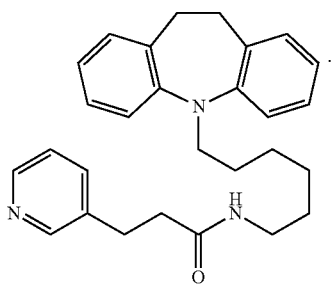 [SMILES: O=C(CCc1cccnc1)NCCCCCCN1c2ccccc2CCc2ccccc21]

Synthesis of the NAMPT Inhibitors

The compounds of the disclosure can be synthesized by any method known to one skilled in the art.

The silylindoline compounds can generally be prepared from aryl azides using Rh2(II)-catalyzed sp$^3$ C—H bond amination technology. In particular, a desired ortho-silyl substituted aryl azide can be reacted with a rhodium catalyst to form a desired benzo[1,3]azasilole compound. The benzo [1,3]azasilole can be reacted with a desired 2-(1,3-dioxoisoindolin-2-yl)acetyl chloride, base, hydrazine, and (E)-(pyridin-3-yl)acrylic acid to form the desired silylindoline analog, as shown in Scheme 1, below.

Scheme 1

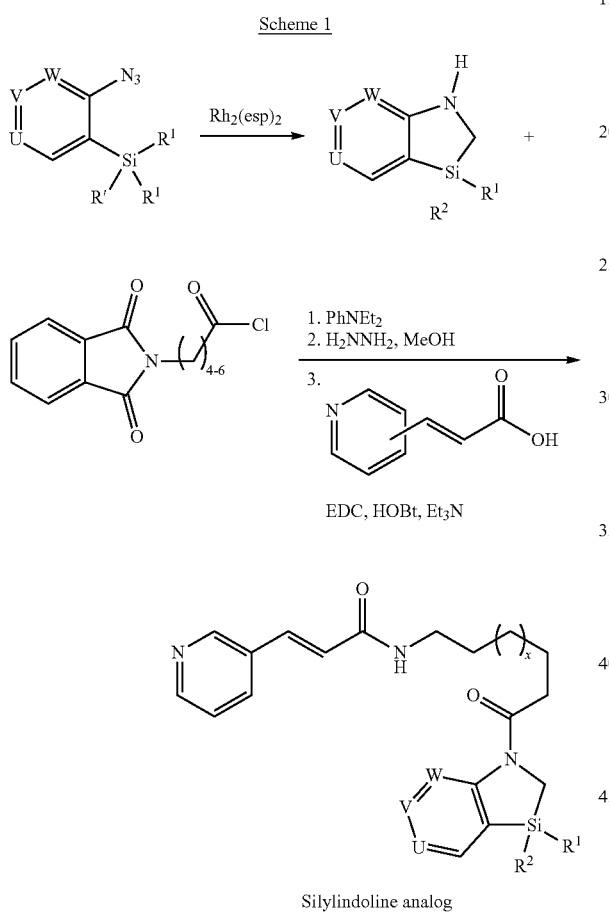

Silylindoline analog

The indole compounds can be synthesized by reacting a desired indole and a desired phthalimide with KH and crown ether, or alternatively NaH, to form a desired N-(6-indolehexyl)-phthalimide. The phthalimide can be reacted with desired (E)-(pyridin-3-yl)acrylic acid to form the desired indole product as shown in Scheme 2, below.

Scheme 2

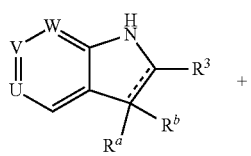

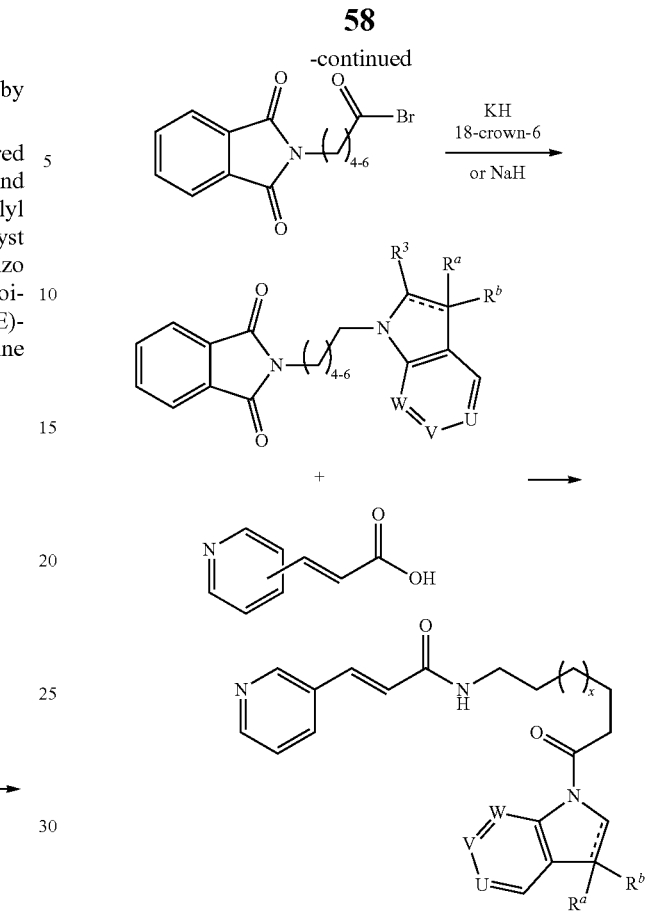

If desired, the double bond of the acrylamidyl group can be saturated with hydrogen or deuterium using techniques known to those skilled in the art.

Additional synthetic procedures for preparing the compounds disclosed herein can be found in the Examples section.

Methods

The compounds of the disclosure can inhibit nicotinamide phosphoribosyltransferase ("NAMPT") in a cell with nanomolar potency, and have been found to treat disorders and diseases, such as pulmonary arterial hypertension ("PAH") cancer, lung disorders, and metabolic disease.

Therefore, one aspect of the disclosure relates to a method of inhibiting NAMPT in a cell, comprising contacting the cell with a compound described herein (e.g., a compound or salt of Formula (II), a compound or salt of Formula (III), Formula (III'), a compound or salt of Formula (IV), a compound of Formula (IV'), a compound or salt of Formula (V), a compound of Formula (V'), a compound listed in Table A or salt thereof, a compound listed in Table B or salt thereof, a compound listed in Table C or salt thereof, DGMS-RAR-2, or a combination thereof) in an amount effective to inhibit NAMPT. As used herein, the term "pharmaceutically acceptable" means that the referenced substance, such as a compound of the present disclosure or a composition containing the compound, or a particular excipient, are safe and suitable for administration to a subject or patient.

The compounds disclosed herein can inhibit NAMPT in a cell by contacting the cell in vitro or in vivo. In some embodiments, the contacting occurs in vitro. In other embodiments, the contacting occurs in vivo. The compounds can contact NAMPT in vivo by administering the compound to a subject or patient in need of regulation of NAMPT. As used herein, the terms "patient" and "subject" may be used interchangeably and mean animals, such as dogs, cats, cows, horses, and sheep (i.e., non-human animals) and humans. Particular patients are mammals (e.g., humans). Put another way, in various embodiments, the invention includes administering one or more compounds of the disclosure to a subject or patient, such as a human, in need thereof. In some of these embodiments, the patient suffers from a disease associated with deregulation of NAMPT or form a disease or disorder wherein inhibition of NAMPT would provide a benefit (e.g., pulmonary arterial hypertension, cancer, lung disorders, pulmonary fibrosis, and metabolic disease).

Another aspect of the disclosure relates to a method of treating a disease associated with deregulation of NAMPT in a subject, comprising administering to the subject a therapeutically effective amount of a compound described herein (e.g., a compound or salt of Formula (II), a compound or salt of Formula (III), Formula (III'), a compound or salt of Formula (IV), a compound of Formula (IV'), a compound or salt of Formula (V), a compound of Formula (V'), a compound listed in Table A or salt thereof, a compound listed in Table B or salt thereof, a compound listed in Table C or salt thereof, DGMS-RAR-2, or a combination thereof). A further aspect of the disclosure relates to a method of treating a subject having a disease or disorder wherein inhibition of nicotinamide phosphoribosyltransferase would provide a benefit comprising administering to the subject a therapeutically effective amount of a compound described herein (e.g., a compound or salt of Formula (II), a compound or salt of Formula (III), Formula (III'), a compound or salt of Formula (IV), a compound of Formula (IV'), a compound or salt of Formula (V), a compound of Formula (V'), a compound listed in Table A or salt thereof, a compound listed in Table B or salt thereof, a compound listed in Table C or salt thereof, DGMS-RAR-2, or a combination thereof). As used herein, the phrase "deregulation of nicotinamide phosphoribosyltransferase" or "deregulation of the NAMPT" refers to an abnormality in the regulatory ability of NAMPT, resulting excess NAMPT activity. As used herein, the term "therapeutically effective amount" refers to an amount of a compound or combination of therapeutically active compounds (e.g., a compound described herein, or a combination of compounds) that ameliorates, attenuates or eliminates one or more symptoms of a particular disease or condition (e.g., pulmonary arterial hypertension or cancer), or prevents or delays the onset of one of more symptoms of a particular disease or condition. As used herein the terms "treating", "treat" or "treatment" and the like include preventative (e.g., prophylactic) and palliative treatment. In some embodiments, the disease or condition is pulmonary arterial hypertension. In various embodiments, disease or condition can include, for example, cancer (see Lee et al., Gastroenterology 155(3):799 (2018); Moore et al., Cell Death & Disease 6:e1599 (2015)), lung disorders (see Camp et al., Scientific Reports 5:13135 (2015)), and metabolic disease. See, Saddi-Rosa et al., Diabetol Metab Syndr. 2:21 (2010)). In some cases, the cancer is can include cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma. In various cases, the lung disorder can include acute respiratory distress syndrome, acute lung injury, pulmonary fibrosis, and ventilator-induced lung injury. In some embodiments, the metabolic disease can include phenylketonuria, tyrosinemia, homocystinuria, and non-ketotic hyperglycinemia.

Use of a compound disclosed herein, or a pharmaceutically acceptable salt thereof (e.g., a compound or salt of Formula (II), a compound or salt of Formula (III), Formula (III'), a compound or salt of Formula (IV), a compound of Formula (IV'), a compound or salt of Formula (V), a compound of Formula (V'), a compound listed in Table A or salt thereof, a compound listed in Table B or salt thereof, a compound listed in Table C or salt thereof, DGMS-RAR-2, or a combination thereof) to treat a condition resulting from deregulation of NAMPT in a subject, as well as use of the inhibitor in the preparation of a medicament for treating the condition, also are contemplated. Likewise, use of a compound disclosed herein, or a pharmaceutically acceptable salt thereof (e.g., a compound or salt of Formula (II), a compound or salt of Formula (III), Formula (III'), a compound or salt of Formula (IV), a compound of Formula (IV'), a compound or salt of Formula (V), a compound of Formula (V'), a compound listed in Table A or salt thereof, a compound listed in Table B or salt thereof, a compound listed in Table C or salt thereof, DGMS-RAR-2, or a combination thereof) to treat a disease or disorder wherein inhibition of nicotinamide phosphoribosyltransferase would provide a benefit, as well as use of the inhibitor in the preparation of a medicament for treating the condition, also are contemplated.

Further guidance of using the compounds disclosed herein for inhibiting NAMPT can be found in the Examples section, below.

Pharmaceutical Formulations

Also provided herein are pharmaceutical formulations that include the compounds of the disclosure, and one or more pharmaceutically acceptable excipients. As used herein, the term "excipient" refers to any pharmaceutically acceptable additive, carrier, diluent, adjuvant, or other ingredient, other than the active pharmaceutical ingredient ("API"). The term "pharmaceutically acceptable carrier" refers to a medium that does not interfere with the effectiveness of the biological activity of the active ingredient(s) and is not toxic to the host to which it is administered.

The compound or salts of the disclosure can be administered to a subject or patient in a therapeutically effective amount. The compound or salts can be administered alone or as part of a pharmaceutically acceptable composition or formulation. In addition, the compounds or salts can be administered all at once, as for example, by a bolus injection, multiple times, e.g. by a series of tablets, or delivered substantially uniformly over a period of time, as for example, using transdermal delivery. It is also noted that the dose of the compound can be varied over time.

The compounds or salts disclosed herein can be administered in combination with one or more additional pharmaceutically active compounds/agents. The additional pharmaceutically active compounds/agents may be traditional small organic chemical molecules or can be macromolecules such as a proteins, antibodies, peptibodies, DNA, RNA or fragments of such macromolecules.

The compounds or salts disclosed herein and other pharmaceutically active compounds, if desired, can be administered to a subject or patient by any suitable route, e.g. orally, rectally, parenterally, (for example, intravenously, intramuscularly, or subcutaneously) intracisternally, intravaginally, intraperitoneally, intravesically, or as a buccal, inhalation, or nasal spray. The administration can be to provide a systemic effect (e.g. eneteral or parenteral). All methods that can be used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferably suppositories, which can be prepared by mixing the compounds of the disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

The compounds of the disclosure can be administered to a subject or patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that will be used can potentially depend on a number of factors, including the requirements of the subject or patient, the severity of the condition or disease being treated, and the pharmacological activity of the compound being administered. The determination of dosage ranges and optimal dosages for a particular subject or patient is within the ordinary skill in the art.

When a subject or patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

In jurisdictions that forbid the patenting of methods that are practiced on the human body, the meaning of "administering" of a composition to a human subject or patient shall be restricted to prescribing a controlled substance that a human subject or patient will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

EXAMPLES

The following examples are provided for illustration and are not intended to limit the scope of the invention.

General $^1$H NMR and $^{13}$C NMR spectra were recorded at ambient temperature using 500 MHz or 300 MHz spectrometers. The data are reported as follows: chemical shift in ppm from internal tetramethylsilane on the δ scale, multiplicity (br=broad, s=singlet, d=doublet, t=triplet, q=quartet, m=multiplet), coupling constants (Hz) and integration. High-resolution mass spectra were obtained by peak matching. Melting points are reported uncorrected. Infrared spectroscopy was obtained using a diamond attenuated total reflectance (ATR) accessory. Analytical thin layer chromatography was performed on 0.25 mm extra hard silica gel plates with UV254 fluorescent indicator. Liquid chromatography was performed using forced flow (flash chromatography) of the indicated solvent system on 60 Å (40-60 μm) mesh silica gel ($SiO_2$). Medium pressure liquid chromatography (MPLC) was performed using pumps to force flow the indicated solvent system down columns that had been packed with 60 Å (40-60 μm) mesh silica gel ($SiO_2$). All reactions were carried out under an atmosphere of nitrogen in glassware, which had been oven-dried. Unless otherwise noted, all reagents were commercially obtained and, where appropriate, purified prior to use. Acetonitrile, methanol, toluene, THF, $Et_2O$, and $CH_2Cl_2$ were dried by filtration through alumina according to the procedure of Grubbs. See Pangborn et al., Organometallics 15:1518 (1996). Metal salts were stored in a nitrogen atmosphere dry box. The vinyl triflates used in our study were synthesized following literature reports. See Kong et al., Org. Lett. 17:802 (2015) and Kong et al., Tetrahedron Lett. 56:3262 (2015).

I. Preparation of ortho-Silyl Substituted Aryl Azide Substrates

A. Substrate synthesis overview. ortho-Silyl substituted aryl azide substrates were synthesized from 2-iodoaniline or 2-bromoaniline following Method A outlined in Scheme s1 or Method B outlined in Scheme s2.

Method A:

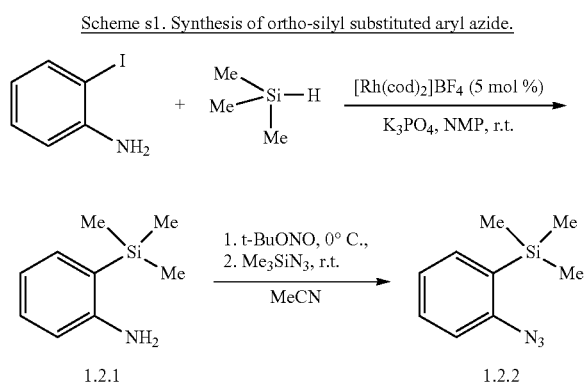

Method B:

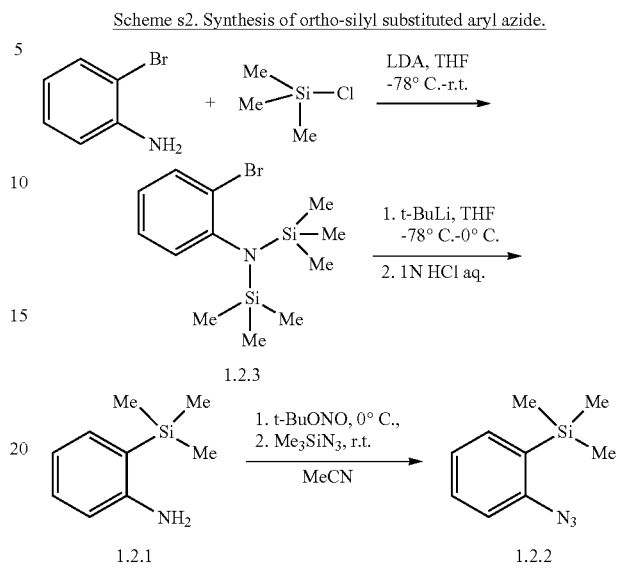

B. Synthesis of 2-bromo-N,N-disilyl substituted Aniline.

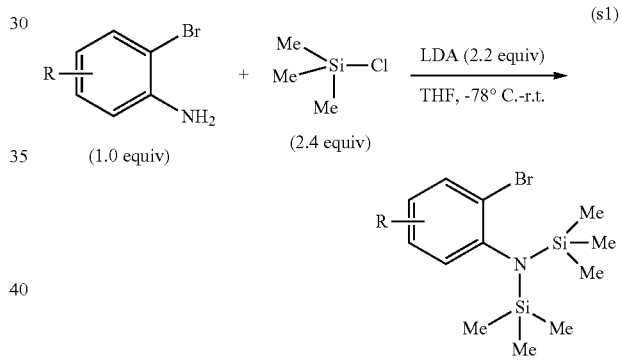

Synthesis of 2-bromo-N,N-disilyl substituted aniline was performed following the procedure reported by Storozhenko, Belyakova and co-workers. See Storozhenko et al., Russian J. Gen. Chem. 78:892 (2008). To an oven-dried round bottom flask was added a 0.2 M solution of 2-bromoaniline in THF under a $N_2$ atmosphere. The flask was then cooled to −78° C. The first portion of a 2.0 M solution of LDA (1.1 equiv) in THF was added to the reaction mixture over 5 min. After an additional 5 min, the first portion of trimethylsilyl chloride (1.2 equiv) was added into the reaction mixture over 5 min. After 15 min, the second portion of a 2.0 M solution of LDA (1.1 equiv) in THF was added over 5 min. After 20 min, the second portion of trimethylsilyl chloride (1.2 equiv) was added over 5 min. After 20 min, the reaction mixture was warmed to room temperature. After an additional 30 min, the reactives were quenched by the addition of 20 mL of a saturated aqueous solution of $NaHCO_3$. The resulting mixture was diluted with 20 mL of EtOAc. The mixture was washed with 2×20 mL of water and 20 mL of brine. The resulting organic phase was dried over $Na_2SO_4$, filtered and the filtrate was concentrated in vacuo. The resulting residue was purified by MPLC to afford the product.

Characterization Data for 2-bromo-N,N-disilyl-substituted Aniline.

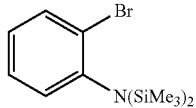

1.2.3a

2-Bromo-N,N-disilyl substituted aniline 1.2.3a. The general procedure was followed using 344 mg of 2-bromoaniline (2.0 mmol) in 10 mL of THF, 2.20 mL of a 2.0 M LDA solution in THF (4.4 mmol), 471 mg of trimethylsilyl chloride (4.80 mmol). Purification by MPLC chromatography (hexanes) afforded 1.2.3a as a clear oil (606 mg, 96% yield). The spectral data of 1.2.3a matched that reported by Storozhenko et al. $^1$H NMR (500 MHz, CDCl$_3$) δ 7.57 (dd, J=8.0, 1.5 Hz, 1H), 7.17 (td, J=8.0, 1.5 Hz, 1H), 7.02 (dd, J=7.5, 1.5 Hz, 1H), 6.94 (td, J=7.5, 1.5 Hz, 1H), 0.12 (s, 18H); $^{13}$C NMR (125 MHz, CDCl$_3$) δ 147.2 (C), 133.0 (CH), 131.8 (CH), 127.6 (CH), 126.9 (C), 125.2 (CH), 1.9 (CH$_3$); $^{29}$Si NMR (99.46 MHz, CDCl$_3$) δ 6.13. IR (thin film): 2955, 1463, 1251, 1225, 1028, 958, 913, 839, 750, 681 cm$^{-1}$. HRMS (ESI) m/z calculated for C$_{12}$H$_{22}$BrNSi$_2$ (M)$^+$: 315.0474, found: 315.0470.

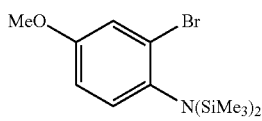

1.2.3b

2-Bromo-N,N-disilyl substituted aniline 1.2.3b. The general procedure was followed using 404 mg of 2-bromoaniline (2.0 mmol) in 10 mL of THF, 4.40 mL of a 2.0 M LDA solution in THF (4.40 mmol), 521 mg of trimethylsilyl chloride (4.80 mmol). Purification by MPLC chromatography (hexanes) afforded 1.2.3b as a clear oil (650 mg, 94% yield): $^1$H NMR (500 MHz, CDCl$_3$) δ 7.13 (d, J=3.0 Hz, 1H), 6.92 (d, J=8.5 Hz, 1H), 6.74 (dd, J=8.5, 3.0 Hz, 1H), 3.75 (s, 3H), 0.12 (s, 18H); $^{13}$C NMR (125 MHz, CDCl$_3$) δ 156.3 (C), 139.7 (C), 131.6 (CH), 126.7 (C), 117.8 (CH), 113.5 (CH), 55.4 (CH$_3$), −2.0 (CH$_3$); $^{29}$Si NMR (99.46 MHz, CDCl$_3$) δ 6.17. IR (thin film): 2954, 2899, 1597, 1483, 1439, 1264, 1213, 1204, 1042, 958, 839, 825 cm$^{-1}$. HRMS (ESI) m/z calculated for C$_7$H$_9$BrNO (M−2(SiMe$_3$)+3H)$^+$: 201.9868, found: 201.9863.

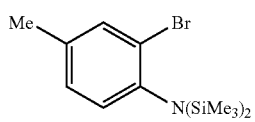

1.2.3c

2-Bromo-N,N-disilyl substituted aniline 1.2.3c. The general procedure was followed using 930 mg of 2-bromoaniline (5.0 mmol) in 25 mL of THF, 11.0 mL of a 2.0 M LDA solution in THF (11.0 mmol), 1.32 g of trimethylsilyl chloride (12.0 mmol). Purification by MPLC chromatography (hexanes) afforded 1.2.3c as a clear oil (1.55 g, 94% yield): $^1$H NMR (500 MHz, CDCl$_3$) δ 7.37 (d, J=1.0 Hz, 1H), 6.96 (dd, J=8.0, 1.5 Hz, 1H), 6.87 (d, J=8.0 Hz, 1H), 2.28 (s, 3H), 0.10 (s, 18H); $^{13}$C NMR (125 MHz, CDCl$_3$) δ 144.2 (C), 134.9 (C), 133.4 (CH), 131.3 (CH), 128.4 (CH), 126.4 (C), 20.4 (CH$_3$), 1.9 (CH$_3$); $^{29}$Si NMR (99.46 MHz, CDCl$_3$) δ 5.91. IR (thin film): 2955, 1480, 1267, 1251, 1233, 1043, 962, 934, 918, 868, 840, 682 cm$^{-1}$. HRMS (ESI) m/z calculated for C$_{17}$H$_{17}$O$_3$F$_3$Na (M+Na)$^+$: 349.1207, found: 349.1207.

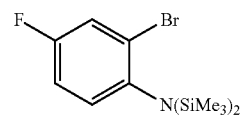

1.2.3d

2-Bromo-N,N-disilyl substituted aniline 1.2.3d. The general procedure was followed using 570 mg of 2-bromoaniline (3.0 mmol) in 15 mL of THF, 6.60 mL of a 2.0 M LDA solution in THF (6.60 mmol), 782 mg of trimethylsilyl chloride (7.20 mmol). Purification by MPLC chromatography (hexanes) afforded 1.2.3d as a clear oil (800 mg, 80% yield): $^1$H NMR (500 MHz, CDCl$_3$) δ 7.30 (dd, J=8.0, 3.0 Hz, 1H), 6.95 (dd, J=8.0, 5.0 Hz, 1H), 6.77 (td, J=8.0, 3.0 Hz, 1H), 0.10 (s, 18H); $^{13}$C NMR (125 MHz, CDCl$_3$) δ 158.8 (d, J$_{CF}$=244.4 Hz, C), 143.3 (C), 131.8 (d, J$_{CF}$=7.9 Hz, CH), 126.6 (d, J$_{CF}$=10.1 Hz, C), 119.8 (d, J$_{CF}$=25.8 Hz, CH), 114.4 (d, J$_{CF}$=22.0 Hz, CH), 1.9 (CH$_3$); $^{29}$Si NMR (99.46 MHz, CDCl$_3$) δ 6.59. IR (thin film): 2955, 1593, 1474, 1250, 1186, 1034, 957, 922, 873, 756, 684 cm$^{-1}$. HRMS (ESI) m/z calculated for C$_{12}$H$_{21}$BrFNSi$_2$ (M)$^+$: 333.0380, found: 333.0392.

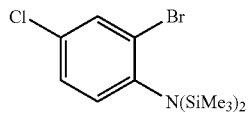

1.2.3e

2-Bromo-N,N-disilyl substituted aniline 1.2.3e. The general procedure was followed using 1.03 g of 2-bromoaniline (5.0 mmol) in 25 mL of THF, 11.0 mL of a 2.0 M LDA solution in THF (11.0 mmol), 1.30 g of trimethylsilyl chloride (12.0 mmol). Purification by MPLC chromatography (hexanes) afforded 1.2.3a as a clear oil (1.55 g, 89% yield): $^1$H NMR (500 MHz, CDCl$_3$) δ 7.56 (d, J=2.5 Hz, 0.84H), 7.15 (dd, J=8.5, 2.5 Hz, 1H), 6.92 (d, J=8.5 Hz, 0.9H), 0.10 (s, 15H); Diagnostic data for minor rotamer: $^1$H NMR (500 MHz, CDCl$_3$) δ 6.89 (d, J=8.0 Hz, 0.15H), 0.09 (s, 3H); $^{13}$C NMR (125 MHz, CDCl$_3$) δ 146.1 (C), 132.5 (CH), 132.2 (CH), 129.6 (C), 127.7 (CH), 127.2 (C), 1.90 (CH$_3$); Diagnostic data for minor rotamer: $^{13}$C NMR (125 MHz, CDCl$_3$) δ 132.1 (C), 129.4 (C), 3.9 (CH$_3$); $^{29}$Si NMR (99.46 MHz, CDCl$_3$) δ 6.58. IR (thin film): 2955, 2898, 1462, 1411, 1252, 1040, 959, 928, 904, 840, 773, 684 cm$^{-1}$. HRMS (ESI) m/z calculated for C$_9$H$_{14}$BrClNSi (M−SiMe$_3$+2H)$^+$: 277.9767, found: 277.9754.

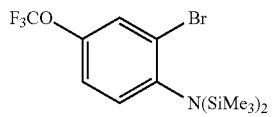

1.2.3f

2-Bromo-N,N-disilyl substituted aniline 1.2.3f. The general procedure was followed using 1.28 g of 2-bromoaniline (5.0 mmol) in 25 mL of THF, 11.0 mL of a 2.0 M LDA solution in THF (11.0 mmol), 1.30 g of trimethylsilyl chloride (12.0 mmol). Purification by MPLC chromatography (hexanes) afforded 1.2.3f as a clear oil (1.55 g, 89% yield): $^1$H NMR (500 MHz, CDCl$_3$) δ 7.45 (d, J=2.0 Hz, 1H), 7.05 (dd, J=9.0, 2.0 Hz, 1H), 7.00 (d, J=9.0 Hz, 1H), 0.11 (s, 18H); $^{13}$C NMR (125 MHz, CDCl$_3$) δ 146.3 (C), 145.2 (C), 131.8 (CH), 126.8 (C), 125.5 (CH), 120.4 (q, $J_{CF}$=255.1 Hz, C) 120.0 (CH), 1.8 (CH$_3$); $^{29}$Si NMR (99.46 MHz, CDCl$_3$) δ 6.80. IR (thin film): 2957, 1475, 1250, 1218, 1170, 959, 928, 908, 842, 684 cm$^{-1}$. HRMS (ESI) m/z calculated for C$_{10}$H$_{14}$BrF$_3$NOSi (M-SiMe$_3$+2H)$^+$: 327.9980, found: 327.9966.

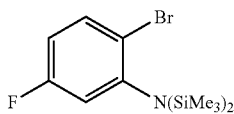

1.2.3g

2-Bromo-N,N-disilyl substituted aniline 1.2.3g. The general procedure was followed using 570 mg of 2-bromoaniline (3.0 mmol) in 15 mL of THF, 6.60 mL of a 2.0 M LDA solution in THF (6.60 mmol), 782 mg of trimethylsilyl chloride (7.20 mmol). Purification by MPLC chromatography (hexanes) afforded 1.2.3g as a clear oil (960 mg, 96% yield): $^1$H NMR (500 MHz, CDCl$_3$) δ 7.51-7.48 (m, 1H), 6.76-6.65 (m, 2H), 0.12 (s, 18H); $^{13}$C NMR (125 MHz, CDCl$_3$) δ 161.8 (d, $J_{CF}$=245.9 Hz, C), 149.0 (C), 133.3 (d, $J_{CF}$=9.4 Hz, CH), 121.3 (d, $J_{CF}$=3.6 Hz, C), 118.6 (d, $J_{CF}$=20.2 Hz, CH), 112.5 (d, $J_{CF}$=22.0 Hz, CH), 1.9 (CH$_3$); $^{29}$Si NMR (99.46 MHz, CDCl$_3$) δ 6.74. IR (thin film): 2956, 1592, 1574, 1457, 1392, 1282, 1250, 1154, 985, 946, 877, 840, 823 cm$^{-1}$. HRMS (ESI) m/z calculated for C$_9$H$_{14}$BrFNSi (M-SiMe$_3$+2H)$^+$: 262.0063, found: 262.0056.

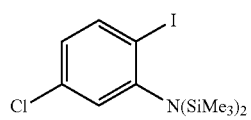

1.2.3h

2-Bromo-N,N-disilyl substituted aniline 1.2.3h. The general procedure was followed using 1.27 g of 2-iodoaniline (5.0 mmol) in 25 mL of THF, 11.0 mL of a 2.0 M LDA solution in THF (11.0 mmol), 1.30 g of trimethylsilyl chloride (12.0 mmol). Purification by MPLC chromatography (hexanes) afforded 1.2.3h as a clear oil (1.70 g, 85% yield): $^1$H NMR (500 MHz, CDCl$_3$) δ 7.74 (d, J=8.5 Hz, 1H), 7.00 (d, J=2.5 Hz, 1H), 6.80 (dd, J=8.5, 2.5 Hz, 1H), 0.14 (s, 18H); $^{13}$C NMR (125 MHz, CDCl$_3$) δ 152.2 (C), 139.8 (CH), 134.2 (C), 130.0 (CH), 125.8 (CH), 103.9 (C), 2.1 (CH$_3$); $^{29}$Si NMR (99.46 MHz, CDCl$_3$) δ 7.07. IR (thin film): 2954, 1564, 1454, 1441, 1370, 1251, 1218, 933, 865, 840, 823 cm$^{-1}$. HRMS (ESI) m/z calculated for C$_{12}$H$_{21}$ClINSi$_2$ (M)$^+$: 396.9946, found: 396.9932.

1.2.3i

2-Bromo-N,N-disilyl substituted aniline 1.2.3i. The general procedure was followed using 404 mg of 2-bromoaniline (2.0 mmol) in 10 mL of THF, 4.40 mL of a 2.0 M LDA solution in THF (4.40 mmol), 521 mg of trimethylsilyl chloride (4.80 mmol). Purification by MPLC chromatography (hexanes) afforded 1.2.3i as a clear oil (560 mg, 81% yield): $^1$H NMR (500 MHz, CDCl$_3$) δ 7.18 (dd, J=8.5, 1.0 Hz, 1H), 6.90 (t, J=8.0 Hz, 1H), 6.77 (dd, J=8.0, 1.0 Hz, 1H), 3.77 (s, 3H), 0.13 (s, 18H); $^{13}$C NMR (125 MHz, CDCl$_3$) δ 156.6 (C), 137.0 (C), 127.8 (C), 124.8 (CH), 124.4 (CH), 109.2 (CH), 55.1 (CH$_3$), 2.1 (CH$_3$); $^{29}$Si NMR (99.46 MHz, CDCl$_3$) δ 6.28. IR (thin film): 2954, 1565, 1463, 1443, 1246, 1041, 953, 908, 841, 824, 768, 681 cm$^{-1}$. HRMS (ESI) m/z calculated for C$_{13}$H$_{25}$BrNOSi$_2$ (M+H)$^+$: 346.0658, found: 346.0673.

1.2.3k

2-Bromo-N,N-disilyl substituted aniline 1.2.3k. The general procedure was followed using 516 mg of 2-bromoaniline (3.0 mmol) in 15 mL of THF, 6.60 mL of a 2.0 M LDA solution in THF (6.60 mmol), 1.23 g of methyldiphenylsilyl chloride (7.20 mmol). Purification by MPLC chromatography (hexanes) afforded 1.2.3k as a cloudy white oil (1.02 g, 77% yield): $^{29}$Si NMR (99.46 MHz, CDCl$_3$) δ −1.11. IR (thin film): 2956, 1462, 1427, 1250, 1220, 1111, 953, 895, 799, 697, 647 cm$^{-1}$. HRMS (ESI) m/z calculated for C$_{22}$H$_{27}$BrNSi$_2$ (M+H)$^+$: 440.0865, found: 440.0851. The product contains inseparable impurities. The product mixture was submitted to the next step without further purification.

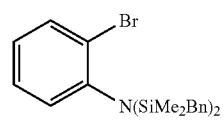

1.2.3l

2-Bromo-N,N-disilyl substituted aniline 1.2.3l. The general procedure was followed using 516 mg of 2-bromoaniline (3.0 mmol) in 15 mL of THF, 6.60 mL of a 2.0 M LDA solution in THF (6.60 mmol), 1.33 g of benzyldimethylsilyl chloride (7.20 mmol). Purification by MPLC chromatography (hexanes) afforded 1.2.3k as a cloudy white oil (1.10 g, 74% yield): $^1$H NMR (500 MHz, CDCl$_3$) δ 7.60 (dd, J=8.0, 1.5 Hz, 1H), 7.22-7.17 (m, 5H), 7.09-7.06 (m, 2H), 7.00-6.94 (m, 6H), 2.29 (d, J=13.3 Hz, 2H), 2.24 (d, J=13.3 Hz, 2H), 0.13 (s, 6H), 0.06 (s, 6H); $^{13}$C NMR (125 MHz, CDCl$_3$) δ 146.3 (C), 139.7 (C), 133.2 (CH), 132.2 (CH), 128.5 (CH), 128.2 (CH), 127.9 (CH), 126.8 (C), 125.7 (CH), 124.1 (CH), 28.4 (CH$_2$), −0.1 (CH$_3$), −0.6 (CH$_3$); $^{29}$Si NMR (99.46

MHz, CDCl$_3$) δ 5.61. IR (thin film): 3022, 2957, 1492, 1461, 1250, 1222, 1027, 952, 833, 760, 697 cm$^{-1}$. HRMS (ESI) m/z calculated for C$_{24}$H$_{31}$BrNSi$_2$ (M+H)$^+$: 468.1178, found: 468.1196.

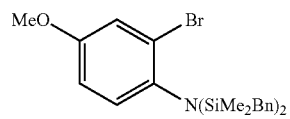

1.2.3m

2-Bromo-N,N-disilyl substituted aniline 1.2.3m. The general procedure was followed using 607 mg of 2-bromoaniline (2.0 mmol) in 15 mL of THF, 6.60 mL of a 2.0 M LDA solution in THF (6.60 mmol), 1.33 g of benzyldimethylsilyl chloride (7.20 mmol). Purification by MPLC chromatography (hexanes) afforded 1.2.3m as a clear oil (1.31 g, 87% yield): $^1$H NMR (500 MHz, CDCl$_3$) δ 7.41-7.36 (m, 5H), 7.26 (t, J=7.5 Hz, 2H), 7.21 (d, J=7.5 Hz, 4H), 7.01 (d, J=8.5 Hz, 1H), 6.91 (d, J=8.5 Hz, 1H), 3.86 (s, 3H), 2.52 (d, J=13.5 Hz, 2H), 2.46 (d, J=13.5 Hz, 2H), 0.36 (s, 6H), 0.30 (s, 6H); $^{13}$C NMR (125 MHz, CDCl$_3$) δ 156.9 (C), 139.9 (C), 139.0 (C), 132.3 (CH), 128.7 (CH), 128.4 (CH), 127.0 (C), 124.4 (CH), 118.2 (CH), 114.0 (CH), 55.6 (CH$_3$), 28.7 (CH$_2$), 0.2 (CH$_3$), –0.3 (CH$_3$); $^{29}$Si NMR (99.46 MHz, CDCl$_3$) δ 5.68. IR (thin film): 3023, 2956, 1598, 1482, 1249, 1201, 1152, 1030, 955, 922, 835, 807, 760, 697 cm$^{-1}$. HRMS (ESI) m/z calculated for C$_{25}$H$_{33}$BrNOSi$_2$ (M+H)$^+$: 498.1284, found: 298.1270.

C. Synthesis of 2-silyl Substituted Anilines.

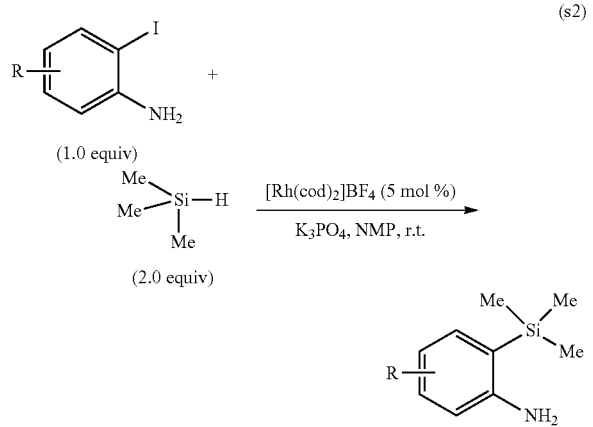

(s2)

Method A. Rhodium-catalyzed silylation of aryl halides with trialkylsilane was performed following the report of Yamanoi and Nishihara. See Yamanoi et al., J. Org. Chem. 73:6671 (2008). An oven-dried Schlenk flask or round bottom flask with a magnetic stir bar was charged with [Rh(cod)$_2$]BF$_4$ (5 mol %) and K$_3$PO$_4$ (3.0 equiv) under nitrogen atmosphere. Then a 0.5 M solution of aryl halides (1.0 equiv) in NMP and trimethyl silanes (1.0 mmol) were added to the reaction mixture in one portion. The flask was capped with a rubber septum and stirred at room temperature for up to 3 days. Once analysis of the reaction progress by thin layer chromatography revealed consumption of the aryl halide, the reactives were quenched with the addition of 10 mL of H$_2$O. The aqueous layer was extracted with 3×10 mL of DCM. The combined organic phases were dried over Na$_2$SO$_4$, filtered and the filtrate was concentrated in vacuo. The resulting residue was purified by MPLC to afford the product.

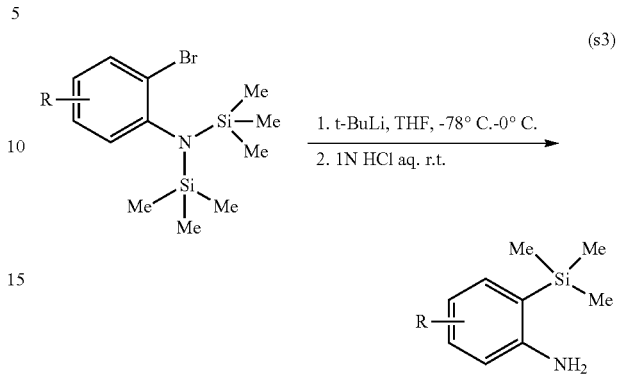

(s3)

Method B. The synthesis of 2-silyl substituted aniline from the 2-bromo-N,N-disilyl substituted aniline was achieved following the report by Storozhenko, Belyakova and co-workers.$^3$ A cooled (–78° C.) 0.2 M solution of N,N-disilyl substituted aniline (1.0 equiv) in THF was treated with a 1.9 M solution of t-BuLi (2.1 equiv) in pentanes. After 15 min, the reaction mixture was warmed to 0° C. After 15 min, the reaction mixture was treated with 10 mL of a 3 M aqueous solution of HCl. After 1 h, the reaction mixture was warmed to room temperature. The reaction mixture was extracted with 2×10 mL of EtOAc and the combined organic layers was washed with 2×10 mL H$_2$O, 10 mL of brine. The resulting organic phase was dried over Na$_2$SO$_4$, filtered and the filtrate was concentrated in vacuo. The resulting residue was purified by MPLC to afford the product.

Characterization Data for 2-Silyl Substituted Anilines.

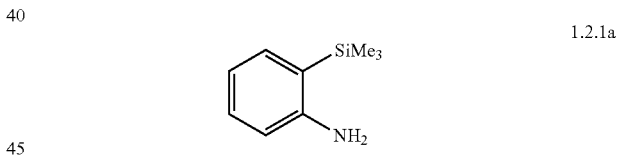

1.2.1a

2-Silyl substituted aniline 1.2.1a. (a) Method A was followed using 1.09 g of 2-iodoaniline (5.0 mmol), 0.742 g of trimethylsilane (10.0 mmol), 101.5 mg of [Rh(cod)$_2$]BF$_4$ (0.25 mmol), 3.18 g of K$_3$PO$_4$ (15.0 mmol) in 10 mL of NMP. Purification by MPLC chromatography (5:95 EtOAc: hexanes) 1.2.1a as a yellow gel (363 mg, 44% yield). (b) Method B was followed using 1.0 g of 2-bromo-N,N-disilyl substituted aniline (3.16 mmol), 3.50 mL of a 1.9 M t-BuLi solution in pentanes (6.64 mmol), and 18.0 mL of THF. Purification by MPLC chromatography (5:95 EtOAc: hexanes) afforded 1.2.1b as a yellow gel (497 mg, 95% yield). The spectral data of 1.2.1a matched that reported by Storozhenko, Belyakova and co-workers. $^3$ $^1$H NMR (500 MHz, CDCl$_3$) δ 7.33 (dd, J=7.0, 1.0 Hz, 1H), 7.21 (td, J=8.0, 1.0 Hz, 1H), 6.81 (td, J=7.0, 1.0 Hz, 1H), 6.65 (d, J=8.0 Hz, 1H), 3.67 (br s, 2H), 0.38 (s, 9H); $^{13}$C NMR (125 MHz, CDCl$_3$) δ 151.4 (C), 135.1 (CH), 130.6 (CH), 122.7 (C), 118.4 (CH), 115.4 (CH), 0.7 (CH$_3$); $^{29}$Si NMR (99.46 MHz, CDCl$_3$) δ –5.59. IR (thin film): 3473, 3382, 3063, 2954, 1621, 1589, 1478, 1438, 1311, 1287, 1250, 1102, 836, 752, 718 cm$^{-1}$. HRMS (ESI) m/z calculated for C$_9$H$_{16}$NSi (M+H)$^+$: 166.1052, found: 166.1047.

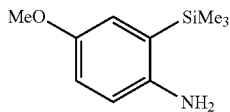

2-Silyl substituted aniline 1.2.1b. Method B was followed using 347 mg of 2-bromo-N,N-disilyl substituted aniline (1.0 mmol), 1.10 mL of a 1.9 M t-BuLi solution in pentanes (2.10 mmol) and 6.0 mL of THF. Purification by MPLC chromatography (5:95 EtOAc:hexanes) afforded 1.2.1b as a yellow gel (53.0 mg, 27% yield): $^1$H NMR (500 MHz, CDCl$_3$) δ 6.90 (d, J=2.5 Hz, 1H), 6.77 (dd, J=8.5, 2.5 Hz, 1H), 6.61 (d, J=8.5 Hz, 1H), 3.76 (s, 3H), 3.52 (br s, 2H), 0.36 (s, 9H); 13C NMR (125 MHz, CDCl$_3$) δ 152.5 (C), 145.0 (C), 125.0 (C), 120.7 (CH), 116.8 (CH), 115.6 (CH), 55.8 (CH$_3$), −0.8 (CH$_3$); $^{29}$Si NMR (99.46 MHz, CDCl$_3$) δ 6.17. IR (thin film): 2918, 2851, 1733, 1558, 1540, 1508, 1247, 1039, 839 cm$^{-1}$. HRMS (ESI) m/z calculated for C$_{10}$H$_{18}$NOSi (M+H)$^+$: 196.1158, found: 196.1158.

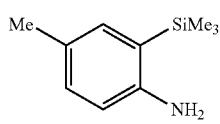

2-silyl substituted aniline 1.2.1c. Method B was followed using 991 mg of 2-bromo-N,N-disilyl substituted aniline (3.0 mmol), 3.3 mL of a 1.9 M t-BuLi solution in pentanes (6.2 mmol) and 15 mL of THF. Purification by MPLC chromatography (5:95 EtOAc:hexanes) afforded 1.2.1c as a yellow gel (474 mg, 88% yield): $^1$H NMR (500 MHz, CDCl$_3$) δ 7.34 (d, J=2.0 Hz, 1H), 7.21 (dd, J=8.0, 1.5 Hz, 1H), 6.74 (d, J=8.0 Hz, 1H), 3.82 (br s, 2H), 2.49 (s, 3H), 0.58 (s, 9H); $^{13}$C NMR (125 MHz, CDCl$_3$) δ 149.3 (C), 135.6 (CH), 131.4 (CH), 127.3 (C), 123.0 (C), 115.9 (CH), 20.8 (CH$_3$), −0.4 (CH$_3$); $^{29}$Si NMR (99.46 MHz, CDCl$_3$) δ −5.71. IR (thin film): 3464, 3375, 2954, 1621, 1488, 1391, 1249, 1105, 887, 834, 726, 686 cm$^{-1}$. HRMS (ESI) m/z calculated for C$_9$H$_{14}$NSi (M-Me)$^+$: 164.0896, found: 164.0894.

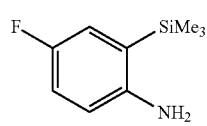

2-Silyl substituted aniline 1.2.1d. Method B was followed using 668 mg of 2-bromo-N,N-disilyl substituted aniline (2.0 mmol), 2.21 mL of a 1.9 M t-BuLi solution in pentanes (4.2 mmol) and 10 mL of THF. Purification by MPLC chromatography (5:95 EtOAc:hexanes) afforded 1.2.1d as a yellow gel (220 mg, 60% yield): $^1$H NMR (500 MHz, CDCl$_3$) δ 7.05 (dd, J=9.0, 3.0 Hz, 1H), 6.91 (td, J=8.5, 3.0 Hz, 1H), 6.81 (dd, J=9.0, 4.0 Hz, 1H), 3.70 (br s, 2H), 0.40 (s, 9H); $^{13}$C NMR (125 MHz, CDCl$_3$) δ 156.5 (d, J$_{CF}$=235.0 Hz, C), 147.4 (C), 125.1 (C), 120.7 (d, J$_{CF}$=20 Hz, CH), 116.9 (d, J$_{CF}$=23.4 Hz, CH), 116.7 (d, J$_{CF}$=7.4 Hz, CH), −1.0 (CH$_3$); $^{29}$Si NMR (99.46 MHz, CDCl$_3$) δ 6.17. IR (thin film): 3467, 3382, 2955, 2925, 2853, 1482, 1400, 1253, 1200, 838 cm$^{-1}$. HRMS (ESI) m/z calculated for C$_8$H$_{11}$FNSi (M-Me)$^+$: 168.0645, found: 168.0644.

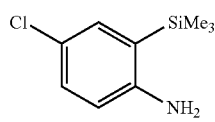

2-Silyl substituted aniline 1.2.1e. Method B was followed using 1.05 g of 2-bromo-N,N-disilyl substituted aniline (3.0 mmol), 3.26 mL of a 1.9 M t-BuLi solution in pentanes (6.2 mmol) and 15 mL of THF. Purification by MPLC chromatography (5:95 EtOAc:hexanes) afforded 1.2.1e as an orange gel (315 mg, 53% yield): $^1$H NMR (500 MHz, CDCl$_3$) δ 7.24 (d, J=2.5 Hz, 1H), 7.13 (dd, J=8.0, 2.5 Hz, 1H), 6.56 (t, J=8.0 Hz, 1H), 3.79 (br, 2H), 0.37 (s, 9H); $^{13}$C NMR (125 MHz, CDCl$_3$) δ 149.8 (C), 134.3 (CH), 130.1 (CH), 125.1 (C), 123.4 (C), 116.7 (CH), −0.9 (CH$_3$); $^{29}$Si NMR (99.46 MHz, CDCl$_3$) δ 6.17. IR (thin film): 3479, 3392, 2955, 1621, 1470, 1383, 1252, 1113, 862, 835, 761 cm$^{-1}$. HRMS (ESI) m/z calculated for C$_8$H$_{11}$ClNSi (M-Me)$^+$: 184.0349, found: 184.0346.

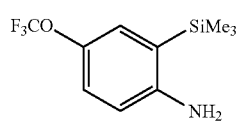

2-Silyl substituted aniline 1.2.1f. Method B was followed using 700 mg of 2-bromo-N,N-disilyl substituted aniline (1.75 mmol), 1.94 mL of a 1.9 M t-BuLi solution in pentanes (3.68 mmol) and 8.8 mL of THF. Purification by MPLC chromatography (5:95 EtOAc:hexanes) afforded 1.2.1f as a yellow gel (300 mg, 69% yield): $^1$H NMR (500 MHz, CDCl$_3$) δ 7.11 (d, J=2.0 Hz, 1H), 7.02 (dd, J=8.5, 2.0 Hz, 1H), 6.59 (d, J=8.5 Hz, 1H), 3.81 (br s, 2H), 0.36 (s, 9H); $^{13}$C NMR (125 MHz, CDCl$_3$) δ 150.0 (C), 141.4 (C), 127.6 (CH), 124.4 (C), 123.4 (CH), 120.7 (q, J$_{CF}$=253.4 Hz, C), 115.9 (CH), −1.1 (CH$_3$); $^{29}$Si NMR (99.46 MHz, CDCl$_3$) δ −4.60. IR (thin film): 3481, 3397, 2958, 1625, 1482, 1402, 1250, 1220, 1194, 1156, 1142, 867, 836, 761 cm$^{-1}$. HRMS (ESI) m/z calculated for C$_{10}$H$_{15}$F$_3$NOSi (M+H)$^+$: 250.0875, found: 250.0869.

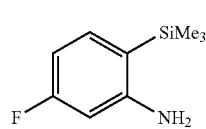

2-Silyl substituted aniline 1.2.1g. Method B was followed using 668 mg of 2-bromo-N,N-disilyl substituted aniline (2.0 mmol), 2.21 mL of a 1.9 M t-BuLi solution in pentanes (4.2 mmol) and 10 mL of THF. Purification by MPLC chromatography (5:95 EtOAc:hexanes) afforded 1.2.1g as a yellow gel (330 mg, 90% yield): $^1$H NMR (500 MHz, CDCl$_3$) δ 7.33 (t, J=7.5 Hz, 1H), 6.56 (td, J=8.5, 2.5 Hz, 1H), 6.38 (dd, J=10.5, 2.5 Hz, 1H), 3.95 (br, 2H), 0.43 (s, 9H); $^{13}$C NMR (125 MHz, CDCl$_3$) δ 125.1 (d, $J_{CF}$=244.25 Hz, C), 153.5 (C, $J_{CF}$=10.9 Hz, C), 136.8 (d, $J_{CF}$=9.2 Hz, CH), 118.1 (C), 105.1 (d, $J_{CF}$=20.1 Hz, CH), 101.0 (d, $J_{CF}$=23.1 Hz, CH), −0.66 (CH$_3$). $^{29}$Si NMR (99.46 MHz, CDCl$_3$) δ −5.66. IR (thin film): 3488, 3396, 2955, 1622, 1597, 1579, 1490, 1419, 1288, 1250, 1171, 1095, 1022, 976, 835, 759, 690 cm$^{-1}$. HRMS (ESI) m/z calculated for C$_9$H$_{15}$FNSi (M+H)$^+$: 184.0958, found: 184.0955. The product contains inseparable impurities. The product mixture was submitted to the next step without further purification.

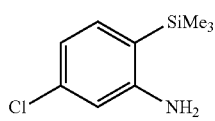

2-Silyl substituted aniline 1.2.1h. Method B was followed using 796 mg of 2-iodo-N,N-disilyl substituted aniline (2.0 mmol), 2.2 mL of a 1.9 M t-BuLi solution in pentanes (4.2 mmol) and 10 mL of THF. Purification by MPLC chromatography (5:95 EtOAc:hexanes) afforded 1.2.1h as a yellow gel (32 mg, 8% yield): $^1$H NMR (500 MHz, CDCl$_3$) δ 7.19 (d, J=8.0 Hz, 1H), 6.74 (dd, J=8.0, 2.0 Hz, 1H), 6.62 (d, J=2.0 Hz, 1H), 3.84 (br s, 2H), 0.34 (s, 9H); $^{13}$C NMR (125 MHz, CDCl$_3$) δ 152.5 (C), 136.2 (CH), 120.9 (C), 118.3 (CH), 114.9 (CH), −0.8 (CH$_3$), only visible signals; $^{29}$Si NMR (99.46 MHz, CDCl$_3$) δ 5.97. IR (thin film): 3446, 3384, 2924, 1620, 1597, 1485, 1320, 1265, 1077, 993, 888, 848, 769 cm$^{-1}$. HRMS (ESI) m/z calculated for C$_{17}$H$_{17}$O$_3$F$_3$Na (M+Na)$^+$: 349.1207, found: 349.1207.

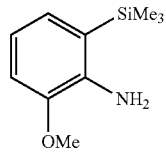

2-silyl substituted aniline 1.2.1i. Method B was followed using 346 mg of 2-bromo-N,N-disilyl substituted aniline (1.0 mmol), 1.1 mL of a 1.9 M t-BuLi solution in pentanes (2.1 mmol) and 5 mL of THF. Purification by MPLC chromatography (5:95 EtOAc:hexanes) afforded 1.2.1i as a yellow gel (130 mg, 67% yield): $^1$H NMR (500 MHz, CDCl$_3$) δ 6.98 (d, J=7.0 Hz, 1H), 6.88 (d, J=7.5 Hz, 1H), 6.81 (t, J=8.0 Hz, 1H), 4.07 (br s, 2H), 3.90 (s, 3H), 0.41 (s, 9H); $^{13}$C NMR (125 MHz, CDCl$_3$) δ 146.8 (C), 141.0 (C), 126.5 (CH), 122.7 (C), 118.1 (CH), 111.4 (CH), 55.5 (CH$_3$), −0.7 (CH$_3$); $^{29}$Si NMR (99.46 MHz, CDCl$_3$) δ 6.17. IR (thin film): 3483, 3391, 2954, 2834, 1608, 1568, 1451, 1434, 1275, 1250, 1208, 1182, 1049, 860, 836, 751, 690 cm$^{-1}$. HRMS (ESI) m/z calculated for C$_{17}$H$_{17}$O$_3$F$_3$Na (M+Na)$^+$: 349.1207, found: 349.1207.

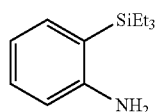

2-Silyl substituted aniline 1.2.1j. Method A was followed using 1.09 g of 2-iodoaniline (5.0 mmol), 1.16 g of trimethylsilane (10.0 mmol), 101.5 mg of [Rh(cod)$_2$]BF$_4$ (0.25 mmol), 3.18 g of K$_3$PO$_4$ (15.0 mmol) in 10 mL of NMP. Purification by MPLC chromatography (5:95 EtOAc: hexanes) 1.2.1a as a yellow gel (467 mg, 45% yield) The spectral data of 1.2.1j matched that reported by Yamanoi and Nishihara:[4] $^1$H NMR (500 MHz, CDCl$_3$) δ 7.32 (dd, J=7.5, 1.5 Hz, 1H), 7.21 (td, J=7.5, 1.5 Hz, 1H), 6.80 (t, J=7.5 Hz, 1H), 6.65 (d, J=8.0 Hz, 1H), 3.69 (br s, 2H), 1.04 (t, J=7.5 Hz, 9H), 0.91 (q, J=7.5 Hz, 6H); $^{13}$C NMR (125 MHz, CDCl$_3$) δ 151.9 (C), 136.1 (CH), 130.4 (CH), 119.7 (C), 118.2 (CH), 115.3 (CH), 7.6 (CH$_3$), 3.8 (CH$_2$); $^{29}$Si NMR (99.46 MHz, CDCl$_3$) δ 6.17. IR (thin film): 3474, 3383, 2953, 2909, 2874, 1619, 589, 1438, 1310, 1288, 1237, 1098, 1003, 712 cm$^{-1}$. HRMS (ESI) m/z calculated for C$_{12}$H$_{22}$NSi (M+H)$^+$: 208.1522, found: 208.1515.

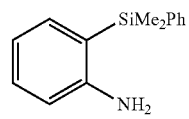

2-Silyl substituted aniline 1.2.1k. Method B was followed using 632 mg of 2-bromo-N,N-disilyl substituted aniline (2.0 mmol), 2.2 mL of a 1.9 M t-BuLi solution in pentanes (4.2 mmol) and 12 mL of THF. Purification by MPLC chromatography (5:95 EtOAc:hexanes) afforded 1.2.1k as a cloudy gel (260 mg, 57% yield): $^1$H NMR (500 MHz, CDCl$_3$) δ 7.61-7.60 (m, 2H), 7.43-7.39 (m, 4H), 7.24 (ddd, J=7.9, 7.4, 1.6 Hz, 1H), 6.84 (td, J=7.3, 1.0 Hz, 1H), 6.61 (d, J=8.0 Hz, 1H), 3.38 (br s, 2H), 0.60 (s, 6H); $^{13}$C NMR (125 MHz, CDCl$_3$) δ 151.8 (C), 138.1 (C), 135.8 (CH), 134.1 (CH), 131.0 (CH), 129.5 (CH), 128.3 (CH), 120.5 (C), 118.3 (CH), 115.5 (CH), −2.33 (CH$_3$); $^{29}$Si NMR (99.46 MHz, CDCl$_3$) δ −9.12. IR (thin film): 3443, 3366, 3065, 2955, 1620, 1588, 1478, 1438, 1289, 1250, 1112, 810, 776, 699 cm$^{-1}$. HRMS (ESI) m/z calculated for C$_{14}$H$_{18}$NSi (M+H)$^+$: 228.1209, found: 228.1210. The product contains inseparable impurities. The product mixture was submitted to the next step without further purification.

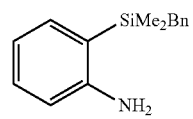

2-Silyl substituted aniline 1.2.1l. Method B was followed using 497 mg of 2-bromo-N,N-disilyl substituted aniline (1.0 mmol), 1.1 mL of a 1.9 M t-BuLi solution in pentanes (2.1 mmol) and 6 mL of THF. Purification by MPLC chromatography (5:95 EtOAc:hexanes) afforded 1.2.1l as a light yellow gel (240 mg, 94% yield): $^1$H NMR (500 MHz, CDCl$_3$) δ 7.39 (dd, J=7.5, 1.5 Hz, 1H), 7.33-7.29 (m, 3H), 7.20 (t, J=7.5 Hz, 1H), 7.12 (d, J=7.0 Hz, 2H), 6.89 (td, J=7.5, 1.0 Hz, 1H), 6.70 (d, J=8.5 Hz, 1H), 3.62 (br s, 2H), 2.51 (s. 2H), 0.45 (s, 6H); $^{13}$C NMR (125 MHz, CDCl$_3$) δ 151.8 (C), 139.9 (C), 135.6 (CH), 130.9 (CH), 128.4 (CH), 128.4 (CH), 124.4 (CH), 121.1 (C), 118.5 (CH), 115.7 (CH), 26.0 (CH$_2$), −2.50 (CH$_3$); $^{29}$Si NMR (99.46 MHz, CDCl$_3$) 6-4.42. IR (thin film): 3381, 3024, 2957, 1600, 1493, 1451, 1251, 1207, 1055, 833, 758, 697 cm$^{-1}$. HRMS (ESI) m/z calculated for $C_{15}H_{20}NSi$ (M+H)$^+$: 242.1365, found: 242.1371.

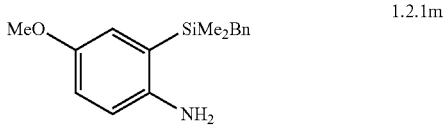

1.2.1m

2-Silyl substituted aniline 1.2.1m. Method B was followed using 1.0 g of 2-bromo-N,N-disilyl substituted aniline (2.0 mmol), 2.2 mL of a 1.9 M t-BuLi solution in pentanes (4.2 mmol) and 12 mL of THF. Purification by MPLC chromatography (5:95 EtOAc:hexanes) afforded 1.2.1m as an orange gel (420 mg, 77% yield): $^1$H NMR (500 MHz, CDCl$_3$) δ 7.31 (t, J=7.5 Hz, 2H), 7.20 (t, J=7.4 Hz, 1H), 7.12 (d, J=7.6 Hz, 2H), 6.99 (d, J=2.3 Hz, 1H), 6.90 (dd, J=8.6, 1.6 Hz, 1H), 6.67 (d, J=8.6 Hz, 1H), 3.83 (s, 3H), 3.38 (br s, 2H), 2.52 (s, 2H), 0.45 (s, 6H); $^{13}$C NMR (125 MHz, CDCl$_3$) δ 152.5 (C), 145.4 (C), 139.8 (C), 128.39 (CH), 128.36 (CH), 124.4 (CH), 123.4 (C), 121.1 (CH), 117.2 (CH), 116.0 (CH), 55.8 (CH$_3$), 25.8 (CH$_2$), −2.6 (CH$_3$); $^{29}$Si NMR (99.46 MHz, CDCl$_3$) δ −4.01. IR (thin film): 3445, 3363, 3022, 2952, 2830, 1599, 1483, 1399, 1278, 1236, 1218, 1153, 1041, 882, 817, 763, 699 cm$^{-1}$. HRMS (ESI) m/z calculated for $C_{16}H_{22}NOSi$ (M+H)$^+$: 272.1471, found: 272.1464.

D. Synthesis of ortho-Silyl Substituted Aryl Azide from 2-Silyl Substituted Aniline.

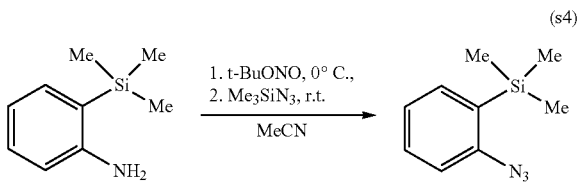 [SMILES: "MeCN" ; C[Si](C)(C)c1ccccc1N ; C[Si](C)(C)c1ccccc1N=[N+]=[N-]]

(s4)

Following the procedure reported by Zhang and Moses (see Zhang et al., Org. Lett. 11:1587 (2009)), to a cooled solution of aniline in MeCN (0.2 M) at 0° C. was added t-BuNO$_2$ (4.0 equiv) dropwise over 15 min. After 30 min, the reaction mixture was warmed to room temperature followed by the addition of azidotrimethylsilane (3.9 equiv) dropwise over 10 min. When monitoring of the reaction progress using thin layer chromatography indicated that the starting materials were consumed (approximately 1 h), the reaction was diluted with 10 mL of water and was extracted with 3×10 mL of DCM. The combined organic phases were washed with 10 mL of brine. The resulting organic phase was dried over Na$_2$SO$_4$, filtered, and the filtrate was concentrated in vacuo. Purification of the residue by MPLC afforded the azide product.

Characterization Data for ortho-Silyl Substituted Aryl Azide.

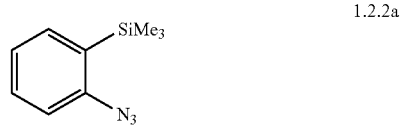

1.2.2a ortho-Silyl aryl azide 1.2.2a. The general procedure was followed using 400 mg of 2-silyl substituted aniline (2.4 mmol), 1.16 mL of t-BuNO$_2$ (9.7 mmol), 1.26 mL of azidotrimethylsilane (9.5 mmol) in 24 mL of MeCN. Purification by MPLC chromatography (1:20 EtOAc:hexanes) afforded 1.2.2a as a yellow gel (450 mg, 97% yield): $^1$H NMR (500 MHz, CDCl$_3$) δ 7.52 (dd, J=7.0, 1.0 Hz, 1H), 7.46 (td, J=8.0, 1.5 Hz, 1H), 7.22-7.18 (m, 2H), 0.41 (s, 9H); $^{13}$C NMR (125 MHz, CDCl$_3$) δ 145.1 (C), 135.4 (CH), 131.6 (C), 130.7 (CH), 124.4 (CH), 117.6 (CH), −0.7 (CH$_3$); $^{29}$Si NMR (99.46 MHz, CDCl$_3$) δ −3.09. IR (thin film): 2955, 2116, 2081, 1566, 1467, 1434, 1274, 1246, 1122, 835, 750, 713, 647, 620 cm$^{-1}$. HRMS (ESI) m/z calculated for $C_9H_{13}N_3Si$ (M)$^+$: 191.0879, found: 191.0874.

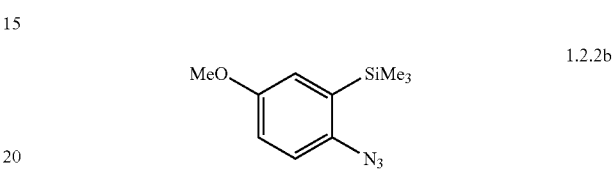

1.2.2b ortho-Silyl aryl azide 1.2.2b. The general procedure was followed using 40 mg of 2-silyl substituted aniline (0.20 mmol), 0.096 mL of t-BuNO$_2$ (0.80 mmol), 0.104 mL of azidotrimethylsilane (0.78 mmol) in 2 mL of MeCN. Purification by MPLC chromatography (1:10 EtOAc:hexanes) afforded 1.2.2b as an orange gel (29 mg, 66% yield): $^1$H NMR (500 MHz, CDCl$_3$) δ 7.09 (d, J=8.5 Hz, 1H), 6.97 (s, 1H), 6.92 (d, J=8.5 Hz, 1H), 3.80 (s, 3H), 0.31 (s, 9H); $^{13}$C NMR (125 MHz, CDCl$_3$) δ 156.4 (C), 137.3 (C), 133.1 (C), 121.1 (CH), 118.7 (CH), 115.2 (CH), 55.5 (CH$_3$), 0.9 (CH$_3$); $^{29}$Si NMR (99.46 MHz, CDCl$_3$) δ 24.89. IR (thin film): 2924, 2114, 1733, 1558, 1506, 1464, 1248, 1038, 840 cm$^{-1}$. HRMS (ESI) m/z calculated for $C_{17}H_{17}O_3F_3Na$ (M+Na)$^+$: 349.1207, found: 349.1207.

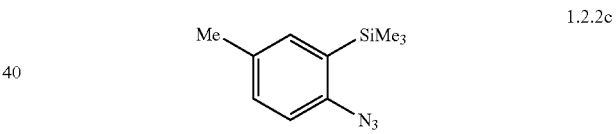

1.2.2c ortho-Silyl aryl azide 1.2.2c. The general procedure was followed using 359 mg of 2-silyl substituted aniline (2.0 mmol), 0.96 mL of t-BuNO$_2$ (8.0 mmol), 1.04 mL of azidotrimethylsilane (7.8 mmol) in 20 mL MeCN. Purification by MPLC chromatography (1:20 EtOAc:hexanes) afforded 1.2.2c as a yellow gel (220 mg, 54% yield): $^1$H NMR (500 MHz, CDCl$_3$) δ 7.28 (s, 1H), 7.25 (d, J=8.0 Hz, 1H), 7.09 (d, J=8.0 Hz, 1H), 2.38 (s, 3H), 0.36 (s, 9H); $^{13}$C NMR (125 MHz, CDCl$_3$) δ 142.3 (C), 136.0 (CH), 133.7 (C), 131.3 (C), 131.2 (CH), 117.5 (CH), 21.0 (CH$_3$), −0.7 (CH$_3$); $^{29}$Si NMR (99.46 MHz, CDCl$_3$) δ −3.97. IR (thin film): 2955, 2109, 2065, 1473, 1291, 1270, 1246, 1156, 1059, 885, 836, 809 764, 692 cm$^{-1}$. HRMS (ESI) m/z calculated for $C_{10}H_{15}N_3Si$ (M)$^+$: 205.1035, found: 205.1039.

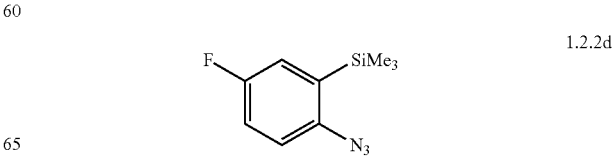

1.2.2d ortho-Silyl aryl azide 1.2.2d. The general procedure was followed using 183 mg of 2-silyl substituted aniline (1.0 mmol), 0.48 mL of t-BuNO$_2$ (4.0 mmol), 0.52 mL of azidotrimethylsilane (3.9 mmol) in 10 mL MeCN. Purification by MPLC chromatography (hexanes) afforded 1.2.2d as a yellow gel (110 mg, 53% yield): $^1$H NMR (500 MHz, CDCl$_3$) δ 7.13-7.06 (m, 3H), 0.33 (s, 9H); $^{13}$C NMR (125 MHz, CDCl$_3$) δ 159.7 (d, $J_{CF}$=244.1 Hz, C), 140.5 (C), 134.3 (C), 121.7 (d, $J_{CF}$=20.5 Hz, CH), 119.0 (d, $J_{CF}$=7.5 Hz, CH), 117.1 (d, $J_{CF}$=23.9 Hz, CH), −1.0 (CH$_3$); $^{29}$Si NMR (99.46 MHz, CDCl$_3$) δ 6.17. IR (thin film): 2957, 2116, 2074, 1470, 1297, 1260, 1208, 1138, 840, 812 cm$^{-1}$. HRMS (ESI) m/z calculated for C$_9$H$_{12}$FN$_3$Si (M)$^+$: 209.0785, found: 209.0785.

ortho-Silyl aryl azide 1.2.2g. The general procedure was followed using 183 mg of 2-silyl substituted aniline (1.0 mmol), 0.48 mL of t-BuNO$_2$ (4.0 mmol), 0.52 mL of azidotrimethylsilane (3.9 mmol) in 10 mL MeCN. Purification by MPLC chromatography (hexanes) afforded 1.2.2g as a yellow gel (120 mg, 57% yield): $^1$H NMR (500 MHz, CDCl$_3$) δ 7.93 (t, J=7.5 Hz, 1H), 6.88-6.82 (m, 2H), 0.31 (s, 9H); $^{13}$C NMR (125 MHz, CDCl$_3$) δ164.5 (d, $J_{CF}$=247.8 Hz, C), 146.8 (d, $J_{CF}$=7.2 Hz, C), 136.9 (d, $J_{CF}$=9.1 Hz, CH), 127.0 (d, $J_{CF}$=3.1 Hz, C), 111.5 (d, $J_{CF}$=18.5 Hz, CH), 105.1 (d, $J_{CF}$=23.8 Hz, CH), −0.82 (CH$_3$). $^{29}$Si NMR (99.46 MHz, CDCl$_3$) δ 0.05. IR (thin film): 2956, 2110, 1582, 1483, 1389, 1290, 1248, 1202, 990, 840, 764 cm$^{-1}$. HRMS (ESI) m/z calculated for C$_9$H$_{12}$FN$_3$Si (M)$^+$: 209.0785, found: 209.0775.

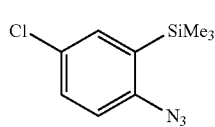

1.2.2e ortho-Silyl aryl azide 1.2.2e. The general procedure was followed using 250 mg of 2-silyl substituted aniline (1.25 mmol), 0.60 mL of t-BuNO$_2$ (5.0 mmol), 0.65 mL of azidotrimethylsilane (4.9 mmol) in 12.5 mL MeCN. Purification by MPLC chromatography (1:20 EtOAc:hexanes) afforded 1.2.2e as a yellow gel (230 mg, 82% yield): $^1$H NMR (500 MHz, CDCl$_3$) δ 7.38-7.34 (m, 2H), 7.08 (d, J=8.5 Hz, 1H), 0.34 (s, 9H); $^{13}$C NMR (125 MHz, CDCl$_3$) δ 143.4 (C), 135.1 (CH), 134.0 (C), 130.4 (CH), 130.1 (C), 118.9 (CH), −1.0 (CH$_3$); $^{29}$Si NMR (99.46 MHz, CDCl$_3$) δ −3.00. IR (thin film): 2956, 2123, 1459, 1371, 1288, 1261, 1248, 1104, 839, 825, 811, 763 cm$^{-1}$. HRMS (ESI) m/z calculated for C$_9$H$_{12}$ClN$_3$Si (M)$^+$: 225.0489, found: 225.0495.

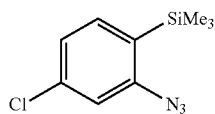

1.2.2h ortho-Silyl aryl azide 1.2.2h. The general procedure was followed using 200 mg of 2-silyl substituted aniline (1.0 mmol), 0.48 mL of t-BuNO$_2$ (4.0 mmol), 0.52 mL of azidotrimethylsilane (3.9 mmol) in 10 mL MeCN. Purification by MPLC chromatography (1:15 EtOAc:hexanes) afforded 1.2.2h as a yellow gel (144 mg, 64% yield): $^1$H NMR (500 MHz, CDCl$_3$) δ 7.35 (d, J=8.0 Hz, 1H), 7.14-7.09 (m, 2H), 0.31 (s, 9H); $^{13}$C NMR (125 MHz, CDCl$_3$) δ 146.3 (C), 142.4 (C), 136.4 (CH), 129.9 (C), 124.6 (CH), 117.7 (CH), −0.9 (CH$_3$); $^{29}$Si NMR (99.46 MHz, CDCl$_3$) δ 6.17. IR (thin film): 2955, 2100, 1576, 1552, 1469, 1378, 1278, 1248, 1105, 882, 838, 814, 763 cm$^{-1}$. HRMS (ESI) m/z calculated for C$_9$H$_{12}$ClN$_3$Si (M)$^+$: 225.0489, found: 225.0481.

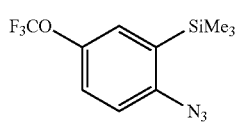

1.2.2f ortho-Silyl aryl azide 1.2.2f. The general procedure was followed using 250 mg of 2-silyl substituted aniline (1.0 mmol), 0.48 mL of t-BuNO$_2$ (4.0 mmol), 0.52 mL of azidotrimethylsilane (3.9 mmol) in 10 mL MeCN. Purification by MPLC chromatography (2:98 EtOAc:hexanes) afforded 1.2.2f as a yellow gel (195 mg, 71% yield): $^1$H NMR (500 MHz, CDCl$_3$) δ 7.25-7.24 (m, 2H), 7.16-7.14 (m, 1H), 0.33 (s, 9H); 13C NMR (125 MHz, CDCl$_3$) δ 145.8 (C), 143.5 (C), 134.1 (C), 127.8 (CH), 123.1 (CH), 120.5 (q, $J_{CF}$=255.2 Hz, C), 118.7 (CH), −1.1 (CH$_3$); $^{29}$Si NMR (99.46 MHz, CDCl$_3$) δ −2.97. IR (thin film): 2119, 1472, 1254, 1200, 1166, 1058, 866, 840 cm$^{-1}$. HRMS (ESI) m/z calculated for C$_{10}$H$_{12}$F$_3$N$_3$OSi (M)$^+$: 275.0702, found: 275.0705.

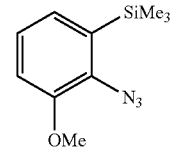

1.2.2i ortho-Silyl aryl azide 1.2.2i. The general procedure was followed using 100 mg of 2-silyl substituted aniline (0.51 mmol), 0.25 mL of t-BuNO$_2$ (2.0 mmol), 0.27 mL of azidotrimethylsilane (2.0 mmol) in 5 mL MeCN. Purification by MPLC chromatography (1:20 EtOAc:hexanes) afforded 1.2.2i as a yellow gel (100 mg, 45% yield): $^1$H NMR (500 MHz, CDCl$_3$) δ 7.12 (t, J=7.5 Hz, 1H), 7.03 (dd, J=7.5, 1.5 Hz, 1H), 6.93 (dd, J=8.0, 1.5 Hz, 1H), 3.92 (s, 3H), 0.35 (s, 9H); $^{13}$C NMR (125 MHz, CDCl$_3$) 153.6 (C), 133.6 (C), 133.0 (C), 126.6 (CH), 125.4 (CH), 113.0 (CH), 55.8 (CH$_3$), −0.7 (CH$_3$); $^{29}$Si NMR (99.46 MHz, CDCl$_3$) δ 6.17. IR (thin film): 2955, 2116, 2087, 1569, 1464, 1423, 1299, 1246, 1226, 1204, 1155, 1053, 879, 835, 780, 755, 629 cm$^{-1}$. HRMS (ESI) m/z calculated for C$_{17}$H$_{17}$O$_3$F$_3$Na (M+Na)$^+$: 349.1207, found: 349.1207.

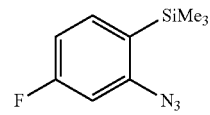

1.2.2g

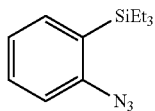

1.2.5a ortho-Silyl aryl azide 1.2.5a. The general procedure was followed using 100 mg of 2-silyl substituted aniline (0.48 mmol), 0.23 mL of t-BuNO$_2$ (1.9 mmol), 0.25 mL of azidotrimethylsilane (1.9 mmol) in 5 mL MeCN. Purification by MPLC chromatography (hexanes) afforded 1.2.5a as a yellow gel (106 mg, 95% yield): $^1$H NMR (500 MHz, CDCl$_3$) δ 7.43-7.39 (m, 2H), 7.18-7.12 (m, 2H), 1.00-0.95 (m, 9H), 0.91-0.86 (m, 6H); $^{13}$C NMR (125 MHz, CDCl$_3$) δ 145.2 (C), 136.4 (CH), 130.5 (CH), 128.9 (C), 124.2 (CH), 117.5 (CH), 7.5 (CH$_3$), 3.5 (CH$_2$); $^{29}$Si NMR (99.46 MHz, CDCl$_3$) δ 3.52. IR (thin film): 2953, 2874, 2118, 2083, 1567, 1468, 1434, 1276, 1238, 1064, 1005, 753, 727, 687 cm$^{-1}$. HRMS (ESI) m/z calculated for C$_{12}$H$_{19}$N$_3$Si (M)$^+$: 233.1348, found: 233.1344.

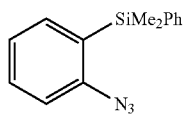

1.2.5b ortho-Silyl aryl azide 1.2.5b. The general procedure was followed using 100 mg of 2-silyl substituted aniline (0.44 mmol), 0.21 mL of t-BuNO$_2$ (1.8 mmol), 0.23 mL of azidotriimethylsilane (1.7 mmol) in 4.4 mL MeCN. Purification by MPLC chromatography (1:20 EtOAc:hexanes) afforded 1.2.5b as a yellow gel (37 mg, 33% yield): $^1$H NMR (500 MHz, CDCl$_3$) δ 7.59-7.57 (m, 2H), 7.45-7.36 (m, 5H), 7.18 (d, J=8.0 Hz, 1H), 7.12 (t, J=7.5 Hz, 1H), 0.64 (s, 9H); $^{13}$C NMR (125 MHz, CDCl$_3$) δ 145.3 (C), 138.1 (C), 136.5 (CH), 134.2 (CH), 131.0 (CH), 129.6 (C), 129.1 (CH), 127.8 (CH), 124.4 (CH), 117.7 (CH), -2.0 (CH$_3$); $^{29}$Si NMR (99.46 MHz, CDCl$_3$) δ 6.17. IR (thin film): 2923, 2851, 2124, 1465, 1259, 1084, 1015, 795, 754, 668 cm$^{-1}$. HRMS (ESI) m/z calculated for C$_{17}$H$_{17}$O$_3$F$_3$Na (M+Na)$^+$: 349.1207, found: 349.1207.

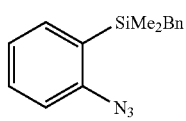

1.2.5c ortho-Silyl aryl azide 1.2.5c. The general procedure was followed using 177 mg of 2-silyl substituted aniline (0.67 mmol), 0.32 mL of t-BuNO$_2$ (2.7 mmol), 0.35 mL of azidotrimethylsilane (2.6 mmol) in 7 mL MeCN. Purification by MPLC chromatography (hexanes) afforded 1.2.5c as a yellow gel (110 mg, 61% yield): $^1$H NMR (500 MHz, CDCl$_3$) δ 7.45 (td, J=7.5, 1.5 Hz, 0.81H), 7.39 (dd, J=7.5, 1.5 Hz, 0.82H), 7.24-7.19 (m, 2.8H), 7.13 (t, J=7.5 Hz, 0.8H), 7.09 (t, J=7.5 Hz, 0.8H), 7.00 (d, J=7.5 Hz, 1.6H), 2.47 (s, 1.6H), 0.3 (s, 4.9H); Diagnostic data for minor rotamer: $^1$H NMR (500 MHz, CDCl$_3$) δ 7.73 (d, J=7.5 Hz, 0.2H), 7.64 (d, J=8.0 Hz, 0.2H), 7.58 (dd, J=7.0, 1.0 Hz, 0.2H), 7.51 (td, J=7.5, 1.5 Hz, 0.2H), 7.34 (t, J=7.5 Hz, 0.2H), 7.29 (td, J=7.0, 2.0 Hz, 0.2H), 2.21 (s, 0.4H), 0.26 (s, 1.2H); $^{13}$C NMR (125 MHz, CDCl$_3$) δ 145.1 (C), 140.0 (C), 135.9 (CH), 131.0 (CH), 129.8 (C), 128.4 (CH), 128.1 (CH), 124.4 (CH), 124.2 (CH), 117.6 (CH), 25.6 (CH$_2$), -2.9 (CH$_3$); Diagnostic data for minor rotamer: $^{13}$C NMR (125 MHz, CDCl$_3$) δ 144.6 (C), 137.7 (C), 136.3 (C), 132.6 (CH), 131.3 (CH), 130.3 (CH), 128.0 (CH), 127.6 (CH), 126.7 (CH), 126.2 (CH), 21.4 (CH$_2$), -4.2 (CH$_3$); $^{29}$Si NMR (99.46 MHz, CDCl$_3$) δ 6.17. IR (thin film): 3024, 2956, 2120, 2082, 1566, 1493, 1468, 1434, 1275, 1149, 828, 794, 754, 698 cm$^{-1}$. HRMS (ESI) m/z calculated for C$_{15}$H$_{17}$N$_3$Si (M)$^+$: 267.1192, found: 267.1200.

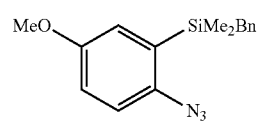

1.2.5d ortho-Silyl aryl azide 1.2.5d. The general procedure was followed using 271 mg of 2-silyl substituted aniline (1.0 mmol), 0.48 mL of t-BuNO$_2$ (4.0 mmol), 0.52 mL of azidotrimethylsilane (3.9 mmol) in 10 mL MeCN. Purification by MPLC chromatography (1:10 EtOAc:hexanes) afforded 1.2.5d as a yellow gel (270 mg, 91% yield): $^1$H NMR (500 MHz, CDCl$_3$) δ 7.22 (t, J=7.5 Hz, 2H), 7.15 (d, J=8.5 Hz, 1H), 7.10 (t, J=7.5 Hz, 1H), 7.02 (d, J=7.0 Hz, 2H), 6.99-6.94 (m, 2H), 3.80 (s, 3H), 2.48 (s, 2H), 0.32 (s, 6H); $^{13}$C NMR (125 MHz, CDCl$_3$) δ 156.4 (C), 139.8 (C), 137.4 (C), 131.4 (C), 128.4 (CH), 128.2 (CH), 124.2 (CH), 121.5 (CH), 118.7 (CH), 115.6 (CH), 55.5 (CH$_3$), 25.6 (CH$_2$), -2.9 (CH$_3$); $^{29}$Si NMR (99.46 MHz, CDCl$_3$) δ -2.87. IR (thin film): 2955, 2113, 1599, 1493, 1474, 1398, 1281, 1236, 1206, 1153, 1057, 1036, 878, 821, 699 cm$^{-1}$. HRMS (ESI) m/z calculated for C$_{16}$H$_{19}$N$_3$OSi (M)$^+$: 297.1297, found: 297.1292.

II. Formation of benzo[1,3]azasiloles from ortho-Silyl Substituted Azides

A. Development of Optimal Reaction Conditions.

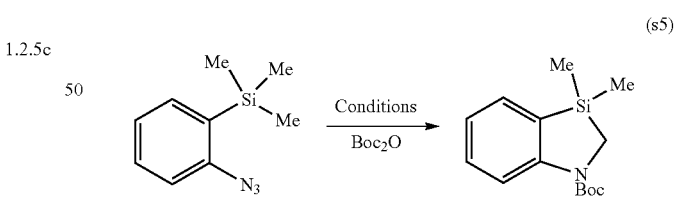

(s5)

In an oven-dried bomb under nitrogen atmosphere, a solution of ortho-silyl substituted aryl azide (1.0 equiv, 0.1 M) was added to a mixture of metal catalyst and Boc$_2$O (1.0 equiv). The resulting mixture was sealed and heated. After 16 h, the reaction mixture was cooled to room temperature. The reactives were quenched by 10 mL of water and extracted with 3×5 mL of EtOAc. The combined organic phases were washed with 10 mL of brine and dried over Na$_2$SO$_4$ and filtered. The filtrate was concentrated in vacuo, and the residue was analyzed using $^1$H NMR spectroscopy using CH$_2$Br$_2$ as the internal standard.

TABLE s1

Development of optimal reaction conditions.

| Entry | Catalyst | mol % | solvent | temperature (° C.) | yield (%)[a] |
|---|---|---|---|---|---|
| 1 | Rh$_2$(esp)$_2$ | 5 | toluene | 90 | 40 |
| 2 | Rh$_2$(esp)$_2$ | 5 | toluene | 100 | 70 |
| 3 | Rh$_2$(esp)$_2$ | 5 | toluene | 100[b] | 47 |
| 4 | Rh$_2$(esp)$_2$ | 5 | toluene | 120 | 100[c] |
| 5 | Rh$_2$(OAc)$_4$ | 5 | toluene | 120 | 44 |
| 6 | no cat | ... | toluene | 120 | 8 |
| 7 | Rh$_2$(esp)$_2$ | 1 | toluene | 120 | 100[c] |
| 8 | Rh$_2$(esp)$_2$ | 1 | toluene | 140 | 100 |

[a]Yield determined by NMR using CH$_2$Br$_2$ as internal standard.
[b]Reaction performed in air condition.
[c]Isolated yield.

B. Optimal Reaction Conditions.

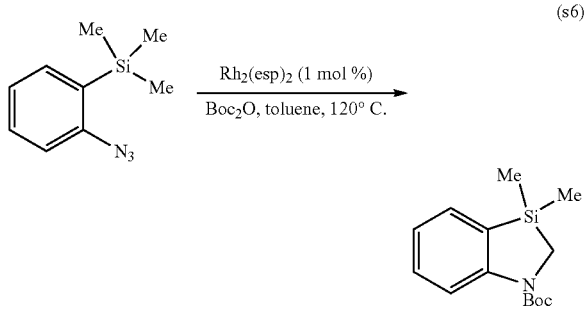

(s6)

In an oven-dried bomb under a nitrogen atmosphere, a solution of ortho-silyl substituted aryl azide (1.0 equiv, 0.1 M) in toluene was added to a mixture of Rh$_2$esp$_2$ (1 mol %) and Boc$_2$O (1.1 equiv). The resulting mixture was sealed and heated to 120° C. After 16 h, the reaction mixture was cooled to room temperature. The reactives were quenched by 10 mL of water and extracted with 3×5 mL of EtOAc. The combined organic phases were washed with 10 mL of brine and dried over Na$_2$SO$_4$ and filtered. The filtrate was concentrated in vacuo. Purification by MPLC afforded the product.

C. Characterization Data for benzo[1,3]azasiloles.

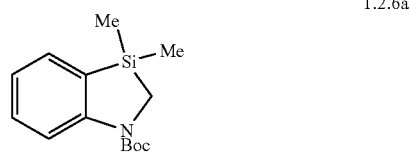

1.2.6a tert-Butyl 3,3-dimethyl-2,3-dihydro-1H-benzo[d][1,3]azasilole-1-carboxylate 1.2.6a. The general procedure was followed using 19.1 mg of ortho-silyl substituted aryl azide 1.2.2a (0.10 mmol) in 1.0 mL of toluene, 0.76 mg of Rh$_2$esp$_2$ (1 mol %), and 24.0 mg of BOC$_2$O (0.11 mmol). Purification by MPLC chromatography (5:95 EtOAc:hexanes) afforded 1.2.6a as a light yellow gel (26.2 mg, 100% yield): $^1$H NMR (500 MHz, CDCl$_3$) δ 8.24 (d, J=6.5 Hz, 1H), 7.44 (dd, J=7.0, 1.5 Hz, 1H) 7.36-7.32 (m, 1H), 6.98 (td, J=7.0, 0.5 Hz, 1H), 3.12 (s, 2H), 1.56 (s, 9H), 0.36 (s, 6H); $^{13}$C NMR (125 MHz, CDCl$_3$) δ 154.6 (C), 151.5 (C), 132.4 (CH), 131.0 (C), 121.9 (CH), 117.8 (CH), 37.3 (CH$_2$), 28.5 (CH$_3$), −1.8 (CH$_3$), only visible signals; $^{29}$Si NMR (99.46 MHz, CDCl$_3$) δ 6.17. IR (thin film): 2975, 1702, 1464, 1446, 1337, 1252, 1168, 1139, 1120, 850, 758 cm$^{-1}$. HRMS (ESI) m/z calculated for C$_{14}$H$_{22}$NO$_2$Si (M+H)$^+$: 264.1420, found: 264.1407.

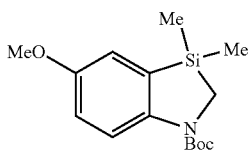

1.2.6b tert-Butyl 5-methoxy-3,3-dimethyl-2,3-dihydro-1H-benzo[d][1,3]azasilole-1-carboxylate 1.2.6b. The general procedure was followed using 22.1 mg of ortho-silyl substituted aryl azide 1.2.2b (0.10 mmol) in 1.0 mL of toluene, 0.76 mg of Rh$_2$esp$_2$ (1 mol %), and 24.0 mg of Boc$_2$O (0.11 mmol). Purification by MPLC chromatography (5:95 EtOAc:hexanes) afforded 1.2.6b as a light yellow gel (24 mg, 83% yield): $^1$H NMR (500 MHz, CDCl$_3$) δ 8.16 (s, 1H), 6.94 (s, 1H), 6.89 (d, J=9.5 Hz, 1H), 3.79 (s, 3H), 3.12 (s, 2H), 1.55 (s, 9H), 0.36 (s, 6H); $^{13}$C NMR (125 MHz, CDCl$_3$) δ 154.6 (C), 145.2 (C), 128.3 (C), 118.8 (CH), 116.6 (CH), 116.5 (CH), 80.3 (C), 55.6 (CH$_3$), 37.4 (CH$_2$), 28.5 (CH$_3$), −1.9 (CH$_3$); Diagnostic data for minor rotamer: $^{13}$C NMR (125 MHz, CDCl$_3$) δ 27.4 (CH$_3$); $^{29}$Si NMR (99.46 MHz, CDCl$_3$) δ 6.17. IR (thin film): 2973, 1698, 1468, 1345, 1277, 1252, 1169, 1142, 1124, 1001, 827, 767 cm$^{-1}$. HRMS (ESI) m/z calculated for C$_{15}$H$_{24}$NO$_3$Si (M+H)$^+$: 294.1525, found: 294.1537.

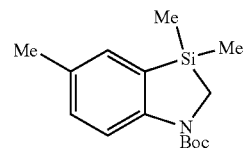

1.2.6c tert-Butyl 3,3,5-trimethyl-2,3-dihydro-1H-benzo[d][1,3]azasilole-1-carboxylate 1.2.6c. The general procedure was followed using 20.5 mg of ortho-silyl substituted aryl azide 1.2.2c (0.10 mmol) in 1.0 mL of toluene, 0.76 mg of Rh$_2$esp$_2$ (1 mol %), and 24.0 mg of Boc$_2$O (0.11 mmol). Purification by MPLC chromatography (5:95 EtOAc:hexanes) afforded 1.2.6c as a light yellow gel (27.7 mg, 100% yield): $^1$H NMR (500 MHz, CDCl$_3$) δ 8.13 (br s, 1H), 7.24 (s, 1H), 7.15 (d, J=8.5 Hz, 1H), 3.12 (s, 2H), 2.30 (s, 3H), 1.56 (s, 9H), 0.36 (s, 6H); $^{13}$C NMR (125 MHz, CDCl$_3$) δ 154.6 (C), 149.3 (C), 132.7 (CH), 131.7 (CH), 131.0 (C), 126.8 (C), 117.6 (CH), 80.4 (C), 37.3 (CH$_2$), 28.5 (CH$_3$), 20.5 (CH$_3$), −1.8 (CH$_3$); $^{29}$Si NMR (99.46 MHz, CDCl$_3$) δ 6.17. IR (thin film): 2974, 2926, 1699, 1467, 1337, 1268, 1251, 1167, 1144, 1123, 1003, 846, 823, 768 cm$^{-1}$. HRMS (ESI) m/z calculated for C$_{15}$H$_{23}$NO$_2$SiNa (M+Na)$^+$: 300.1396, found: 300.1383.

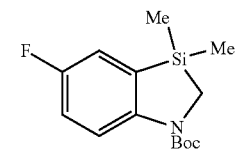

1.2.6d tert-Butyl 5-fluoro-3,3-dimethyl-2,3-dihydro-1H-benzo[d][1,3]azasilole-1-carboxylate 1.2.6d. The general procedure was followed using 21.0 mg of ortho-silyl substituted aryl azide 1.2.2d (0.10 mmol) in 1.0 mL of toluene, 0.76 mg of Rh$_2$esp$_2$ (1 mol %), and 24.0 mg of Boc$_2$O (0.11 mmol). Purification by MPLC chromatography (1:15 EtOAc:hexanes) afforded 1.2.6d as a light yellow gel (28.1 mg, 100% yield): $^1$H NMR (500 MHz, CDCl$_3$) δ 8.23 (br s, 1H), 7.08 (dd, J=7.5, 3.0 Hz, 1H), 7.00 (td, J=8.5, 3.0 Hz, 1H), 3.15 (s, 2H), 1.55 (s, 9H), 0.37 (s, 6H); $^{19}$C NMR (125 MHz, CDCl$_3$) δ 158.1 (d, $J_{CF}$=242.1 Hz, C), 154.6 (C), 147.4 (C), 119.2 (d, $J_{CF}$=7.1 Hz, CH), 117.8 (d, $J_{CF}$=20.1 Hz, CH), 117.5 (d, $J_{CF}$=22.0 Hz, CH), 80.6 (C), 37.6 (CH$_2$), 28.5 (CH$_3$), -2.0 (CH$_3$), only peaks visible; $^{29}$Si NMR (99.46 MHz, CDCl$_3$) δ 6.17. IR (thin film): 2976, 1699, 1464, 1340, 1252, 1167, 1136, 1120, 1004, 848, 795, 651 cm$^{-1}$. HRMS (ESI) m/z calculated for C$_{14}$H$_{21}$FNO$_2$Si (M+H)$^+$: 282.1326, found: 282.1324.

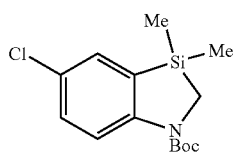

1.2.6e tert-Butyl 5-chloro-3,3-dimethyl-2,3-dihydro-1H-benzo[d][1,3]azasilole-1-carboxylate 1.2.6e. The general procedure was followed using 22.6 mg of ortho-silyl substituted aryl azide 1.2.2e (0.10 mmol) in 1.0 mL of toluene, 0.76 mg of Rh$_2$esp$_2$ (1 mol %), and 24.0 mg of Boc$_2$O (0.11 mmol). Purification by MPLC chromatography (Hexanes) afforded 1.2.6a as a light yellow gel (18.0 mg, 60% yield): $^1$H NMR (500 MHz, CDCl$_3$) δ 8.21 (br s, 1H), 7.35 (d, J=2.0 Hz, 1H), 7.27-7.25 (m, 1H), 3.13 (s, 2H), 1.55 (s, 9H), 0.37 (s, 6H); $^{13}$C NMR (125 MHz, CDCl$_3$) δ 154.4 (C), 150.0 (C), 131.7 (CH), 130.7 (CH), 129.2 (C), 127.1 (C), 119.1 (CH), 80.9 (C), 37.4 (CH$_2$), 28.4 (CH$_3$), -1.9 (CH$_3$); $^{29}$Si NMR (99.46 MHz, CDCl$_3$) δ 6.17. IR (thin film): 2976, 2929, 1702, 1457, 1335, 1252, 1166, 1146, 1100, 1002, 853, 826, 769 cm$^{-1}$. HRMS (ESI) m/z calculated for C$_{14}$H$_{20}$ClNO$_2$SiNa (M+Na)$^+$: 320.0850, found: 320.0854.

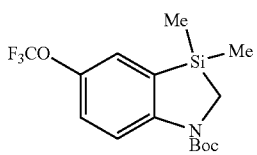

1.2.6f tert-Butyl 3,3-dimethyl-5-trifluoromethoxy-2,3-dihydro-1H-benzo[d][1,3]azasilole-1-carboxylate 1.2.6f. The general procedure was followed using 27.5 mg of ortho-silyl substituted aryl azide 1.2.2f (0.10 mmol) in 1.0 mL of toluene, 0.76 mg of Rh$_2$esp$_2$ (1 mol %), and 24.0 mg of Boc$_2$O (0.11 mmol). Purification by MPLC chromatography (hexanes) afforded 1.2.6f as a light yellow gel (34.6 mg, 100% yield): $^1$H NMR (500 MHz, CDCl$_3$) δ 8.28 (d, J=7.5 Hz, 1H), 7.23 (d, J=2.0 Hz, 1H), 7.16 (dd, J=9.5, 2.5 Hz, 1H), 3.16 (s, 2H), 1.56 (s, 9H), 0.38 (s, 6H); $^{13}$C NMR (125 MHz, CDCl$_3$) δ 154.5 (C), 150.0 (C), 143.8 (C), 128.8 (C), 124.3 (CH), 123.7 (CH), 120.6 (q, $J_{CF}$=255.1 Hz, C), 118.8 (CH), 80.9 (C), 37.6 (CH$_2$), 28.4 (CH$_3$), -2.0 (CH$_3$); Diagnostic data for minor rotamer: $^{13}$C NMR (125 MHz, CDCl$_3$) δ 146.8 (C), 85.2 (C), 27.4 (CH$_3$); $^{29}$Si NMR (99.46 MHz, CDCl$_3$) δ -6.58. IR (thin film): 2977, 1703, 1466, 1338, 1220, 1141, 1123, 1004, 830, 770 cm$^{-1}$. HRMS (ESI) m/z calculated for C$_{15}$H$_{21}$F$_3$NO$_3$Si (M+H)$^+$: 348.1243, found: 348.1238.

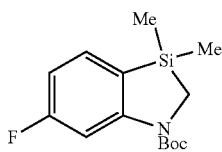

1.2.6g tert-Butyl 6-fluoro-3,3-dimethyl-2,3-dihydro-1H-benzo[d][1,3]azasilole-1-carboxylate 1.2.6g. The general procedure was followed using 21.0 mg of ortho-silyl substituted aryl azide 1.2.2g (0.10 mmol) in 1.0 mL of toluene, 0.76 mg of Rh$_2$esp$_2$ (1 mol %), and 24.0 mg of Boc$_2$O (0.11 mmol). Purification by MPLC chromatography (1:15 EtOAc:hexanes) afforded 1.2.6g as a light yellow gel (27.5 mg, 98% yield): $^1$H NMR (500 MHz, CDCl$_3$) δ8.03 (d, J=12.5 Hz, 1H), 7.35 (t, J=7.5 Hz, 1H), 6.69 (td, J=8.0, 2.5 Hz, 1H), 3.14 (s, 2H), 1.56 (s, 9H), 0.35 (s, 6H); $^{13}$C NMR (125 MHz, CDCl$_3$) δ165.3 (d, $J_{CF}$=242.9 Hz, C), 154.4 (C), 146.8 (C), 133.3 (d, $J_{CF}$=9.4 Hz, CH), 121.8 (C), 109.1 (d, $J_{CF}$=21.9 Hz, CH), 105.6 (d, $J_{CF}$=27.9 Hz, CH), 38.0 (CH$_2$), 27.4 (CH$_3$), -1.7 (CH$_3$). $^{29}$Si NMR (99.46 MHz, CDCl$_3$) δ 6.17. IR (thin film): 2977, 1702, 1594, 1470, 1338, 1253, 1170, 1116, 849, 770 cm$^{-1}$. HRMS (ESI) m/z calculated for C$_{14}$H$_{21}$FNO$_2$Si (M+H)$^+$: 282.1326, found: 282.324.

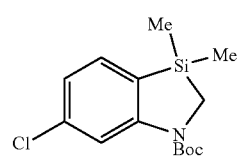

1.2.6h tert-Butyl 6-chloro-3,3-dimethyl-2,3-dihydro-1H-benzo[d][1,3]azasilole-1-carboxylate 1.2.6h. The general procedure was followed using 22.6 mg of ortho-silyl substituted aryl azide 1.2.2h (0.10 mmol) in 1.0 mL of toluene, 0.76 mg of Rh$_2$esp$_2$ (1 mol %), and 24.0 mg of Boc$_2$O (0.11 mmol). Purification by MPLC chromatography (hexanes) afforded 1.2.6h as a light yellow gel (26 mg, 87% yield): $^1$H NMR (500 MHz, CDCl$_3$) δ 8.33 (s, 1H), 7.33 (d, J=7.5 Hz, 1H), 6.96 (dd, J=7.5, 1.5 Hz, 1H), 3.13 (s, 2H), 1.56 (s, 9H), 0.36 (s, 6H); $^{13}$C NMR (125 MHz, CDCl$_3$) δ 154.4 (C), 152.7 (C), 137.2 (C), 133.0 (CH), 124.9 (C), 122.0 (CH), 118.0 (CH), 81.0 (C), 37.7 (CH$_2$), 28.4 (CH$_3$), -1.8 (CH$_3$); $^{29}$Si NMR (99.46 MHz, CDCl$_3$) δ -6.25. IR (thin film): 2976, 1703, 1580, 1456, 1392, 1335, 1167, 1121, 850, 835, 769 cm$^{-1}$. HRMS (ESI) m/z calculated for C$_{14}$H$_{21}$ClNO$_2$Si (M+H)$^+$: 298.1030, found: 298.1019.

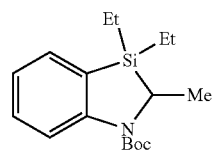

1.2.7a tert-Butyl 3,3-diethyl-2-methyl-2,3-dihydro-1H-benzo[d][1,3]azasilole-1-carboxylate 1.2.7a. The general procedure was followed using 23.3 mg of ortho-silyl substituted aryl azide 1.2.5a (0.10 mmol) in 1.0 mL of toluene, 3.8 mg of Rh$_2$esp$_2$ (5 mol %), and 24.0 mg of Boc$_2$O (0.11 mmol). Purification by MPLC chromatography (hexanes) afforded 1.2.7a as a light yellow gel (30.0 mg, 98% yield): $^1$H NMR (500 MHz, CDCl$_3$) δ 8.07 (d, J=7.5 Hz, 1H), 7.44 (d, J=7.0 Hz, 1H), 7.33 (t, J=7.5 Hz, 1H), 6.98 (t, J=7.0 Hz, 1H), 3.71 (q, J=7.5 Hz, 1H), 1.56 (s, 9H), 1.25 (d, J=7.5 Hz, 3H), 1.14 (t, J=8.0 Hz, 3H), 0.95-0.86 (m, 5H), 0.80-0.74 (m, 2H); $^1$C NMR (125 MHz, CDCl$_3$) δ 154.1 (C), 150.8 (C), 133.0 (CH), 130.7 (CH), 125.2 (C), 122.2 (CH), 119.1 (CH), 80.3 (C), 42.4 (CH), 28.5 (CH$_3$), 16.3 (CH$_3$), 7.7 (CH$_3$), 6.9 (CH$_3$), 4.4 (CH$_2$), 1.6 (CH$_2$); Diagnostic data for minor rotamer: $^{13}$C NMR (125 MHz, CDCl$_3$) δ 27.4 (CH$_3$); $^{29}$Si NMR (99.46 MHz, CDCl$_3$) δ 6.17. IR (thin film): 2960, 2875, 1700, 1462, 1440, 1347, 1308, 1276, 1243, 1168, 1016, 758, 712 cm$^{-1}$. HRMS (ESI) m/z calculated for C$_{17}$H$_{28}$NO$_2$Si (M+H)$^+$: 306.1889, found: 306.1874.

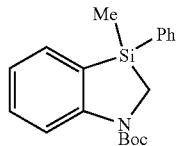

1.2.7b tert-Butyl 3-methyl-3-phenyl-2,3-dihydro-1H-benzo[d][1,3]azasilole-1-carboxylate 1.2.7b. The general procedure was followed using 25.3 mg of ortho-silyl substituted aryl azide 1.2.5b (0.10 mmol) in 1.0 mL of toluene, 0.76 mg of Rh$_2$esp$_2$ (1 mol %), and 24.0 mg of Boc$_2$O (0.11 mmol). Purification by MPLC chromatography (5:95 EtOAc:hexanes) afforded 1.2.7b as a light yellow gel (22 mg, 78% yield): $^1$H NMR (500 MHz, CDCl$_3$) δ 8.34 (d, J=6.5 Hz, 1H), 7.52 (dd, J=8.0, 1.5 Hz, 2H), 7.46 (dd, J=8.0, 1.5 Hz, 1H), 7.43-7.35 (m, 4H), 7.00 (td, J=7.5, 1.0 Hz, 1H), 3.34 (d, J=15.5 Hz, 1H), 3.27 (d, J=15.5 Hz, 1H), 1.56 (s, 9H), 0.68 (s, 3H); $^{13}$C NMR (125 MHz, CDCl$_3$) δ 154.6 (C), 152.4 (C), 135.0 (C), 134.4 (CH), 133.1 (CH), 131.4 (CH), 130.1 (CH), 128.1 (CH), 122.1 (CH), 117.9 (CH), 85.2 (C), 37.3 (CH$_2$), 28.5 (CH$_3$), −4.1 (CH$_3$), only visible signals; Diagnostic data for minor rotamer: $^{13}$C NMR (125 MHz, CDCl$_3$) δ 150.2 (C), 80.7 (C), 27.4 (CH$_3$); $^{29}$Si NMR (99.46 MHz, CDCl$_3$) δ 6.17. IR (thin film): 2975, 2928, 1700, 1587, 1445, 1335, 1252, 1167, 1121, 999, 758 cm$^{-1}$. HRMS (ESI) m/z calculated for C$_{19}$H$_{23}$NO$_2$SiNa (M+Na)$^+$: 348.1396, found: 348.1400.

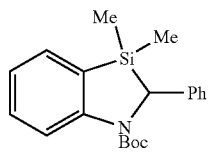

1.2.7c tert-Butyl 3,3-diethyl-2-phenyl-2,3-dihydro-1H-benzo[d][1,3]azasilole-1-carboxylate 1.2.7c. The general procedure was followed using 26.7 mg of ortho-silyl substituted aryl azide 1.2.5c (0.10 mmol) in 1.0 mL of toluene, 0.76 mg of Rh$_2$esp$_2$ (1 mol %), and 24.0 mg of Boc$_2$O (0.11 mmol). Purification by MPLC chromatography (1:10 EtOAc:hexanes) afforded 1.2.7c as a yellow gel (30.0 mg, 88% yield): $^1$H NMR (500 MHz, CDCl$_3$) δ 8.43 (d, J=8.5 Hz, 1H), 7.44-7.41 (m, 2H), 7.21 (t, J=7.5 Hz, 2H) 7.10-7.04 (m, 2H), 6.95 (d, J=7.5 Hz, 2H), 4.68 (s, 1H), 1.28 (s, 9H), 0.43 (s, 3H), −0.12 (s, 3H); $^{13}$C NMR (125 MHz, CDCl$_3$) δ 154.2 (C), 151.9 (C), 143.2 (C), 132.9 (CH), 131.4 (CH), 128.4 (CH), 125.1 (CH), 124.8 (C), 124.1 (CH), 122.6 (CH), 117.6 (CH), 80.6 (C), 54.7 (CH), 28.1 (CH$_3$), −0.9 (CH$_3$), −4.3 (CH$_3$); Diagnostic data for minor rotamer: $^{13}$C NMR (125 MHz, CDCl$_3$) δ 27.4 (CH$_3$); $^{29}$Si NMR (99.46 MHz, CDCl$_3$) δ 9.00. IR (thin film): 2977, 1809, 1702, 1476, 1326, 1314, 1141, 1116, 1064, 858, 761 cm$^{-1}$. HRMS (ESI) m/z calculated for C$_{20}$H$_{26}$NO$_2$Si (M+H)$^+$: 340.1733, found: 340.1726.

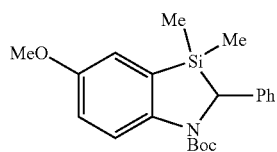

1.2.7d tert-Butyl 5-methoxy-3,3-diethyl-2-phenyl-2,3-dihydro-1H-benzo[d][1,3]azasilole-1-carboxylate 1.2.7d. The general procedure was followed using 89.2 mg of ortho-silyl substituted aryl azide 1.2.5d (0.30 mmol) in 3.0 mL of toluene, 2.28 mg of Rh$_2$esp$_2$ (1 mol %), and 72.0 mg of BOC$_2$O (0.33 mmol). Purification by MPLC chromatography (1:20 EtOAc:hexanes) afforded 1.2.6d as a light yellow gel (98 mg, 88% yield): $^1$H NMR (500 MHz, CDCl$_3$) δ 8.36 (br s, 1H), 7.20 (t, J=7.5 Hz, 2H), 7.08 (t, J=7.5 Hz, 1H), 6.98-6.94 (m, 4H), 4.69 (s, 1H), 3.80 (s, 3H), 1.27 (s, 9H), 0.43 (s, 3H), −0.13 (s, 3H); $^{13}$C NMR (125 MHz, CDCl$_3$) δ 155.2 (C), 154.2 (C), 145.4 (C), 143.2 (C), 128.4 (CH), 126.4 (C), 125.1 (CH), 124.1 (CH), 118.7 (CH), 117.0 (CH), 116.9 (CH), 80.4 (C), 55.6 (CH$_3$), 54.8 (CH), 28.1 (CH$_3$), −1.2 (CH$_3$), −4.4 (CH$_3$); $^{29}$Si NMR (99.46 MHz, CDCl$_3$) δ −1.99. IR (thin film): 2975, 1698, 1466, 1352, 1330, 1273, 1245, 1169, 1116, 1002, 859, 794 cm$^{-1}$. HRMS (ESI) m/z calculated for C$_{21}$H$_{28}$NO$_3$Si (M+H)$^+$: 370.1838, found: 370.1835.

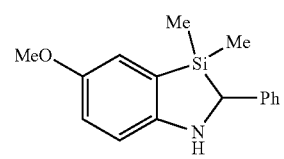

1.2.7dH 5-methoxy-3,3-dimethyl-2-phenyl-2,3-dihydro-1H-benzo[d][1,3]azasilole 1.2.7dH. The general procedure was followed using 29.7 mg of ortho-silyl substituted aryl azide 1.2.5d (0.10 mmol) in 1.0 mL toluene and 0.76 mg of Rh$_2$esp$_2$ (1 mol %). Purification by MPLC chromatography (5:95 EtOAc:hexanes) afforded 1.2.7dH. The reaction mixture was diluted by EtOAc and washed by water and brine. NMR spectroscopy using CBr$_2$H$_2$ revealed the reaction yield as 100%: $^1$H NMR (500 MHz, CDCl$_3$) δ 7.27 (t, J=7.5 Hz, 2H), 7.18 (d, J=7.5 Hz, 2H), 7.12 (t, J=7.5 Hz, 1H), 6.91 (d, J=2.5 Hz, 1H), 6.83 (dd, J=8.5, 2.5 Hz, 1H), 6.54 (d, J=8.5 Hz, 1H), 4.21 (s, 1H), 3.77 (s, 3H), 0.44 (s, 3H), −0.12 (s, 3H), only peaks visible; $^{13}$C NMR (125 MHz, CDCl$_3$) δ 152.4 (C), 144.2 (C), 128.5 (CH), 125.2 (CH), 124.8 (CH), 120.2 (C), 118.2 (CH), 117.8 (CH), 111.1 (CH), 80.6 (C), 56.1 (CH$_3$), 53.7 (CH), −1.4 (CH$_3$), −3.8 (CH$_3$). The crude product was used for the following step without further purification or characterization.

III. Functionalization of benzo[1,3]azasiloles.

A. N-alkylation

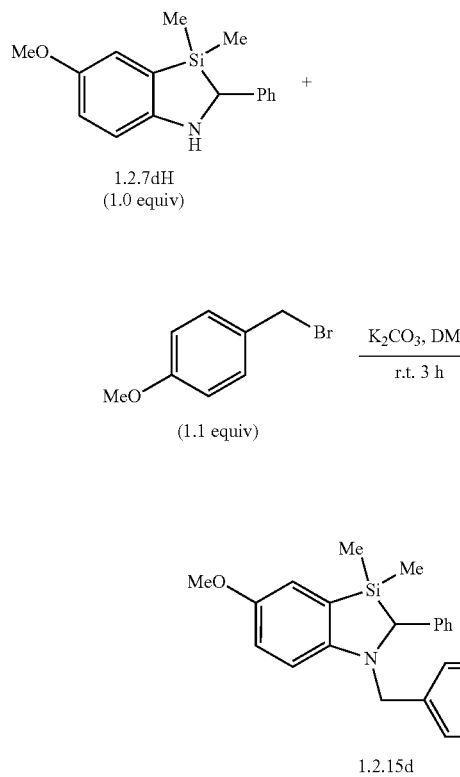

B. N-acylation

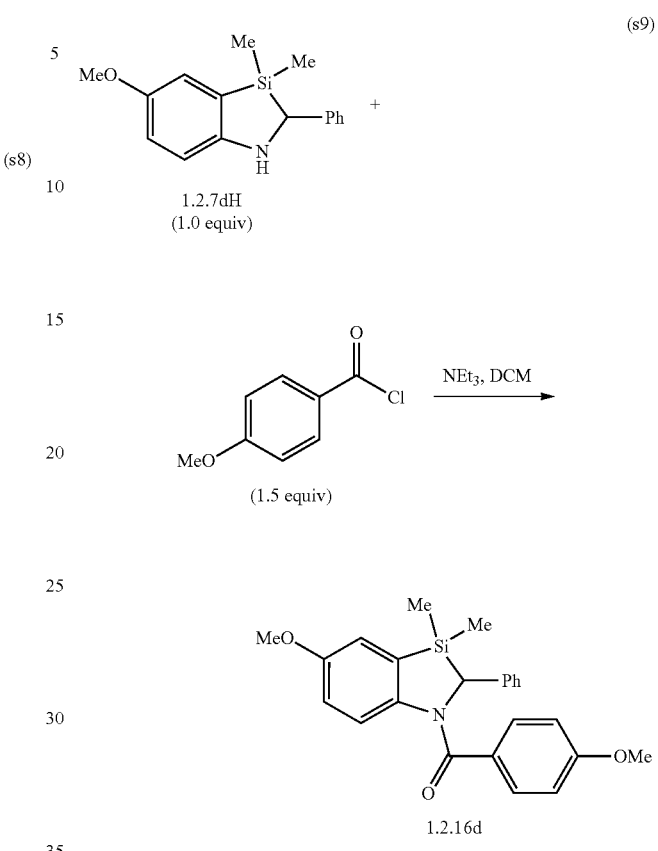

5-Methoxy-1-(4-methoxybenzyl)-3,3-dimethyl-2-phenyl-2,3-dihydro-1H-benzo[d][1,3]azasilole 1.2.15d. To an oven-dried round bottom flask was added 27 mg of [1,3]-silylindoline 1.2.7dH (0.10 mmol, 1.0 equiv) and 30.4 mg of K$_2$CO$_3$ in 1.0 mL DMF under N$_2$ atmosphere. A solution of 22.1 mg 1-(bromomethyl)-4-methoxybenzene (0.11 mmol, 1.1 equiv) in 0.5 mL DMF was added dropwise to the reaction mixture over 10 min. After 3 h, the reactives were quenched by the addition of 5 mL of a saturated aqueous solution of NaHCO$_3$. The resulting mixture was washed with 2×5 mL of water, and the combined aqueous phases were extracted with 3×5 mL of EtOAc. The combined organic phases were dried over Na$_2$SO$_4$, filtered and the filtrate was concentrated in vacuo. The resulting residue was purified by flash chromatography using neutral Al$_2$O$_3$ (1:15 EtOAc:hexanes) to afford the product 1.2.15d: $^1$H NMR (500 MHz, CDCl$_3$) δ 7.27 (t, J=7.5 Hz, 2H), 7.14 (t, J=7.5 Hz, 1H), 7.09-7.07 (m, 4H), 6.95 (d, J=3.0 Hz, 1H), 6.84-6.80 (m, 3H), 6.54 (d, J=8.5 Hz, 1H), 4.61 (d, J=16.5 Hz, 1H), 4.09 (d, J=16.5 Hz, 1H), 4.06 (s, 1H), 3.78 (s, 3H), 3.77 (s, 3H), 0.39 (s, 3H), −0.11 (s, 3H); $^{13}$C NMR (125 MHz, CDCl$_3$) δ 158.4 (C), 153.7 (C), 151.4 (C), 141.9 (C), 130.7 (C), 128.6 (CH), 128.3 (CH), 125.7 (CH), 125.3 (CH), 121.3 (C), 118.6 (CH), 117.6 (CH), 113.8 (CH), 109.0 (CH), 58.5 (CH$_3$), 56.0 (CH$_3$), 55.2 (CH), 50.1 (CH$_2$), −1.29 (CH$_3$), −3.83 (CH$_3$). The compound decomposed rapidly in air.

(5-Methoxy-3,3-dimethyl-2-phenyl-2,3-dihydro-1H-benzo[d][1,3]azasilol-1-yl)(4-methoxyphenyl)methanone 1.2.16d. To an oven-dried round bottom flask was added 27 mg of [1,3]-silylindoline 1.2.7dH (0.10 mmol, 1.0 equiv) and 30.4 mg of triethylamine in 1.0 mL DCM under N$_2$ atmosphere. The resulting mixture was cooled to 0° C., and a solution of 25.6 mg of 4-methoxybenzoyl chloride (0.15 mmol, 1.5 equiv) in 0.5 mL DCM was added dropwise to the reaction mixture over 15 min. The reaction mixture was warmed to room temperature. After 3 h, the reactives were quenched by the addition of 5 mL of a saturated aqueous solution of NaHCO$_3$ The resulting mixture was washed with 2×5 mL of water, and the combined aqueous phases were extracted with 3×5 mL of EtOAc. The combined organic phases were dried over Na$_2$SO$_4$, filtered and the filtrate was concentrated in vacuo. The resulting residue was purified by MPLC (1:5 EtOAc:hexanes) to afford the product 1.2.15d as a yellow gel (30.1 mg, 75%): $^1$H NMR (500 MHz, CDCl$_3$) δ 7.74-7.62 (m, 1H), 7.25 (d, J=8.5 Hz, 2H), 7.19 (t, J=7.5 Hz, 2H), 7.09 (t, J=7.5 Hz, 1H), 6.94-6.85 (m, 4H), 6.75 (d, J=8.5 Hz, 2H), 4.79 (s, 1H), 3.81 (s, 3H), 3.79 (s, 3H), 0.43 (s, 3H), −0.08 (s, 3H); $^{13}$C NMR (125 MHz, CDCl$_3$) δ 160.8 (C), 156.3 (C), 145.0 (C), 141.7 (C), 129.6 (C), 129.2 (CH), 129.0 (C), 128.6 (CH), 125.5 (CH), 124.5 (CH), 122.1 (CH), 117.0 (CH), 116.4 (CH), 113.3 (CH), 58.4 (CH$_3$), 55.5 (CH$_3$), 55.3 (CH), −1.7 (CH$_3$), −5.2 (CH$_3$). $^{29}$Si NMR (99.46 MHz, CDCl$_3$) δ 6.17. IR (thin film): 3308, 2956, 2929, 1606, 1495, 1396, 1302, 1255, 1218, 1176, 1031, 844, 794 cm$^{-1}$; HRMS (ESI) m/z calculated for C$_{17}$H$_{17}$O$_3$F$_3$Na (M+Na)$^+$: 349.1207, found: 349.1207.

D. Synthetic Applications.

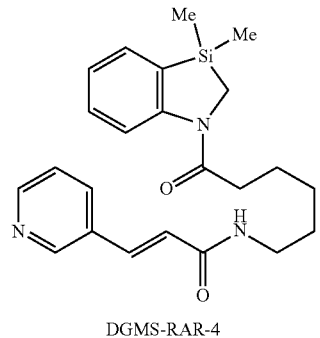 [SMILES: C[Si]1(C)CN(C(=O)CCCCCNC(=O)/C=C/c2cccnc2)c2ccccc21]

DGMS-RAR-4

DGMS-RAR-4. $^1$H NMR (500 MHz, CDCl$_3$) δ 8.69 (s, 1H), 8.63 (br, 1H), 8.51 (d, J=3.5 Hz, 1H), 7.72 (d, J=7.5 Hz, 1H), 7.58 (d, J=15.5 Hz, 1H), 7.46 (d, J=7.0 Hz, 1H), 7.32 (t, J=7.5 Hz, 1H), 7.24 (t, J=6.0 Hz, 1H), 7.05 (t, J=7.0 Hz, 1H), 6.89 (br, 1H), 6.59 (d, J=15.5 Hz, 1H), 3.43 (q, J=6.0 Hz, 2H), 3.11 (br, 2H), 2.61 (t, J=7.0 Hz, 2H), 1.79-1.71 (m, 2H), 1.65-1.60 (m, 2H), 1.49-1.43 (m, 2H), 0.37 (s, 3H); $^{13}$C NMR (125 MHz, CDCl$_3$) δ 174.4 (C), 165.4 (C), 151.7 (C), 150.1 (CH), 149.1 (CH), 136.6 (CH), 134.3 (CH), 132.4 (CH), 131.0 (CH), 131.0 (CH), 123.7 (CH), 123.6 (CH), 123.5 (CH), 119.7 (CH), 39.2 (CH$_2$), 37.8 (CH$_2$), 36.6 (CH$_2$), 28.9 (CH$_2$), 26.4 (CH$_2$). 24.0 (CH$_2$), −1.9 (CH$_3$), only peaks visible; $^{29}$Si NMR (99.46 MHz, CDCl$_3$) δ 6.17. IR (thin film): 3292, 2927, 2857, 1660, 1629, 1584, 1549, 1461, 1440, 1381, 1234, 980, 850, 830, 764, 724 cm$^{-1}$; HRMS (ESI) m/z calculated for C$_{23}$H$_{30}$N$_3$O$_2$Si (M+H)$^+$: 408.2107, found: 408.2101.

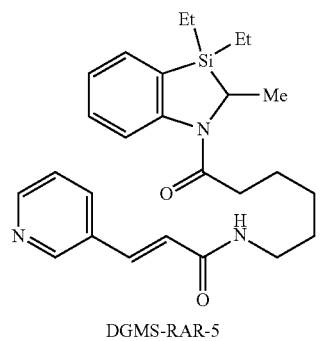 [SMILES: CC[Si]1(CC)c2ccccc2N(C(=O)CCCCCNC(=O)/C=C/c2cccnc2)C1C]

DGMS-RAR-5

DGMS-RAR-5. $^1$H NMR (500 MHz, CDCl$_3$) δ 8.72 (s, 1H), 8.54 (d, J=2.5 Hz, 1H), 8.15 (br, 1H), 7.74 (d, J=7.5 Hz, 1H), 7.59 (d, J=15.5 Hz, 1H), 7.49 (d, J=6.5 Hz, 1H), 7.34 (t, J=7.5 Hz, 1H), 7.28-7.26 (m, 1H), 7.08 (t, J=7.5 Hz, 1H), 6.54 (d, J=15.5 Hz, 2H), 3.71 (br, 1H), 3.47-3.40 (m, 2H), 2.71-2.67 (m, 1H), 2.60-2.54 (m, 1H), 1.78-1.76 (m, 2H), 1.62 (br, 2H), 1.46 (br, 2H), 1.23 (d, J=7.0 Hz, 3H), 1.14 (t, J=7.5 Hz, 3H), 0.95-0.75 (m, 7H); $^{13}$C NMR (125 MHz, CDCl$_3$) δ 172.8 (C), 165.3 (C), 150.6 (C), 150.2 (CH), 149.2 (CH), 136.8 (CH), 134.2 (CH), 133.3 (CH), 130.9 (C), 130.4 (CH), 124.0 (CH), 123.6 (CH), 123.4 (CH), 39.1 (CH$_2$), 34.9 (CH$_2$), 29.7 (CH), 28.8 (CH$_2$), 26.4 (CH$_2$), 24.5 (CH$_2$), 16.6 (CH$_3$), 7.6 (CH$_3$), 7.0 (CH$_3$), 4.0 (CH$_2$), 1.3 (CH$_2$), only peaks visible; $^{29}$Si NMR (99.46 MHz, CDCl$_3$) δ 6.17; IR (thin film): 3295, 2953, 2873, 1658, 1628, 1585, 1548, 1437, 1382, 1290, 1267, 1229, 980, 762, 739, 715 cm$^{-1}$; HRMS (ESI) m/z calculated for C$_{26}$H$_{36}$N$_3$O$_2$Si (M+H)$^+$: 450.2577, found: 450.2573.

Salt Formation.

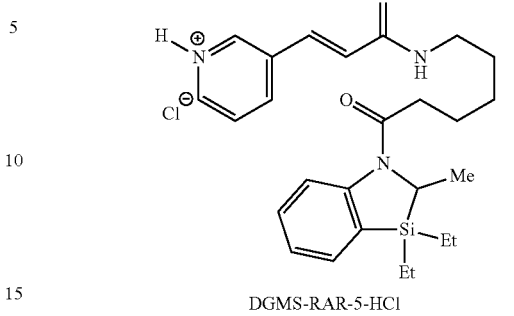

DGMS-RAR-5-HCl

DGMS-RAR-5-HCl. The general procedure was followed using 13.5 mg of DGMS-RAR-5 (0.030 mmol) in 3 mL DCM, and 0.015 mL Of 2.0 M of HCl solution in ether (0.030 mmol). After evaporating the solvent, the product DGMS-RAR-5-HCl was afforded as a clear gel (14.6 mg, 100% yield). $^1$H NMR (500 MHz, CDCl$_3$) δ 9.14 (s, 1H), 8.76 (d, J=4.0 Hz, 1H), 8.39 (d, J=7.5 Hz, 1H), 7.91 (t, J=6.0 Hz, 1H), 7.66 (s, 1H), 7.61 (d, J=15.5 Hz, 1H), 7.48 (d, J=7.0 Hz, 1H), 7.36-7.32 (m, 2H), 7.07 (t, J=7.5 Hz, 1H), 3.72 (br, 1H), 3.44-3.36 (m, 2H), 2.70-2.64 (m, 1H), 2.59-2.53 (m, 1H), 1.82-1.72 (m, 2H), 1.67-1.62 (m, 2H), 1.49-1.46 (m, 2H), 1.23 (d, J=7.5 Hz, 3H), 1.13 (t, J=8.0 Hz, 3H), 0.95-0.85 (m, 5H), 0.78-0.73 (m, 2H); $^{13}$C NMR (125 MHz, CDCl$_3$) δ 172.9 (C), 164.1 (C), 150.1 (C), 143.8 (CH), 143.8 (CH), 139.8 (CH), 139.3 (CH), 136.2 (C), 133.3 (CH), 131.1 (CH), 130.4 (CH), 127.2 (CH), 123.9 (CH), 39.6 (CH$_2$), 35.0 (CH$_2$), 28.9 (CH$_2$), 26.7 (CH$_2$), 25.1 (CH$_2$), 7.6 (CH$_3$), 7.0 (CH$_3$), 4.0 (CH$_2$), 1.3 (CH$_2$), only peaks visible. IR (thin film): 3419, 3000, 2916, 1661, 1436, 1406, 1313, 1016, 952, 701, 670 cm$^{-1}$; HRMS (ESI) m/z calculated for C$_{26}$H$_{36}$N$_3$O$_2$Si (M+H)$^+$: 450.2577, found: 450.2569 same as the mass of the parent compound.

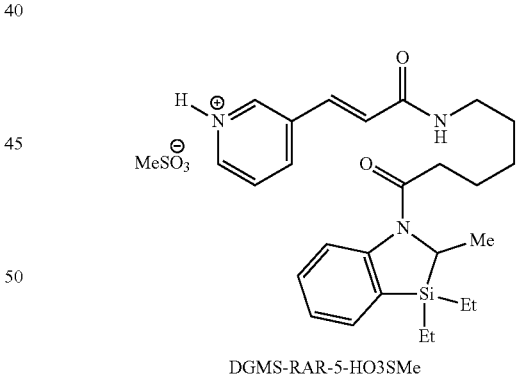

DGMS-RAR-5-HO3SMe

DGMS-RAR-5-HO$_3$SMe. The general procedure was followed using 13.5 mg of DGMS-RAR-5 (0.030 mmol) in 3 mL DCM, and 0.030 mL Of a 1.0 M of HO$_3$SMe solution in ether (0.030 mmol). After evaporating the solvent, the product DGMS-RAR-5- HO$_3$SMe was afforded as a clear gel (16.4 mg, 100% yield). $^1$H NMR (500 MHz, CDCl$_3$) δ 9.30 (s, 1H), 8.87 (d, J=5.5 Hz, 1H), 8.45 (d, J=8.0 Hz, 1H), 7.95 (t, J=6.5 Hz, 1H), 7.84 (s, 1H), 7.58 (d, J=15.5 Hz, 1H), 7.48 (d, J=7.0 Hz, 1H), 7.34 (t, J=7.5 Hz, 1H), 7.26 (d, J=15.5 Hz, 1H)), 7.07 (t, J=7.5 Hz, 1H), 3.73 (br, 1H), 3.37 (q, J=6.0 Hz, 2H), 2.88 (s, 3H), 2.69-2.64 (m, 1H), 2.59-2.54 (m, 1H), 1.80-1.73 (m, 2H), 1.66-1.60 (m, 2H), 1.50-1.41

(m, 2H), 1.23 (d, J=7.0 Hz, 3H), 1.14 (t, J=8.0 Hz, 3H), 0.97-0.84 (m, 5H), 0.79-0.72 (m, 2H); $^{13}$C NMR (125 MHz, CDCl$_3$) δ 172.9 (C), 164.3 (C), 150.1 (C), 144.1 (CH), 140.8 (CH), 140.3 (CH), 139.3 (C), 136.2 (CH), 133.9 (C), 133.3 (CH), 131.3 (CH), 130.4 (CH), 130.1 (CH), 127.3 (CH), 123.9 (CH), 39.73 (CH$_3$), 39.67 (CH$_2$), 35.1 (CH$_2$), 29.0 (CH$_2$), 26.8 (CH$_2$), 25.3 (CH$_2$), 7.6 (CH$_3$), 7.0 (CH$_3$), 4.0 (CH$_2$), 1.3 (CH$_2$), only peaks visible. IR (thin film): 3420, 2996, 2913, 1661, 1436, 1406, 1310, 1210, 1018, 951, 698, 667 cm$^{-1}$; HRMS (ESI) m/z calculated for C$_{26}$H$_{36}$N$_3$O$_2$Si (M+H)$^+$: 450.2577, found: 450.2570 same as the mass of the parent compound.

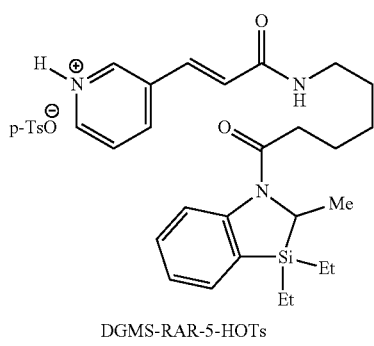 [SMILES: CC[Si]1(CC)c2ccccc2N(C(=O)CCCCCNC(=O)/C=C/c2ccc[nH+]c2)C1C]

DGMS-RAR-5-HOTs

DGMS-RAR-5-HOTs. The general procedure was followed using 13.5 mg of DGMS-RAR-5 (0.030 mmol) and 5.7 mg of TsOH (0.030 mmol) in 3 mL DCM. After evaporating the solvent, the product DGMS-RAR-5-HOTs was afforded as a clear gel (18.7 mg, 100% yield). $^1$H NMR (500 MHz, CDCl$_3$) δ 9.35 (s, 1H), 8.86 (d, J=5.5 Hz, 1H), 8.38 (d, J=8.5 Hz, 1H), 7.91-7.87 (m, 2H), 7.77 (d, J=7.5 Hz, 2H), 7.52 (d, J=15.5 Hz, 1H), 7.48 (d, J=7.0 Hz, 1H), 7.35-7.29 (m, 2H), 7.10 (d, J=7.5 Hz, 2H), 7.07 (t, J=7.5 Hz, 1H), 3.72 (br, 1H), 3.35-3.32 (m, 2H), 2.67-2.61 (m, 1H), 2.56-2.50 (m, 1H), 2.30 (s, 3H), 1.77-1.72 (m, 2H), 1.62-1.56 (m, 2H), 1.47-1.39 (m, 2H), 1.22 (d, J=7.5 Hz, 3H), 1.14 (t, J=8.0 Hz, 3H), 0.96-0.83 (m, 5H), 0.78-0.73 (m, 2H); $^{13}$C NMR (125 MHz, CDCl$_3$) δ 173.0 (C), 164.4 (C), 150.1 (C), 144.2 (CH), 141.6 (C), 140.7 (CH), 140.3 (CH), 136.2 (C), 133.2 (CH), 131.2 (CH), 130.4 (CH), 130.2 (CH), 129.1 (CH), 127.2 (CH), 125.9 (CH), 123.9 (CH), 39.7 (CH$_2$), 35.1 (CH$_2$), 29.0 (CH$_2$), 26.8 (CH$_2$), 25.4 (CH$_2$), 21.3 (CH$_3$), 16.5 (CH$_3$), 7.7 (CH$_3$), 7.0 (CH$_3$), 4.0 (CH$_3$), 1.3 (CH$_3$), only peaks visible. IR (thin film): cm$^{-1}$; HRMS (ESI) m/z calculated for C$_{17}$H$_{17}$O$_3$F$_3$Na (M+Na)$^+$: 349.1207, found: 349.1207.

II. Preparation of Indole Compounds.

A. Synthesis of N-(6-indolehexyl)-phthalimide. (Route A)

General Procedure A.

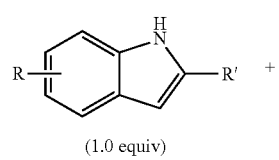

(s1)

(1.0 equiv)

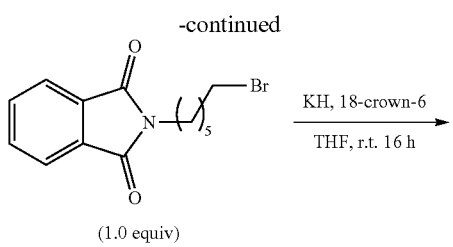

(1.0 equiv)

KH, 18-crown-6
THF, r.t. 16 h

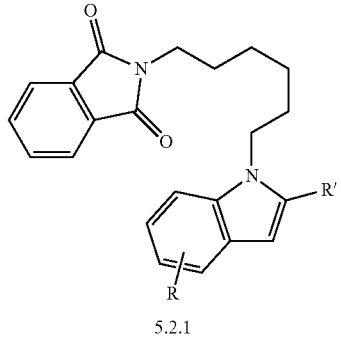

5.2.1

To a stirred 0.5 M solution of 18-crown-6 (1.5 equiv) and KH (1.5 equiv, 30% w/w suspension in mineral oil) in dry THF was added a 0.5 M solution of indole (1.0 equiv) in dry THF dropwise over 10 min under N$_2$ atmosphere. After stirring at room temperature for 30 min, a 0.5 M solution of N-(6-bromohexyl) phthalimide (1.2 equiv) in dry THF was added to the reaction mixture dropwise over 10 min. The reaction mixture was allowed to stir at room temperature overnight. The reactives were then quenched by the addition of 20 mL of water. The resulting mixture was extracted by 3×15 mL of EtOAc. The combined organic extracts were washed with 2×20 mL of water and 20 mL of brine. The resulting organic phase was dried over Na$_2$SO$_4$, filtered and the filtrate was concentrated in vacuo. The resulting residue was purified by MPLC to afford the product.

General Procedure B.

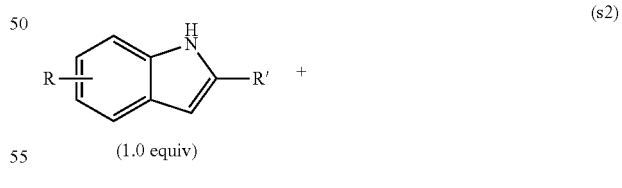

(s2)

(1.0 equiv)

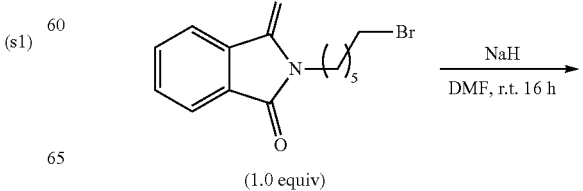

(1.0 equiv)

NaH
DMF, r.t. 16 h

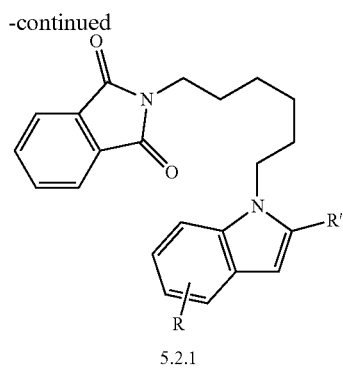

5.2.1

In a three-necked flask, equipped with a magnetic stir bar, was charged with indole (1.0 equiv). Dry DMF (3 ml/1 mmol of indole) was added under Ar atmosphere and the reaction mixture cooled to 0° C. NaH (2.0 equiv, 60% w/w in mineral oil) was added in a single portion and the reaction mixture stirred at 0° C. After 10 minutes, the reaction was warmed to room temperature. After 1 h, the reaction mixture was cooled to 0° C. and N-(6-bromohexyl) phthalimide (2.0 equiv) dissolved in 2 mL of dry DMF was added dropwise over 10 min. The reaction mixture was slowly warmed to room temperature and stirred overnight. The reactives were then quenched by addition of 20 mL of water. The resulting mixture was extracted with 3×15 mL of EtOAc. The combined organic extracts were washed with 2×20 mL of water and 20 mL of brine. The resulting organic phase was dried over Na$_2$SO$_4$, filtered and the filtrate was concentrated in vacuo. The resulting residue was purified by MPLC to afford the product.

B. Characterization Data for N-(6-indolehexyl)-phthalimides 5.2.1

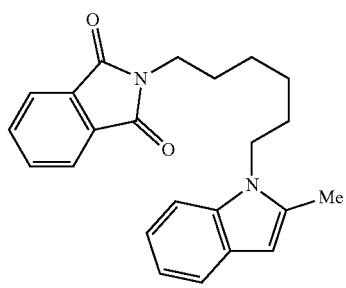

5.2.1a

N-(6-Indolehexyl)-phthalimide 5.2.1a. The general procedure was followed using 131.2 mg of 2-2ethylindole (1.0 mmol), 620.4 mg of N-(6-bromohexyl) phthalimide (2.0 mmol), 80 mg of 60% w/w NaH in mineral oil (2.0 mmol) in total 5 mL of DMF. Purification by MPLC chromatography (10:1 hexanes:EtOAc) afforded 5.2.1a as a yellow oil (54 mg, 15% yield). $^1$H NMR (500 MHz, CDCl$_3$) δ 7.85-7.82 (m, 2H), 7.72-7.69 (m, 2H), 7.50 (d, J=8.0 Hz, 1H), 7.24 (d, J=8.0 Hz, 1H), 7.11 (dt, J=8.0 Hz, 1.0 Hz, 1H), 7.05-7.02 (m, 1H), 6.22 (s, 1H), 4.04 (t, J=7.5 Hz, 2H), 3.67 (t, J=7.0 Hz, 2H), 2.41 (s, 3H), 1.75 (quin, J=7.0 Hz, 2H), 1.67 (quin, J=7.0 Hz, 2H), 1.44-1.34 (m, 4H); $^{13}$C NMR (125 MHz, CDCl$_3$) δ 168.4 (C), 136.6 (C), 136.3 (C), 133.9 (CH), 132.1 (C), 128.0 (C), 123.2 (CH), 120.3 (CH), 119.6 (CH), 119.1 (CH), 109.0 (CH), 99.9 (CH), 43.1 (CH$_2$), 37.8 (CH$_2$), 30.1 (CH$_2$), 28.5 (CH$_2$), 26.6 (CH$_2$), 26.6 (CH$_2$), 12.8 (CH$_3$). ATR-FTIR (thin film): 3054, 2935, 2858, 1771, 1707, 1614, 1550, 1465, 1395, 1357, 1055, 718 cm$^{-1}$. HRMS (ESI) m/z calculated for C$_{23}$H$_{25}$N$_2$O$_2$ [M+H]$^+$: 361.1916, found: 361.1911.

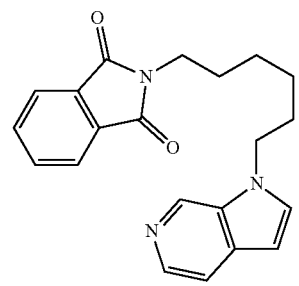

5.2.1b

N-(6-Indolehexyl)-phthalimide 5.2.1b. The general procedure was followed using 118.1 mg of 6-azaindole (1.0 mmol), 620.4 mg of N-(6-bromohexyl) phthalimide (2.0 mmol), 80 mg of 60% w/w NaH in mineral oil (2.0 mmol) in total 5 mL of DMF. Purification by MPLC chromatography (5:1-1:1 hexanes:EtOAc-100% EtOAc) afforded 5.2.1b as a yellow oil (70 mg, 20% yield). $^1$H NMR (500 MHz, CDCl$_3$) δ 8.71 (s, 1H), 8.17 (d, J=5.5 Hz, 1H), 7.78-7.75 (m, 2H), 7.66-7.63 (m, 2H), 7.44 (dd, J=5.5 Hz, 1.0 Hz, 1H), 7.16 (d, J=3.0 Hz, 1H), 6.41 (d, J=3.0 Hz, 1H), 4.13 (t, J=7.5 Hz, 2H), 3.60 (t, J=7.0 Hz, 2H), 1.82 (quin, J=3.5 Hz, 2H), 1.63-1.57 (m, 2H), 1.33-1.29 (m, 4H); $^{13}$C NMR (125 MHz, CDCl$_3$) δ 168.4 (C), 138.4 (CH), 133.9 (CH), 133.2 (C), 133.0 (C), 132.8 (CH), 132.0 (C), 131.3 (CH), 123.1 (CH), 115.3 (CH), 100.5 (CH), 46.6 (CH$_2$), 37.7 (CH$_2$), 30.3 (CH$_2$), 28.4 (CH$_2$), 26.4 (CH$_2$), 26.4 (CH$_2$). ATR-FTIR (thin film): 3044, 2934, 2858, 1771, 1707, 1668, 1395, 1090, 818, 719 cm$^{-1}$. HRMS (ESI) m/z calculated for C$_{21}$H$_{22}$N$_3$O$_2$ [M+H]$^+$ 348.1712, found: 348.1708.

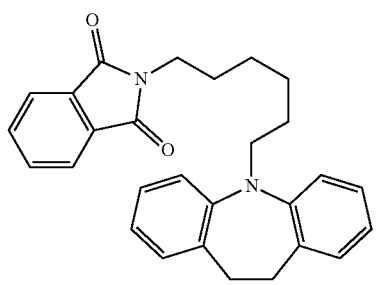

5.2.1c

N-(6-Indolehexyl)-phthalimide 5.2.1c. The general procedure was followed using 195.3 mg of iminodibenzyl (1.0 mmol), 372.2 mg of N-(6-bromohexyl) phthalimide (1.2 mmol), 60.2 mg of 30% w/w KH suspension in mineral oil (1.5 mmol) and 396.2 mg of 18-crown-6 (1.5 mmol) in total 6 mL of THF. Purification by MPLC chromatography (10:1 hexanes:EtOAc) afforded 5.2.1c as a yellow oil (198 mg, 47% yield) as a mixture of inseparable impurities, which was taken to the next step without any further purification or characterization.

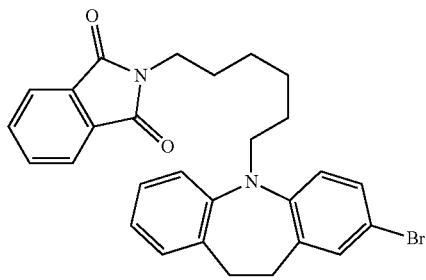

5.2.1d

N-(6-Indolehexyl)-phthalimide 5.2.1d. The general procedure was followed using 274.2 mg of 2-bromo-10,11-dihydro-5H-dibenzo[b,f]azepine (1.0 mmol), 372.2 mg of N-(6-bromohexyl) phthalimide (1.2 mmol), 60.2 mg of 30% w/w KH suspension in mineral oil (1.5 mmol) and 396.2 mg of 18-crown-6 (1.5 mmol) in total 6 mL of THF. Purification by MPLC chromatography (10:1 hexanes:EtOAc) afforded 5.2.1d as a yellow oil (259 mg, 51% yield) as a mixture of inseparable impurities, which was taken to the next step without any further purification or characterization.

5.2.1e

N-(6-Indolehexyl)-phthalimide 5.2.1e. The general procedure was followed using 195.2 mg of 2-phenylindoline (1.0 mmol), 372.2 mg of N-(6-bromohexyl) phthalimide (1.2 mmol), 60.2 mg of 30% w/w KH suspension in mineral oil (1.5 mmol) and 396.2 mg of 18-crown-6 (1.5 mmol) in total 6 mL of THF. Purification by MPLC chromatography (10:1 hexanes:EtOAc) afforded 5.2.1e as a yellow oil (260 mg, 61% yield) as a mixture of inseparable impurities, which was taken to the next step without any additional purification or characterization.

5.2.1f

N-(6-indolehexyl)-phthalimide 5.2.1f. The general procedure was followed using 147 mg of indole (1.00 mmol), 310 mg of N-(6-bromohexyl) phthalimide (1.50 mmol), 60.2 mg of 30% w/w KH in mineral oil (1.50 mmol), 396 mg of 18-crown-6 in a total of 6 mL of THF. Purification by MPLC chromatography (1:10 EtOAc:hexanes) afforded 5.2.1f as a yellow oil (280 mg, 74% yield): $^1$H NMR (500 MHz, CDCl$_3$) δ 7.83 (dd, J=5.5, 3.0 Hz, 2H), 7.70 (dd, J=5.5, 3.0 Hz, 2H), 7.20 (d, J=8.5 Hz, 1H), 7.07 (d, J=2.0 Hz, 1H), 7.05 (d, J=3.0 Hz, 1H), 6.85 (dd, J=8.5, 2.0 Hz, 1H), 6.38 (d, J=2.5 Hz, 1H), 4.06 (t, J=7.5 Hz, 2H), 3.84 (s, 3H), 3.66 (t, J=7.5 Hz, 2H), 1.81 (quintet, J=7.0 Hz, 2H), 1.65 (quintet, J=7.0 Hz, 2H), 1.39-1.32 (m, 4H); $^{13}$C NMR (125 MHz, CDCl$_3$) δ 168.4 (C), 153.9 (C), 133.9 (CH), 132.1 (C), 131.3 (C), 128.9 (C), 128.3 (CH), 123.2 (CH), 111.7 (CH), 110.1 (CH), 102.6 (CH), 100.4 (CH), 55.9 (CH$_3$), 46.5 (CH$_2$), 37.8 (CH$_2$), 30.2 (CH$_2$), 28.5 (CH$_2$), 26.6 (CH$_2$), 26.5 (CH$_2$).

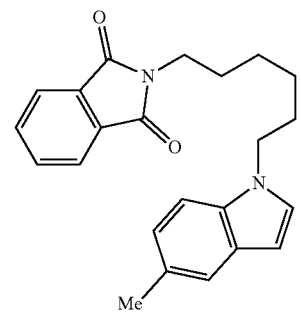

5.2.1g

N-(6-indolehexyl)-phthalimide 5.2.1g. The general procedure was followed using 131 mg of indole (1.00 mmol), 310 mg of N-(6-bromohexyl) phthalimide (1.50 mmol), 60.2 mg of 30% w/w KH in mineral oil (1.50 mmol), 396 mg of 18-crown-6 in a total of 6 mL of THF. Purification by MPLC chromatography (1:10 EtOAc:hexane) afforded 5.2.1g as a yellow oil (250 mg, 69% yield): 1H NMR (500 MHz, CDCl$_3$) δ 7.84 (dd, J=5.3, 3.1 Hz, 2H), 7.70 (dd, J=5.4, 3.0 Hz, 2H), 7.42 (s, 1H), 7.23 (d, J=8.3 Hz, 1H), 7.04 (dd, J=9.6, 5.7 Hz, 2H), 6.40 (d, J=2.9 Hz, 1H), 4.08 (t, J=7.0 Hz, 2H), 3.68 (t, J=7.2 Hz, 2H), 2.47 (s, 3H), 1.89-1.79 (m, 2H), 1.72-1.62 (m, 2H), 1.41-1.34 (m, 4H); $^{13}$C NMR (125 MHz, CDCl$_3$) δ 168.5 (C), 134.4 (C), 133.9 (CH), 132.2 (C), 128.9 (C), 128.3 (C), 127.9 (CH), 123.2 (CH), 123.0 (CH), 120.6 (CH), 109.1 (CH), 100.3 (CH), 46.3 (CH$_2$), 37.9 (CH$_2$), 30.1 (CH$_2$), 28.5 (CH$_2$), 26.6 (CH$_2$), 26.5 (CH$_2$), 21.4 (CH$_3$). IR (thin film): 2933, 2858, 1771, 1706, 1436, 1394, 1357, 1333, 1056, 878, 791, 759, 717 cm$^{-1}$; HRMS (ESI) m/z calculated for C$_{23}$H$_{25}$N$_2$O$_2$ (M+H)$^+$: 361.1916, found: 361.1919.

5.2.1h

N-(6-Indolehexyl)-phthalimide 5.2.1h. The general procedure was followed using 189 mg of indole (1.00 mmol), 310 mg of N-(6-bromohexyl) phthalimide (1.5 mmol), 60.2 mg of 30% w/w KH in mineral oil (1.50 mmol), 396 mg of 18-crown-6 in a total of 6 mL of THF. Purification by MPLC chromatography (1:5 EtOAc:hexanes) afforded 5.2.1h as a yellow oil (50 mg, 12% yield): $^1$H NMR (500 MHz, CDCl$_3$) δ 7.84-7.82 (m, 2H), 7.70-7.69 (m, 2H), 7.59 (d, J=8.0 Hz, 1H), 7.28 (d, J=8.5 Hz, 1H), 7.19 (t, J=7.5 Hz, 1H), 7.10 (t, J=7.5 Hz, 1H), 7.07 (s, 1H), 4.06 (t, J=7.0 Hz, 2H), 3.76 (s, 2H), 3.69 (s, 3H), 3.66 (t, J=7.0 Hz, 2H), 1.83-1.81 (m, 2H), 1.69-1.65 (m, 2H), 1.39-1.35 (m, 4H); $^{13}$C NMR (125 MHz, CDCl$_3$) δ 172.6 (C), 168.4 (C), 136.2 (C), 133.9 (CH), 132.1 (C), 127.8 (C), 126.7 (CH), 123.2 (CH), 121.6 (CH), 119.1 (CH), 119.0 (CH), 109.4 (CH), 106.8 (C), 51.9 (CH$_3$), 46.2 (CH$_2$), 37.8 (CH$_2$), 31.1 (CH$_2$), 30.1 (CH$_2$), 28.5 (CH$_2$), 26.6 (CH$_2$), 26.5 (CH$_2$).

mg of N-(6-bromohexyl) phthalimide (3.00 mmol), 120 mg of 30% w/w KH in mineral oil (3.00 mmol), 792 mg of 18-crown-6 in a total of 12 mL of THF. Purification by MPLC chromatography (1:5 EtOAc:hexanes) afforded 5.2.1j as a yellow oil (676 mg, 80% yield): $^1$H NMR (500 MHz, CDCl$_3$) δ 7.85-7.82 (m, 2H), 7.73-7.68 (m, 2H), 7.68-7.66 (m, 1H), 7.62 (t, J=7.8 Hz, 1H), 7.49-7.43 (m, 3H), 7.40-7.32 (m, 2H), 7.23-7.17 (m, 1H), 7.12 (t, J=7.5 Hz, 1H), 6.50 (s, 1H), 4.14-4.11 (m, 1H), 3.68 (q, J=6.9 Hz, 1H), 3.58 (t, J=7.3 Hz, 1H), 3.39 (t, J=6.8 Hz, 1H), 1.91-1.81 (m, 1H), 1.74-1.65 (m, 2H), 1.56-1.45 (m, 2H), 1.43-1.34 (m, 1H), 1.17 (dd, J=15.2, 11.7 Hz, 2H). This phthalimide was taken to the next step without any further purification or characterization.

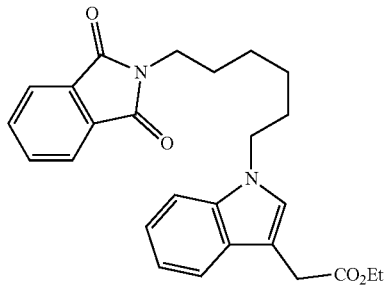

5.2.1i

N-(6-Indolehexyl)-phthalimide 5.2.1i. The general procedure was followed using 406 mg of indole (2.00 mmol), 620 mg of N-(6-bromohexyl) phthalimide (3.00 mmol), 120 mg of 30% w/w KH in mineral oil (3.00 mmol), 792 mg of 18-crown-6 in a total of 12 mL of THF. Purification by MPLC chromatography (1:5 EtOAc:hexanes) afforded 5.2.1i as a yellow oil (165 mg, 19% yield): $^1$H NMR (500 MHz, CDCl$_3$) δ 7.83-7.81 (m, 2H), 7.69-7.67 (m, 2H), 7.60 (d, J=7.5 Hz, 1H), 7.29 (d, J=8.0 Hz, 1H), 7.19 (t, J=7.5 Hz, 1H), 7.11-7.08 (m, 2H), 4.16 (q, J=7.0 Hz, 2H), 4.06 (t, J=7.0 Hz, 2H), 3.75 (s, 2H), 3.66 (t, J=7.5 Hz, 2H), 1.84-1.81 (m, 2H), 1.67-1.65 (m, 2H), 1.39-1.34 (m, 4H), 1.26 (t, J=7.0 Hz, 3H); $^{13}$C NMR (125 MHz, CDCl$_3$) δ 172.1 (C), 168.4 (C), 136.2 (C), 133.9 (CH), 132.1 (C), 127.8 (C), 126.6 (CH), 123.2 (CH), 121.6 (CH), 119.1 (CH), 119.0 (CH), 109.4 (CH), 107.0 (C), 60.7 (CH$_2$), 46.2 (CH$_2$), 37.8 (CH$_2$), 31.4 (CH$_2$), 30.1 (CH$_2$), 28.5 (CH$_2$), 26.6 (CH$_2$), 26.5 (CH$_2$), 14.3 (CH$_3$). IR (thin film): 2934, 2859, 1704, 1613, 1466, 1366, 1187, 1055, 743, 719 cm$^{-1}$; HRMS (ESI) m/z calculated for C$_{26}$H$_{29}$N$_2$O$_4$ (M+H)$^+$: 433.2127, found: 433.2108.

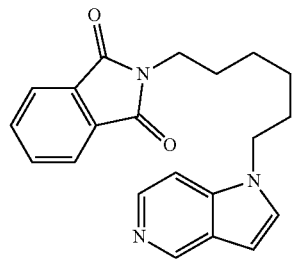

5.2.1k

N-(6-indolehexyl)-phthalimide 5.2.1k. The general procedure was followed using 237 mg of indole (2.00 mmol), 620 mg of N-(6-bromohexyl) phthalimide (3.00 mmol), 120 mg of 30% w/w KH in mineral oil (3.00 mmol), 792 mg of 18-crown-6 in a total of 12 mL of THF. Purification by MPLC chromatography (1:5 EtOAc:hexanes) afforded 5.2.1k as a yellow oil (382 mg, 55% yield): $^1$H NMR (500 MHz, CDCl$_3$) δ 8.13 (dd, J=4.6, 1.1 Hz, 1H), 7.69 (dd, J=7.8, 1.2 Hz, 1H), 7.60 (dt, J=6.8, 3.4 Hz, 2H), 7.50-7.40 (m, 2H), 7.03 (d, J=3.4 Hz, 1H), 6.84 (dd, J=7.8, 4.7 Hz, 1H), 6.24 (d, J=3.4 Hz, 1H), 4.09 (t, J=7.2 Hz, 2H), 3.53-3.33 (m, 2H), 1.70 (dd, J=18.1, 11.3 Hz, 2H), 1.56-1.38 (m, 2H), 1.20 (s, 4H). $^{13}$C NMR (125 MHz, CDCl$_3$) δ 168.1 (C), 147.3 (C), 142.5 (CH), 133.6 (CH), 132.0 (C), 128.5 (CH), 127.8 (CH), 122.9 (CH), 120.4 (C), 115.4 (CH), 99.2 (CH), 44.3 (CH$_2$), 37.7 (CH$_2$), 30.1 (CH$_2$), 28.3 (CH$_2$), 26.34 (CH$_2$), 26.29 (CH$_2$).

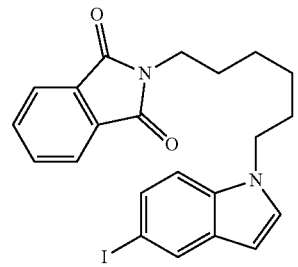

5.2.1l

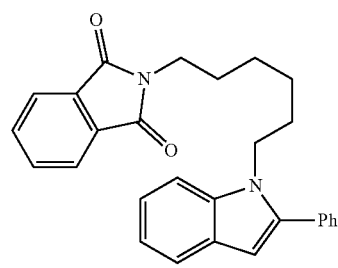

5.2.1j

N-(6-Indolehexyl)-phthalimide 5.2.1j. The general procedure was followed using 386 mg of indole (2.00 mmol), 620

N-(6-Indolehexyl)-phthalimide 5.2.1l. The general procedure was followed using 486 mg of indole (2.00 mmol), 620 mg of N-(6-bromohexyl) phthalimide (3.00 mmol), 120 mg of 30% w/w KH in mineral oil (3.00 mmol), 792 mg of 18-crown-6 in a total of 12 mL of THF. Purification by MPLC chromatography (1:5 EtOAc:hexanes) afforded 5.2.1l as a yellow oil (737 mg, 78% yield): $^1$H NMR (500 MHz, CDCl$_3$) δ 7.89 (d, J=1.2 Hz, 1H), 7.79 (dd, J=5.3, 3.1

Hz, 2H), 7.66 (dd, J=5.4, 3.0 Hz, 2H), 7.37 (dd, J=8.6, 1.4 Hz, 1H), 7.06 (d, J=8.6 Hz, 1H), 7.00 (d, J=3.1 Hz, 1H), 6.35 (d, J=3.0 Hz, 1H), 4.02 (t, J=7.1 Hz, 2H), 3.63 (t, J=7.2 Hz, 2H), 1.82-1.69 (m, 2H), 1.67-1.54 (m, 2H), 1.39-1.27 (m, 4H). $^{13}$C NMR (125 MHz, CDCl$_3$) δ 168.4 (C), 135.0 (C), 133.9 (CH), 132.1 (C), 131.1 (C), 129.7 (CH), 129.6 (CH), 128.6 (CH), 123.2 (CH), 111.4 (CH), 100.4 (CH), 82.7 (C), 46.4 (CH$_2$), 37.8 (CH$_2$), 30.0 (CH$_2$), 28.4 (CH$_2$), 26.5 (CH$_2$), 26.4 (CH$_2$).

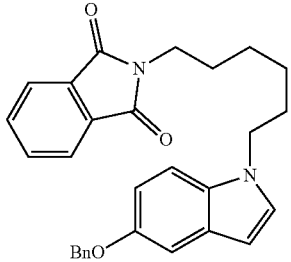

5.2.1m

N-(6-Indolehexyl)-phthalimide 5.2.1m. The general procedure was followed using 447 mg of indole (2.00 mmol), 620 mg of N-(6-bromohexyl) phthalimide (3.00 mmol), 120 mg of 30% w/w KH in mineral oil (3.00 mmol), 792 mg of 18-crown-6 in a total of 12 mL of THF. Purification by MPLC chromatography (1:5 EtOAc:hexanes) afforded 5.2.1m as a yellow oil (842 mg, 93% yield): $^1$H NMR (500 MHz, CDCl$_3$) δ 7.73 (dd, J=5.0, 3.0 Hz, 2H), 7.53 (dd, J=5.0, 3.0 Hz, 2H), 7.48 (d, J=7.4 Hz, 2H), 7.36 (t, J=7.4 Hz, 2H), 7.29 (t, J=7.2 Hz, 1H), 7.20 (d, J=8.9 Hz, 2H), 7.03 (d, J=2.6 Hz, 1H), 6.97 (dd, J=8.7, 1.6 Hz, 1H), 6.40 (d, J=2.5 Hz, 1H), 5.07 (s, 2H), 3.95 (t, J=6.8 Hz, 2H), 3.62 (t, J=7.1 Hz, 2H), 1.71 (dd, J=21.2, 15.0 Hz, 2H), 1.66-1.50 (m, 2H), 1.28 (d, J=12.8 Hz, 4H). $^{13}$C NMR (125 MHz, CDCl$_3$) δ 168.2 (C), 153.2 (C), 138.0 (C), 133.8 (C), 132.1 (CH), 131.6 (C), 129.0 (C), 128.5 (CH), 128.4 (CH), 127.7 (CH), 127.6 (CH), 123.0 (CH), 112.4 (CH), 110.2 (CH), 104.2 (CH), 100.7 (CH), 70.7 (CH$_2$), 60.3 (CH$_2$), 46.3 (CH$_2$), 37.8 (CH$_2$), 30.2 (CH$_2$), 28.5 (CH$_2$), 26.5 (CH$_2$). ATR-FTIR (thin film): 2933, 2858, 1770, 1705, 1486, 1395, 1233, 1151, 1056, 717 cm$^{-1}$. HRMS (ESI) m/z calculated for C$_{29}$H$_{29}$N$_2$O$_3$ [M+H]$^+$: 453.2178, found: 453.2175.

B. Synthesis of 2-(6-(indolin-1-yl)-6-oxohexyl) phthalimide. (Route B)

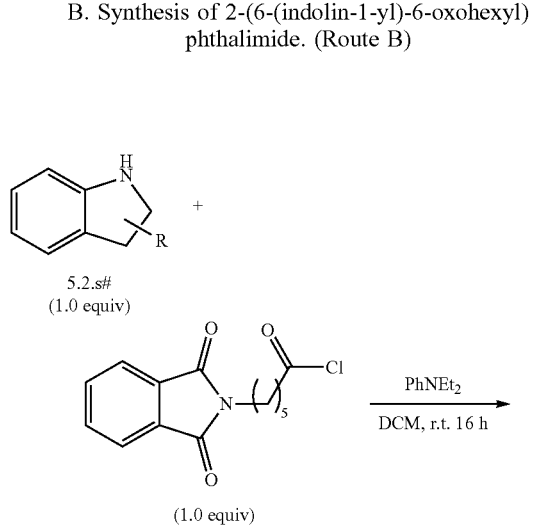

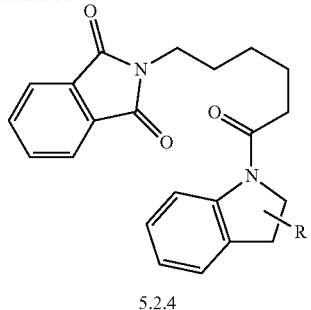

5.2.4

The synthesis of 2-(6-(indolin-1-yl)-6-oxohexyl)phthalimide 5.2.4 was performed following the report of Krasnov and co-workers (see Krasnov et al., Mendeleev Commun. 25:412 (2015)): To a stirred solution of aniline (1.0 equiv) and N,N-diethylaniline (1.0 equiv) in 0.2 M dry CH$_2$Cl$_2$ was added a 0.2 M solution of acid chloride (1.0 equiv) in dry CH$_2$Cl$_2$ dropwise over 10 min. After stirring at room temperature for 16 h, a 1.0 N aq soln of HCl was added to the reaction mixture. After 30 min, the reactives were diluted with 20 mL of EtOAc and washed with 2×20 mL of water and 20 mL of a 5% aq soln of NaHCO$_3$. The resulting organic phase was dried over Na$_2$SO$_4$, filtered and the filtrate was concentrated in vacuo. The resulting residue was purified by MPLC to afford the product.

Characterization Data of 2-(6-(indolin-1-yl)-6-oxohexyl)phthalimides 5.2.4

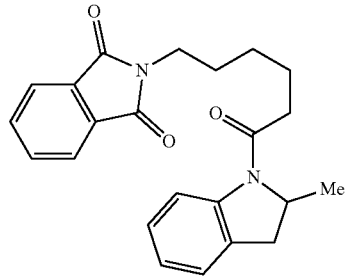

5.2.4a 2-(6-(Indolin-1-yl)-6-oxohexyl)phthalimide 5.2.4a. The general procedure was followed using 133.2 mg of 2-methylindoline (1.0 mmol), 149.2 mg of N,N-diethylaniline (1.0 mmol) and 279.7 mg of acid chloride (1.0 mmol) in a total 4 mL of CH$_2$Cl$_2$. Purification by MPLC chromatography (5:1-2:1 hexanes:EtOAc) afforded 5.2.4a as a yellow oil (320 mg, 85% yield): $^1$H NMR (500 MHz, CDCl$_3$) δ 8.10 (d, J=8.0 Hz, 1H), 7.76-7.74 (m, 2H), 7.64-7.62 (m, 2H), 7.11 (t, J=7.0 Hz, 2H), 6.94 (t, J=7.5 Hz, 1H), 4.44 (s, 1H), 3.64 (t, J=7.5 Hz, 2H), 3.36-3.31 (m, 1H), 2.60-2.35 (m, 3H), 1.77 (q, J=8.0 Hz, 2H), 1.69 (quin, J=7.5 Hz, 2H), 1.41 (quin, J=8.0 Hz, 2H), 1.22-1.17 (m, 3H); $^{13}$C NMR (125 MHz, CDCl$_3$) δ 170.6 (C), 168.3 (C), 141.7 (C), 133.9 (CH), 132.1 (C), 130.2 (C), 127.4 (CH), 124.9 (CH), 123.7 (CH), 123.1 (CH), 117.9 (CH), 55.4 (CH), 37.8 (CH$_2$), 36.4 (CH$_2$), 34.7 (CH$_2$), 28.5 (CH$_2$), 26.7 (CH$_2$), 24.7 (CH$_2$), 21.9 (CH$_3$). ATR-FTIR (thin film): 3317, 2972, 2928, 2879, 1774, 1717, 1636, 1482, 1378, 1087, 1046, 880, 721 cm$^{-1}$. HRMS (ESI) m/z calculated for C$_{23}$H$_{25}$N$_2$O$_3$ [M+H]$^+$: 377.1865, found: 377.1863.

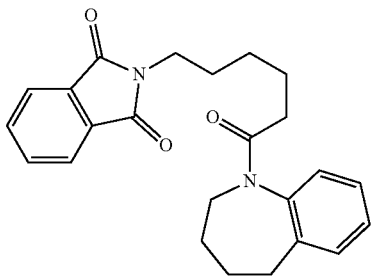

5.2.4b 2-(6-(Indolin-1-yl)-6-oxohexyl)phthalimide 5.2.4b. The general procedure was followed using 147.2 mg of 2,3,4,5-tetrahydro-1H-benzo[b]azepine (1.0 mmol), 149.2 mg of N,N-diethylaniline (1.0 mmol) and 279.7 mg of acid chloride (1.0 mmol) in a total 4 mL of $CH_2Cl_2$. Purification by MPLC chromatography (5:1-2:1 hexanes:EtOAc) afforded 5.2.4b as a yellow oil (218 mg, 56% yield): $^1$H NMR (500 MHz, $CDCl_3$) δ 7.75-7.73 (m, 2H), 7.64-7.62 (m, 2H), 7.16-7.13 (m, 3H), 7.03 (q, J=4.5 Hz, 1H), 4.63 (td, J=7.0 Hz, 3.5 Hz, 1H), 3.55 (t, J=7.5 Hz, 2H), 2.69-2.59 (m, 2H), 2.53-2.47 (m, 1H), 2.12 (quin, J=7.5 Hz, 1H), 1.92-1.79 (m, 3H), 1.70-1.67 (m, 1H), 1.54 (sextet, J=7.5 Hz, 4H), 1.34-1.25 (m, 1H), 1.22-1.15 (m, 2H); $^{13}$C NMR (125 MHz, $CDCl_3$) δ 171.6 (C), 168.3 (C), 143.2 (C), 140.6 (C), 133.8 (CH), 132.1 (C), 130.1 (CH), 127.8 (CH), 127.6 (CH), 127.2 (CH), 123.1 (CH), 47.0 ($CH_2$), 37.8 ($CH_2$), 34.5 ($CH_2$), 33.9 ($CH_2$), 29.1 ($CH_2$), 28.4 ($CH_2$), 26.6 ($CH_2$), 26.5 ($CH_2$), 24.9 ($CH_2$). ATR-FTIR (thin film): 3054, 2936, 2854, 1772, 1707, 1645, 1492, 1394, 1265, 768, 718 cm$^{-1}$. HRMS (ESI) m/z calculated for $C_{24}H_{27}N_2O_3$ [M+H]$^+$: 391.2022, found: 391.2016.

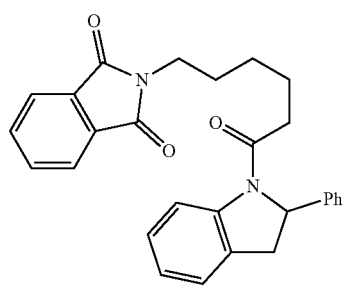

5.2.4c 2-(6-(Indolin-1-yl)-6-oxohexyl)phthalimide 5.2.4c. The general procedure was followed using 195.2 mg of 2-phenylindoline (1.0 mmol), 149.2 mg of N,N-diethylaniline (1.0 mmol) and 279.7 mg of acid chloride (1.0 mmol) in a total 4 mL of $CH_2Cl_2$. Purification by MPLC chromatography (5:1-2:1 hexanes:EtOAc) afforded 5.2.4b as a yellow oil (200 mg, 46% yield): $^1$H NMR (500 MHz, $CDCl_3$) δ 8.32 (d, J=8.0 Hz, 1H), 7.83-7.81 (m, 2H), 7.71-7.69 (m, 2H), 7.28-7.19 (m, 4H), 7.15-7.11 (m, 3H), 7.03 (t, J=7.0 Hz, 1H), 5.41 (d, J=10.0 Hz, 1H), 3.81-3.75 (m, 1H), 3.61 (t, J=7.0 Hz, 2H), 2.96 (d, J=16.0 Hz, 1H), 2.40-2.35 (m, 1H), 2.10-2.04 (m, 1H), 1.71-1.55 (m, 4H), 1.27-1.23 (m, 2H); $^{13}$C NMR (125 MHz, $CDCl_3$) δ 171.9 (C), 168.4 (C), 143.5 (C), 143.3 (C), 133.9 (CH), 132.2 (C), 129.1 (CH), 127.7 (CH), 125.0 (CH), 124.8 (CH), 124.0 (CH), 123.1 (CH), 117.0 (CH), 62.7 (CH), 38.9 ($CH_2$), 37.8 ($CH_2$), 35.3 ($CH_2$), 28.3 ($CH_2$), 26.4 ($CH_2$), 24.3 ($CH_2$); only visible signals. ATR-FTIR (thin film): 3030, 2944, 2862, 1771, 1705, 1656, 1393, 1267, 1046, 734 cm$^{-1}$. HRMS (ESI) m/z calculated for $C_{28}H_{27}N_2O_3$[M+H]$^+$:439.2022, found: 439.2011.

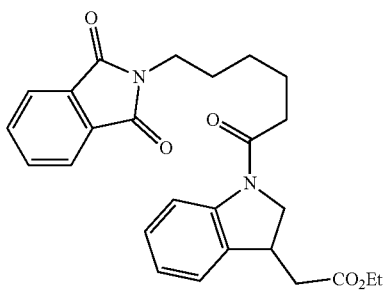

5.2.4f 2-(6-(Indolin-1-yl)-6-oxohexyl)phthalimide 5.2.4f. The general procedure was followed using 492 mg of indoline 5.2.s3 (2.40 mmol), 559 mg of acid chloride (2.40 mmol), 358 mg of $Et_2NPh$ (2.00 mmol) in a total 20 mL of DCM. Purification by MPLC chromatography (1:5 EtOAc: hexanes) afforded 5.2.4f as a yellow gel (660 mg, 76% yield): $^1$H NMR (500 MHz, $CDCl_3$) δ 8.12-8.09 (m, 1H), 7.73-7.72 (m, 2H), 7.62-7.60 (m, 2H), 7.11 (t, J=7.5 Hz, 1H), 7.06 (d, J=7.5 Hz, 1H), 6.92 (t, J=7.5 Hz, 1H), 4.20 (t, J=10.0 Hz, 1H), 4.10 (q, J=7.5 Hz, 2H), 3.73-3.57 (m, 4H), 2.76-2.62 (m, 1H), 2.47 (dd, J=16.5, 10.0 Hz, 1H), 2.35-2.24 (m, 2H), 1.72-1.59 (m, 4H), 1.40-1.32 (m, 2H), 1.19 (t, J=7.5 Hz, 3H); $^{13}$C NMR (125 MHz, $CDCl_3$) δ 171.7 (C), 171.0 (C), 168.3 (C), 142.7 (C), 133.8 (CH), 133.1 (C), 132.1 (C), 128.2 (CH), 123.6 (CH), 123.5 (CH), 123.1 (CH), 117.0 (CH), 60.8 ($CH_2$), 54.2 ($CH_2$), 39.8 ($CH_2$), 37.8 ($CH_2$), 36.5 ($CH_3$), 35.6 ($CH_2$), 28.4 ($CH_2$), 26.5 ($CH_2$), 24.0 ($CH_2$), 14.2 ($CH_3$). IR (thin film): 2939, 1771, 1706, 1661, 1481, 1396, 1372, 1267, 1177, 1047, 1026, 757, 720 cm$^{-1}$; HRMS (ESI) m/z calculated for $C_{26}H_{29}N_2O_5$ (M+H)$^+$: 449.2076, found: 449.2081.

C. Synthesis of N-(6-indolehexyl)-amine and 6-amino-1-(indolin-1-yl)hexan-1-one

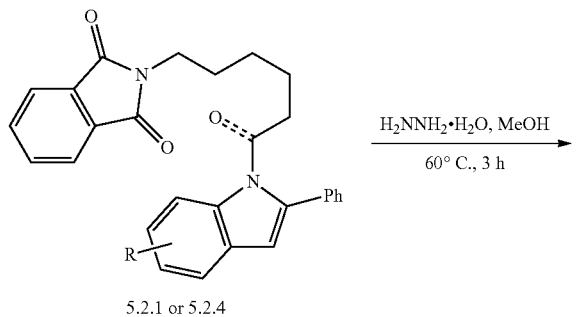

(s4)

5.2.1 or 5.2.4

-continued

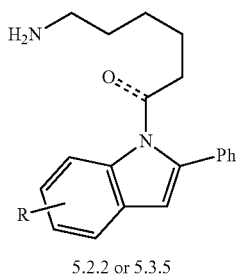

5.2.2 or 5.3.5

To a solution of N-(6-indolehexyl)-phthalimide 5.2.1 (1.0 equiv) or 2-(6-(indolin-1-yl)-6-oxohexyl)phthalimide 5.2.4 (1.0 equiv) in 0.1 M MeOH was added a solution of hydrazine hydrate (N₂H₄.H₂O, 5.0 equiv). The resulting reaction mixture was heated to reflux at 60° C. for 4 h with monitoring the reaction progress by thin layer chromatography (TLC).

After complete consumption of the starting materials, the reaction was cooled to room temperature and 20 mL of a 1 N aq soln of NaOH was added. The resulting mixture was then diluted and extracted by 3×20 mL of DCM. After additional washes with 2×20 mL of a 1 N aq soln of NaOH and 2×20 mL of water, the organic phase was dried over Na₂SO₄, filtered and the filtrate was concentrated in vacuo. The amine product was used in the subsequent coupling reaction without additional characterization or purification.

Characterization Data of
2-(6-(indolin-1-yl)-6-oxohexyl)phthalimides 5.2.2 or 5.3.5

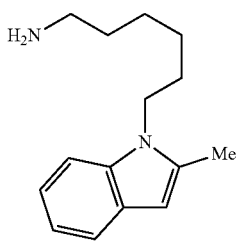

5.2.2a

N-(6-Indolehexyl)-amine 5.2.2a. The general procedure was followed using 36.0 mg of 5.2.1a (0.10 mmol), 25.0 mg of hydrazine hydrate (0.5 mmol) in 1.0 mL of MeOH. The crude product 5.2.2a was afforded as a yellow gel (23 mg, quant. yield): $^1$H NMR (500 MHz, CDCl$_3$) δ 7.51 (d, J=8.0 Hz, 1H), 7.27-7.25 (m, 1H), 7.15-7.11 (m, 1H), 7.05 (t, J=7.5 Hz, 1H), 6.23 (s, 1H), 4.05 (t, J=7.5 Hz, 2H), 2.88 (s, 2H), 2.70 (t, J=7.5 Hz, 2H), 2.42 (s, 3H), 1.75 (quin, J=7.0 Hz, 2H), 1.48 (quin, J=7.0 Hz, 2H), 1.39-1.35 (m, 4H). The amine product was used in the subsequent coupling reaction without additional purification or characterization.

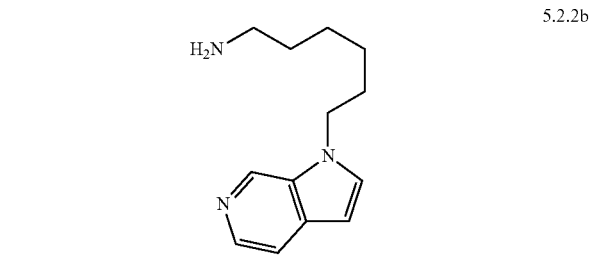 [SMILES: NCCCCCCn1ccc2ccncc21]

5.2.2b

N-(6-Indolehexyl)-amine 5.2.2b. The general procedure was followed using 34.7 mg of 5.2.1b (0.10 mmol), 25.0 mg of hydrazine hydrate (0.5 mmol) in 1.0 mL of MeOH. The crude product 5.2.2a was afforded as a yellow gel (21 mg, quant. yield): $^1$H NMR (500 MHz, CDCl$_3$) δ 8.74 (s, 1H), 8.19 (d, J=5.5 Hz, 1H), 7.47 (dd, J=5.5 Hz, 1.0 Hz, 1H), 7.18 (d, J=3.0 Hz, 1H), 6.44 (d, J=3.0 Hz, 1H), 4.16 (t, J=7.0 Hz, 2H), 2.61 (t, J=7.0 Hz, 2H), 1.84 (quin, J=7.0 Hz, 2H), 1.45-1.23 (m, 8H). The amine product was used in the subsequent coupling reaction without additional purification or characterization.

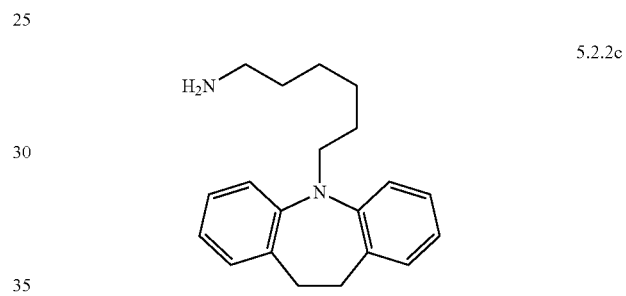

5.2.2c

N-(6-Indolehexyl)-amine 5.2.2c. The general procedure was followed using 42.5 mg of 5.2.1c (0.10 mmol), 25.0 mg of hydrazine hydrate (0.5 mmol) in 1.0 mL of MeOH. The crude product 5.2.2c was afforded as a yellow gel (29 mg, quant. yield). $^1$H NMR (500 MHz, CDCl$_3$) δ 7.16-7.07 (m, 6H), 6.92 (dt, J=7.0 Hz, 1.5 Hz, 2H), 3.73 (t, J=7.0 Hz, 2H), 3.18 (s, 4H), 2.65 (t, J=7.5 Hz, 2H), 2.34 (s, 2H), 1.58 (quin, J=7.5 Hz, 2H), 1.42 (quin, J=7.5 Hz, 2H), 1.38-1.24 (m, 4H). The amine product was used in the subsequent coupling reaction without additional purification or characterization.

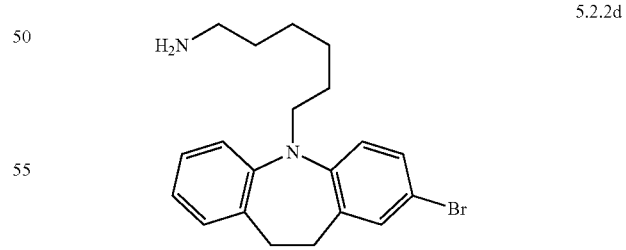

5.2.2d

N-(6-Indolehexyl)-amine 5.2.2d. The general procedure was followed using 50.0 mg of 5.2.1d (0.10 mmol), 25.0 mg of hydrazine hydrate (0.5 mmol) in 1.0 mL of MeOH. The crude product 5.2.2d was afforded as a yellow gel (37 mg, quant. yield) as a mixture of rotamers: $^1$H NMR (500 MHz, CDCl$_3$) δ 7.22-7.20 (m, 1.83H), 7.15-7.05 (m, 3.22H), 6.95-6.90 (m, 2H), 3.73 (t, J=7.0 Hz, 0.25H), 3.68 (t, J=7.0 Hz, 1.59H), 3.63 (t, J=7.0 Hz, 0.17H), 3.17-3.09 (m, 3.92H), 2.63 (t, J=7.0 Hz, 1.95H), 1.59-1.51 (m, 2H), 1.41-1.23 (m, 6.22H), 1.12 (s, 1.95H). The amine product was used in the subsequent coupling reaction without additional purification or characterization.

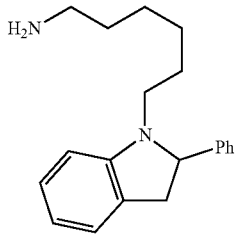

N-(6-Indolehexyl)-amine 5.2.2e. The general procedure was followed using 42.4 mg of 5.2.1e (0.10 mmol), 25.0 mg of hydrazine hydrate (0.5 mmol) in 1.0 mL of MeOH. The crude product 5.2.2e was afforded as a yellow gel (29 mg, quant. yield): $^1$H NMR (500 MHz, CDCl$_3$) δ 7.43-7.41 (m, 2H), 7.37-7.34 (m, 2H), 7.32-7.29 (m, 1H), 7.11 (t, J=7.5 Hz, 1H), 7.04 (d, J=7.0 Hz, 1H), 6.66 (t, J=7.5 Hz, 1H), 6.47 (d, J=7.5 Hz, 1H), 4.64 (t, J=10.0 Hz, 1H), 3.37 (dd, J=16.0 Hz, 9.5 Hz, 1H), 3.11-3.05 (m, 1H), 2.96-2.87 (m, 2H), 2.63 (t, J=7.0 Hz, 2H), 1.47 (quin, J=7.0 Hz, 2H), 1.39-1.34 (m, 2H), 1.27-1.20 (m, 4H), 1.13 (s, 2H). The amine product was used in the subsequent coupling reaction without additional purification or characterization.

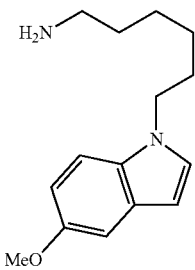

N-(6-Indolehexyl)-amine 5.2.2f. The general procedure was followed using 188 mg of 5.2.1f (0.50 mmol), 125 mg of hydrazine hydrate (2.50 mmol) in 5 mL of MeOH. Purification by MPLC chromatography (1:5 Et$_3$N:DCM) afforded 5.2.2f as a yellow gel (100 mg, 81% yield): $^1$H NMR (500 MHz, CDCl$_3$) δ 7.21 (d, J=9.0 Hz, 1H), 7.07 (dd, J=17.0, 2.0 Hz, 2H), 6.86 (dd, J=9.0, 2.0 Hz, 1H), 6.39 (d, J=2.5 Hz, 1H), 4.06 (t, J=7.0 Hz, 2H), 3.84 (s, 3H), 1.84-1.79 (m, 2H), 1.43-1.39 (m, 4H), 1.32-1.26 (m, 4H). IR (thin film): 3367, 2932, 2857, 1668, 1621, 1488, 1450, 1237, 1150, 1031, 801, 720 cm$^{-1}$; HRMS (ESI) m/z calculated for C$_{15}$H$_{23}$N$_2$O (M+H)$^+$: 247.1810, found: 247.1801. The amine product was used in the subsequent coupling reaction without additional purification or characterization.

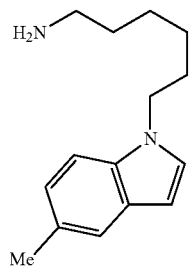

N-(6-Indolehexyl)-amine 5.2.2g. The general procedure was followed using 188 mg of 5.2.1g (0.500 mmol), 125 mg of hydrazine hydrate (2.50 mmol) in 5 mL of MeOH. Purification by MPLC chromatography (1:5 Et$_3$N:DCM) afforded 5.2.2g as a yellow gel (110 mg, 96% yield): $^1$H NMR (500 MHz, CDCl$_3$) δ 7.42 (s, 1H), 7.23 (d, J=8.5 Hz, 1H), 7.05-7.02 (m, 2H), 6.39 (d, J=2.5 Hz, 1H), 4.08 (t, J=7.5 Hz, 2H), 2.46 (s, 3H), 1.83 (quintet, J=7.0 Hz, 2H), 1.42-1.32 (m, 8H). IR (thin film): 3236, 2930, 2858, 1668, 1489, 1455, 1396, 1333, 1298, 791, 759, 718 cm$^{-1}$; HRMS (ESI) m/z calculated for C$_{15}$H$_{23}$N$_2$(M+H)$^+$: 231.1861, found: 231.1856. The amine product was used in the subsequent coupling reaction without additional purification or characterization.

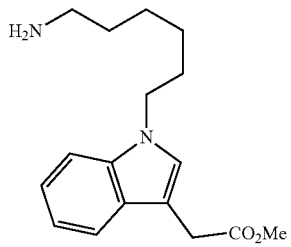

N-(6-Indolehexyl)-amine 5.2.2h. The general procedure was followed using 42.0 mg of 5.2.1h (0.100 mmol), 25.0 mg of hydrazine hydrate (0.500 mmol) in 1.0 mL of MeOH. The crude product 5.2.2h was afforded as a yellow gel (29 mg, 100% yield). $^1$H NMR (500 MHz, CDCl$_3$) δ 7.60 (d, J=8.0 Hz, 1H), 7.30 (d, J=8.5 Hz, 1H), 7.21 (t, J=7.5 Hz, 1H), 7.12 (t, J=7.5 Hz, 1H), 7.08 (s, 1H), 4.06 (t, J=7.0 Hz, 2H), 3.76 (s, 2H), 3.69 (s, 3H), 3.66 (t, J=7.0 Hz, 2H), 1.83-1.81 (m, 2H), 1.40-1.33 (m, 8H). The amine product was used in the subsequent coupling reaction without additional purification or characterization.

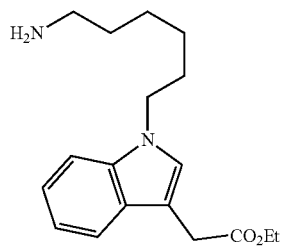

N-(6-Indolehexyl)-amine 5.2.2i. The general procedure was followed using 160 mg of 5.2.1i (0.37 mmol), 93.0 mg of hydrazine hydrate (1.85 mmol) in 4.0 mL of MeOH. Purification by MPLC chromatography (1:5 MeOH:DCM) afforded 5.2.2i as a yellow gel (110 mg, 100% yield): $^1$H NMR (500 MHz, CDCl$_3$) δ 7.61 (d, J=7.5 Hz, 1H), 7.31 (d, J=8.0 Hz, 1H), 7.21 (t, J=7.0 Hz, 1H), 7.13-7.09 (m, 2H), 4.16 (q, J=7.0 Hz, 2H), 4.07 (t, J=7.0 Hz, 2H), 3.76 (s, 2H), 2.66-2.64 (m, 2H), 1.84-1.82 (m, 2H), 1.41-1.25 (m, 11H). IR (thin film): 3295, 2929, 2856, 1732, 1652, 1552, 1468, 1368, 1261, 1152, 1033, 1014, 740 cm$^{-1}$; HRMS (ESI) m/z calculated for $C_{18}H_{27}N_2O_2$ (M+H)$^+$: 303.2073, found: 303.2071. The amine product was used in the subsequent coupling reaction without additional purification or characterization.

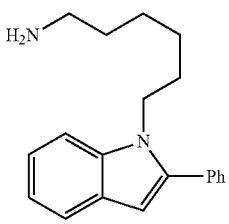

5.2.2j

N-(6-Indolehexyl)-amine 5.2.2j. The general procedure was followed using 156 mg of 5.2.1j (0.37 mmol), 93.0 mg of hydrazine hydrate (1.85 mmol) in 4.0 mL of MeOH. Purification by MPLC chromatography (1:5 MeOH:DCM) afforded 5.2.2j as a yellow gel (105 mg, 97% yield): $^1$H NMR (500 MHz, CDCl$_3$) δ 7.63 (t, J=9.1 Hz, 1H), 7.53-7.44 (m, 4H), 7.44-7.33 (m, 2H), 7.30-7.18 (m, 1H), 7.14 (dd, J=9.5, 5.3 Hz, 1H), 6.53 (d, J=2.9 Hz, 1H), 4.14 (dd, J=13.7, 6.2 Hz, 2H), 2.62 (t, J=7.0 Hz, 2H), 1.73-1.62 (m, 2H), 1.44-1.27 (m, 2H), 1.22-1.07 (m, 4H). The amine product was used in the subsequent coupling reaction without additional purification or characterization.

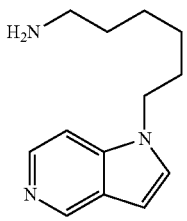

5.2.2k

N-(6-indolehexyl)-amine 5.2.2k. The general procedure was followed using 102 mg of 5.2.1k (0.370 mmol), 93.0 mg of hydrazine hydrate (1.85 mmol) in 4.0 mL of MeOH. Purification by MPLC chromatography (1:5 MeOH:DCM) afforded 5.2.2k as a yellow gel (15.3 mg, 19% yield): $^1$H NMR (500 MHz, CDCl$_3$) δ 8.28 (d, J=3.8 Hz, 1H), 7.85 (d, J=7.7 Hz, 1H), 7.17 (d, J=2.5 Hz, 1H), 7.00 (dd, J=7.2, 4.8 Hz, 1H), 6.40 (d, J=2.7 Hz, 1H), 4.24 (t, J=6.9 Hz, 2H), 3.55 (br s, 2H), 2.66 (t, J=6.4 Hz, 2H), 1.85-1.81 (m, 2H), 1.43 (d, J=6.5 Hz, 2H), 1.31 (s, 4H). $^{13}$C NMR (125 MHz, CDCl$_3$) δ 147.4 (C), 142.6 (CH), 128.7 (CH), 127.9 (CH), 120.6 (C), 115.5 (CH), 99.3 (CH), 44.4 (CH$_2$), 41.4 (CH$_2$), 32.1 (CH$_2$), 30.3 (CH$_2$), 26.6 (CH$_2$), 26.4 (CH$_2$). The amine product was used in the subsequent coupling reaction without additional purification or characterization.

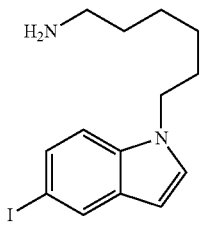

5.2.2l

N-(6-Indolehexyl)-amine 5.2.2l. The general procedure was followed using 127 mg of 5.2.1l (0.370 mmol), 93.0 mg of hydrazine hydrate (1.85 mmol) in 4.0 mL of MeOH. Purification by MPLC chromatography (1:5 MeOH:DCM) afforded 5.2.2l as a yellow gel (97 mg, 77% yield): $^1$H NMR (500 MHz, CDCl$_3$) δ 7.93 (s, 1H), 7.40 (d, J=8.6 Hz, 1H), 7.06 (d, J=8.6 Hz, 1H), 6.99 (d, J=2.6 Hz, 1H), 6.37 (d, J=2.5 Hz, 1H), 4.00 (t, J=7.0 Hz, 2H), 2.62 (s, 2H), 1.75 (dt, J=13.6, 6.9 Hz, 4H), 1.36 (d, J=6.5 Hz, 2H), 1.25 (d, J=10.0 Hz, 4H). $^{13}$C NMR (125 MHz, CDCl$_3$) δ 135.1 (C), 131.2 (C), 129.7 (CH), 129.6 (CH), 128.7 (C), 111.5 (CH), 100.3 (CH), 82.7 (C), 46.4 (CH$_2$), 41.9 (CH$_2$), 33.4 (CH$_2$), 30.2 (CH$_2$), 26.8 (CH$_2$), 26.5 (CH$_2$). The amine product was used in the subsequent coupling reaction without additional purification or characterization.

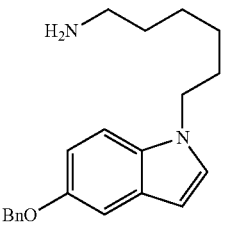

5.2.2m

N-(6-Indolehexyl)-amine 5.2.2m. The general procedure was followed using 167 mg of 5.2.1m (0.37 mmol), 93.0 mg of hydrazine hydrate (1.85 mmol) in 4.0 mL of MeOH. Purification by MPLC chromatography (1:5 MeOH:DCM) afforded 5.2.2m as a yellow gel (78 mg, 65% yield): $^1$H NMR (500 MHz, CDCl$_3$) δ 7.53 (d, J=7.4 Hz, 2H), 7.43 (t, J=7.4 Hz, 2H), 7.37 (d, J=7.2 Hz, 1H), 7.27 (d, J=11.0 Hz, 2H), 7.08 (d, J=2.3 Hz, 1H), 7.04 (d, J=8.7 Hz, 1H), 6.47 (d, J=1.9 Hz, 1H), 5.13 (s, 2H), 4.03 (t, J=6.9 Hz, 2H), 2.65 (t, J=6.5 Hz, 2H), 1.91-1.72 (m, 2H), 1.40 (d, J=6.3 Hz, 2H), 1.37-1.25 (m, 4H). $^{13}$C NMR (125 MHz, CDCl$_3$) δ 153.2 (C), 138.0 (C), 131.6 (C), 129.0 (C), 128.6 (C), 128.5 (CH), 127.8 (CH), 127.6 (CH), 112.5 (CH), 110.2 (CH), 104.2 (CH), 100.6 (CH), 70.89 (CH$_2$), 46.5 (CH$_2$), 42.2 (CH$_2$), 33.7 (CH$_2$), 30.4 (CH$_2$), 26.9 (CH$_2$), 26.6 (CH$_2$). The amine product was used in the subsequent coupling reaction without additional purification or characterization.

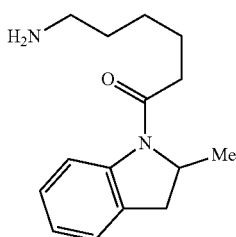

5.3.5a

6-Amino-1-(indolin-1-yl)hexan-1-one 5.3.5a. The general procedure was followed using 42.0 mg of 5.2.4a (0.10 mmol), 25.0 mg of hydrazine hydrate (0.5 mmol) in 1.0 mL of MeOH. The crude product 5.3.5a was afforded as a yellow gel (29 mg, quant. yield). $^1$H NMR (500 MHz, CDCl$_3$) δ 8.15 (d, J=8.5 Hz, 1H), 7.17 (t, J=7.5 Hz, 2H), 6.99 (t, J=7.5 Hz, 1H), 4.47 (t, J=7.0 Hz, 1H), 3.99-3.24 (m, 1H), 2.70 (t, J=7.0 Hz, 2H), 2.65-2.58 (m, 1H), 2.54-2.39 (m, 2H), 1.76 (quin, J=7.5 Hz, 2H), 1.60-1.38 (m, 6H), 1.27-1.19 (m, 3H). The amine product was used in the subsequent coupling reaction without additional purification or characterization.

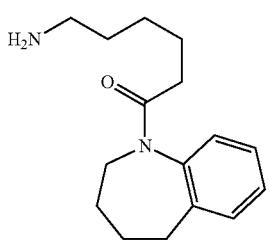

5.3.5b

6-Amino-1-(indolin-1-yl)hexan-1-one 5.3.5b. The general procedure was followed using 39.0 mg of 5.2.4b (0.10 mmol), 25.0 mg of hydrazine hydrate (0.5 mmol) in 1.0 mL of MeOH. The crude product 5.3.5b was afforded as a yellow gel (26 mg, quant. yield): $^1$H NMR (500 MHz, CDCl$_3$) δ 7.18-7.13 (m, 3H), 7.03 (t, J=4.5 Hz, 1H), 4.65-4.61 (m, 1H), 2.64 (quin, J=8.0 Hz, 2H), 2.55 (t, J=8.0 Hz, 2H), 2.48 (d, J=13.0 Hz, 1H), 2.11 (quin, J=7.5 Hz, 1H), 2.14-1.79 (m, 5H), 1.71-1.67 (m, 1H), 1.52-1.45 (m, 2H), 1.31-1.26 (m, 3H), 1.19-1.12 (m, 2H). The amine product was used in the subsequent coupling reaction without additional purification or characterization.

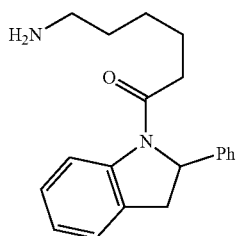

5.3.5c

6-Amino-1-(indolin-1-yl)hexan-1-one 5.3.5c. The general procedure was followed using 43.8 mg of 5.2.4c (0.10 mmol), 25.0 mg of hydrazine hydrate (0.5 mmol) in 1.0 mL of MeOH. The crude product 5.3.5c was afforded as a yellow gel (30 mg, quant. yield): $^1$H NMR (500 MHz, CDCl$_3$) δ 8.34 (d, J=8.0 Hz, 1H), 7.28-7.23 (m, 4H), 7.15-7.10 (m, 3H), 7.04-7.01 (m, 1H), 5.40 (d, J=10.0 Hz, 1H), 3.78-3.73 (m, 1H), 2.95 (d, J=16.0 Hz, 1H), 2.60 (s, 2H), 2.41-2.35 (m, 1H), 2.11-2.04 (m, 1H), 1.65-1.50 (m, 2H), 1.32-1.20 (m, 6H). The amine product was used in the subsequent coupling reaction without additional purification or characterization.

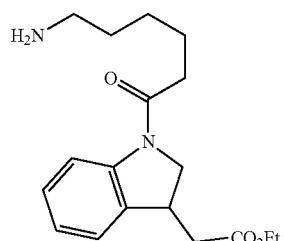

5.2.5f

6-Amino-1-(indolin-1-yl)hexan-1-one 5.3.5f. The general procedure was followed using 434 mg of 5.3.5f (1.00 mmol), 250 mg of hydrazine hydrate (5.00 mmol) in 10 mL of MeOH. The crude product 5.3.5f was afforded as a yellow gel (304 mg, 100% yield): $^1$H NMR (500 MHz, CDCl$_3$) δ 8.19 (d, J=7.5 Hz, 1H), 7.17 (t, J=7.5 Hz, 1H), 7.10 (d, J=7.0 Hz, 1H), 6.97 (t, J=7.0 Hz, 1H), 4.25 (t, J=9.5 Hz, 1H), 4.16-4.11 (m, 2H), 3.77-3.70 (m, 2H), 2.79-2.76 (m, 1H), 2.67 (t, J=6.0 Hz, 2H), 2.50 (dd, J=16.0, 10.0 Hz, 1H), 2.38 (t, J=6.5 Hz, 2H), 1.73-1.67 (m, 2H), 1.47-1.22 (m, 9H); IR (thin film): 3293, 2928, 2858, 1729, 1652, 1596, 1481, 1460, 1407, 1264, 1177, 1024, 755, 732 cm$^{-1}$; HRMS (ESI) m/z calculated for C$_{18}$H$_{27}$N$_2$O$_3$ (M+H)$^+$: 319.2022, found: 319.2026. The amine product was used in the subsequent coupling reaction without additional purification or characterization.

D. Synthesis of Acrylamide Analogues

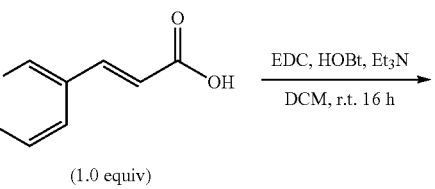

-continued

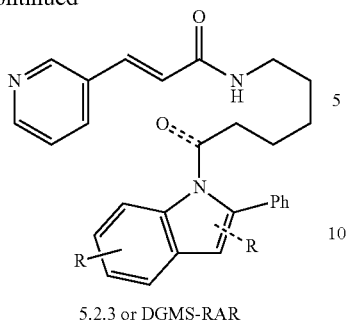

5.2.3 or DGMS-RAR

To a solution of trans-3-(3-pyridyl) acrylic acid (1.0 equiv) in 0.1 M dry CH$_2$Cl$_2$ was added N-(3-dimethylaminopropyl)-N'-ethylcarbodiimide hydrochloride (EDC, 2.0 equiv), 1-hydroxybenzotriazole hydrate (HOBt, 1.5 equiv), and triethylamine (1.5 equiv) sequentially. After stirring at room temperature for 5 min, a solution of amine 5.2.2 (1.2 equiv) or 5.2.5 (1.2 equiv) in DCM was added slowly to the reaction mixture. The reaction was allowed to stir at room temperature for overnight. After complete consumption of the starting materials indicated by thin layer chromatography (TLC), the reactives were quenched by the addition of 10 mL of a saturated NaHCO$_3$ aqueous solution. The reaction mixture was then washed with 2×20 mL water and extracted with 2×20 mL of CH$_2$Cl$_2$. The combined organic phases were dried over Na$_2$SO$_4$, filtered and the filtrate was concentrated in vacuo. The crude product was purified by MPLC.

Characterization Data.

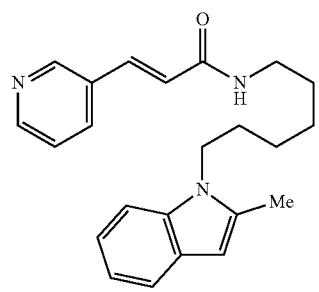

5.2.3a (E)-N-(6-(1H-Indol-1-yl)hexyl)-3-(pyridin-3-yl)acrylamide 5.2.3a. The general procedure was followed using 46.1 mg of 5.2.2a (0.20 mmol), 25.0 mg of trans-3-(3-pyridyl) acrylic acid (0.170 mmol), 65.1 mg of EDC.HCl (0.34 mmol), 35.1 mg of HOBt (0.26 mmol), and 26.3 mg of Et$_3$N (0.26 mmol) in 4 mL of CH$_2$Cl$_2$. Purification by MPLC chromatography (2:98 MeOH:CH$_2$Cl$_2$) afforded 5.2.3a as a yellow gel (40 mg, 65%): $^1$H NMR (500 MHz, CDCl$_3$) δ 8.72 (d, J=2.0 Hz, 1H), 8.55 (d, J=5.0 Hz, 1H), 7.75 (td, J=4.0 Hz, 2.0 Hz, 1H), 7.58 (d, J=15.5 Hz, 1H), 7.52 (d, J=7.5 Hz, 1H), 7.29-7.24 (m, 2H), 7.12 (t, J=7.5 Hz, 1H), 7.05 (t, J=7.5 Hz, 1H), 6.41 (d, J=15.5 Hz, 1H), 6.23 (s, 1H), 5.84 (t, J=6.0 Hz, 1H), 4.04 (t, J=7.5 Hz, 2H), 3.33 (quin, J=7.0 Hz, 2H), 2.41 (s, 3H), 1.74 (quin, J=7.5 Hz, 2H), 1.52 (quin, J=7.0 Hz, 2H), 1.40-1.30 (m, 4H); $^{13}$C NMR (125 MHz, ODCl$_3$) δ 165.1 (C), 150.3 (CH), 149.1 (CH), 137.2 (CH), 136.6 (C), 136.4 (C), 134.4 (CH), 130.7 (C), 128.1 (C), 123.7 (CH), 122.9 (CH), 120.3 (CH), 119.7 (CH), 119.2 (CH), 109.0 (CH), 99.9 (CH), 43.1 (CH$_2$), 39.7 (CH$_2$), 30.1 (CH$_2$), 29.5 (CH$_2$), 26.8 (CH$_2$), 26.7 (CH$_2$), 12.9 (CH$_3$). ATR-FTIR (thin film): 3417, 3000, 2915, 1660, 1436, 1385, 1016, 952 701 cm$^{-1}$. HRMS (ESI) m/z calculated for C$_{23}$H$_{28}$N$_3$O [M+H]$^+$: 362.2232, found: 362.2231.

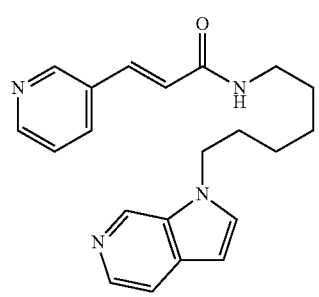

5.2.3b (E)-N-(6-(1H-indol-1-yl)hexyl)-3-(pyridin-3-yl)acrylamide 5.2.3b. The general procedure was followed using 43.5 mg of 5.2.2b (0.2 mmol), 25.0 mg of trans-3-(3-pyridyl) acrylic acid (0.17 mmol), 65.1 mg of EDC.HCl (0.34 mmol), 35.1 mg of HOBt (0.26 mmol), and 26.3 mg of Et$_3$N (0.26 mmol) in 4 mL of CH$_2$Cl$_2$. Purification by MPLC chromatography (2:98 MeOH:CH$_2$Cl$_2$) afforded 5.2.3b as a yellow gel (44 mg, 74%): $^1$H NMR (500 MHz, CDCl$_3$) δ 8.73 (s, 1H), 8.67 (s, 1H), 8.50 (d, J=5.0 Hz, 1H), 8.20 (d, J=5.5 Hz, 1H), 7.70 (d, J=8.0 Hz, 1H), 7.57 (d, J=15.5 Hz, 1H), 7.49 (d, J=5.5 Hz, 1H), 7.25-7.22 (m, 1H), 7.19 (d, J=2.5 Hz, 1H), 6.64 (t, J=5.5 Hz, 1H), 6.49 (d, J=15.5 Hz, 1H), 6.46 (d, J=2.5 Hz, 1H), 4.16 (t, J=7.0 Hz, 2H), 3.33 (q, J=7.0 Hz, 2H), 1.82 (quin, J=7.5 Hz, 2H), 1.51 (quin, J=7.0 Hz, 2H), 1.37-1.25 (m, 4H); $^{13}$C NMR (125 MHz, CDCl$_3$) δ 165.3 (C), 150.2 (CH), 149.1 (CH), 138.2 (CH), 136.9 (CH), 134.3 (CH), 133.3 (C), 133.1 (C), 132.6 (CH), 131.6 (CH), 130.8 (C), 123.7 (CH), 123.1 (CH), 115.5 (CH), 100.6 (CH), 46.7 (CH$_2$), 39.6 (CH$_2$), 30.3 (CH$_2$), 29.5 (CH$_2$), 26.5 (CH$_2$), 26.5 (CH$_2$); ATR-FTIR (thin film): 3418, 3000, 2914, 1651, 1436, 1407, 1313, 1017, 952, 701 cm$^{-1}$. HRMS (ESI) m/z calculated for C$_{21}$H$_{25}$N$_4$O [M+H]$^+$: 349.2028, found: 349.2020.

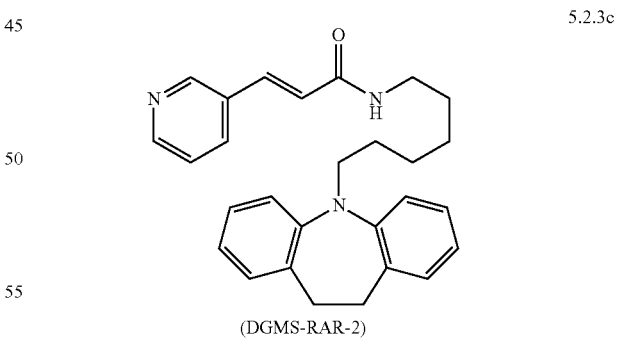

(DGMS-RAR-2)

(E)-N-(6-(1H-Indol-1-yl)hexyl)-3-(pyridin-3-yl)acrylamide 5.2.3c (DGMS-RAR-2). The general procedure was followed using 58.9 mg of 5.2.2c (0.2 mmol), 25.0 mg of trans-3-(3-pyridyl) acrylic acid (0.17 mmol), 65.1 mg of EDC.HCl (0.34 mmol), 35.1 mg of HOBt (0.26 mmol), and 26.3 mg of Et$_3$N (0.26 mmol) in 4 mL of CH$_2$Cl$_2$. Purification by MPLC chromatography (2:98 MeOH:CH$_2$Cl$_2$) afforded DGMS-RAR-2 as a yellow gel (46 mg, 63%): $^1$H NMR (500 MHz, CDCl$_3$) δ 8.70 (d, J=2.0 Hz, 1H), 8.51 (dd, J=5.0 Hz, 1.5 Hz, 1H), 7.71 (td, J=4.0 Hz, 2.0 Hz, 1H), 7.57 (d, J=16.0 Hz, 1H), 7.23 (dd, J=8.0 Hz, 5.0 Hz, 1H), 7.13-7.04 (m, 6H), 6.90 (dt, J=7.0 Hz, 1.0 Hz, 2H), 6.49 (d, J=16.0 Hz, 1H), 6.41 (t, J=6.0 Hz, 1H), 3.69 (t, J=7.0 Hz, 2H), 3.31 (q, J=7.0 Hz, 2H), 3.13 (s, 4H), 1.57-1.47 (m, 4H), 1.36-1.24 (m, 4H); $^{13}$C NMR (125 MHz, CDCl$_3$) δ 165.2 (C), 150.1 (CH), 148.9 (CH), 148.4 (C), 136.9 (CH), 134.5 (CH), 134.2 (C), 130.9 (C), 129.8 (CH), 126.3 (CH), 123.7 (CH), 123.3 (CH), 122.3 (CH), 120.0 (CH), 50.6 (CH$_2$), 39.8 (CH$_2$), 32.3 (CH$_2$), 29.5 (CH$_2$), 27.8 (CH$_2$), 26.8 (CH$_2$), 26.7 (CH$_2$). ATR-FTIR (thin film): 3280, 3060, 2923, 2853, 1659, 1621, 1552, 1486, 1472, 1229, 978, 764, 751, 741 cm$^{-1}$. HRMS (ESI) m/z calculated for C$_{28}$H$_{32}$N$_3$O [M+H]$^+$: 426.2545, found: 426.2546.

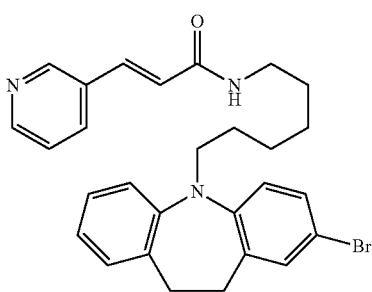

5.2.3d (E)-N-(6-(1H-Indol-1-yl)hexyl)-3-(pyridin-3-yl)acrylamide 5.2.3d. The general procedure was followed using 74.6 mg of 5.2.2d (0.2 mmol), 25.0 mg of trans-3-(3-pyridyl) acrylic acid (0.17 mmol), 65.1 mg of EDC.HCl (0.34 mmol), 35.1 mg of HOBt (0.26 mmol), and 26.3 mg of Et$_3$N (0.26 mmol) in 4 mL of CH$_2$Cl$_2$. Purification by MPLC chromatography (2:98 MeOH:CH$_2$Cl$_2$) afforded 5.2.3d as a yellow gel (50 mg, 58%) as a 3:1 mixture of rotamers. $^1$H NMR (500 MHz, CDCl$_3$ δ 8.72 (s, 0.99H), 8.55 (d, J=5.0 Hz, 0.98H), 7.74 (d, J=8.0 Hz, 1.03H), 7.59 (d, J=15.5 Hz, 1H), 7.29-7.26 (m, 1.23H), 7.22-7.19 (m, 2.21H), 7.14-7.08 (m, 1.84H), 7.03 (d, J=8.0 Hz, 0.82H), 6.94-6.88 (m, 1.97H), 6.44 (d, J=15.5 Hz, 1.01H), 5.89 (s, 0.97H), 3.66 (t, J=7.0 Hz, 1.43H), 3.61 (t, J=7.0 Hz, 0.46H), 3.32 (q, J=7.0 Hz, 2.10H), 3.14-3.07 (m, 3.87H), 1.56-1.47 (m, 4.22H), 1.36-1.25 (m, 4.70H), (only visible signals); $^{13}$C NMR (125 MHz, CDCl$_3$) δ 165.1 (C), 150.3 (C), 149.1 (C), 148.1 (CH), 147.3 (C), 147.0 (C), 137.2 (C), 136.1 (C), 136.1 (C), 134.4 (CH), 134.2 (C), 132.5 (CH), 132.4 (CH), 130.7 (C), 129.7 (CH), 129.3 (CH), 129.1 (CH), 126.5 (CH), 123.7 (CH), 122.9 (CH), 122.8 (CH), 121.8 (CH), 121.7 (CH), 120.2 (CH), 115.3 (C), 114.7 (C), 50.8 (CH$_2$), 50.6 (CH$_2$), 39.7 (CH$_2$), 32.2 (CH$_2$), 31.7 (CH$_2$), 29.5 (CH$_2$), 27.7 (CH$_2$), 27.6 (CH$_2$), 26.7 (CH$_2$), 26.7 (CH$_2$), 26.6 (CH$_2$) (only visible signals). ATR-FTIR (thin film): 3425, 2997, 2914, 1651, 1482, 1436, 1407, 1312, 1013, 951, 735 cm$^{-1}$. HRMS (ESI) m/z calculated for C$_{28}$H$_{31}$N$_3$OBr [M+H]$^+$: 504.1651, found: 504.1652.

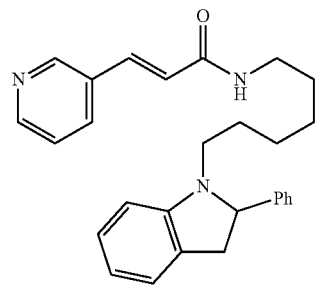

5.2.3e (E)-N-(6-(1H-Indol-1-yl)hexyl)-3-(pyridin-3-yl)acrylamide 5.2.3e (DGMS-RAR-7). The general procedure was followed using 58.9 mg of 5.2.2e (0.2 mmol), 25.0 mg of trans-3-(3-pyridyl) acrylic acid (0.17 mmol), 65.1 mg of EDC.HCl (0.34 mmol), 35.1 mg of HOBt (0.26 mmol), and 26.3 mg of Et$_3$N (0.26 mmol) in 4 mL of DCM. Purification by MPLC chromatography (2% MeOH in DCM) afforded a yellow gel (38 mg, 52% yield). $^1$H NMR (500 MHz, CDCl$_3$) δ 8.73 (d, J=2.5 Hz, 1H), 8.56 (dd, J=4.5 Hz, 1.5 Hz, 1H), 7.76 (td, J=4.0 Hz, 2.0 Hz, 1H), 7.60 (d, J=16.0 Hz, 1H), 7.41-7.39 (m, 2H), 7.34 (t, J=7.5 Hz, 2H), 7.30-7.28 (m, 2H), 7.10 (t, J=8.0 Hz, 1H), 7.03 (d, J=7.0 Hz, 1H), 6.66 (t, J=7.5 Hz, 1H), 6.46 (s, 1H), 6.43 (d, J=7.5 Hz, 1H), 5.82 (t, J=6.0 Hz, 1H), 4.62 (t, J=9.5 Hz, 1H), 3.36-3.31 (m, 3H), 3.07 (quin, J=7.5 Hz, 1H), 2.95-2.86 (m, 2H), 1.52-1.42 (m, 4H), 1.30-1.20 (m, 4H); $^{13}$C NMR (125 MHz, CDCl$_3$) δ 165.1 (C), 152.3 (C), 150.3 (CH), 149.1 (CH), 143.1 (C), 137.3 (CH), 134.4 (CH), 130.7 (C), 128.5 (CH), 128.2 (C), 127.6 (CH), 127.6 (CH), 127.4 (CH), 124.1 (CH), 123.7 (CH), 122.9 (CH), 117.2 (CH), 106.3 (CH), 69.0 (CH), 46.5 (CH$_2$), 39.8 (CH$_2$), 39.6 (CH$_2$), 29.5 (CH$_2$), 26.9 (CH$_2$), 26.7 (CH$_2$), 26.1 (CH$_2$); ATR-FTIR (thin film): 3265, 3054, 2992, 2928, 2856, 1667, 1625, 1548, 1023, 767 cm$^{-1}$. HRMS (ESI) m/z calculated for C$_{28}$H$_{30}$N$_3$O [M+H]$^+$: 424.2389, found: 424.2388.

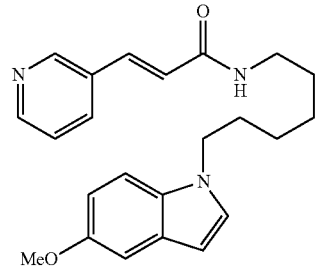

5.2.3f (E)-N-(6-(1H-Indol-1-yl)hexyl)-3-(pyridin-3-yl)acrylamide 5.2.3f. The general procedure was followed using 49.3 mg of 5.2.2f (0.200 mmol), 25.0 mg of trans-3-(3-pyridyl) acrylic acid (0.170 mmol), 76.7 mg of EDC.HCl (0.400 mmol), 40.5 mg of HOBt (0.300 mmol), and 30.4 mg of Et$_3$N (0.300 mmol) 4 mL of DCM. Purification by MPLC chromatography (2% MeOH in DCM) afforded 5.2.3f as a yellow gel (63 mg, 100% yield): $^1$H NMR (500 MHz, CDCl$_3$) δ 8.72 (d, J=1.5 Hz, 1H), 8.55 (dd, J=4.5, 1.0 Hz, 1H), 7.75 (dt, J=7.5, 1.5 Hz, 1H), 7.59 (d, J=16.0 Hz, 1H), 7.28 (dd, J=8.0, 5.0 Hz, 1H), 7.21 (d, J=9.0 Hz, 1H), 7.09 (d, J=2.0 Hz, 1H), 7.05 (d, J=3.0 Hz, 1H), 6.86 (dd, J=9.0, 2.0 Hz, 1H), 6.43-6.39 (m, 2H), 5.79 (t, J=5.5 Hz, 1H), 4.07 (t, J=7.0 Hz, 2H), 3.84 (s, 3H), 3.32 (q, J=7.0 Hz, 2H), 1.81 (quintet, J=7.0 Hz, 2H), 1.51 (quintet, J=7.0 Hz, 2H), 1.37-1.30 (m, 4H); 13C NMR (125 MHz, CDCl$_3$) δ 165.1 (C), 153.9 (C), 150.4 (CH), 149.2 (CH), 137.3 (CH), 134.4 (CH), 131.3 (C), 130.7 (C), 128.9 (C), 128.4 (CH), 123.7 (CH), 122.8 (CH), 111.8 (CH), 110.1 (CH), 102.6 (CH), 100.4 (CH), 55.9 (CH$_3$), 46.5 (CH$_2$), 39.6 (CH$_2$), 30.1 (CH$_2$), 29.5 (CH$_2$), 26.7 (CH$_2$), 26.6 (CH$_2$). IR (thin film): 3444, 2996, 2912, 1662, 1436, 1406, 1310, 1042, 952, 697, 667 cm$^{-1}$; HRMS (ESI) m/z calculated for C$_{23}$H$_{28}$N$_3$O$_2$ (M+H)$^+$: 380.2338, found: 380.2337.

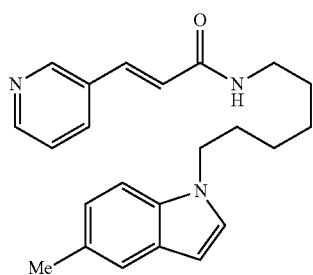

5.2.3g (E)-N-(6-(1H-indol-1-yl)hexyl)-3-(pyridin-3-yl)acrylamide 5.2.3g. The general procedure was followed using 46.1 mg of 5.2.2g (0.200 mmol), 25.0 mg of trans-3-(3-pyridyl) acrylic acid (0.170 mmol), 76.7 mg of EDC.HCl (0.400 mmol), 40.5 mg of HOBt (0.300 mmol), and 30.4 mg of Et$_3$N (0.300 mmol) in 4 mL of DCM. Purification by MPLC chromatography (2% MeOH in DCM) afforded 5.2.3g as a yellow gel (60 mg, 100% yield): $^1$H NMR (500 MHz, CDCl$_3$) δ 8.73 (s, 1H), 8.56 (d, J=4.0 Hz, 1H), 7.76 (d, J=8.0 Hz, 1H), 7.59 (d, J=20.5 Hz, 1H), 7.41 (s, 1H), 7.29 (dd, J=7.5, 5.0 Hz, 1H), 7.22 (d, J=8.5 Hz, 1H), 7.04-7.01 (m, 2H), 6.43-6.38 (m, 2H), 5.76 (t, J=5.0 Hz, 1H), 4.08 (t, J=7.0 Hz, 2H), 3.33 (q, J=6.5 Hz, 2H), 2.44 (s, 3H), 1.82 (quintet, J=7.0 Hz, 2H), 1.51 (quintet, J=7.0 Hz, 2H), 1.37-1.29 (m, 4H); $^{13}$C NMR (125 MHz, CDCl$_3$) δ 165.1 (C), 150.4 (CH), 149.2 (CH), 137.3 (CH), 134.4 (CH), 134.3 (C), 130.7 (C), 128.8 (C), 128.4 (C), 127.9 (CH), 123.7 (CH), 123.0 (CH), 122.8 (CH), 120.6 (CH), 109.1 (CH), 100.3 (CH), 46.4 (CH$_2$), 39.7 (CH$_2$), 30.1 (CH$_2$), 29.5 (CH$_2$), 26.7 (CH$_2$), 26.6 (CH$_2$), 21.4 (CH$_3$). HRMS (ESI) m/z calculated for C$_{23}$H$_{28}$N$_3$O (M+H)$^+$: 362.2232, found: 362.2233.

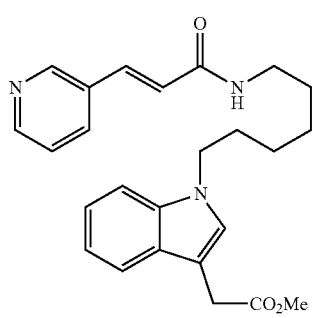

5.2.3h (E)-N-(6-(1H-Indol-1-yl)hexyl)-3-(pyridin-3-yl)acrylamide 5.2.3h. The general procedure was followed using 28.8 mg of 5.2.2h (0.100 mmol), 12.0 mg of trans-3-(3-pyridyl) acrylic acid (0.0800 mmol), 30.7 mg of EDC.HCl (0.160 mmol), 16.2 mg of HOBt (0.120 mmol), and 12.1 mg of Et$_3$N (0.120 mmol) in 1.6 mL of DCM. Purification by MPLC chromatography (5% MeOH in DCM) afforded 5.2.3h as a yellow gel (15 mg, 36% yield): $^1$H NMR (500 MHz, CDCl$_3$) δ 8.73 (d, J=1.5 Hz, 1H), 8.56 (dd, J=4.5, 1.0 Hz, 1H), 7.76 (td, J=8.0, 1.5 Hz, 1H), 7.60 (d, J=3.5 Hz, 1H), 7.58 (d, J=4.0 Hz, 1H), 7.31-7.28 (m, 2H), 7.20 (t, J=8.0 Hz, 1H), 7.10 (t, J=8.0 Hz, 1H), 7.07 (s, 1H), 6.43 (d, J=15.5 Hz, 1H), 5.80 (br s, 1H), 4.08 (t, J=7.0 Hz, 2H), 3.77 (s, 2H), 3.70 (s, 3H), 3.32 (q, J=6.5 Hz, 2H), 1.84-1.80 (m, 2H), 1.53-1.49 (m, 2H), 1.35-1.32 (m, 4H); 13C NMR (125 MHz, CDCl$_3$) δ 172.7 (C), 165.1 (C), 150.3 (CH), 149.2 (CH), 137.3 (CH), 136.2 (C), 134.3 (CH), 130.7 (C), 127.8 (C), 126.7 (CH), 123.7 (CH), 122.9 (CH), 121.7 (CH), 119.2 (CH), 119.0 (CH), 109.5 (CH), 106.8 (C), 52.0 (CH$_3$), 46.2 (CH$_2$), 39.6 (CH$_2$), 31.1 (CH$_2$), 30.0 (CH$_2$), 29.4 (CH$_2$), 26.6 (CH$_2$), 26.5 (CH$_2$). IR (thin film): 3302, 2929, 2859, 1734, 1663, 1556, 1509, 1426, 1373, 1242, 1046, 805, 730 cm$^{-1}$; HRMS (ESI) m/z calculated for C$_{25}$H$_{30}$N$_3$O$_3$(M+H)$^+$: 420.2263, found: 420.2271.

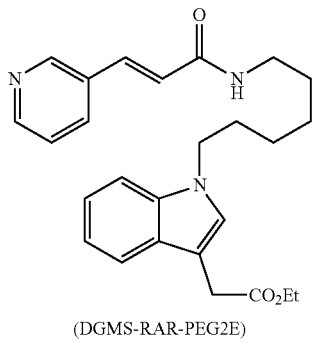

5.2.3i (DGMS-RAR-PEG2E)

(E)-N-(6-(1H-Indol-1-yl)hexyl)-3-(pyridin-3-yl)acrylamide 5.2.3i (DGMS-RAR-PEG2E). The general procedure was followed using 140 mg of 5.2.2 i (0.460 mmol), 57.6 mg of trans-3-(3-pyridyl) acrylic acid (0.390 mmol), 148 mg of EDC.HCl (0.770 mmol), 78.2 mg of HOBt (0.580 mmol), and 58.6 mg of Et$_3$N (0.580 mmol) in 10 mL of DCM. Purification by MPLC chromatography (2% MeOH in DCM) afforded DGMS-RAR-PEG2E as a light yellow gel (120 mg, 72% yield): $^1$H NMR (500 MHz, CDCl$_3$) δ 8.69 (s, 1H), 8.51 (d, J=4.0 Hz, 1H), 7.68 (d, J=7.0 Hz, 1H), 7.59 (d, J=8.0 Hz, 1H), 7.56 (d, J=15.5 Hz, 1H), 7.27 (d, J=8.0 Hz, 1H), 7.22 (dd, J=7.5, 4.5 Hz, 1H), 7.17 (t, J=7.5 Hz, 1H), 7.09 (t, J=7.5 Hz, 1H), 7.05 (s, 1H), 6.46 (d, J=15.5 Hz, 1H), 6.41 (t, J=5.0 Hz, 1H), 4.14 (q, J=7.0 Hz, 2H), 4.02 (t, J=7.0 Hz, 2H), 3.74 (s, 3H), 3.27 (q, J=6.5 Hz, 2H), 1.78-1.75 (m, 2H), 1.48-1.45 (m, 2H), 1.30-1.28 (m, 4H), 1.25 (t, J=7.0 Hz, 3H); 13C NMR (125 MHz, CDCl$_3$) δ 172.3 (C), 165.3 (C), 150.2 (CH), 149.0 (CH), 136.8 (C), 136.2 (C), 134.4 (CH), 130.9 (C), 127.8 (C), 126.7 (CH), 123.7 (CH), 123.3 (CH), 121.6 (CH), 119.10 (CH), 119.08 (CH), 109.5 (CH), 106.9 (C), 60.8 (CH$_2$), 46.2 (CH$_2$), 39.6 (CH$_2$), 31.4 (CH$_2$), 30.1 (CH$_2$), 29.4 (CH$_2$), 26.7 (CH$_2$), 26.5 (CH$_2$), 14.3 (CH$_3$). HRMS (ESI) m/z calculated for C$_{26}$H$_{32}$N$_3$O$_3$ (M+H)$^+$: 434.2444, found: 434.2432.

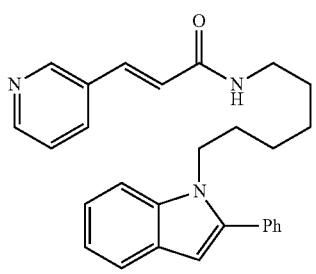

(DGMS-RARI)                                                     5.2.3j (E)-N-(6-(1H-indol-1-yl)hexyl)-3-(pyridin-3-yl)acrylamide 5.2.3j (DGMS-RARI). The general procedure was followed using 29.2 mg of 5.2.2j (0.100 mmol), 12.0 mg of trans-3-(3-pyridyl) acrylic acid (0.080 mmol), 30.7 mg of EDC.HCl (0.160 mmol), 16.2 mg of HOBt (0.120 mmol), and 12.1 mg of Et$_3$N (0.120 mmol) in 1.6 mL of DCM. Purification by MPLC chromatography (5% MeOH in DCM) afforded DGMS-RARI as a yellow gel (39.7 mg, 94% yield): $^1$H NMR (501 MHz, CDCl$_3$) δ 8.69 (s, 1H), 8.50 (d, J=4.4 Hz, 1H), 7.68 (d, J=7.8 Hz, 1H), 7.63 (d, J=7.8 Hz, 1H), 7.56 (d, J=15.7 Hz, 1H), 7.43 (m, 5H), 7.35 (d, J=8.3 Hz, 1H), 7.21 (t, J=6.4 Hz, 2H), 7.13 (t, J=7.4 Hz, 1H), 6.51 (s, 1H), 6.45 (d, J=15.7 Hz, 1H), 6.35 (d, J=5.0 Hz, 1H), 4.13 (t, J=7.6 Hz, 2H), 3.24 (t, J=6.6 Hz, 2H), 1.64 (t, J=7.1 Hz, 2H), 1.39 (t, J=7.1 Hz, 2H), 1.14 (m, 4H); $^{13}$C NMR (125 MHz, CDCl$_3$) δ 165.1 (C), 150.2 (CH), 149.0 (CH), 141.4 (C), 137.4 (C), 137.1 (CH), 134.4 (CH), 133.2 (C), 130.8 (C), 129.4 (CH), 128.6 (CH), 128.2 (C), 128.0 (CH), 123.7 (CH), 123.0 (CH), 121.5 (CH), 120.6 (CH), 119.8 (CH), 110.1 (CH), 102.1 (CH), 43.7 (CH$_2$), 39.7 (CH$_2$), 29.7 (CH$_2$), 29.4 (CH$_2$), 26.4 (CH$_2$), 26.4 (CH$_2$). IR (thin film): 3440, 2997, 2913, 1666, 1436, 1406, 1311, 1018, 952, 698, 667 cm$^{-1}$; HRMS (ESI) m/z calculated for C$_{28}$H$_{30}$N$_3$O (M+H)$^+$: 424.2389, found: 424.2385.

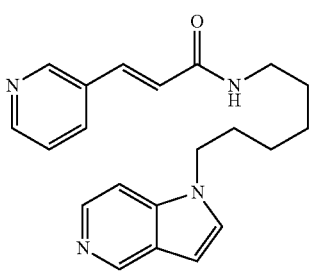

5.2.3k (E)-N-(6-(1H-Indol-1-yl)hexyl)-3-(pyridin-3-yl)acrylamide 5.2.3k. The general procedure was followed using 21.7 mg of 5.2.2k (0.100 mmol), 12.0 mg of trans-3-(3-pyridyl) acrylic acid (0.080 mmol), 30.7 mg of EDC.HCl (0.160 mmol), 16.2 mg of HOBt (0.120 mmol), and 12.1 mg of Et$_3$N (0.120 mmol) in 1.6 mL of DCM. Purification by MPLC chromatography (5% MeOH in DCM) afforded 5.2.3k as a brown gel (31.1 mg, 89% yield): $^1$H NMR (501 MHz, CDCl$_3$) δ 8.64 (d, J=1.2 Hz, 1H), 8.50-8.43 (m, 1H), 8.25 (dd, J=4.7, 1.3 Hz, 1H), 7.85 (dd, J=7.8, 1.4 Hz, 1H), 7.67 (d, J=7.9 Hz, 1H), 7.55 (d, J=15.7 Hz, 1H), 7.20 (dd, J=7.8, 4.8 Hz, 1H), 7.15 (d, J=3.4 Hz, 1H), 6.99 (dd, J=7.8, 4.7 Hz, 1H), 6.72 (t, J=5.3 Hz, 1H), 6.51 (d, J=15.7 Hz, 1H), 6.40 (d, J=3.4 Hz, 1H), 4.21 (t, J=7.2 Hz, 2H), 3.30 (dd, J=13.0, 6.7 Hz, 2H), 1.84-1.73 (m, 2H), 1.53-1.44 (m, 2H), 1.31 (m, 4H); $^{13}$C NMR (125 MHz, CDCl$_3$) δ 165.3 (C), 150.1 (CH), 149.0 (CH), 147.3 (CH), 142.5 (C), 136.8 (CH), 134.3 (CH), 130.8 (C), 128.8 (CH), 128.0 (CH), 123.7 (CH), 123.3 (CH), 120.6 (C), 115.6 (CH), 99.4 (CH), 44.3 (CH$_2$), 39.6 (CH$_2$), 30.3 (CH$_2$), 29.3 (CH$_2$), 26.4 (CH$_2$), 26.3 (CH$_2$); IR (thin film): 3443, 2995, 2912, 1667, 1436, 1406, 1309, 1260, 1042, 952, 930, 802, 697, 667 cm$^{-1}$; HRMS (ESI) m/z calculated for C$_{21}$H$_{25}$N$_4$O (M+H)$^+$: 349.2028, found: 349.2020.

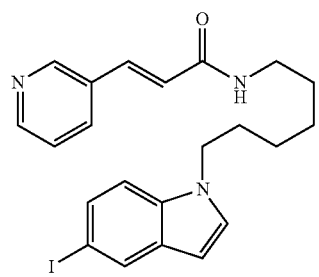

5.2.3l (E)-N-(6-(1H-Indol-1-yl)hexyl)-3-(pyridin-3-yl)acrylamide 5.2.3l. The general procedure was followed using 34.7 mg of 5.2.2l (0.100 mmol), 12.0 mg of trans-3-(3-pyridyl) acrylic acid (0.080 mmol), 30.7 mg of EDC.HCl (0.160 mmol), 16.2 mg of HOBt (0.120 mmol), and 12.1 mg of Et$_3$N (0.120 mmol) in 1.6 mL of DCM. Purification by MPLC chromatography (5% MeOH in DCM) afforded 5.2.3l as a brown gel (39.5 mg, 83% yield): $^1$H NMR (500 MHz, CDCl$_3$) δ 8.68 (s, 1H), 8.49 (d, J=4.2 Hz, 1H), 7.91 (s, 1H), 7.71 (d, J=7.7 Hz, 1H), 7.55 (d, J=15.7 Hz, 1H), 7.39 (d, J=8.6 Hz, 1H), 7.24 (dd, J=7.7, 5.3 Hz, 1H), 7.06 (d, J=8.6 Hz, 1H), 7.00 (d, J=2.5 Hz, 1H), 6.46 (d, J=15.7 Hz, 1H), 6.41-6.24 (m, 2H), 4.02 (t, J=6.9 Hz, 2H), 3.30 (dd, J=12.9, 6.5 Hz, 2H), 1.84-1.70 (m, 2H), 1.55-1.39 (m, 2H), 1.36-1.14 (m, 4H); $^{13}$C NMR (125 MHz, CDCl$_3$) δ 165.3 (C), 150.0 (CH), 148.8 (CH), 137.0 (CH), 135.0 (C), 134.6 (CH), 131.1 (C), 130.9 (C), 129.7 (CH), 129.6 (CH), 128.6 (CH), 123.8 (CH), 123.2 (CH), 111.4 (CH), 100.3 (CH), 82.7 (C), 46.4 (CH$_2$), 39.7 (CH$_2$), 30.0 (CH$_2$), 29.4 (CH$_2$), 26.6 (CH$_2$), 26.5 (CH$_2$); IR (thin film): 3398, 2996, 2913, 1660, 1436, 1406, 1315, 1014, 951, 703, 671 cm$^{-1}$; HRMS (ESI) m/z calculated for C$_{22}$H$_{25}$IN$_3$O (M+H)$^+$: 474.1042, found: 474.1049.

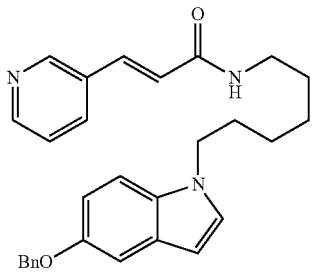

(DGMS-RAR-6)                                                    5.2.3m (E)-N-(6-(1H-Indol-1-yl)hexyl)-3-(pyridin-3-yl)acrylamide 5.2.3m (DGMS-RAR-6). The general procedure was followed using 32.1 mg of 5.2.2m (0.100 mmol), 12.0 mg of trans-3-(3-pyridyl) acrylic acid (0.080 mmol), 30.7 mg of EDC.HCl (0.160 mmol), 16.2 mg of HOBt (0.120 mmol), and 12.1 mg of Et₃N (0.120 mmol) in 1.6 mL of DCM. Purification by MPLC chromatography (5% MeOH in DCM) afforded DGMS-RAR-6 as a yellow gel (14.9 mg, 33% yield): $^1$H NMR (500 MHz, CDCl₃) δ 8.71 (d, J=1.1 Hz, 1H), 8.53 (d, J=3.8 Hz, 1H), 7.70 (d, J=8.0 Hz, 1H), 7.58 (d, J=15.7 Hz, 1H), 7.46 (d, J=7.2 Hz, 2H), 7.37 (t, J=7.5 Hz, 2H), 7.31 (d, J=7.3 Hz, 1H), 7.27-7.20 (m, 2H), 7.18 (d, J=2.3 Hz, 1H), 7.04 (d, J=3.0 Hz, 1H), 6.95 (dd, J=8.8, 2.4 Hz, 1H), 6.42 (d, J=15.7 Hz, 1H), 6.39 (d, J=3.0 Hz, 1H), 6.07 (t, J=5.5 Hz, 1H), 5.09 (s, 2H), 4.04 (t, J=7.0 Hz, 2H), 3.30 (dd, J=13.2, 6.8 Hz, 2H), 1.95-1.65 (m, 2H), 1.53-1.44 (m, 2H), 1.34-1.27 (m, 4H); $^{13}$C NMR (125 MHz, CDCl₃) δ 165.2 (C), 153.1 (C), 150.2 (CH), 149.0 (CH), 137.7 (C), 137.1 (CH), 134.4 (CH), 131.5 (C), 130.8 (C), 128.9 (C), 128.5 (CH), 128.4 (CH), 127.8 (CH), 127.6 (CH), 123.7 (CH), 123.1 (CH), 112.5 (CH), 110.1 (CH), 104.2 (CH), 100.5 (CH), 71.0 (CH₂), 46.5 (CH₂), 39.7 (CH₂), 30.2 (CH₂), 29.5 (CH₂), 26.7 (CH₂), 26.6 (CH₂); IR (thin film): 3404, 3002, 2919, 1659, 1436, 1406, 1314, 1015, 951, 702, 671 cm⁻¹.

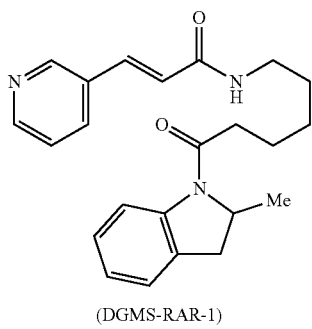

(DGMS-RAR-1)

(E)-N-(6-(1H-Indol-1-yl)hexyl)-3-(pyridin-3-yl)acrylamide 5.2.3n (DGMS-RAR-1). The general procedure was followed using 49.3 mg of 5.3.5a (0.2 mmol), 25.0 mg of trans-3-(3-pyridyl) acrylic acid (0.17 mmol), 65.1 mg of EDC.HCl (0.34 mmol), 35.1 mg of HOBt (0.26 mmol), and 26.3 mg of Et₃N (0.26 mmol) in 4 mL of CH₂Cl₂. Purification by MPLC chromatography (2:98 MeOH:CH₂Cl₂) afforded DGMS-RAR-1 as a yellow gel (49 mg, 75%): $^1$H NMR (500 MHz, DMSO-d₆) δ 8.73 (d, J=8.5 Hz, 1H), 8.52 (t, J=6.0 Hz, 1H), 8.16 (dd, J=11.0, 5.5 Hz, 1H), 8.01 (d, J=8.5 Hz, 1H), 7.94 (d, J=8.5 Hz, 1H), 7.45-7.38 (m, 2H), 7.20 (t, J=7.5 Hz, 1H), 7.12 (t, J=7.5 Hz, 1H), 6.97 (t, J=7.5 Hz, 1H), 6.73-6.69 (m, 1H), 4.60 (d, J=10.0 Hz, 1H), 3.35-3.17 (m, 1H), 3.18 (q, J=6.5 Hz, 2H), 2.61-2.37 (m, 3H), 1.61 (q, J=7.5 Hz, 2H), 1.49 (q, J=7.5 Hz, 2H), 1.35 (quin, J=7.5 Hz, 2H), 1.16-1.13 (m, 3H); $^{13}$C NMR (125 MHz, DMSO-d₆) δ 170.9 (C), 164.8 (C), 150.5 (CH), 149.5 (CH), 142.0 (C), 135.5 (CH), 134.3 (CH), 131.2 (C), 127.4 (CH), 125.6 (CH), 124.8 (CH), 124.4 (CH), 123.8 (CH), 117.4 (CH), 55.3 (CH), 39.1 (CH₂), 36.3 (CH₂), 34.4 (CH₂), 29.6 (CH₂), 26.7 (CH₂), 24.8 (CH₂), 22.0 (CH₂), 14.5 (CH₃); ATR-FTIR (thin film): 3416, 3001, 2882, 1672, 1629, 1421, 1313, 1016, 952, 702 cm⁻¹. HRMS (ESI) m/z calculated for C₂₃H₂₈N₃O₂ [M+H]⁺: 378.2182, found: 378.2176.

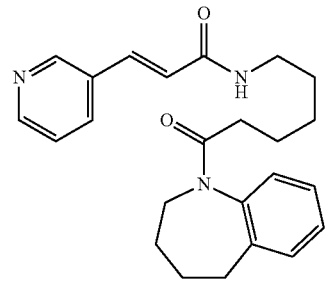

(DGMS-RAR-3)

(E)-N-(6-(1H-indol-1-yl)hexyl)-3-(pyridin-3-yl)acrylamide 5.2.3o (DGMS-RAR-3). The general procedure was followed using 52.1 mg of 5.3.5b (0.2 mmol), 25.0 mg of trans-3-(3-pyridyl) acrylic acid (0.17 mmol), 65.1 mg of EDC.HCl (0.34 mmol), 35.1 mg of HOBt (0.26 mmol), and 26.3 mg of Et₃N (0.26 mmol) in 4 mL of DCM. Purification by MPLC chromatography (2% MeOH in DCM) afforded DGMS-RAR-3 as a yellow gel (36 mg, 54% yield): $^1$H NMR (500 MHz, CDCl₃) δ 8.75 (s, 1H), 8.55 (s, 1H), 7.78 (d, J=8.0 Hz, 1H), 7.59 (d, J=15.5 Hz, 1H), 7.30-7.20 (m, 4H), 7.10-7.08 (m, 1H), 6.55 (d, J=16.0 Hz, 1H), 6.47 (t, J=6.0 Hz, 1H), 4.73-4.69 (m, 1H), 3.49-3.32 (m, 2H), 2.74-2.66 (m, 2H), 2.62-2.57 (m, 2H), 2.25-2.19 (m, 1H), 1.98-1.86 (m, 3H), 1.78-1.74 (m, 1H), 1.61-1.49 (m, 3H), 1.44-1.35 (m, 1H), 1.30 (quin, J=7.5 Hz, 2H); $^{13}$C NMR (125 MHz, CDCl₃) δ 172.0 (C), 165.3 (C), 150.0 (CH), 149.0 (CH), 143.0 (C), 140.5 (C), 136.5 (CH), 134.3 (CH), 131.0 (C), 130.2 (CH), 128.0 (CH), 127.5 (CH), 127.3 (CH), 123.7 (CH), 123.6 (CH), 47.2 (CH₂), 39.2 (CH₂), 34.5 (CH₂), 33.9 (CH₂), 29.1 (CH₂), 28.8 (CH₂), 26.5 (CH₂), 26.4 (CH₂), 24.3 (CH₂). ATR-FTIR (thin film): 3434, 3289, 3049, 2929, 2855, 1645, 1633, 1492, 1402, 1025, 952, 730 cm⁻¹. HRMS (ESI) m/z calculated for C₂₄H₃₀N₃O₂ [M+H]⁺: 392.2338, found: 392.2337.

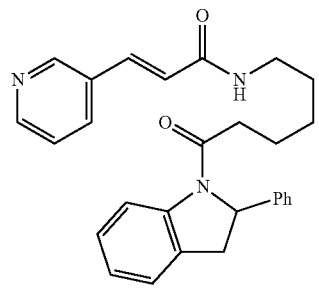

(DGMS-RAR-7)

(E)-N-(6-(1H-indol-1-yl)hexyl)-3-(pyridin-3-yl)acrylamide 5.2.3p (DGMS-RAR-7). The general procedure was followed using 61.7 mg of 5.3.5c (0.2 mmol), 25.0 mg of trans-3-(3-pyridyl) acrylic acid (0.17 mmol), 65.1 mg of EDC.HCl (0.34 mmol), 35.1 mg of HOBt (0.26 mmol), and 26.3 mg of Et₃N (0.26 mmol) in 4 mL of DCM. Purification by MPLC chromatography (2% MeOH in DCM) afforded DGMS-RAR-7 as a yellow gel (45 mg, 60% yield): $^1$H NMR (500 MHz, CDCl₃) δ 8.71 (d, J=2.5 Hz, 1H), 8.53 (d, J=5.0 Hz, 1H), 8.35 (d, J=8.0 Hz, 1H), 7.74 (d, J=8.0 Hz, 1H), 7.58 (d, J=16.0 Hz, 1H), 7.29-7.22 (m, 4H), 7.14-7.11 (m, 3H), 7.04 (t, J=7.5 Hz, 1H), 6.63 (t, J=5.5 Hz, 1H), 6.55 (d, J=16.0 Hz, 1H), 5.40 (d, J=10.0 Hz, 1H), 3.80-3.75 (m, 1H), 3.39-3.31 (m, 2H), 2.96 (d, J=16.0 Hz, 1H), 2.44-2.38 (m, 1H), 2.16-2.05 (m, 1H), 1.64-1.44 (5H), 1.30-1.22 (m, 2H); $^{13}$C NMR (125 MHz, CDCl$_3$) δ 172.1 (C), 165.2 (C), 150.2 (CH), 149.2 (CH), 143.4 (C), 143.1 (C), 136.7 (CH), 134.2 (CH), 132.0 (C), 130.9 (C), 129.2 (CH), 127.8 (CH), 127.7 (CH), 125.0 (CH), 124.9 (CH), 124.3 (CH), 123.7 (CH), 123.4 (CH), 116.9 (CH), 62.7 (CH), 39.0 (CH$_2$), 38.9 (CH$_2$), 35.1 (CH$_2$), 28.7 (CH$_2$), 26.1 (CH$_2$), 23.5 (CH$_2$); ATR-FTIR (thin film): 3277, 3049, 1727, 1661, 1628, 1402, 1267, 1024, 730 cm$^{-1}$. HRMS (ESI) m/z calculated for C$_{28}$H$_{30}$N$_3$O$_2$ [M+H]$^+$: 440.2338, found: 440.2335.

(E)-N-(6-(1H-Indol-1-yl)hexyl)-3-(pyridin-3-yl)acrylamide 5.2.3q (DGMS-RAR-PEG3E). The general procedure was followed using 304 mg of 5.2.5f (1.00 mmol), 124.2 mg of trans-3-(3-pyridyl) acrylic acid (0.830 mmol), 320 mg of EDC.HCl (1.67 mmol), 169 mg of HOBt (1.25 mmol), and 126 mg of Et$_3$N (1.25 mmol) in 20 mL of DCM. Purification by MPLC chromatography (5% MeOH in DCM) afforded DGMS-RAR-PEG3E as a light yellow gel (420 mg, 92% yield): $^1$H NMR (500 MHz, CDCl$_3$) δ 8.71 (s, 1H), 8.53 (d, J=2.5 Hz, 1H), 8.22 (d, J=8.0 Hz, 1H), 7.75 (d, J=7.5 Hz, 1H), 7.57 (d, J=15.5 Hz, 1H), 7.27-7.13 (m, 3H), 7.02 (t, J=7.5 Hz, 1H), 6.65 (br, 1H), 6.56 (d, J=16.0 Hz, 1H), 4.28 (t, J=8.5 Hz, 1H), 4.17-4.08 (m, 2H), 3.80-3.71 (m, 2H), 3.44 (q, J=7.0 Hz, 2H), 2.81 (d, J=15.5 Hz, 1H), 2.53 (dd, J=16.0, 9.5 Hz, 1H), 2.45-2.40 (m, 2H), 1.78-1.73 (m, 2H), 1.65-1.60 (m, 2H), 1.49-1.45 (m, 2H), 1.25 (t, J=7.0 Hz, 3H); $^{13}$C NMR (125 MHz, CDCl$_3$) δ 171.8 (C), 171.3 (C), 165.3 (C), 150.2 (CH), 149.2 (CH), 142.7 (C), 136.8 (CH), 134.3 (CH), 133.1 (C), 130.9 (C), 128.4 (CH), 123.9 (CH), 123.71 (CH), 123.66 (CH), 123.4 (CH), 117.0 (CH), 60.9 (CH$_2$), 54.3 (CH$_2$), 39.9 (CH$_2$), 39.0 (CH$_2$), 36.6 (CH), 35.5 (CH$_2$), 28.8 (CH$_2$), 26.3 (CH$_2$), 23.3 (CH$_2$), 14.2 (CH$_3$); IR (thin film): 3295, 2934, 2865, 1728, 1660, 1634, 1481, 1412, 1284, 1179, 1025, 978, 806, 756, 733 cm$^{-1}$; HRMS (ESI) m/z calculated for C$_{26}$H$_{32}$N$_3$O$_4$ (M+H)$^+$: 450.2393, found: 450.2375.

E. Expanding RARI Analogue Compound Library

1. Hydrogenation.

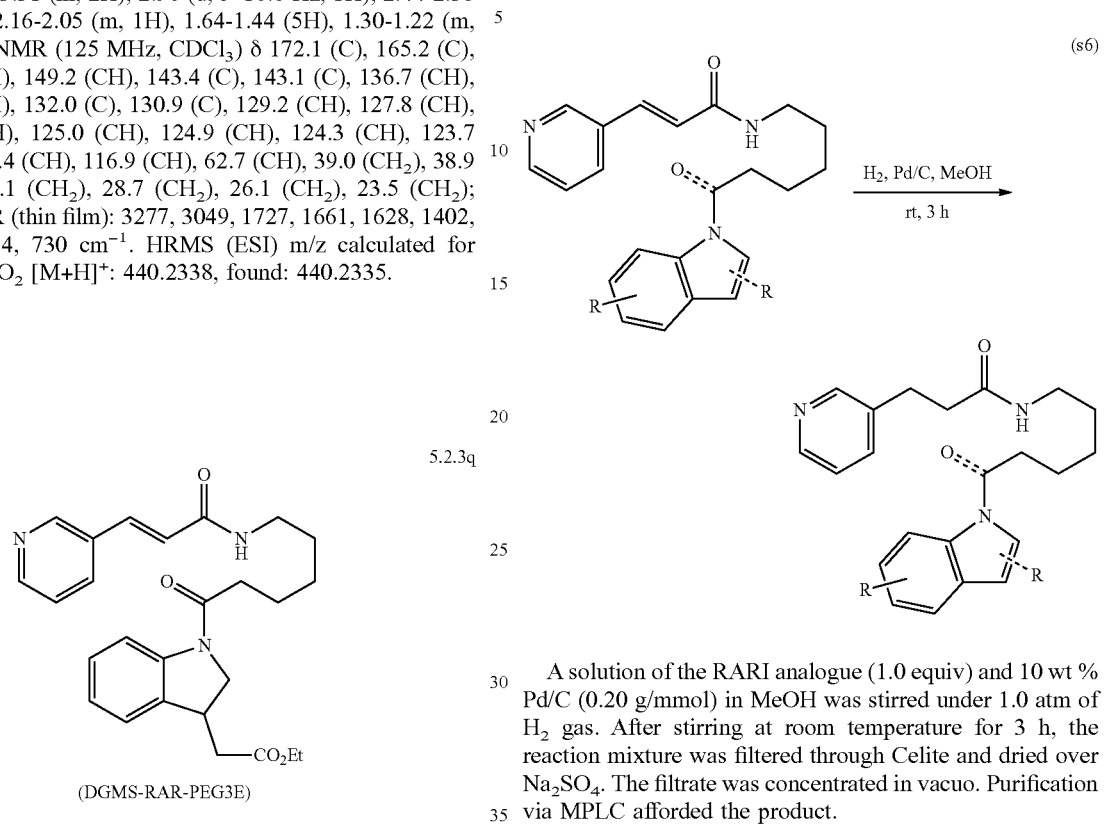

A solution of the RARI analogue (1.0 equiv) and 10 wt % Pd/C (0.20 g/mmol) in MeOH was stirred under 1.0 atm of H$_2$ gas. After stirring at room temperature for 3 h, the reaction mixture was filtered through Celite and dried over Na$_2$SO$_4$. The filtrate was concentrated in vacuo. Purification via MPLC afforded the product.

Characterization Data.

DGMS-RAR-5.2.3b H2. The general procedure was followed using 15.0 mg (0.043 mmol) of 5.2.3b, 8.6 mg of Pd/C in 1.0 mL of MeOH under H$_2$ atmosphere. Purification by MPLC chromatography (2% MeOH in DCM) afforded DGMS-RAR-5.2.3b H2 as a yellow gel (12.2 mg, 80% yield): $^1$H NMR (500 MHz, CDCl$_3$) δ 8.72 (s, 1H), 8.40-8.37 (m, 2H), 8.18 (d, J=5.5 Hz, 1H), 7.49-7.47 (m, 2H), 7.20 (d, J=3.0 Hz, 1H), 7.15-7.12 (m, 1H), 6.46 (d, J=3.5 Hz, 1H), 6.06 (t, J=6.0 Hz, 1H), 4.16 (t, J=7.0 Hz, 2H), 3.15 (q, J=6.5 Hz, 2H), 2.93 (t, J=7.5 Hz, 2H), 2.42 (t, J=7.5 Hz, 2H), 1.81 (quin, J=7.0 Hz, 2H), 1.37 (t, J=7.0 Hz, 2H), 1.28-1.23 (m, 4H); $^{13}$C NMR (125 MHz, CDCl$_3$) δ 171.4 (C), 149.7 (CH), 147.6 (CH), 138.1 (CH), 136.4 (C), 136.1 (CH), 133.3 (C), 133.1 (C), 132.6 (CH), 131.6 (CH), 123.4 (CH), 115.4 (CH), 100.6 (CH), 46.7 (CH$_2$), 39.3 (CH$_2$), 37.8 (CH$_2$), 30.3

(CH$_2$), 29.4 (CH$_2$), 28.8 (CH$_2$), 26.5 (CH$_2$), 26.4 (CH$_2$). ATR-FTIR (thin film): 3271, 3043, 2926, 2855, 1645, 1552, 1500, 1320, 1028, 817, 775, 730 cm$^{-1}$. HRMS (ESI) m/z calculated for C$_{21}$H$_{27}$N$_4$O [M+H]$^+$: 351.2185, found: 351.2186.

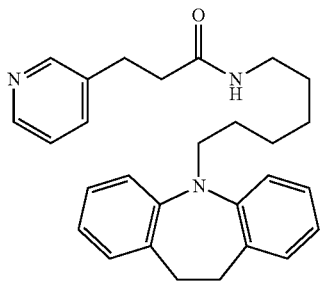

DGMS-RAR-5.2.3c H2

DGMS-RAR-5.2.3c H2. The general procedure was followed using 15.0 mg (0.035 mmol) of 5.2.3c, 7.0 mg of Pd/C in 0.8 mL of MeOH under H$_2$ atmosphere. Purification by MPLC chromatography (2% MeOH in DCM) afforded DGMS-RAR-5.2.3c H2 as a yellow gel (12.0 mg, 80% yield): $^1$H NMR (500 MHz, CDCl$_3$) δ 8.44-8.41 (m, 2H), 7.51 (td, J=4.0 Hz, 2.0 Hz, 1H), 7.16 (dd, J=8.0 Hz, 5.0 Hz, 1H), 7.13-7.05 (m, 6H), 6.92-6.89 (m, 2H), 5.41 (s, 1H), 3.70 (t, J=7.0 Hz, 2H), 3.17-3.13 (m, 6H), 2.95 (t, J=7.5 Hz, 2H), 2.41 (t, J=7.5 Hz, 2H), 1.53 (quin, J=7.0 Hz, 2H), 1.39-1.24 (m, 4H), 1.20-1.14 (m, 2H); $^{13}$C NMR (125 MHz, CDCl$_3$) δ 171.2 (C), 149.8 (CH), 148.4 (C), 147.7 (CH), 136.3 (C), 136.1 (CH), 134.2 (C), 129.8 (CH), 126.3 (CH), 123.4 (CH), 122.3 (CH), 120.0 (CH), 50.5 (CH$_2$), 39.4 (CH$_2$), 37.9 (CH$_2$), 32.2 (CH$_2$), 29.5 (CH$_2$), 28.8 (CH$_2$), 27.8 (CH$_2$), 26.8 (CH$_2$), 26.5 (CH$_2$). ATR-FTIR (thin film): 3501, 2995, 2912, 1661, 1487, 1436, 1407, 1309, 1042, 952, 930, 697 cm$^{-1}$. HRMS (ESI) m/z calculated for C$_{28}$H$_{34}$N$_3$O [M+H]$^+$: 428.2702, found: 428.2696.

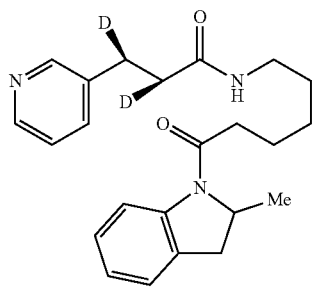

DGMS-RAR-1 D2

DGMS-RAR-1 D2. The general procedure was followed using 10.0 mg (0.026 mmol) of 5.2.3f, 5.2 mg of Pd/C in 0.6 mL of MeOD under D$_2$ atmosphere. Purification by MPLC chromatography (2% MeOH in DCM) afforded DGMS-RAR-1 D2 as a yellow gel (8.5 mg, 86% yield): $^1$H NMR (500 MHz, CDCl$_3$) δ 8.39 (d, J=6.5 Hz, 2H), 8.11 (d, J=8.0 Hz, 1H), 7.49 (d, J=8.0 Hz, 1H), 7.17-7.13 (m, 3H), 7.00 (t, J=7.0 Hz, 1H), 6.31 (s, 1H), 4.47 (t, J=7.5 Hz, 1H), 3.40-3.33 (m, 1H), 3.23 (q, J=6.5 Hz, 1H), 2.94-2.91 (m, 1H), 2.65-2.58 (m, 1H), 2.53-2.46 (m, 1H), 2.44-2.37 (m, 2H), 1.74-1.67 (m, 2H), 1.50-1.44 (m, 2H), 1.37-1.21 (m, 5H); $^{13}$C NMR (125 MHz, CDCl$_3$) δ 171.5 (C), 170.9 (C), 149.7 (CH), 147.5 (CH), 141.6 (C), 136.5 (C), 136.1 (CH), 130.3 (C), 127.4 (CH), 125.0 (CH), 123.9 (CH), 123.4 (CH), 117.9 (CH), 55.5 (CH), 39.0 (CH$_2$), 37.51 (q, J=19.1 Hz, CHD), 36.4 (CH$_2$), 34.6 (CH$_2$), 29.0 (CH$_2$), 28.54 (q, J=19.8 Hz, CHD), 26.4 (CH2), 24.1 (CH$_2$), 21.8 (CH$_3$). ATR-FTIR (thin film): 3487, 2996, 2912, 1668, 1557, 1436, 1386, 1310, 1018, 952, 931, 698 cm$^{-1}$. HRMS (ESI) m/z calculated for C$_{23}$H$_{28}$D$_2$N$_3$O$_2$ [M+H]$^+$: 382.2464, found: 382.2463.

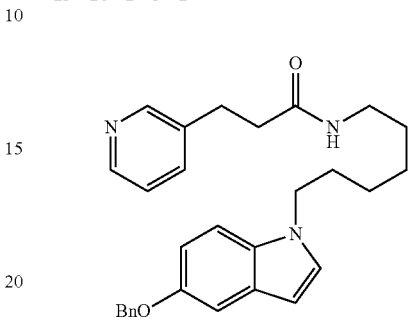

DGMS-RAR-6 H2

DGMS-RAR-6 H2. The general procedure was followed using 45.3 mg (0.100 mmol) of DGMS-RAR-6, 5.2 mg of Pd/C in 0.6 mL of MeOH under H$_2$ atmosphere for 1 hour. Purification by MPLC chromatography (2% MeOH in DCM) afforded DGMS-RAR-6 H2 as a purple gel (27.4 mg, 60% yield): $^1$H NMR (500 MHz, CDCl$_3$) δ 8.46-8.39 (m, 2H), 7.52 (d, J=7.8 Hz, 1H), 7.47 (d, J=7.3 Hz, 2H), 7.38 (t, J=7.5 Hz, 2H), 7.32 (d, J=7.3 Hz, 1H), 7.21 (d, J=8.9 Hz, 1H), 7.16 (d, J=2.4 Hz, 2H), 7.04 (d, J=3.0 Hz, 1H), 6.94 (dd, J=8.8, 2.4 Hz, 1H), 6.38 (d, J=2.9 Hz, 1H), 5.47 (s, 1H), 5.09 (s, 2H), 4.05 (t, J=6.9 Hz, 2H), 3.15 (dd, J=13.1, 6.8 Hz, 2H), 2.95 (t, J=7.5 Hz, 2H), 2.42 (t, J=7.6 Hz, 2H), 1.83-1.70 (m, 2H), 1.42-1.34 (m, 2H), 1.30-1.21 (m, 4H); $^{13}$C NMR (125 MHz, CDCl$_3$) δ 171.5 (C), 153.1 (C), 149.3 (CH), 147.2 (CH), 137.7 (C), 136.7 (C), 136.5 (CH), 131.5 (C), 128.9 (C), 128.5 (CH), 128.4 (CH), 127.8 (CH), 127.6 (CH), 123.6 (CH), 112.4 (CH), 110.1 (CH), 104.2 (CH), 100.5 (CH), 71.0 (CH), 46.4 (CH$_2$), 39.4 (CH$_2$), 37.6 (CH$_2$), 30.2 (CH$_2$), 29.4 (CH$_2$), 28.8 (CH$_2$), 26.6 (CH$_2$), 26.5 (CH$_2$); IR (thin film): 3386, 2256, 1651, 1047, 1023, 993, 824, 762, 630 cm$^{-1}$; HRMS (ESI) m/z calculated for C$_{29}$H$_{34}$N$_3$O$_2$ (M+H)$^+$: 456.2651, found: 456.2645.

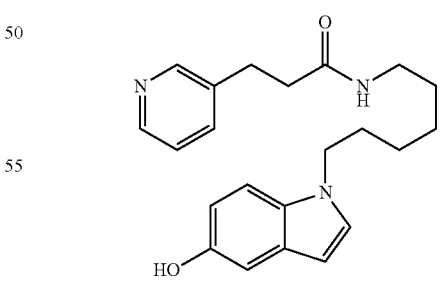

5.2.3t H2

5.2.3t H2. The general procedure was followed using 45.3 mg (0.100 mmol) of DGMS-RAR-6, 5.2 mg of Pd/C in 0.6 mL of MeOH under H$_2$ atmosphere for 4 hours. Purification by MPLC chromatography (2% MeOH in DCM) afforded 5.2.3t H2 as a purple gel (36.5 mg, 80% yield): $^1$H NMR (500 MHz, CDCl$_3$) δ 8.47-8.31 (m, 2H), 7.51 (d, J=7.8 Hz, 1H), 7.16 (dd, J=7.7, 4.8 Hz, 1H), 7.12 (d, J=8.7 Hz, 1H), 7.04 (d, J=2.2 Hz, 1H), 6.98 (d, J=3.0 Hz, 1H), 6.80 (dd, J=8.7, 2.3 Hz, 1H), 6.29 (d, J=2.9 Hz, 1H), 5.65 (t, J=5.4 Hz, 1H), 3.98 (s, 2H), 3.09 (dd, J=13.1, 6.8 Hz, 2H), 2.92 (t, J=7.5 Hz, 2H), 2.39 (t, J=7.5 Hz, 2H), 1.77-1.64 (m, 2H), 1.31 (dt, J=14.4, 7.3 Hz, 2H), 1.23-1.05 (m, 4H); $^{13}$C NMR (125 MHz, CDCl$_3$) δ 171.5 (C), 150.2 (C), 149.3 (CH), 147.2 (CH), 136.6 (CH), 131.2 (C), 129.2 (C), 128.5 (CH), 123.6 (CH), 111.6 (CH), 110.0 (C), 109.9 (CH), 105.4 (CH), 99.9 (CH), 46.3 (CH$_2$), 39.4 (CH$_2$), 37.7 (CH$_2$), 30.0 (CH$_2$), 29.3 (CH$_2$), 28.7 (CH$_2$), 26.5 (CH$_2$), 26.4 (CH$_2$); IR (thin film): 3278, 3093, 2930, 2858, 1644, 1555, 1485, 1455, 1373, 1149, 1048, 1027, 948, 846, 800, 714, 630 cm$^{-1}$; HRMS (ESI) m/z calculated for C$_{22}$H$_{28}$N$_3$O$_2$ (M+H)$^+$: 366.2182, found: 366.2172.

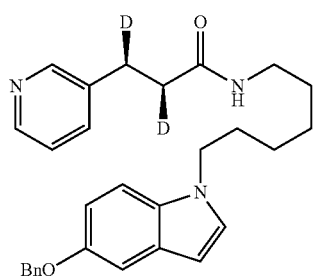

DGMS-RAR-6 D2

DGMS-RAR-5.2.3o D2. The general procedure was followed using 45.3 mg (0.100 mmol) of DGMS-RAR-6, 5.2 mg of Pd/C in 0.6 mL of MeOH under D$_2$ atmosphere for 1 hour. Purification by MPLC chromatography (2% MeOH in DCM) afforded DGMS-RAR-6 D2 as a purple gel (18.7 mg, 30% yield): $^1$H NMR (500 MHz, CDCl$_3$) δ 8.47-8.37 (m, 2H), 7.51 (d, J=7.9 Hz, 1H), 7.47 (d, J=7.4 Hz, 2H), 7.36 (dd, J=21.1, 13.4 Hz, 2H), 7.32 (d, J=7.3 Hz, 1H), 7.22 (d, J=8.9 Hz, 1H), 7.16 (t, J=3.5 Hz, 2H), 7.04 (d, J=3.0 Hz, 1H), 6.94 (dd, J=8.8, 2.3 Hz, 1H), 6.38 (d, J=2.9 Hz, 1H), 5.49 (s, 1H), 5.09 (s, 2H), 4.05 (t, J=7.0 Hz, 2H), 3.15 (dd, J=13.2, 6.9 Hz, 2H), 2.93 (t, J=7.9 Hz, 1H), 2.40 (t, J=7.2 Hz, 1H), 1.78 (dd, J=14.5, 7.1 Hz, 2H), 1.38 (dd, J=14.2, 7.2 Hz, 2H), 1.30-1.17 (m, 4H); $^{13}$C NMR (125 MHz, CDCl$_3$) δ 171.3 (C), 153.1 (C), 149.8 (CH), 147.7 (CH), 137.8 (C), 136.3 (C), 136.1 (CH), 131.5 (C), 128.9 (C), 128.5 (CH), 128.4 (CH), 127.8 (CH), 127.5 (CH), 123.4 (CH), 112.5 (CH), 110.1 (CH), 104.2 (CH), 100.5 (CH), 70.9 (CH$_2$), 46.5 (CH$_2$), 39.4 (CH$_2$), 37.8-37.5 (m, CDH), 30.2 (CH$_2$), 29.4 (CH$_2$), 28.7-28.4 (m, CDH), 26.6 (CH$_2$), 26.5 (CH$_2$); IR (thin film): 3404, 3002, 2921, 1652, 1436, 1314, 1015, 952, 702, 670 cm$^{-1}$; HRMS (ESI) m/z calculated for C$_{29}$H$_{32}$D$_2$N$_3$O$_2$(M+H)$^+$: 458.2777, found: 458.2766.

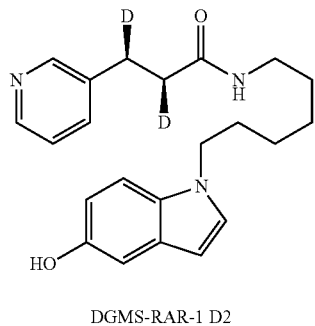 [SMILES: [2H][C@H](C(=O)NCCCCCCn1ccc2cc(O)ccc21)[C@H]([2H])c1cccnc1]

DGMS-RAR-1 D2

DGMS-RAR-1 D2. The general procedure was followed using 45.3 mg (0.100 mmol) of DGMS-RAR-6, 5.2 mg of Pd/C in 0.6 mL of MeOH under D$_2$ atmosphere for 4 hours. Purification by MPLC chromatography (2% MeOH in DCM) afforded DGMS-RAR-1 D2 as a purple gel (35.1 mg, 77% yield): $^1$H NMR (500 MHz, CDCl$_3$) δ 8.43 (dd, J=14.5, 6.7 Hz, 2H), 7.55-7.46 (m, 1H), 7.20-7.11 (m, 2H), 7.02 (dd, J=15.9, 2.6 Hz, 2H), 6.80 (dd, J=8.7, 2.3 Hz, 1H), 6.31 (d, J=2.8 Hz, 1H), 5.44 (s, 1H), 4.02 (t, J=6.9 Hz, 2H), 3.11 (dd, J=13.1, 6.9 Hz, 2H), 2.93 (t, J=7.9 Hz, 1H), 2.38 (d, J=7.0 Hz, 1H), 1.75 (dd, J=14.5, 7.1 Hz, 2H), 1.37-1.29 (m, 2H), 1.24-1.12 (m, 5H); $^{13}$C NMR (125 MHz, CDCl$_3$) δ 171.4 (C), 150.0 (C), 149.5 (CH), 147.4 (CH), 136.5 (CH), 136.3 (C), 131.3 (C), 129.2 (C), 128.5 (CH), 123.6 (CH), 111.6 (CH), 110.0 (CH), 105.4 (CH), 100.0 (CH), 46.4 (CH$_2$), 39.4 (CH$_2$), 37.7-37.3 (m, CDH), 30.0 (CH$_2$), 29.3 (CH$_2$), 28.8-28.5 (m, CDH), 26.5 (CH$_2$), 26.4 (CH$_2$); IR (thin film): 3396, 3000, 2917, 2858, 1653, 1437, 1406, 1314, 1015, 951, 704, 669 cm$^{-1}$; HRMS (ESI) m/z calculated for C22H26D2N3O2 (M+H)$^+$: 368.2307, found: 368.2294.

2. Salt Formation.

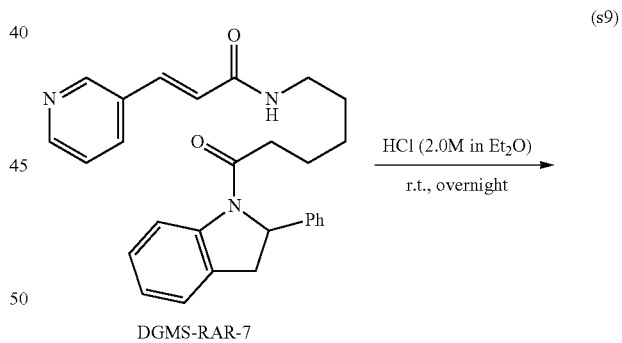

DGMS-RAR-7

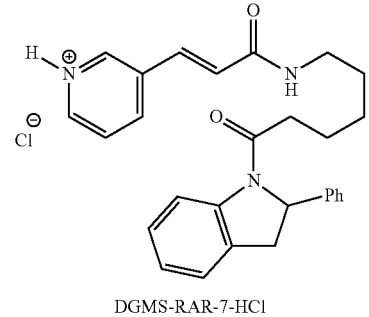

DGMS-RAR-7-HCl

To a solution of RARI analogue DGMS-RAR-7 was added a 2.0 M Et$_2$O solution of protic acid (1.0 equiv). The reaction mixture was allowed to stir at room temperature for overnight. The resulting reaction mixture was filtered through Celite and washed by MeOH. The filtrate was then dried over Na$_2$SO$_4$ and concentrated in vacuo to afford the pure product without additional purification.

Characterization Data.

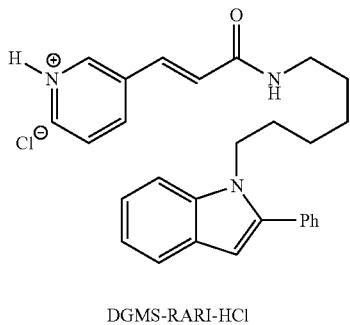 [SMILES: O=C(/C=C/c1ccc[nH+]c1)NCCCCCCn1c(-c2ccccc2)cc2ccccc21 ; [Cl-]]

DGMS-RARI-HCl

DGMS-RARI-HCl. The general procedure was followed using 11.4 mg of DGMS-RARI (0.030 mmol) in 3 mL of DCM, and 0.015 mL Of 2.0 M of HCl solution in ether (0.030 mmol). After evaporating the solvent, the product DGMS-RARI-HCl was afforded as a dark brown gel (12.3 mg, 99% yield). $^1$H NMR (500 MHz, DMSO-d$_6$) δ 8.81 (s, 1H), 8.76 (d, J=5.3 Hz, 1H), 8.47 (d, J=7.9 Hz, 1H), 8.06-7.92 (m, 1H), 7.87 (s, 1H), 7.43 (d, J=7.3 Hz, 3H), 7.39-7.27 (m, 4H), 7.10 (d, J=1.8 Hz, 1H), 6.83 (d, J=8.7 Hz, 1H), 6.28 (d, J=2.5 Hz, 1H), 5.72 (s, 1H), 5.06 (s, 2H), 4.06 (t, J=6.7 Hz, 2H), 3.00 (t, J=7.1 Hz, 2H), 1.65 (s, 2H), 1.25 (s, 2H), 1.13 (d, J=5.6 Hz, 4H); $^{13}$C NMR (125 MHz, DMSO-d$_6$) 164.1 (C), 159.2 (CH), 142.8 (CH), 142.6 (C), 138.4 (C), 135.2 (C), 132.5 (CH), 131.2 (C), 131.2 (CH), 129.4 (CH), 129.2 (CH), 129.0 (CH), 128.7 (CH), 127.9 (C), 127.6 (CH), 124.7 (CH), 123.2 (CH), 119.4 (CH), 113.2 (CH), 110.9 (CH), 39.3 (CH$_2$), 34.7 (CH$_2$), 29.4 (CH$_2$), 29.2 (CH$_2$), 26.2 (CH$_2$), 26.0 (CH$_2$); IR (thin film): 3389, 3000, 2915, 1652, 1436, 1406, 1315, 1013, 951, 704, 671 cm$^{-1}$; HRMS (ESI) m/z calculated for C$_{28}$H$_{29}$N$_3$OCl (M−H)$^+$: 458.1999, found: 458.1991; also parent compound observed m/z calculated for C$_{28}$H$_{30}$N$_3$O (M+H)$^+$: 424.2389, found: 424.2379.

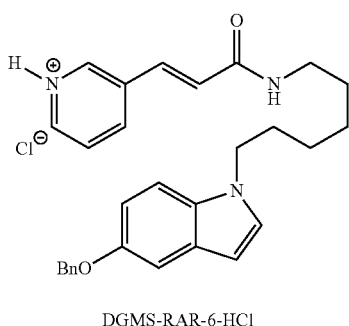 [SMILES: O=C(/C=C/c1ccc[nH+]c1)NCCCCCCn1ccc2cc(OCc3ccccc3)ccc21 ; [Cl-]]

DGMS-RAR-6-HCl

DGMS-RAR-6-HCl. The general procedure was followed using 9.1 mg of DGMS-RAR-6 (0.020 mmol) in 3 mL of DCM, and 0.010 mL Of 2.0 M of HCl solution in ether (0.020 mmol). After evaporating the solvent, the product DGMS-RAR-6-HCl was afforded as a dark brown gel (9.8 mg, 99% yield). $^1$H NMR (500 MHz, DMSO-d$_6$) δ 8.56-8.51 (m, 2H), 7.93 (d, J=7.3 Hz, 2H), 7.82-7.76 (m, 2H), 7.55-7.52 (m, 1H), 7.48-7.43 (m, 2H), 7.40-7.33 (m, 2H), 7.32-7.27 (m, 2H), 7.10 (s, 1H), 6.90-6.82 (m, 2H), 6.28 (s, 1H), 5.07 (s, 2H), 4.09-4.05 (m, 2H), 2.95-2.92 (m, 2H), 2.40 (t, J=7.3 Hz, 2H), 1.77-1.66 (m, 2H), 1.25-1.22 (m, 4H); $^1$C NMR (125 MHz, DMSO-d$_6$) δ 170.9 (C), 153.4 (C), 146.5 (CH), 144.3 (CH), 140.6 (CH), 139.2 (C), 138.1 (C), 133.0 (C), 129.8 (C), 129.6 (CH), 128.1 (CH), 125.2 (CH), 113.0 (CH), 112.1 (CH), 111.8 (CH), 110.9 (CH), 110.0 (CH), 104.2 (CH), 102.2 (CH), 100.4 (CH), 70.2 (CH2), 38.8 (CH$_2$), 36.4 (CH$_2$), 29.4 (CH$_2$), 28.4 (CH2), 26.4 (CH2), 26.2 (CH2). IR (thin film): 3394, 2986, 2881, 1652, 1436, 1406, 1315, 1013, 951, 704 cm$^{-1}$; HRMS (ESI) m/z calculated for C$_{29}$H34N$_3$O$_2$(M+3H)$^+$: 456.2651, found: 456.2641 same as the mass of the parent compound.

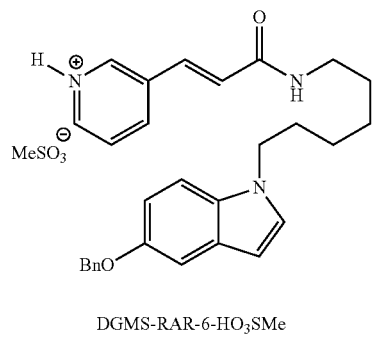 [SMILES: "MeSO3" ; O=C(/C=C/c1ccc[nH+]c1)NCCCCCCn1ccc2cc(OCc3ccccc3)ccc21]

DGMS-RAR-6-HO$_3$SMe

DGMS-RAR-6-HO$_3$SMe. The general procedure was followed using 9.1 mg of DGMS-RAR-6 (0.020 mmol) in 3 mL of DCM, and 0.010 mL Of 2.0 M of HCl solution in ether (0.020 mmol). After evaporating the solvent, the product DGMS-RAR-6-HO$_3$SMe was afforded as a dark brown gel (10.9 mg, 99% yield). $^1$H NMR (500 MHz, DMSO-d$_6$) δ 8.80-8.76 (m, 2H), 8.47-8.45 (m, 2H), 7.99-7.97 (m, 2H), 7.84-7.82 (m, 2H), 7.48-7.23 (m, 6H), 7.10 (s, 1H), 6.83 (d, J=8.6 Hz, 1H), 6.28 (s, 1H), 5.07 (s, 2H), 4.08-4.06 (m, 2H), 2.98-2.96 (m, 2H), 2.37 (s, 3H), 1.82 (dd, J=25.0, 11.1 Hz, 2H), 1.72-1.65 (m, 2H), 1.26-1.20 (m, 4H); $^{13}$C NMR (125 MHz, DMSO-d$_6$) δ 170.7 (C), 153.5 (C), 146.7 (CH), 144.7 (C), 141.9 (CH), 140.1 (CH), 138.3 (C), 133.3 (C), 130.1 (C), 129.6 (CH), 128.8 (CH), 128.0 (CH), 127.2 (CH), 112.1 (CH), 111.8 (CH), 110.9 (CH), 110.0 (CH), 104.2 (CH), 102.2 (CH), 100.4 (CH), 70.2 (CH2), 38.8 (CH$_2$), 35.7 (CH$_2$), 29.4 (CH$_2$), 28.2 (CH2), 26.4 (CH2), 26.2 (CH2). IR (thin film): 3394, 2994, 2911, 1652, 1436, 1406, 1310, 1042, 952, 930, 697 cm$^{-1}$; HRMS (ESI) m/z calculated for C$_{29}$H$_{34}$N$_3$O$_2$(M+3H)$^+$: 456.2651, found: 456.2647 same as the mass of the parent compound.

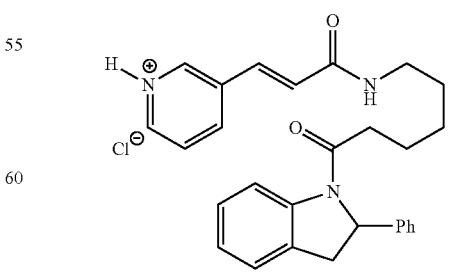

DGMS-RAR-7-HCl

DGMS-RAR-7-HCl. The general procedure was followed using 8.8 mg of DGMS-RAR-7 (0.020 mmol) in 3 mL of DCM, and 0.010 mL Of 2.0 M of HCl solution in ether (0.020 mmol). After evaporating the solvent, the product DGMS-RAR-7-HCl was afforded as a pale yellow solid (9.3 mg, 99% yield). $^1$H NMR (500 MHz, DMSO-d$_6$) δ 9.02 (s, 1H), 8.79 (d, J=5.2 Hz, 1H), 8.54 (d, J=7.9 Hz, 1H), 8.33 (s, 1H), 8.17 (d, J=7.3 Hz, 1H), 7.96-7.90 (m, 1H), 7.52 (d, J=15.9 Hz, 1H), 7.30 (d, J=6.8 Hz, 2H), 7.26-7.14 (m, 3H), 7.12 (d, J=7.7 Hz, 2H), 7.00 (t, J=7.4 Hz, 1H), 6.90 (d, J=15.9 Hz, 1H), 5.67 (d, J=9.4 Hz, 1H), 3.79-3.60 (m, 1H), 3.08 (d, J=5.1 Hz, 2H), 2.81 (d, J=16.1 Hz, 1H), 1.91 (s, 1H), 1.52-1.03 (m, 8H); $^{13}$C NMR (125 MHz, DMSO-d$_6$) δ 171.7 (C), 164.2 (C), 144.2 (C), 143.8 (CH), 143.2 (CH), 141.2 (CH), 134.2 (C), 133.0 (CH), 130.1 (C), 129.5 (CH), 128.0 (CH), 127.9 (CH), 127.7 (CH), 127.0 (CH), 125.6 (CH), 125.2 (CH), 124.2 (CH), 120.4 (C), 116.5 (CH), 62.1 (CH), 39.2 (CH$_2$), 39.0 (CH$_2$), 35.0 (CH), 29.3 (CH$_2$), 26.5 (CH), 24.4 (CH$_2$). IR (thin film): 3266, 3067, 2928, 2858, 1711, 1665, 1591, 1554, 1462, 1410, 1363, 1262, 1222, 1089, 1023, 805, 785 cm$^{-1}$; HRMS (ESI) m/z calculated for C$_{28}$H$_{30}$N$_3$O$_2$(M+H)$^+$: 440.2338, found: 440.2332 same as the mass of the parent compound.

3. PEGylation.
Step 1:

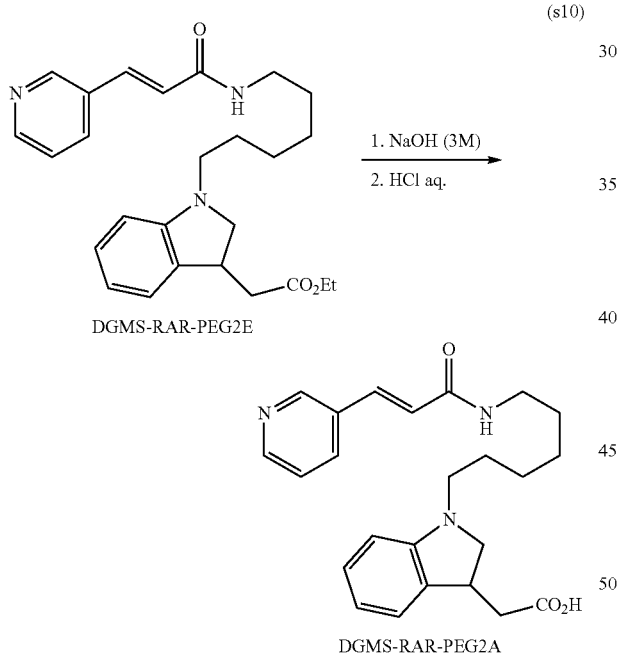

Step 1: The procedure was followed by patent reported by Popovici-Muller ad co-workers (see U.S. Patent 2010-61365072, Jul. 16, 2010: To a 0.1 M solution of (1H-indol-3-yl)-oxo-acetic acid ethyl ester (1.0 equiv) in EtOH was added a 3.0 M solution of NaOH (5.0 equiv) dropwise. The reaction mixture was heated to reflux at 80° C. for 4 h and monitored by thin layer chromatography (TLC). After complete consumption of starting materials, the reaction was cooled to room temperature and EtOH was evaporated in vacuo. The reactives were then acidified by a 1.0 N aqueous solution of HCl until the pH of the mixture was measured to be 7. The resulting reaction mixture was extracted with DCM and washed by 3×20 mL water. The organic phase was collected and dried over Na$_2$SO$_4$. Evaporation of the solvent in vacuo afforded carboxylic acid product and was used in the following reaction without additional purification.

Step 2:

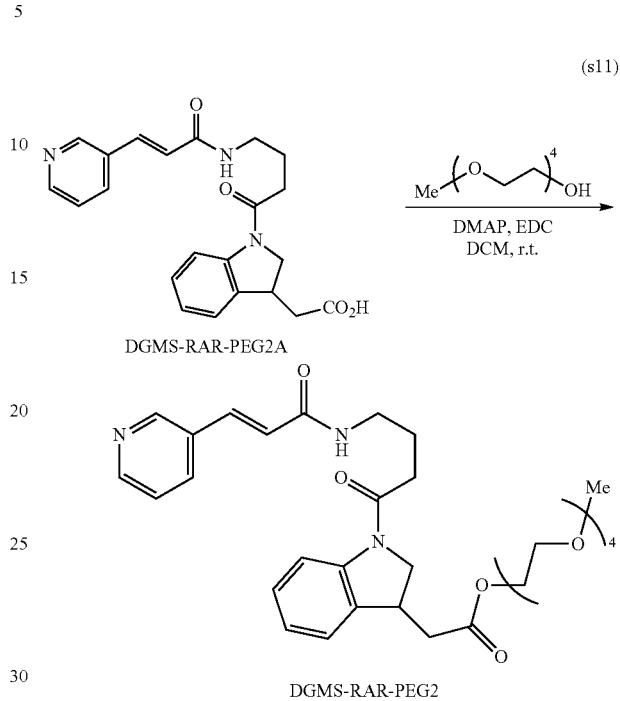

Step 2: The procedure of synthesizing PEGylated DGMS-RARI analogues was followed by patent reported by Yu and Lee (see U.S. Patent Application Publication No. 2008/61058189): To a 0.3 M solution of the carboxylic acid starting material (1.0 equiv) in DCM was added tetraethylene glycol (1.2 equiv), EDC (2.0 equiv), and DAMP (0.2 equiv) sequentially. After allowing the reaction mixture to stir at room temperature overnight, the reactives were quenched by the addition of 10 mL of a saturated NaHCO$_3$ aqueous solution. The reaction mixture was then washed with 2×20 mL water and extracted with DCM. The organic phase was dried over Na$_2$SO$_4$, filtered and the filtrate was concentrated in vacuo. The resulting residue was purified by MPLC to afford the product.

Characterization Data.

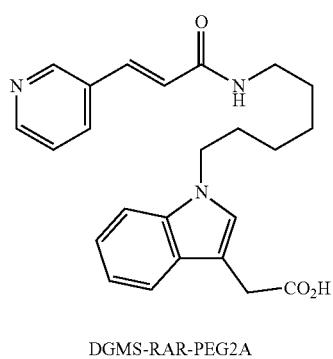 [SMILES: O=C(O)Cc1cn(CCCCCCNC(=O)/C=C/c2cccnc2)c2ccccc12]

DGMS-RAR-PEG2A. The general procedure of Step 1 was followed using 50.0 mg of DGMS-RAR-PEG2E (0.115 mmol) and 0.192 mL of a 5.0 N NaOH aqueous solution in 0.81 mL EtOH. After evaporating the solvent, the crude product DGMS-RAR-PEG2A was afforded as a light yellow foam (50 mg, 100%): $^1$H NMR (500 MHz, DMSO) δ 8.73 (s, 1H), 8.53 (s, 1H), 8.14 (s, 1H), 7.95 (d, J=8.0 Hz, 1H), 7.47 (d, J=7.5 Hz, 1H), 7.43-7.39 (m, 3H), 7.24 (s, 1H), 7.09 (t, J=8.0 Hz, 1H), 6.97 (t, J=7.5 Hz, 1H), 6.69 (d, J=16.0 Hz, 1H), 4.10 (t, J=7.0 Hz, 2H), 3.60 (s, 2H), 3.12 (d, J=6.5 Hz, 2H), 1.71 (t, J=7.0 Hz, 2H), 1.43-1.38 (m, 2H), 1.32-1.24 (m, 5H); HRMS (ESI) m/z calculated for $C_{24}H_{28}N_3O_3$ (M+H)$^+$: 406.2131, found: 406.2142. The product was used in the following reaction without additional purification.

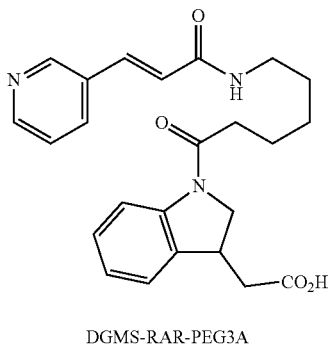 [SMILES: O=C(O)CC1CN(C(=O)CCCCCNC(=O)/C=C/c2cccnc2)c2ccccc21]

DGMS-RAR-PEG3A

DGMS-RAR-PEG3A. The general procedure of Step 1 was followed using 320 mg of DGMS-RAR-PEG3E (0.697 mmol) and 1.16 mL of a 5.0 N NaOH aqueous solution in 6.0 mL EtOH. After evaporating the solvent, the crude product DGMS-RAR-PEG3A was afforded as a red foam (235 mg, 74% yield): HRMS (ESI) m/z calculated for $C_{24}H_{28}N_3O_4$ (M+H)$^+$: 422.2080, found: 422.2092. The product was used in the following reaction without additional purification.

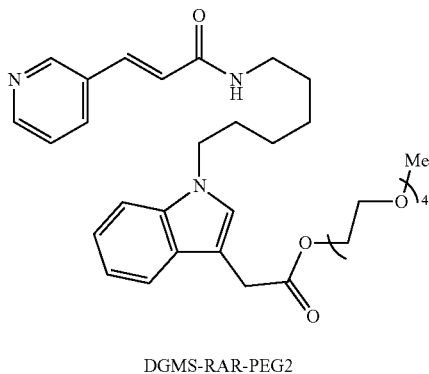

DGMS-RAR-PEG2

DGMS-RAR-PEG2. The general procedure of Step 2 was followed using 50.0 mg of DGMS-RAR-PEG2A (0.123 mmol), 30.8 mg of tetraethylene glycol (0.148 mmol), 47.2 mg of EDC (0.25 mmol), and 3.05 mg of DAMP (0.025 mmol) in 0.41 mL of DCM. Purification by MPLC chromatography (10% MeOH in DCM) afforded DGMS-RAR-PEG2 as a yellow gel (43 mg, 73% yield): $^1$H NMR (500 MHz, CDCl$_3$) δ 8.74 (s, 1H), 8.57 (s, 1H), 7.77 (d, J=8.0 Hz, 1H), 7.61 (s, 1H), 7.58 (d, J=6.5 Hz, 1H), 7.31-7.29 (m, 2H), 7.19 (t, J=8.0 Hz, 1H), 7.11-7.09 (m, 2H), 6.44 (d, J=15.5 Hz, 1H), 5.82 (s, 1H), 4.25 (t, J=5.0 Hz, 2H), 4.08 (t, J=7.0 Hz, 2H), 3.79 (s, 2H), 3.68 (t, J=5.0 Hz, 3H), 3.65-3.61 (m, 6H), 3.59 (s, 3H), 3.54-3.52 (m, 2H), 3.40-3.30 (m, 5H), 1.83 (t, J=7.5 Hz, 2H), 1.52 (t, J=7.0 Hz, 2H), 1.36-1.33 (m, 4H); 13C NMR (125 MHz, CDCl$_3$) 172.1 (C), 165.1 (C), 150.3 (CH), 149.2 (CH), 148.2 (C), 137.2 (CH), 136.2 (C), 134.3 (CH), 130.7 (C), 127.8 (C), 126.8 (CH), 123.7 (CH), 122.9 (CH), 121.6 (CH), 119.1 (CH), 109.4 (CH), 106.7 (CH), 71.9 (CH$_2$), 70.61 (CH$_2$), 70.56 (CH$_2$), 69.1 (CH$_2$), 64.0 (CH$_2$), 59.0 (CH$_3$), 46.2 (CH$_2$), 39.6 (CH$_2$), 31.2 (CH$_2$), 30.0 (CH$_2$), 29.4 (CH$_2$), 26.7 (CH$_2$), 26.5 (CH$_2$) only peaks visible. IR (thin film): 3303, 2924, 2857, 1734, 1664, 1625, 1541, 1469, 1106, 806, 742 cm$^{-1}$; HRMS (ESI) m/z calculated for $C_{33}H_{46}N_3O_7$ (M+H)$^+$: 596.3336, found: 596.3311.

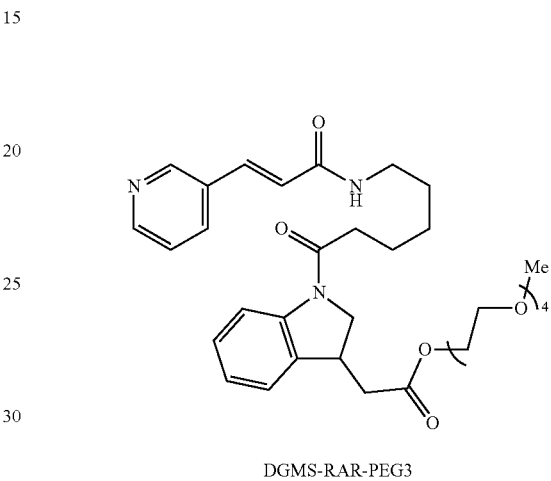

DGMS-RAR-PEG3

DGMS-RAR-PEG3. The general procedure of Step 2 was followed using 200 mg of DGMS-RAR-PEG3A (0.465 mmol), 117 mg of tetraethylene glycol (0.56 mmol), 178 mg of EDC (0.930 mmol), and 11.4 mg of DAMP (0.093 mmol) in 1.55 mL of DCM. Purification by MPLC chromatography (10% MeOH in DCM) afforded DGMS-RAR-PEG3 as a yellow gel (141 mg, 51% yield): 1H NMR (500 MHz, CDCl$_3$) δ 8.70 (s, 1H), 8.51 (d, J=4.5 Hz, 1H), 8.21 (d, J=8.0 Hz, 1H), 7.74 (d, J=7.5 Hz, 1H), 7.57 (d, J=15.5 Hz, 1H), 7.25-7.23 (m, 1H), 7.18 (t, J=8.0 Hz, 1H), 7.14-7.10 (m, 1H), 7.00 (t, J=7.5 Hz, 1H), 6.74-6.72 (m, 1H), 6.56 (d, J=16.0 Hz, 1H), 4.29-4.22 (m, 3H), 3.82-3.72 (m, 2H), 3.67 (t, J=4.5 Hz, 2H), 3.62-3.58 (m, 10H), 3.49 (t, J=4.5 Hz, 2H), 3.44-3.38 (m, 2H), 3.32-3.30 (m, 3H), 2.85 (dd, J=16.5, 4.0 Hz, 1H), 2.55 (dd, J=16.5, 10.0 Hz, 1H), 2.42 (t, J=7.0 Hz, 2H), 1.76-1.70 (m, 2H), 1.64-1.58 (m, 2H), 1.48-1.42 (m, 2H); $^{13}$C NMR (125 MHz, CDCl$_3$) δ 171.7 (C), 171.3 (C), 165.3 (C), 150.2 (CH), 149.2 (CH), 142.7 (C), 136.7 (CH), 134.2 (CH), 133.0 (C), 130.9 (C), 128.4 (CH), 123.9 (CH), 123.7 (CH), 123.6 (CH), 123.5 (CH), 117.0 (CH), 71.9 (CH$_2$), 70.60 (CH$_2$), 70.58 (CH$_2$), 70.55 (CH$_2$), 70.52 (CH$_2$), 69.0 (CH$_2$), 63.9 (CH$_2$), 59.0 (CH), 54.2 (CH$_2$), 39.7 (CH$_2$), 39.0 (CH$_2$), 36.6 (CH$_3$), 35.5 (CH$_2$), 28.8 (CH$_2$), 26.3 (CH$_2$). 23.3 (CH$_2$) only peaks visible; IR (thin film): 3306, 2925, 2869, 1731, 1660, 1544, 1481, 1411, 1283, 1103, 1025, 980, 852, 758 cm$^{-1}$; HRMS (ESI) m/z calculated for $C_{33}H_{46}N_3O_8$ (M+H)$^+$: 612.3285, found: 612.3279.

2. Synthesis of DGMS-RAR-mPEG3.

Step 1:

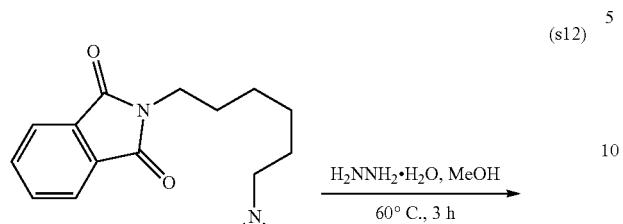

(s12)

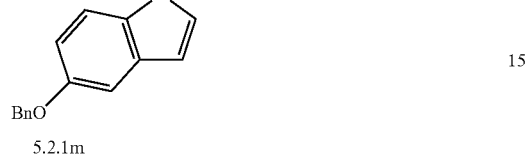

N-(6-Indolehexyl)-amine 5.2.2'a. The general procedure was followed using 45.3 mg of 5.2.1m (0.10 mmol), 25.0 mg of hydrazine hydrate (0.5 mmol) in 1.0 mL of MeOH. The crude product 5.2.2'a was afforded as a yellow gel (33 mg, quant. yield): $^1$H NMR (500 MHz, CDCl$_3$) δ 7.49 (d, J=7.5 Hz, 2H), 7.40 (t, J=7.0 Hz, 2H), 7.33 (t, J=7.5 Hz, 1H), 7.24 (d, J=9.0 Hz, 1H), 7.18 (s, 1H), 7.07 (d, J=3.0 Hz, 1H), 6.96 (d, J=9.0 Hz, 1H), 6.40 (d, J=3.0 Hz, 1H), 5.11 (s, 2H), 4.08 (t, J=7.0 Hz, 2H), 2.67 (t, J=7.0 Hz, 2H), 1.84 (q, J=7.0 Hz, 2H), 1.44-1.28 (m, 8H). The amine product was used in the subsequent reaction without additional purification or characterization.

Step 2:

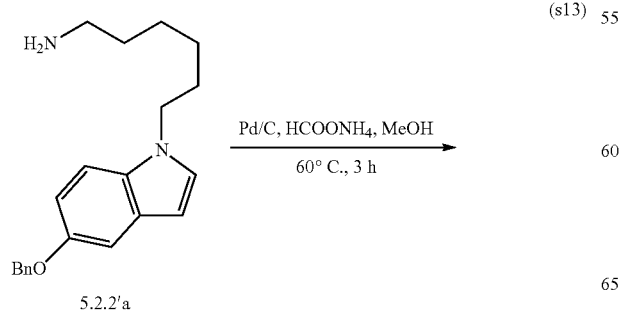

(s13)

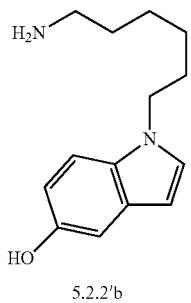

N-(6-Indolehexyl)-amine 5.2.2'b. 32.3 mg of 5.2.2'a (0.10 mmol), 60 mg of 10 wt % Pd/C (60 mg/0.1 mmol of SM) and 32 mg of HCOONH$_4$ (0.5 mmol, 5.0 equiv) was refluxed in 2.0 mL of MeOH for 3 h. When the reaction was complete (as monitored by TLC), the reaction mixture was cooled to room temperature. The reaction mixture was filtered through a small Celite pad. The pad was washed further with 2×5 mL MeOH. The solvent was then evaporated under reduced pressure to give the crude product 5.2.2'b as a yellow gel (23 mg, quant. yield): $^1$H NMR (500 MHz, CDCl$_3$) δ 7.15 (d, J=8.5 Hz, 1H), 7.02-7.00 (m, 2H), 6.77-6.74 (m, 1H), 6.32-6.29 (m, 1H), 4.03 (t, J=7.0 Hz, 2H), 2.68 (t, J=7.0 Hz, 2H), 1.83-1.77 (m, 3H), 1.43 (quin, J=7.0 Hz, 2H), 1.34-1.26 (m, 6H). The product was used in the subsequent reaction without additional purification or characterization.

Step 3:

(s14)

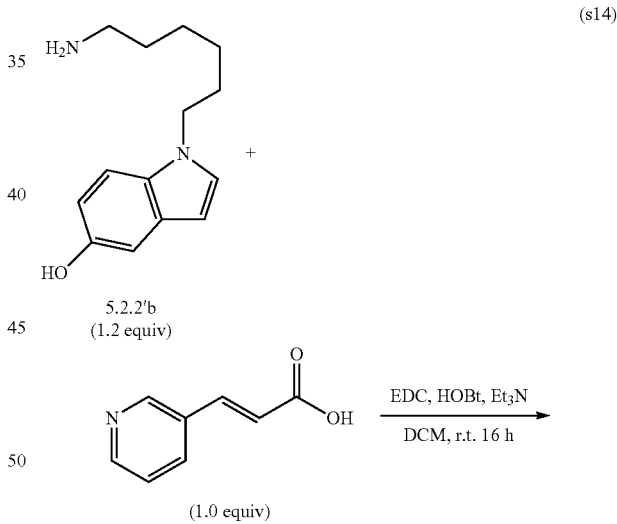

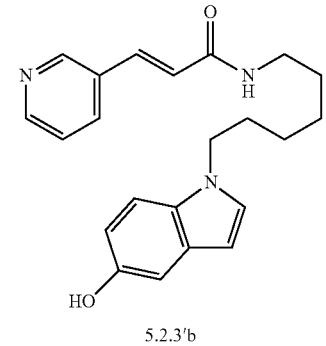

135

(E)-N-(6-(1H-Indol-1-yl)hexyl)-3-(pyridin-3-yl)acrylamide 5.2.3'b. The general procedure was followed using 46.5 mg of 5.2.2'b (0.2 mmol), 25.0 mg of trans-3-(3-pyridyl)acrylic acid (0.17 mmol), 65.1 mg of EDC.HCl (0.34 mmol), 35.1 mg of HOBt (0.26 mmol), and 26.3 mg of Et$_3$N (0.26 mmol) in 4 mL of CH$_2$Cl$_2$. Purification by MPLC chromatography (2% MeOH in CH$_2$Cl$_2$) afforded 5.2.3'b as a yellow gel (57 mg, 78% yield): $^1$H NMR (500 MHz, DMSO-d$_6$) δ 8.73 (d, J=5.5 Hz, 1H), 8.65-8.63 (m, 1H), 8.51 (q, J=4.5 Hz, 1H), 8.11 (q, J=6.5 Hz, 1H), 7.93 (t, J=8.0 Hz, 1H), 7.46-7.36 (m, 2H), 7.21-7.18 (m, 2H), 6.85-6.84 (m, 1H), 6.71 (d, J=15.5 Hz, 1H), 6.63 (d, J=8.0 Hz, 1H), 6.20-6.17 (m, 1H), 4.05-4.00 (m, 2H), 3.14 (t, J=6.5 Hz, 2H), 1.68 (q, J=7.5 Hz, 2H), 1.40 (t, J=7.5 Hz, 2H), 1.31-1.19 (m, 4H); $^{13}$C NMR (125 MHz, DMSO-d$_6$) δ 164.8 (C), 151.1 (C), 150.5 (CH), 149.5 (CH), 135.5 (CH), 134.3 (CH), 131.2 (C), 130.8 (C), 129.3 (C), 129.2 (CH), 124.8 (CH), 124.4 (CH), 111.6 (CH), 110.5 (CH), 104.7 (CH), 99.7 (CH), 45.9 (CH$_2$), 39.1 (CH$_2$), 30.3 (CH$_2$), 29.5 (CH$_2$), 26.5 (CH$_2$), 26.5 (CH$_2$); ATR-FTIR (thin film): 2844, 1750, 1686, 1473, 1425, 1384, 1198, 909 cm$^{-1}$. HRMS (ESI) m/z calculated for C$_{22}$H$_{26}$N$_3$O$_2$ [M+H]$^+$: 364.2025, found: 364.2022.

Step 4:

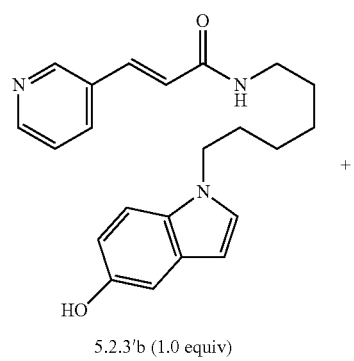

5.2.3'b (1.0 equiv)

+

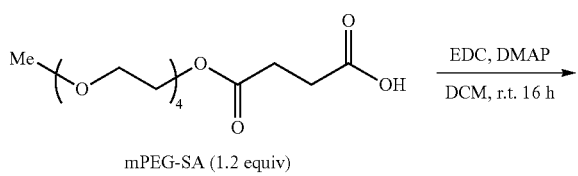

mPEG-SA (1.2 equiv)

EDC, DMAP
DCM, r.t. 16 h

136

-continued

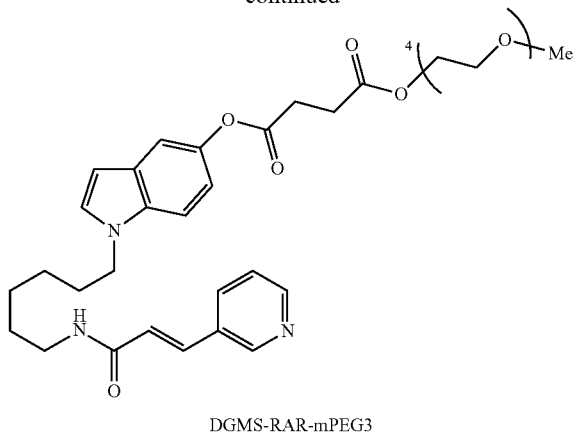

DGMS-RAR-mPEG3

DGMS-RAR-mPEG3. 36.5 mg of 5.2.3'b (0.1 mmol), 37.0 mg of mPEG-SA (see Godeau et al., Macromolecules 45:2509 (2012)) (0.12 mmol), 2.44 mg of DMAP (0.02 mmol) and 38.3 mg of EDC.HCl (0.2 mmol) were weighed in a 10 mL flask equipped with a magnetic stir bar. To the reaction mixture 2 mL of CH$_2$Cl$_2$ was added and the mixture stirred at room temperature for 16 h. After that the reaction mixture was diluted with 5 mL of CH$_2$Cl$_2$ and washed with 3 mL of 2N HCl followed by washing with 3 mL of saturated solution of NaHCO$_3$. The organic layer was then washed with 1×5 mL water followed by washing with 1×5 mL brine. The organic layer was dried over Na$_2$SO$_4$, filtered and the filtrate was concentrated in vacuo. The crude product was purified by MPLC (2% MeOH in CH$_2$Cl$_2$) to afford DGMS-RAR-mPEG3 as a clear oil (13 mg, 21% yield): $^1$H NMR (500 MHz, CDCl$_3$) δ 8.71 (d, J=2.5 Hz, 1H), 8.55-8.53 (m, 1H), 7.77-7.74 (m, 1H), 7.57 (d, J=15.5 Hz, 1H), 7.29-7.25 (m, 3H), 7.07 (d, J=3.0 Hz, 1H), 6.89 (dd, J=8.5 Hz, 2.5 Hz, 1H), 6.44 (d, J=15.5 Hz, 1H), 6.41 (d, J=3.5 Hz, 1H), 5.99 (t, J=6.0 Hz, 1H), 4.26 (t, J=5.0 Hz, 2H), 4.08 (t, J=6.6 Hz, 2H), 3.70-3.68 (m, 2H), 3.66-3.60 (m, 10H), 3.53-3.51 (m, 2H), 3.35 (s, 3H), 3.28 (q, J=6.5 Hz, 2H), 2.89 (t, J=6.5 Hz, 2H), 2.78 (t, J=6.5 Hz, 2H), 1.79 (q, J=6.5 Hz, 2H), 1.47 (q, J=7.0 Hz, 2H), 1.31-1.24 (m, 4H); $^{13}$C NMR (125 MHz, CDCl$_3$) δ 172.2 (C), 171.8 (C), 165.2 (C), 150.3 (CH), 149.2 (CH), 144.0 (C), 137.0 (CH), 134.3 (CH), 133.9 (C), 130.8 (C), 129.1 (CH), 128.7 (C), 123.7 (CH), 123.0 (CH), 115.4 (CH), 112.8 (CH), 109.7 (CH), 101.2 (CH), 71.9 (CH$_2$), 70.6 (CH$_2$), 70.6 (CH$_2$), 70.5 (CH$_2$), 69.1 (CH$_2$), 64.0 (CH$_2$), 59.0 (CH$_3$), 46.6 (CH$_2$), 39.6 (CH$_2$), 30.0 (CH$_2$), 29.4 (CH$_2$), 29.4 (CH$_2$), 29.2 (CH$_2$), 26.6 (CH$_2$), 26.5 (CH$_2$) only peaks visible; ATR-FTIR (thin film): 2878, 1737, 1668, 1626, 1450, 1265, 1219, 1146, 896, 730 cm$^{-1}$. HRMS (ESI) m/z calculated for C$_{35}$H$_{48}$N$_3$O$_9$ [M+H]$^+$: 654.3391, found: 654.3393.

CycLex NAMPT Colorimetric Assay

The ability of the compounds of the disclosure to inhibit NAMPT was determined using the CycLex NAMPT Colorimetric Assay Kit Ver.2 by MBL International Corporation.

Figure 3:
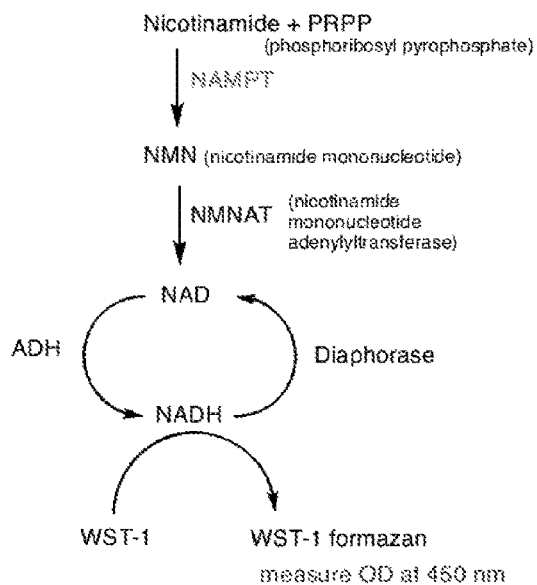
FIG. 3 depicts a schematic of the CycLex NAMPT Colorimetric Assay Kit Ver.2 to determine the ability of compounds to inhibit NAMPT.
Figure 4A:
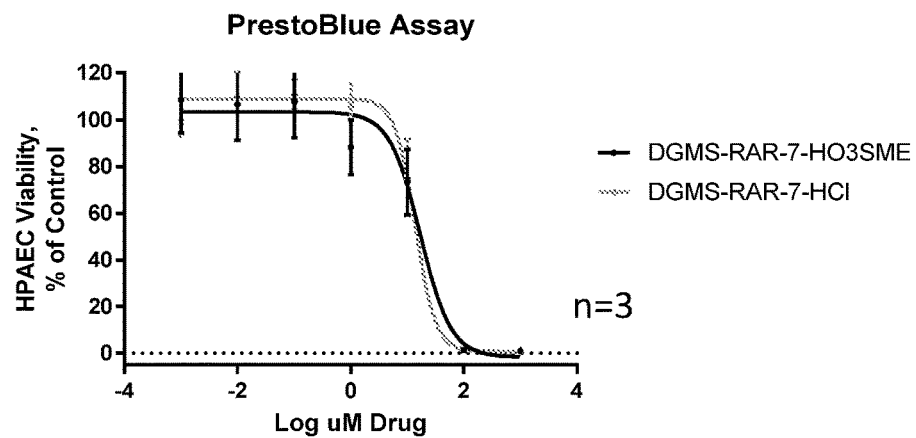
FIG. 4 depicts the effect of compounds (A) DGMS-RAR-7.HO$_3$SMe and DGMS-RAR-7.HCl; (B) DGMS-RAR-7; (C) DGMS-RARI; (D) DGMS-RAR-5-HO$_3$SMe; (E) DGMS-RAR-PEG2; and (F) DGMS-RAR-PEG3 on HPAEC viability compared to a known NAMPT inhibitor (G) FK866. As depicted, these compounds dose-dependently decrease cell viability.
Figure 4B:
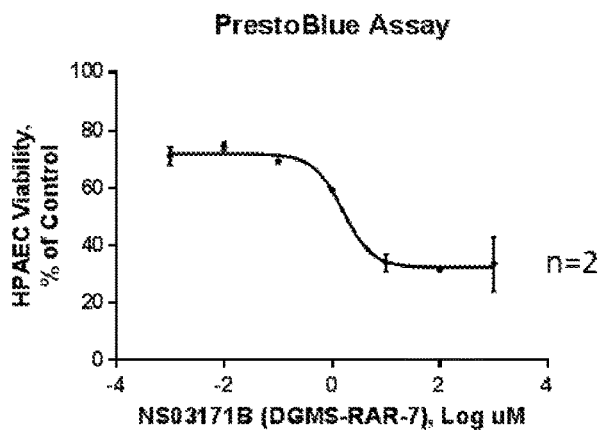
Figure 4C:
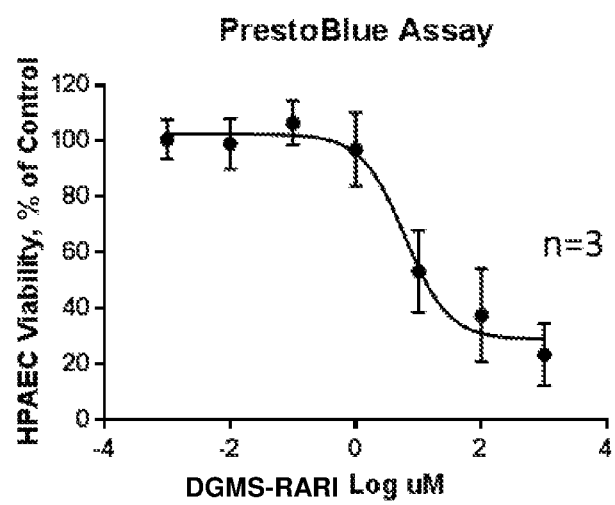
Figure 4D:
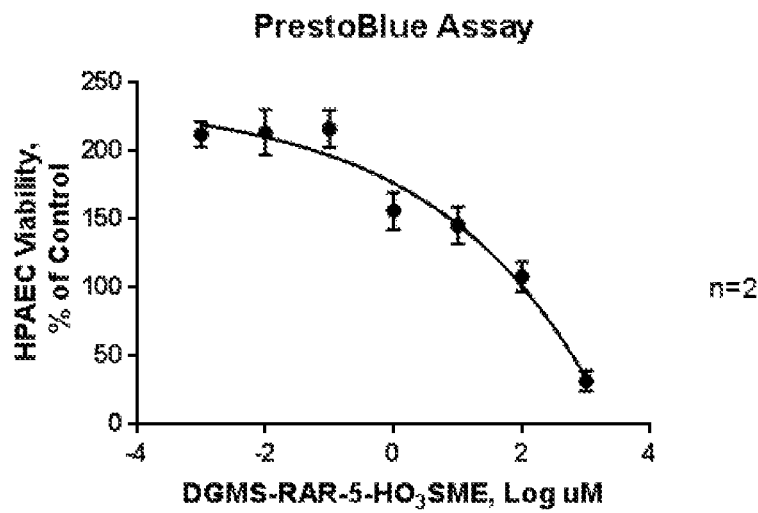
Figure 4E:
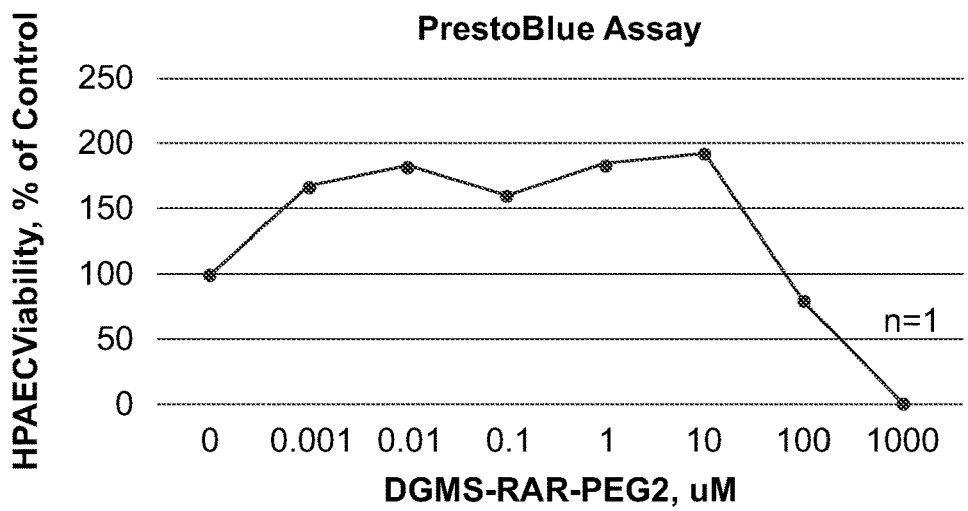
Figure 4F:
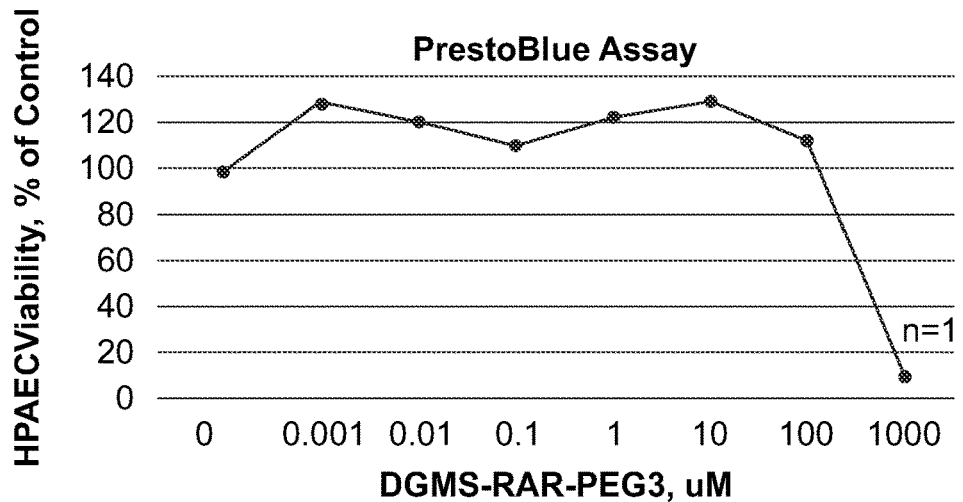
Figure 4G:
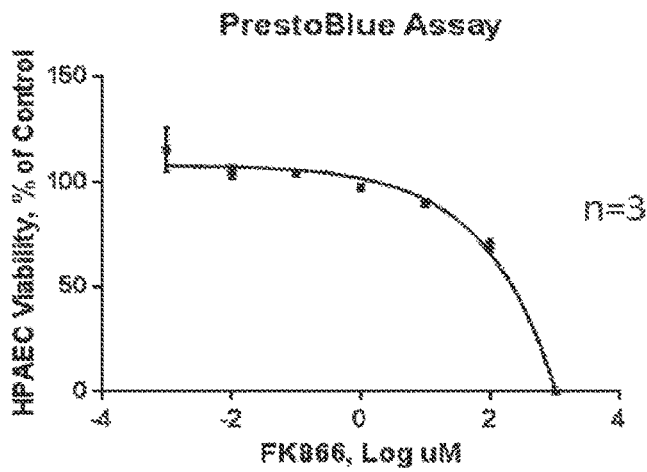
Figure 5A:
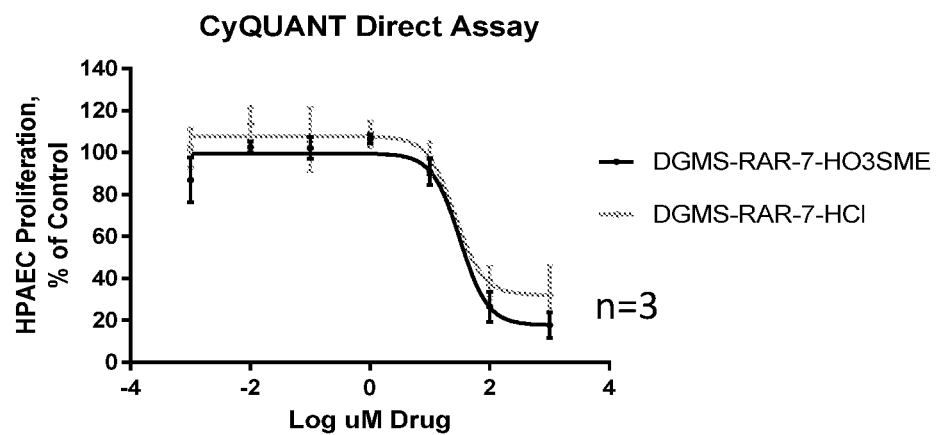
FIG. 5 depicts the effect of compounds (A) DGMS-RAR-7-HO$_3$SMe and DGMS-RAR-7-HCl; (B) DGMS-RAR-7; (C) DGMS-RARI; and (D) DGMS-RAR-PEG3 on HPAEC proliferation compared to a known NAMPT inhibitor (E) FK866 using the CYQuant Direct assay. As depicted, these compounds dose-dependently decrease cell proliferation.
Figure 5B:
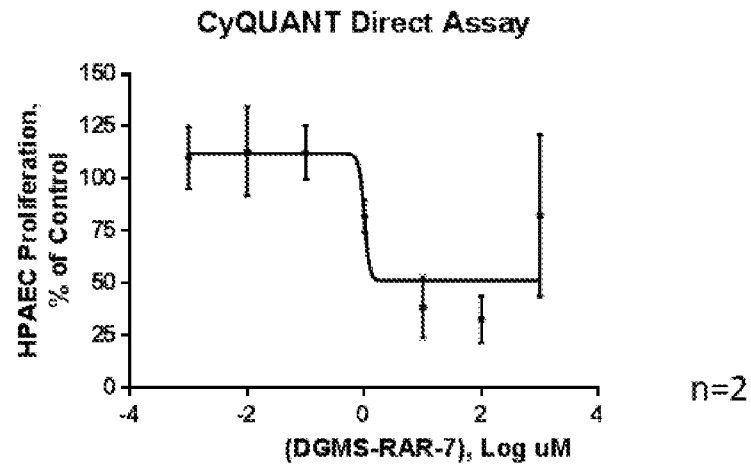
Figure 5C:
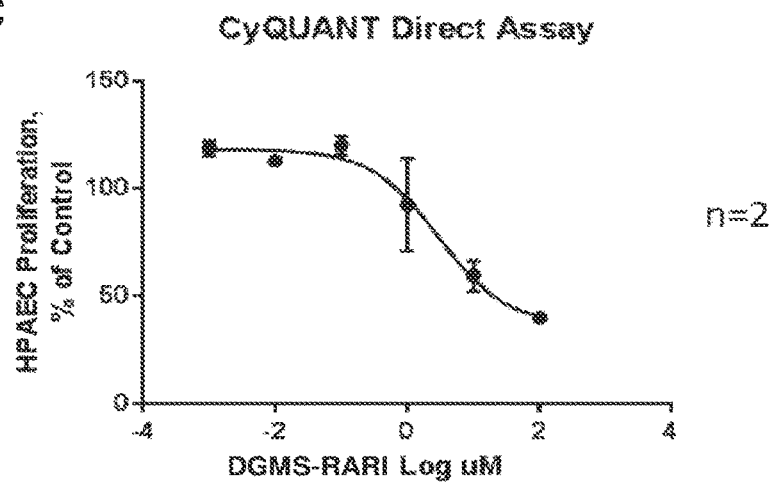
Figure 5D:
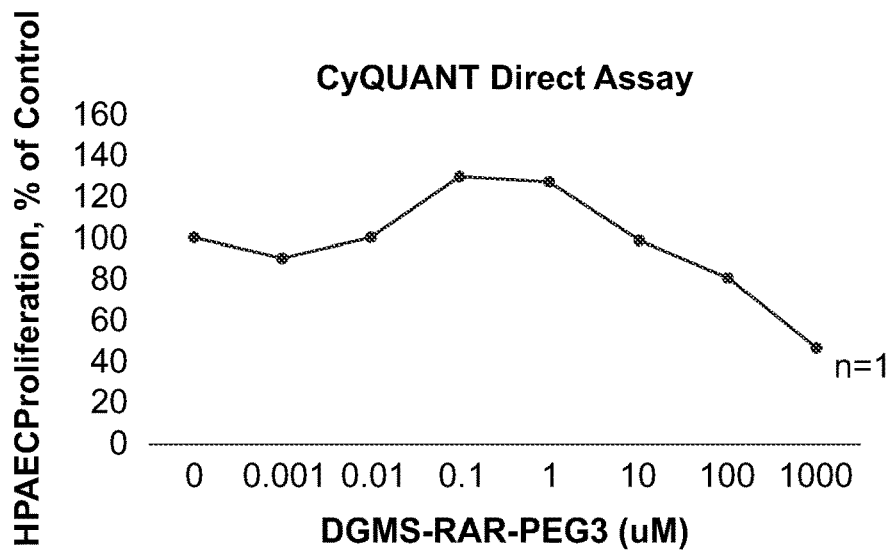
Figure 5E:
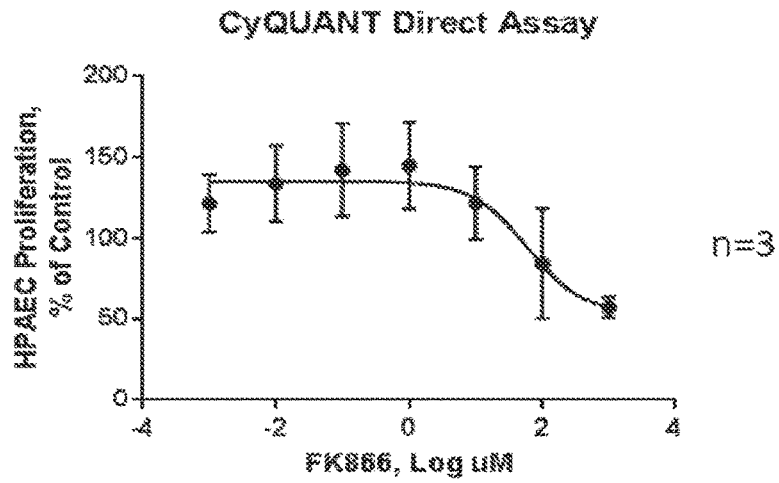
Figure 6A:
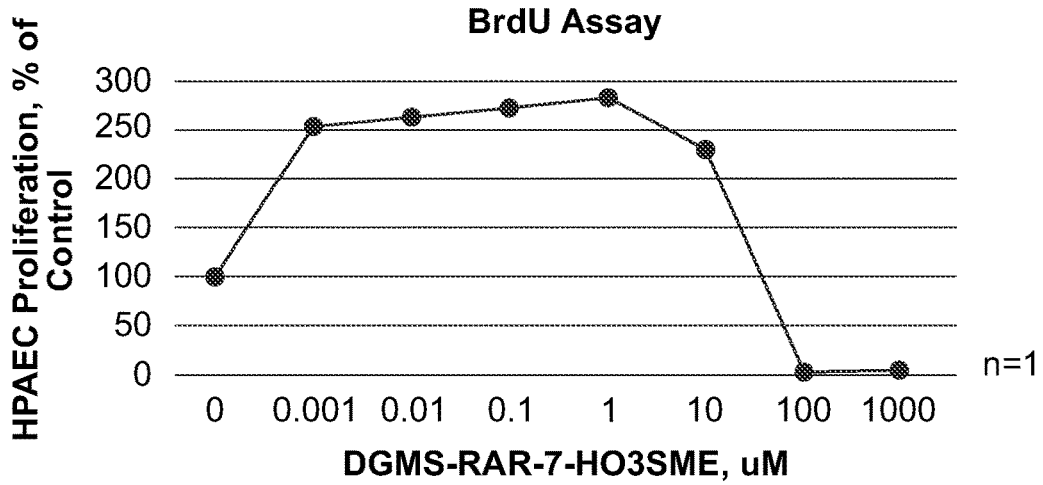
FIG. 6 depicts the effect of compounds (A) DGMS-RAR-7.HO$_3$SMe; (B) DGMS-RAR-7-HCl; (C) DGMS-RAR-7; (D) DGMS-RAR-2; (E) DGMS-RAR-5; and (F) DGMS-RAR-1 on HPAEC proliferation using the BrdU assay. As depicted, these compounds dose-dependently decrease cell proliferation
Figure 6B:
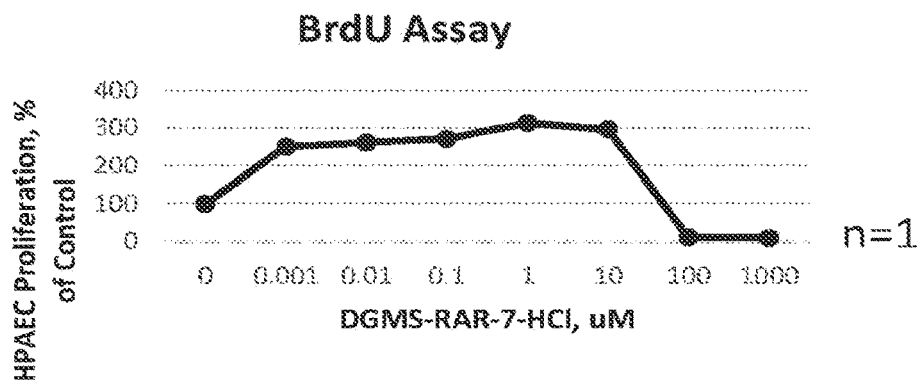
Figure 6C:
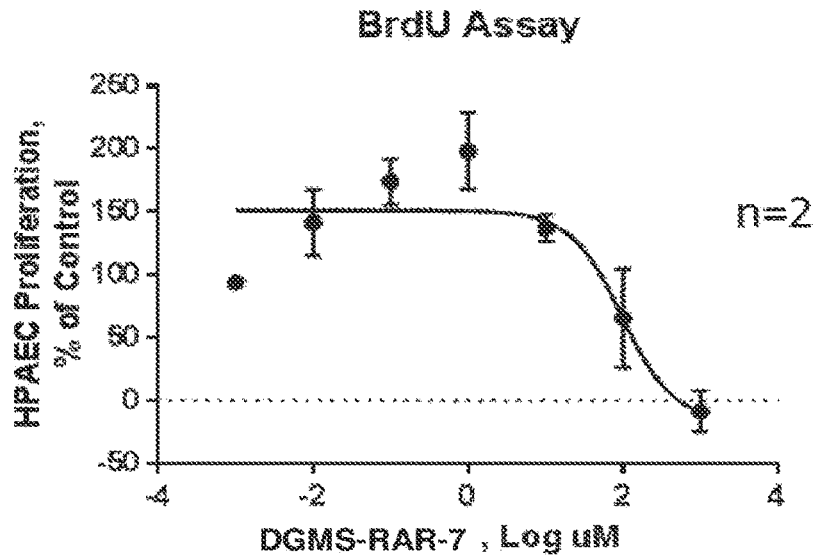
Figure 6D:
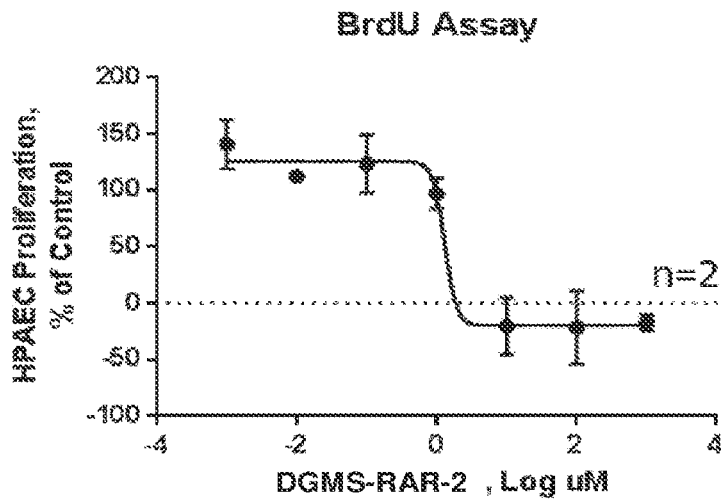
Figure 6E:
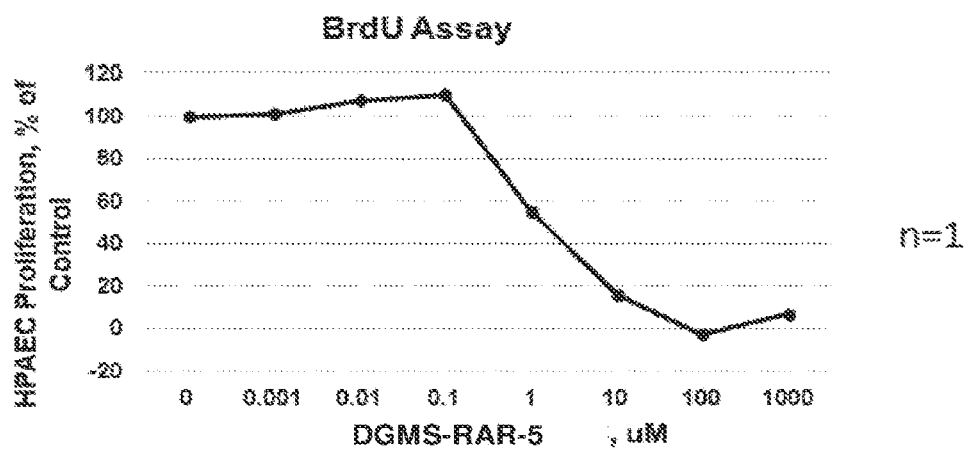
Figure 6F:
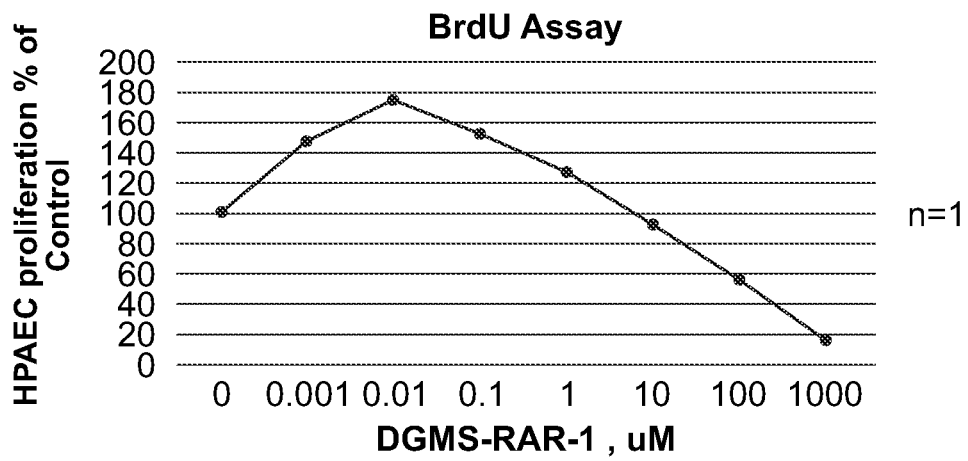
Figure 7A:
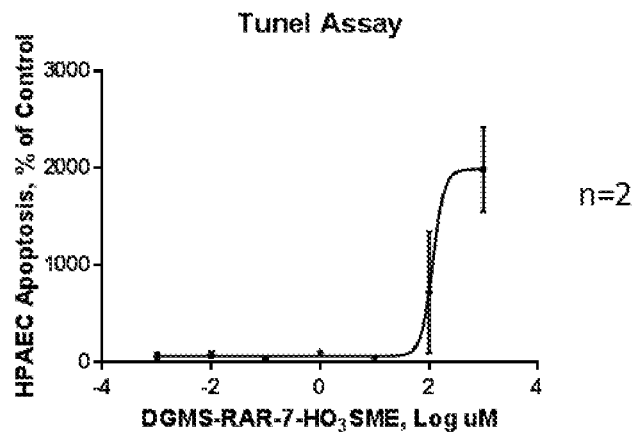
FIG. 7 depicts the effect of compounds (A) DGMS-RAR-7-HO$_3$SMe; and (B) DGMS-RAR-7-HCl on HPAEC apoptosis. As depicted, these compounds dose-dependently decrease apoptosis.
Figure 7B:
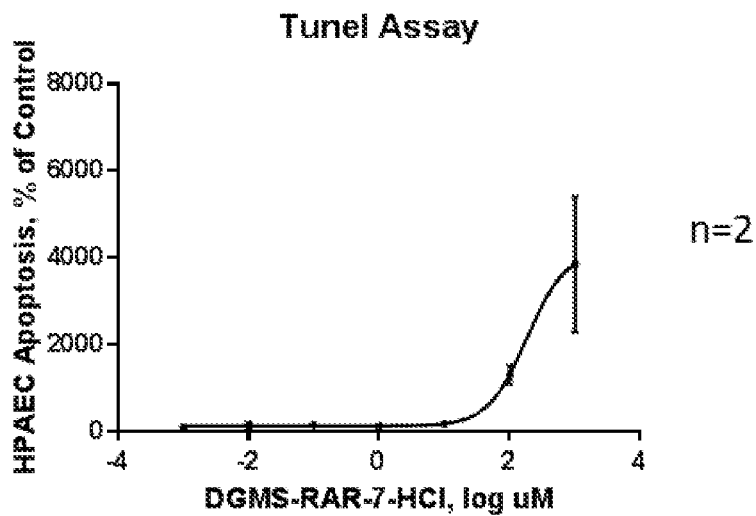
Figure 8A:
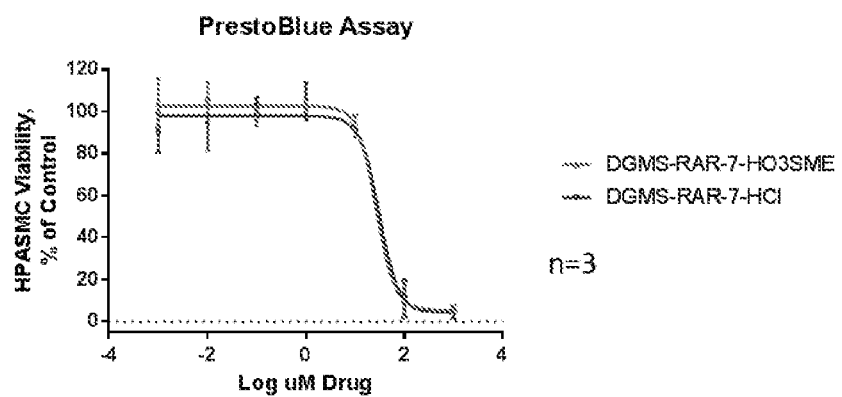
FIG. 8 depicts the effect of compounds (A) DGMS-RAR-7-HO$_3$SMe and DGMS-RAR-7-HCl; (B) DGMS-RARI; and (C) DGMS-RAR-5-HCl; on HPASMC viability compared to a known NAMPT inhibitor (D) FK866. As depicted, these compounds dose-dependently decrease cell viability
Figure 8B:
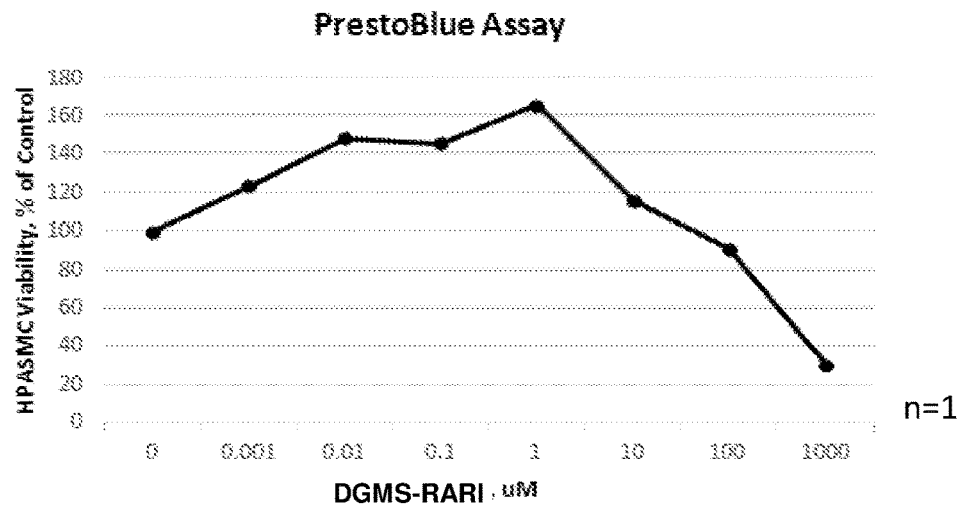
Figure 8C:
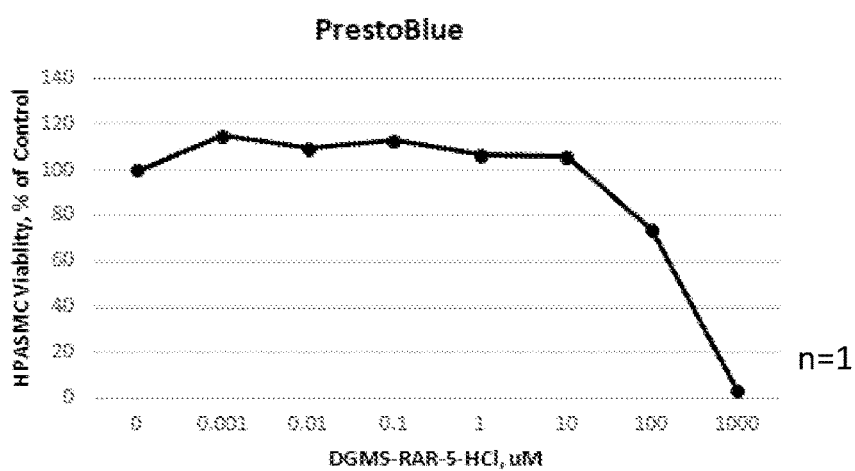
Figure 8D:
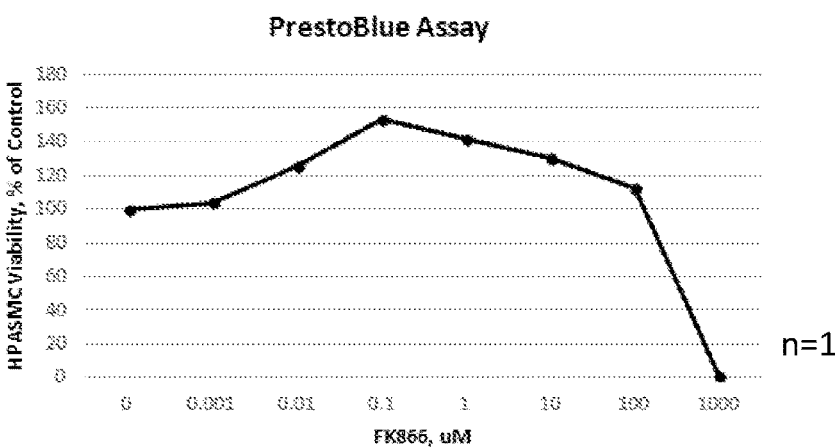
Figure 9A:
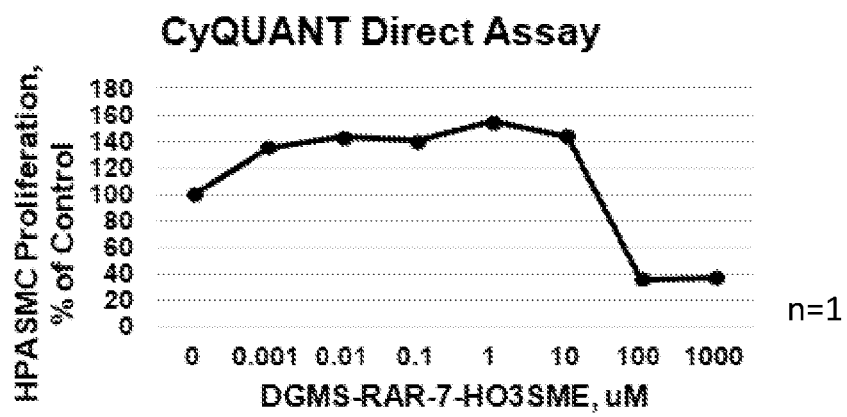
FIG. 9 depicts the effect of compounds (A) DGMS-RAR-7-HO$_3$SMe; (B) DGMS-RAR-7-HCl; and (C) DGMS-RAR-5-HCl on HPASMC proliferation compared to a known NAMPT inhibitor (D) FK866 using the CYQuant Direct assay. As depicted, these compounds dose-dependently decrease cell proliferation.
Figure 9B:
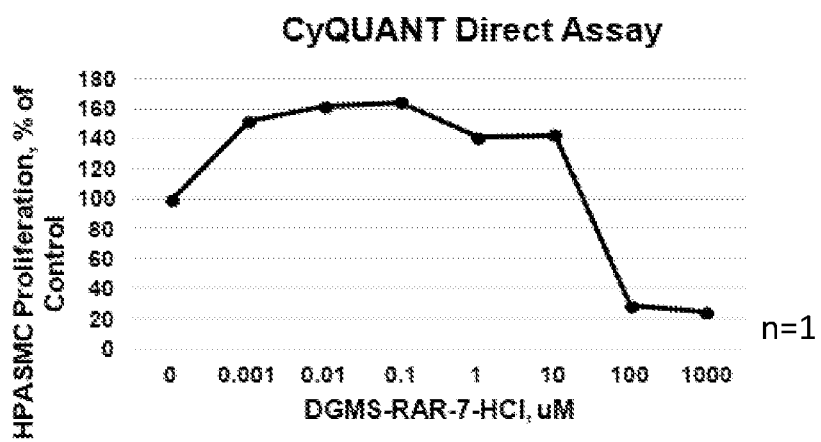
Figure 9C:
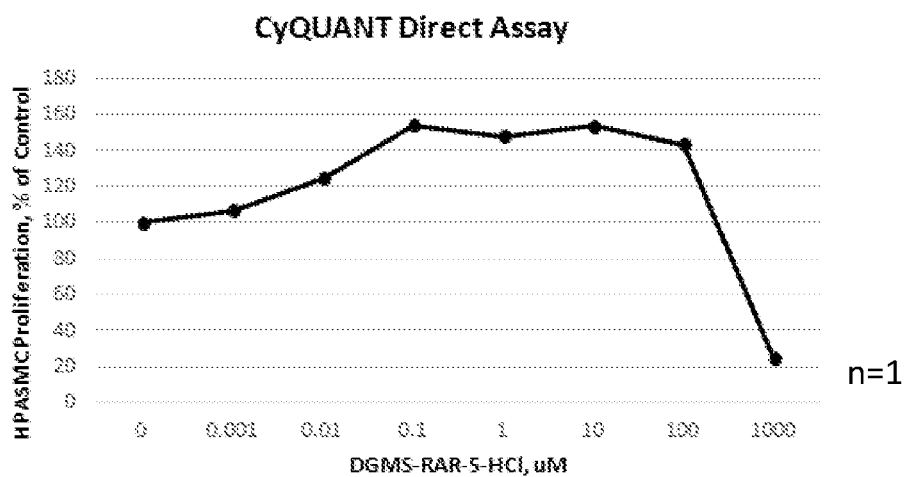
Figure 9D:
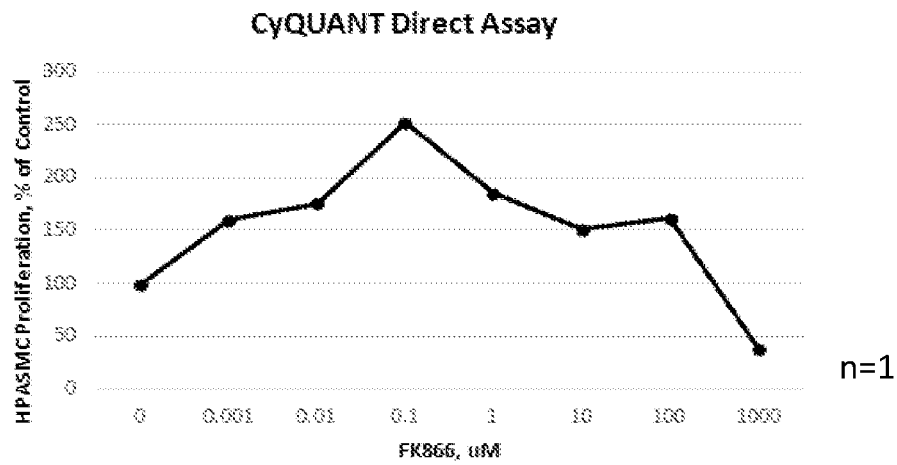
Figure 10A:
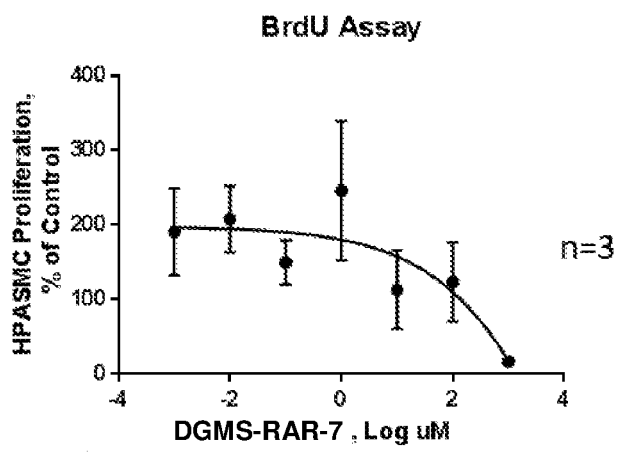
FIG. 10 depicts the effect of compounds (A) DGMS-RAR-7; (B) DGMS-RAR-7-HCl; (C) DGMS-RAR-2; (D) DGMS-RAR-5; and (E) DGMS-RAR-1 on HPASMC proliferation using the BrdU assay.
Figure 10B:
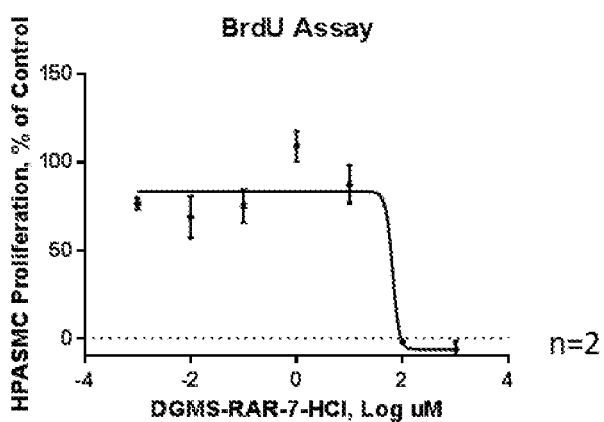
Figure 10C:
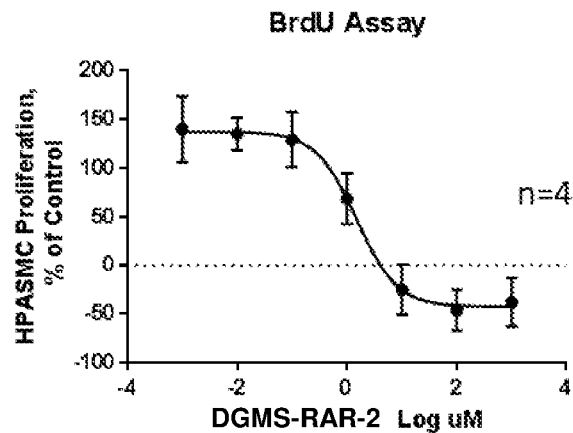
Figure 10D:
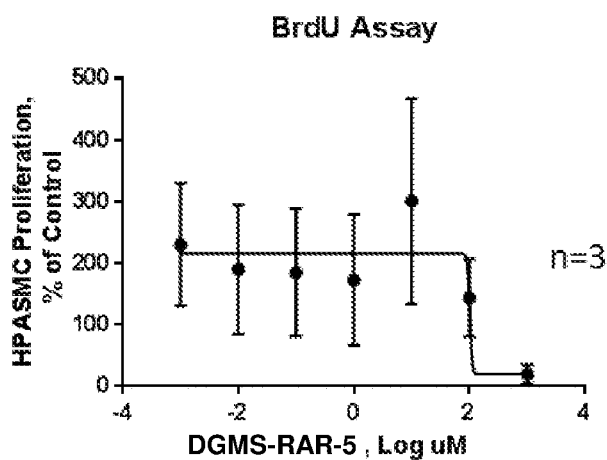
Figure 10E:
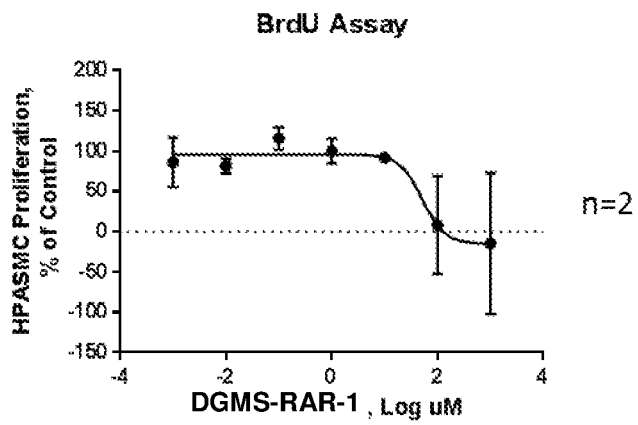
Figure 11A:
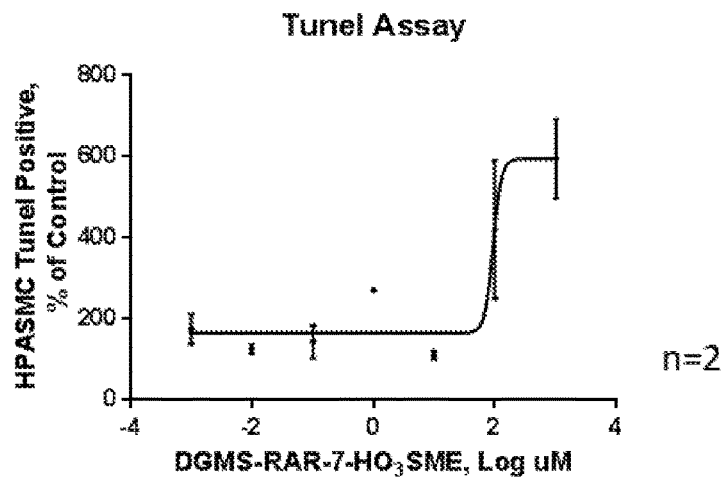
FIG. 11 depicts the effect of compounds (A) DGMS-RAR-7-HO$_3$SMe; and (B) DGMS-RAR-7-HCl on HPASMC apoptosis.
Figure 11B:
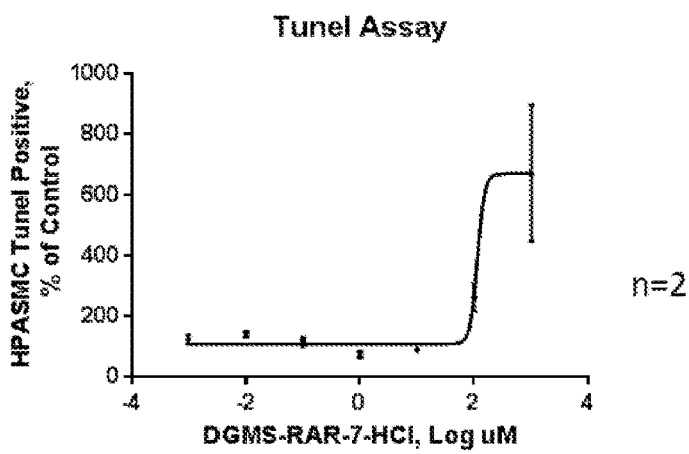

The assay detects NAMPT activity in recombinant NAMPT or endogenous NAMPT immunoprecipitated from cell lysates according to the scheme shown in FIG. 3. In this method, NAMPT converts nicotinamide to nicotinamide mononucleotide ("NMN"). Subsequently, nicotinamide mononucleotide adenylyltransferase 1 ("NMNAT1") converts NMN to NAD$^+$. Resultant NAD$^+$ can be measured by enzyme cycling reaction using alcohol dehydrogenase ("ADH"), diaphorase and WST-1.

As shown in Table 1, below, the compounds function as NAMPT inhibitors with IC$_{50}$ values as low as 10 nM.

TABLE 1

| # | Structure | NAMPT Inhibition IC$_{50}$ (nM)* | % NAMPT Inhibition at 10 µM | Solubility (2.5% v/v DMSO/water) |
|---|---|---|---|---|
| DGMS-RAR-4 | 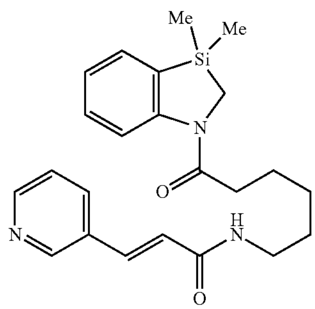 [SMILES: C[Si]1(C)CN(C(=O)CCCCCNC(=O)/C=C/c2cccnc2)c2ccccc21] | 141 | | |
| DGMS-RAR-4H2 | 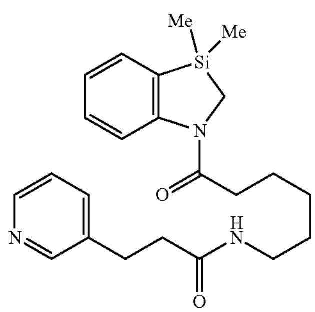 [SMILES: C[Si]1(C)CN(C(=O)CCCCCNC(=O)CCc2cccnc2)c2ccccc21] | 1588 | | |
| DGMS-RAR-4D2 | 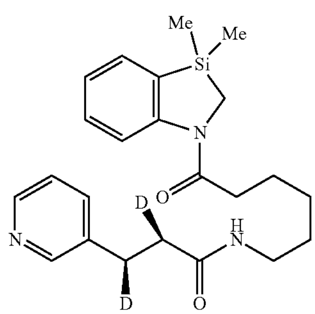 [SMILES: [2H][C@@H](C(=O)NCCCCCC(=O)N1C[Si](C)(C)c2ccccc21)[C@@H]([2H])c1cccnc1] | 2306 | | |
| DGMS-RAR-5 | 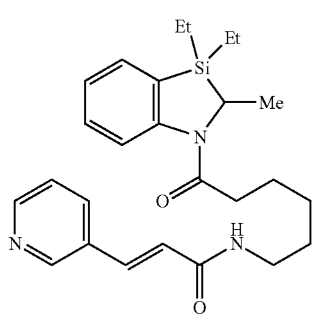 [SMILES: CC[Si]1(CC)c2ccccc2N(C(=O)CCCCCNC(=O)/C=C/c2cccnc2)C1C] | 11 | | |

TABLE 1-continued

| # | Structure | NAMPT Inhibition IC$_{50}$ (nM)* | % NAMPT Inhibition at 10 μM | Solubility (2.5% v/v DMSO/ water) |
|---|---|---|---|---|
| DGMS-RAR-5 • HCl | 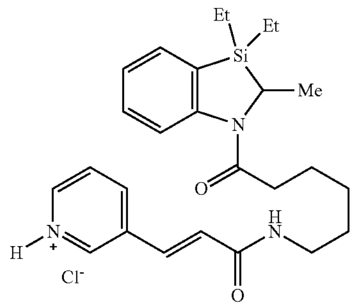 [SMILES: CC[Si]1(CC)c2ccccc2N(C(=O)CCCCCNC(=O)/C=C/c2ccc[nH+]c2)C1C ; [Cl-]] | 23 | 98 | Good |
| DGMS-RAR-5 • O$_3$SMe | 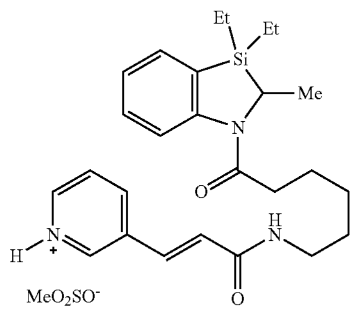 [SMILES: "MeO2SO-" ; CC[Si]1(CC)c2ccccc2N(C(=O)CCCCCNC(=O)/C=C/c2ccc[nH+]c2)C1C] | 14 | 99 | Good |
| DGMS-RAR-5 • OTs | 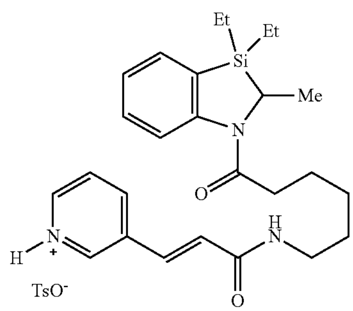 | 10.3 | | |
| DGMS-RAR-5H2 | 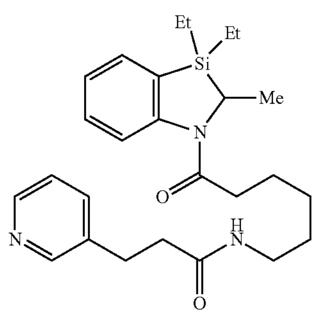 [SMILES: CC[Si]1(CC)c2ccccc2N(C(=O)CCCCCNC(=O)CCc2cccnc2)C1C] | 368 | | |
| DGMS-RAR-5D2 | 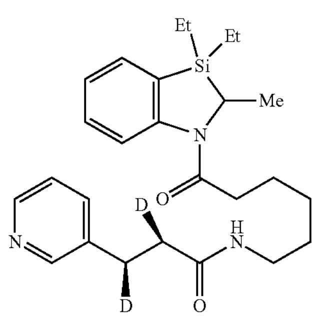 [SMILES: [2H][C@@H](C(=O)NCCCCCC(=O)N1c2ccccc2[Si](CC)(CC)C1C)[C@@H]([2H])c1cccnc1] | 668 | | |

TABLE 1-continued
| # | Structure | NAMPT Inhibition IC$_{50}$ (nM)* | % NAMPT Inhibition at 10 μM | Solubility (2.5% v/v DMSO/ water) |
|---|---|---|---|---|
| DGMS-RARI 5.2.3j | 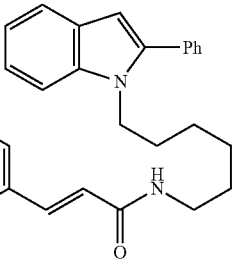 | 14 | 98% | |
| DGMS-RARI • HCl | 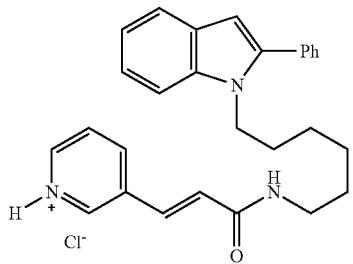 [SMILES: O=C(/C=C/c1ccc[nH+]c1)NCCCCCCn1c(-c2ccccc2)cc2ccccc21 ; [Cl-]] | 32 | 98 | Moderate |
| DGMS-RARI • HO$_3$SMe | 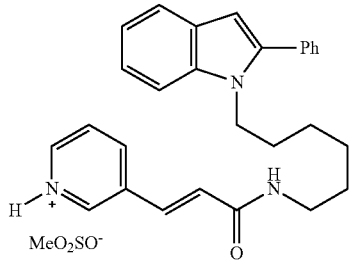 [SMILES: "MeO2SO-" ; O=C(/C=C/c1ccc[nH+]c1)NCCCCCCn1c(-c2ccccc2)cc2ccccc21] | 12 | 98 | |
| | 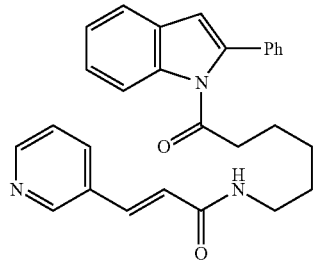 [SMILES: O=C(/C=C/c1cccnc1)NCCCCCC(=O)n1c(-c2ccccc2)cc2ccccc21] | | | |
| | 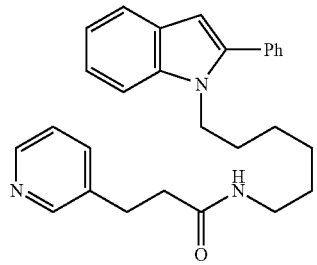 [SMILES: O=C(CCc1cccnc1)NCCCCCCn1c(-c2ccccc2)cc2ccccc21] | ~10,000 | | |

TABLE 1-continued
| # | Structure | NAMPT Inhibition IC$_{50}$ (nM)* | % NAMPT Inhibition at 10 μM | Solubility (2.5% v/v DMSO/water) |
|---|---|---|---|---|
| | 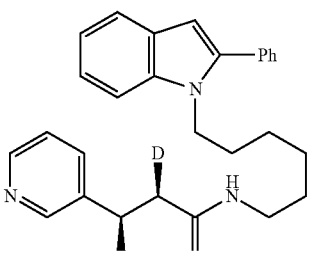 | | 92 | |
| 5.2.3e | 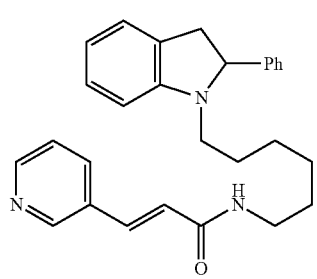 [SMILES: O=C(/C=C/c1cccnc1)NCCCCCCN1c2ccccc2CC1c1ccccc1] | | 26 | |
| DGMS-RAR-7 5.2.3p | 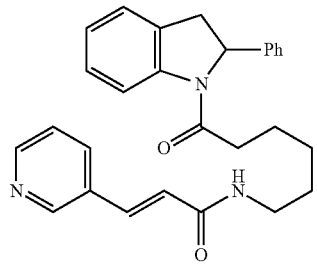 [SMILES: O=C(/C=C/c1cccnc1)NCCCCCC(=O)N1c2ccccc2CC1c1ccccc1] | | 41 | |
| DGMS-RAR-7 • HCl | 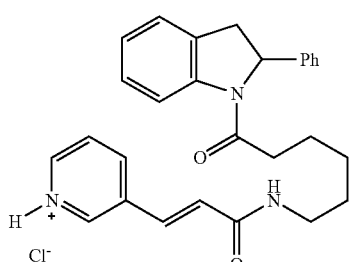 | | 15 | Good |
| DGMS-RAR-7 • HO$_3$SMe | 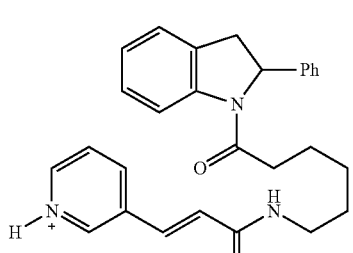 | | | |

TABLE 1-continued

| # | Structure | NAMPT Inhibition IC$_{50}$ (nM)* | % NAMPT Inhibition at 10 μM | Solubility (2.5% v/v DMSO/water) |
|---|---|---|---|---|
| | 5,6-dihydroxy-2-phenyl-indole linked via N-alkyl chain to N-(pyridin-3-yl)acrylamide | 124 | | |
| | 5,6-methylenedioxy-2-phenyl-indole linked via N-alkyl chain to N-(pyridin-3-yl)acrylamide | 386 | | |
| | 5-BnO-2-phenyl-indole linked via N-alkyl chain to N-(pyridin-3-yl)acrylamide | | | |
| DGMS-RAR-6 5.2.3m | 5-BnO-indole linked via N-alkyl chain to N-(pyridin-3-yl)acrylamide | 1009 | | |
| DGMS-RAR-6 · HCl | 5-BnO-indole linked via N-alkyl chain to N-(pyridin-3-yl)acrylamide, pyridinium chloride salt | ~100 | 97 | |

TABLE 1-continued

| # | Structure | NAMPT Inhibition IC$_{50}$ (nM)* | % NAMPT Inhibition at 10 μM | Solubility (2.5% v/v DMSO/ water) |
|---|---|---|---|---|
| DGMS-RAR-6 · HO$_3$SMe | (structure: 5-BnO-indole, N-hexyl linker, pyridinium-acrylamide, MeO$_2$SO$^-$ counterion) | ~100 | 97 | |
| DGMS-RAR-6 H2 | (structure: 5-BnO-indole, N-hexyl linker, saturated pyridyl-propanamide) | 582 | | |
| DGMS-RAR-6 D2 | (structure: 5-BnO-indole, N-hexyl linker, pyridyl-propanamide with D,D labels) | 233 | | |
| 5.2.3a | (structure: 2-Me-indole, N-hexyl linker, pyridyl-acrylamide) | 82 | | |
| | (structure: 2-Me-indole, N-hexyl linker, saturated pyridyl-propanamide) | 970 | | |

TABLE 1-continued

| # | Structure | NAMPT Inhibition IC$_{50}$ (nM)* | % NAMPT Inhibition at 10 μM | Solubility (2.5% v/v DMSO/water) |
|---|---|---|---|---|
| DGMS-RAR1 5.2.3n | 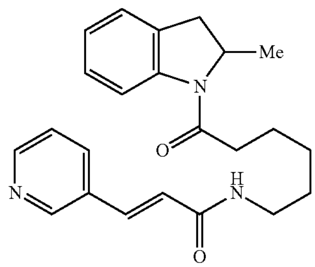 [SMILES: CC1Cc2ccccc2N1C(=O)CCCCCNC(=O)/C=C/c1cccnc1] | | 49 | |
| DGMS-RAR-1 • HCl | 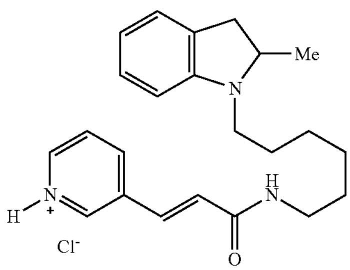 [SMILES: CC1Cc2ccccc2N1CCCCCCNC(=O)/C=C/c1ccc[nH+]c1 ; [Cl-]] | | 47 | |
| DGMS-RAR-1 • HO$_3$SMe | 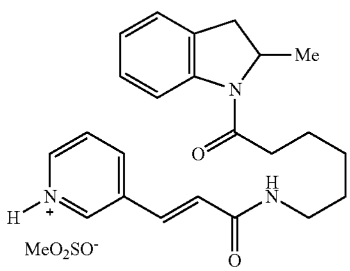 [SMILES: "MeO2SO-" ; CC1Cc2ccccc2N1C(=O)CCCCCNC(=O)/C=C/c1ccc[nH+]c1] | | 34 | |
| DGMS-RAR-1 D2 | 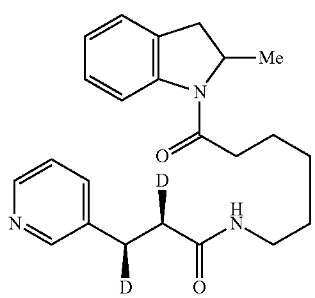 [SMILES: [2H][C@@H](C(=O)NCCCCCC(=O)N1c2ccccc2CC1C)[C@@H]([2H])c1cccnc1] | | 632 | |
| 5.2.3l | 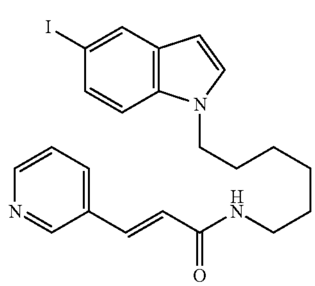 [SMILES: O=C(/C=C/c1cccnc1)NCCCCCCn1ccc2cc(I)ccc21] | | 155 | |

TABLE 1-continued
| # | Structure | NAMPT Inhibition IC$_{50}$ (nM)* | % NAMPT Inhibition at 10 μM | Solubility (2.5% v/v DMSO/ water) |
|---|---|---|---|---|
| | 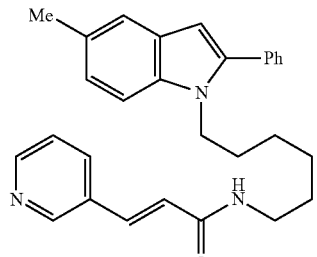 | | | |
| 5.2.3g | 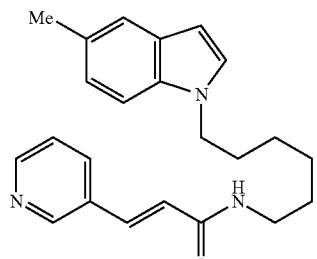 | 170 | | |
| | 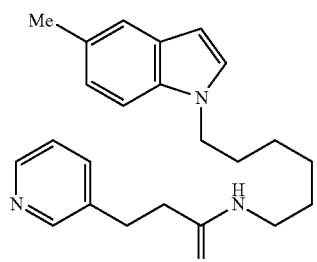 | 1530 | | |
| | 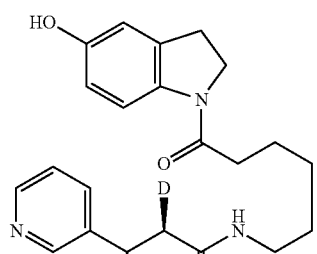 | 189 | | |
| 5.2.3t H2 | 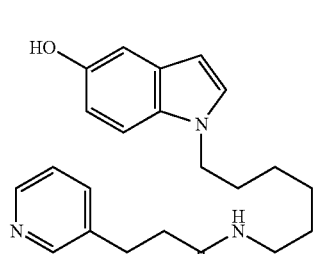 | 1200 | | |

TABLE 1-continued

| # | Structure | NAMPT Inhibition IC$_{50}$ (nM)* | % NAMPT Inhibition at 10 μM | Solubility (2.5% v/v DMSO/water) |
|---|---|---|---|---|
| 5.2.3t D2 | 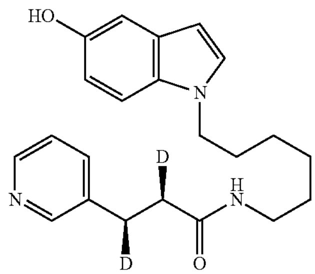 [SMILES: [2H][C@@H](C(=O)NCCCCCCn1ccc2cc(O)ccc21)[C@@H]([2H])c1cccnc1] | | | |
| 5.2.3f | 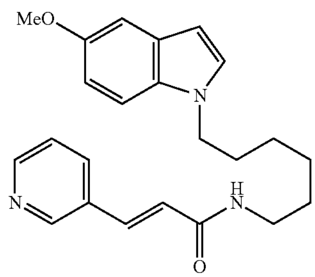 [SMILES: COc1ccc2c(ccn2CCCCCCNC(=O)/C=C/c2cccnc2)c1] | | | |
| | | | | 674 |
| 5.2.3f D2 | 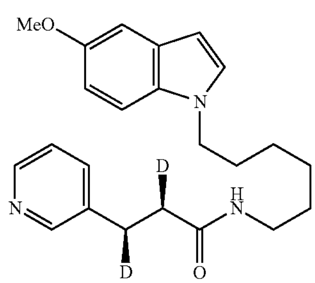 [SMILES: [2H][C@@H](C(=O)NCCCCCCn1ccc2cc(OC)ccc21)[C@@H]([2H])c1cccnc1] | | | 665 |
| 5.2.3h | 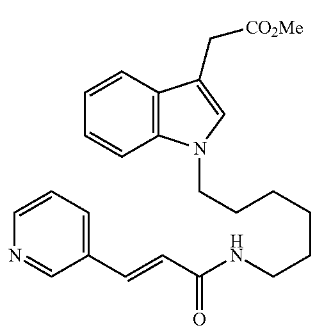 [SMILES: COC(=O)Cc1cn(CCCCCCNC(=O)/C=C/c2cccnc2)c2ccccc12] | | | 100 |

TABLE 1-continued
| # | Structure | NAMPT Inhibition IC$_{50}$ (nM)* | % NAMPT Inhibition at 10 μM | Solubility (2.5% v/v DMSO/water) |
|---|---|---|---|---|
| DGMS-RAR-PEG2E 5.2.3i | 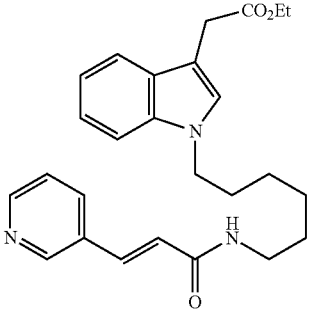 [SMILES: CCOC(=O)Cc1cn(CCCCCCNC(=O)/C=C/c2cccnc2)c2ccccc12] | <10 | 99 | |
| DGMS-RAR-PEG3E 5.2.3q | 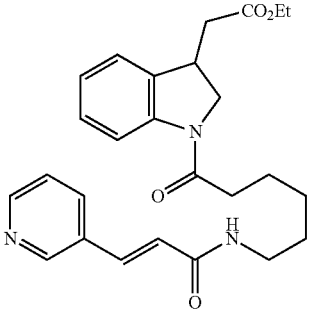 [SMILES: CCOC(=O)CC1CN(C(=O)CCCCCNC(=O)/C=C/c2cccnc2)c2ccccc21] | 44 | | |
| DGMS-RAR-PEG2A | 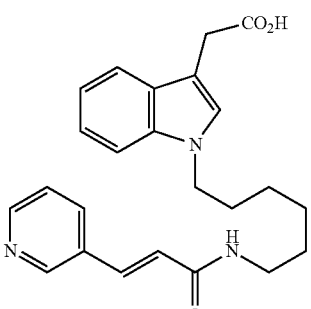 | 40 | 98 | |
| DGMS-RAR-PEG2 | 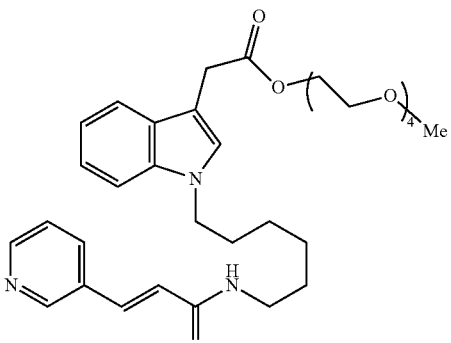 | 21 | 97 | Moderate |

TABLE 1-continued

| # | Structure | NAMPT Inhibition IC$_{50}$ (nM)* | % NAMPT Inhibition at 10 μM | Solubility (2.5% v/v DMSO/water) |
|---|---|---|---|---|
| DGMS-RAR-PEG3A | 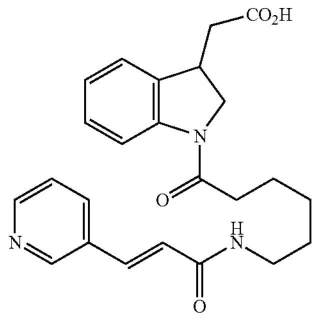 [SMILES: O=C(O)CC1CN(C(=O)CCCCCNC(=O)/C=C/c2cccnc2)c2ccccc21] | 1052 | | |
| DGMS-RAR-PEG3 | 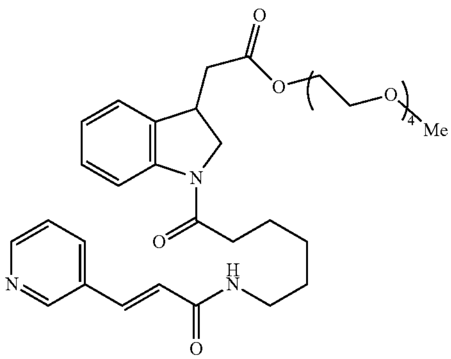 | 21 | | Good |
| DGMS-RAR-mPEG3 | 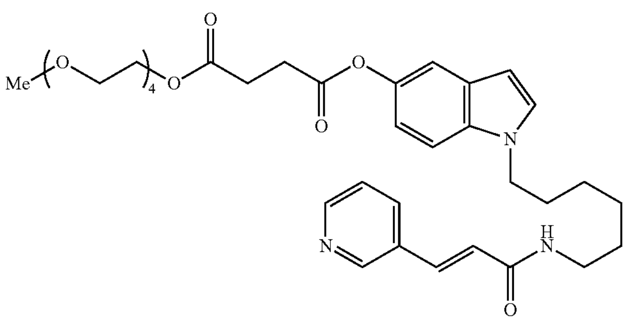 | 20 | 97 | good |
| 5.2.3k | 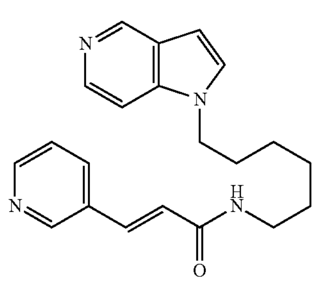 [SMILES: O=C(/C=C/c1cccnc1)NCCCCCCn1ccc2cnccc21] | 110 | | |
| 5.2.3b | 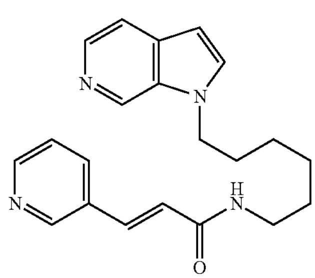 [SMILES: O=C(/C=C/c1cccnc1)NCCCCCCn1ccc2ccncc21] | 230 | | |

TABLE 1-continued

| # | Structure | NAMPT Inhibition IC$_{50}$ (nM)* | % NAMPT Inhibition at 10 μM | Solubility (2.5% v/v DMSO/water) |
|---|---|---|---|---|
| 5.2.3b H2 | 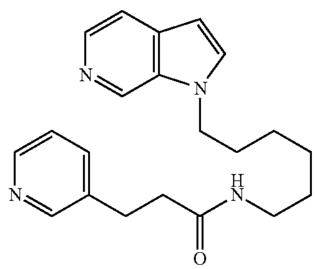 [SMILES: O=C(CCc1cccnc1)NCCCCCCn1ccc2ccncc21] | 2140 | | |
| | | 1540 | | |
| | | 2400 | | |
| DGMS-RAR-2 5.2.3c | 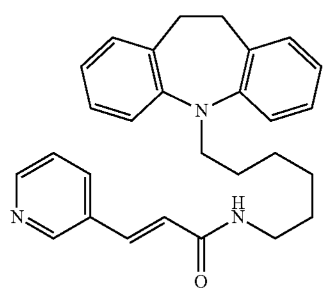 [SMILES: O=C(/C=C/c1cccnc1)NCCCCCCN1c2ccccc2CCc2ccccc21] | 80 | | |
| DGMS-RAR-5.2.3c H2 | 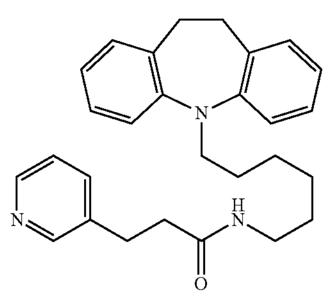 [SMILES: O=C(CCc1cccnc1)NCCCCCCN1c2ccccc2CCc2ccccc21] | 100 | | |

TABLE 1-continued

| # | Structure | NAMPT Inhibition IC$_{50}$ (nM)* | % NAMPT Inhibition at 10 μM | Solubility (2.5% v/v DMSO/water) |
|---|---|---|---|---|
| 5.2.3d | 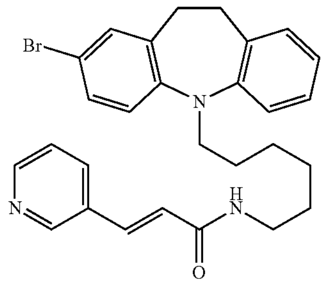 [SMILES: O=C(/C=C/c1cccnc1)NCCCCCCN1c2ccccc2CCc2cc(Br)ccc21] | | 71 | |
| DGMS-RAR-3 5.2.3o | 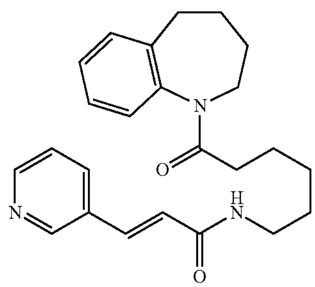 [SMILES: O=C(/C=C/c1cccnc1)NCCCCCC(=O)N1CCCCc2ccccc21] | | 72 | |

*CycLex NAMPT Colorimetric Assay Kit

Cell Viability, Proliferation and Apoptosis Assays

The effect of the compounds disclosed herein on the viability, proliferation, and apoptosis of human pulmonary artery endothelial cells ("hPAECs,") and human pulmonary artery smooth muscle cells ("hPASMCs") was determined using the PrestoBlue Assay (viability), CYQuant Direct or BrdU Assay (proliferation) or Tunel Assay (apoptosis), as described below.

HPAECs ($1 \times 10^4$ cells/well) or HPASMCs ($2.5 \times 10^3$ cells/well) were seeded in 96-well plates for 24 h in full-serum tissue culture medium. The full medium was removed prior to treatment with a NAMPT inhibitor prepared in medium containing 0.1% serum. NAMPT inhibitors were solubilized in 100% DMSO, unless otherwise indicated, prior to preparation of the dose response curve in 100% DMSO. The treatment dose response curve was diluted in 0.1% serum tissue culture medium and administered to cells for 24 h. DMSO diluted in the same medium was used as the vehicle control. Cell viability was measured according to the manufacturer's protocol by adding the PrestoBlue Cell Viability Reagent (ThermoFisher Scientific, #A13261) to cells for 20 min at 37° C. in a tissue culture incubator, followed by reading fluorescence at ex560/em590. Cell proliferation was measured, either in the same wells or in separate experiments, by adding the CyQuant Direct Confirmation Reagent (ThermoFisher Scientific, #C35011) for 1 h at 37° C. in a tissue culture incubator, followed by reading fluorescence at ex485/em538. Proliferation was also measured, in separate experiments, using the BrdU Cell Proliferation Assay (Calbiochem, #QIA58). After treatment with a NAMPT inhibitor for 24 h, BrdU was added to the cells in the presence of the inhibitor, for an additional 24 h and BrdU incorporation was detected according to the manufacturer's protocol. Apoptosis was analyzed by seeding cells ($1 \times 10^5$ cells/well) in 6-well plates for 24 h in full-serum medium, followed by treatment with a NAMPT inhibitor for 24 h in full-serum medium. Tunel staining and detection was performed using the Tunel Assay Kit (Abcam, #ab66110) according to the manufacturer's protocol.

Viability, proliferation and apoptosis assays were performed to determine doses at which NAMPT inhibitory compounds could be toxic to cells. The compounds of the disclosure were found to suppress cell growth and promote apoptosis both in hPASMCs and hPAECs in a dose-dependent manner, as shown in FIGS. 4-11. For example, compounds DGMS-RAR-7.HCl and DGMS-RAR-7.HO$_3$SMe each showed a reduction in the viability and proliferation of HPAECs at high doses. Based on these dose-responsive curve experiments, the IC$_{50}$ values were calculated as provided in Table 2, below.

TABLE 2

| | PrestoBlue Assay IC$_{50}$ (μM) | | CyQUANT Direct Assay IC$_{50}$ (μM) | | BrdU Assay IC$_{50}$ (μM) | | Tunel Assay IC$_{50}$ (μM) | |
|---|---|---|---|---|---|---|---|---|
| | hPAEC | hPASMC | hPAEC | hPASMC | hPAEC | hPASMC | hPAEC | hPASMC |
| FK866 | 108.8 × 10$^9$ | | 60.3 | | | | | |
| DGMS-RARI | 117.4 | | 2.883 | | | | | |
| DGMS-RAR-1 | | | | | | 51.9 | | |
| DGMS-RAR-2 | | | | | 1.309 | 1.496 | | |

TABLE 2-continued

| | PrestoBlue Assay IC$_{50}$ (µM) | | CyQUANT Direct Assay IC$_{50}$ (µM) | | BrdU Assay IC$_{50}$ (µM) | | Tunel Assay IC$_{50}$ (µM) | |
|---|---|---|---|---|---|---|---|---|
| | hPAEC | hPASMC | hPAEC | hPASMC | hPAEC | hPASMC | hPAEC | hPASMC |
| DGMS-RAR-5 | | | | | | 102.5 | | |
| DGMS-RAR-5•HO$_3$SMe | 4.909 × 10$^{14}$ | | | | | | | |
| DGMS-RAR-7•HCl | 13.88 | 31.13 | 26.63 | | | 63.91 | 182.9 | 115.5 |
| DGMS-RAR-7•HO$_3$SMe | 17.08 | 26.56 | 31.88 | | | | 117.4 | 94.11 |
| DGMS-RAR-7 | 1.589 | | 1.003 | | 95.77 | 35422 | | |
| DGMS-RAR-PEG2 | | | | | | | | |
| DGMS-RAR-PEG3 | | | | | | | | |

Seahorse XF Metabolism Assay

The effect of the compounds disclosed herein on metabolism was determined using the Seahorse XF Cell Energy Phenotype Test Kit by Agilent Technologies. See Agilent Seahorse XF Cell Energy Phenotype Test Kit, User Guide, Manual Part Number 103325-400, Kit Part Number 103325-100, First Edition, March 2017 Agilent Technologies, Inc. This assay measures mitochondrial respiration and glycolysis under baseline and stressed conditions to determine baseline phenotype, stressed phenotype, and metabolic potential.

Figure 12A:
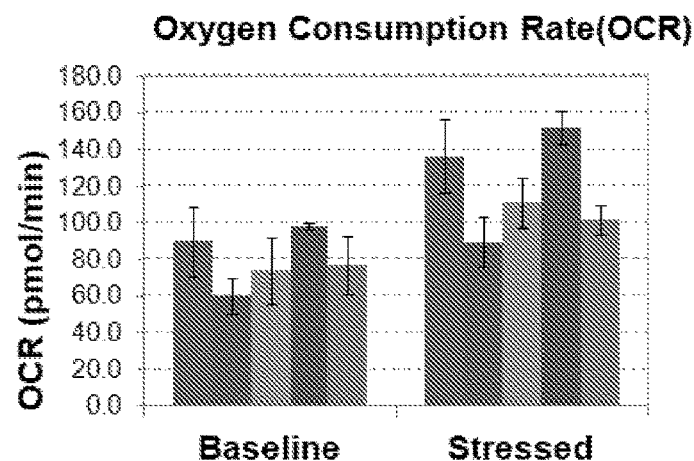
FIG. 12 depicts the effect of compound DGMS-RARI on the metabolic parameters of (A) oxygen consumption rate and (B) extracellular acidification rate.
Figure 12B:
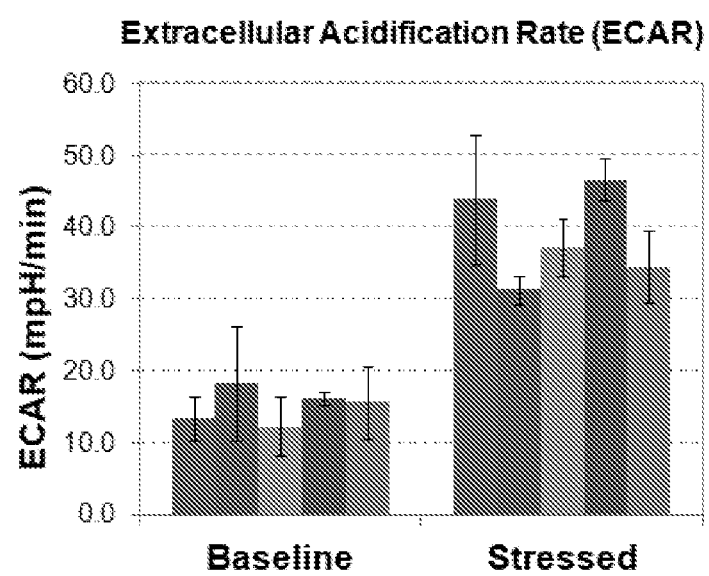
Figure 13:
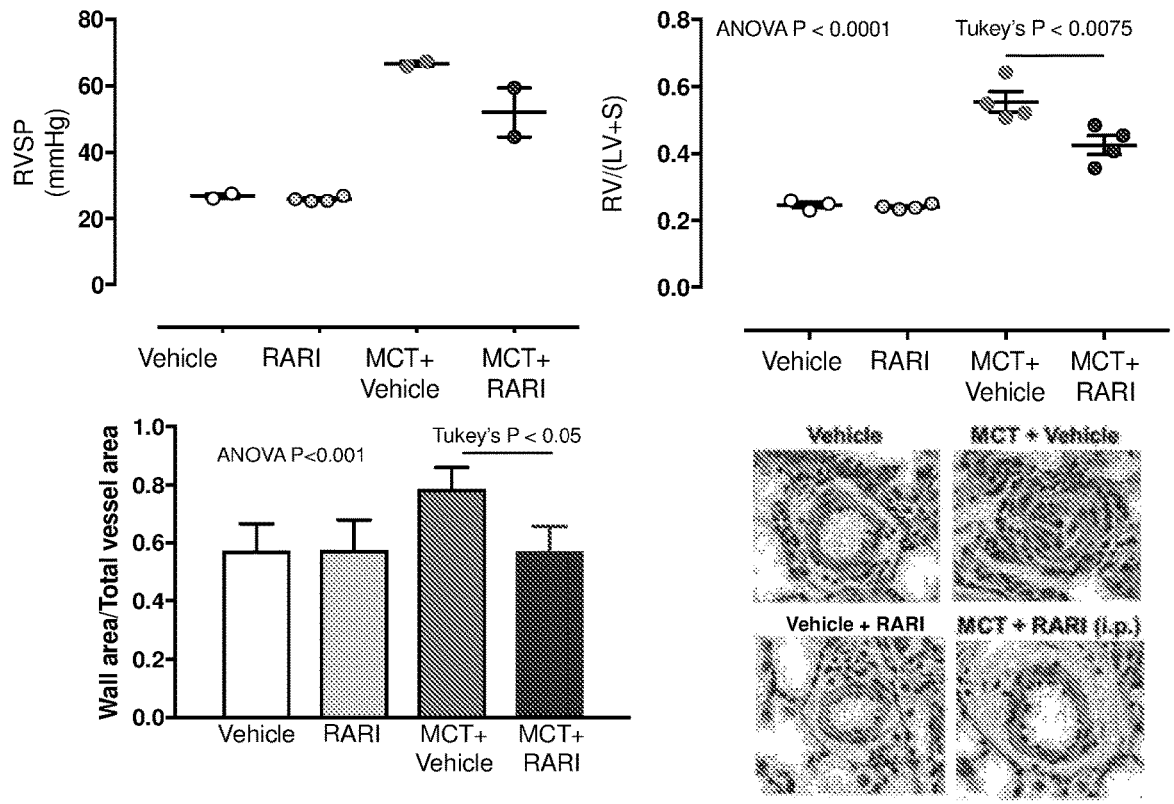
FIG. 13 depicts the therapeutic effect of DGMS-RARI on MCT-induced PAH in rats. DGMS-RARI treatment decreased the severity of elevations in RVSP, the degree of right ventricular hypertrophy, and the degree of pulmonary vascular remodeling induced by the MCT.

FIG. 12, FIG. 13, and Table 3, below, show that these energy phenotype experiments show that high doses of RARI (10 uM) and other NAMPT inhibitors inhibit the maximal oxygen consumption rate of HepG2 cells by approximately 30%. Physiological doses (≤80 nM) in the range detected in animal studies, however, have no effect on cellular respiration. This indicates that therapeutic doses may not adversely effect cellular metabolism.

TABLE 3

Oxygen Consumption Rate ("OCR") Data

| Group Name | Baseline OCR | Baseline OCR StdDev | Stressed OCR | Stressed OCR StdDev | Metabolic Potential (% Baseline OCR) | Metabolic Potential StDev (OCR) |
|---|---|---|---|---|---|---|
| HepG2, Control | 89.97 | 19.04 | 136.32 | 20.22 | 153.40 | 15.14 |
| HepG2, RARI, 10 uM | 60.26 | 10.05 | 89.62 | 14.94 | 148.94 | 10.75 |
| HepG2, RARI, 2 uM | 73.92 | 18.93 | 111.06 | 14.41 | 154.18 | 23.14 |
| HepG2, RARI, 80 nM | 98.19 | 2.56 | 152.08 | 9.33 | 154.82 | 6.27 |
| HepG2, TD3, 10 uM | 76.62 | 16.42 | 101.56 | 8.99 | 135.49 | 20.76 |

TABLE 4

Extracellular Acidification Rate ("ECAR") Data

| Group Name | Baseline ECAR | Baseline ECAR StdDev | Stressed ECAR | Stressed ECAR StdDev | Metabolic Potential (% Baseline ECAR) | Metabolic Potential StDev (ECAR) |
|---|---|---|---|---|---|---|
| HepG2, Control | 13.29 | 3.57 | 43.86 | 9.62 | 333.64 | 25.81 |
| HepG2, RARI, 10 uM | 18.28 | 8.38 | 31.23 | 2.73 | 194.22 | 68.39 |
| HepG2, RARI, 2 uM | 12.28 | 4.85 | 37.11 | 4.65 | 334.84 | 123.71 |
| HepG2, RARI, 80 nM | 16.16 | 1.16 | 46.64 | 3.76 | 288.54 | 10.22 |
| HepG2, TD3, 10 uM | 15.59 | 5.75 | 34.46 | 5.74 | 247.19 | 106.27 |

Animal Model Experiments

The ability of the compounds disclosed herein to attenuate pulmonary vascular remodeling associated with pulmonary arterial hypertension was determined using monocrotaline ("MCT")-induced pulmonary hypertension as well as Sugen-Hypoxia-induced pulmonary hypertension in rats.

MCT 60 mg/kg IP was injected in Sprague Dawley rats. After 21 days when PH was established DGMS-RARI (5 mg/kg every other day) was injected intraperitonealy from days 22-35. At day 35 PH assessments (RVSP measurements via right heart catheterization, RVH measurement via assessment of the ratio between the weight of the right ventricle over the weight of the left ventricle+septum and pulmonary vascular remodeling assessment of H&E stained pulmonary arteries) were performed.

Sugen 10 mg/kg IP was injected in Sprague Dawley rats who were then exposed to 10% hypoxia for 21 days. After 21 rats were returned to normoxia for 14 days. After 35 when PH was established DGMS-RARI (5 mg/kg every other day) was injected intraperitonealy from days 35-49. At day 49 PH assessments (RVSP measurements via right heart catheterization, RVH measurement via assessment of the ratio between the weight of the right ventricle over the weight of the left ventricle+septum and assessment of right ventricular function via echocardiography) were performed.

As shown in FIG. 13, DGMS-RARI treatment decreased the severity of elevations in RVSP, the degree of right ventricular hypertrophy and the degree of pulmonary vascular remodeling induced by MCT.

Figure 14:
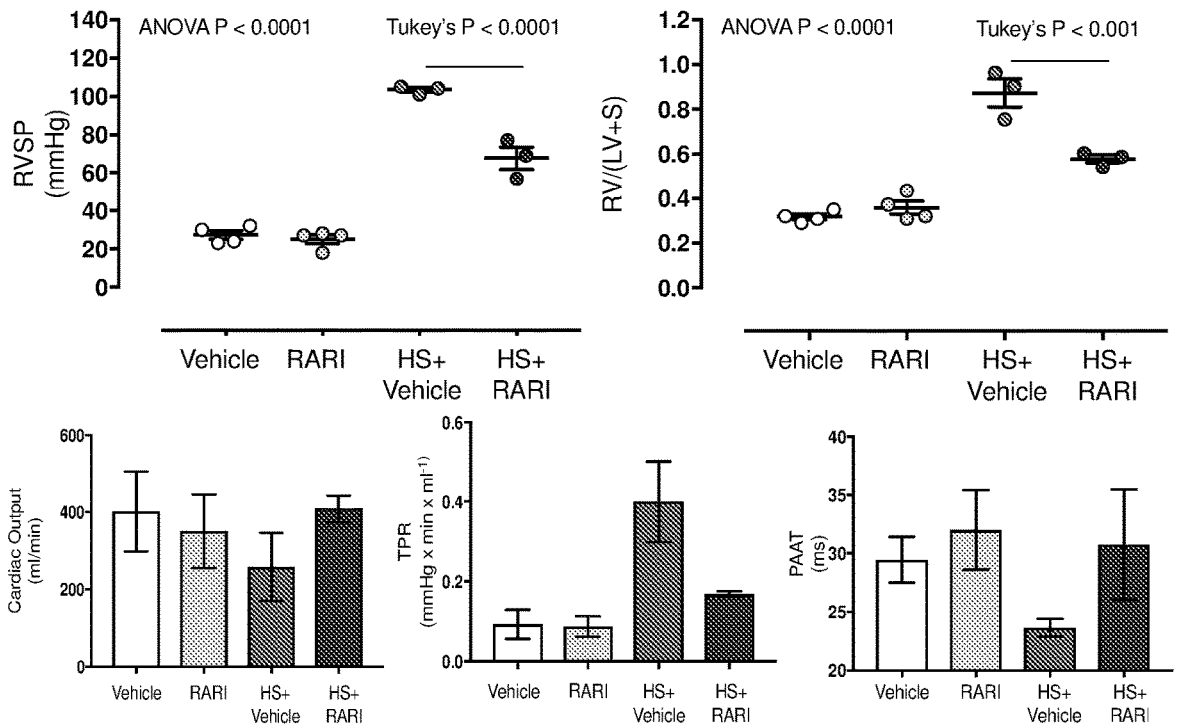
FIG. 14 depicts the therapeutic effect of DGMS-RARI on Sugen-Hypoxia-induced PH in rats. DGMS-RARI treatment decreased the severity of elevations in RVSP, the degree of right ventricular hypertrophy and the degree of right ventricular dysfunction induced by Sugen-Hypoxia exposure.

As shown in FIG. 14, DGMS-RARI treatment decreased the severity of elevations in RVSP, the degree of right ventricular hypertrophy and the degree of right ventricular dysfunction induced by Sugen-Hypoxia exposure.

Figure 15:
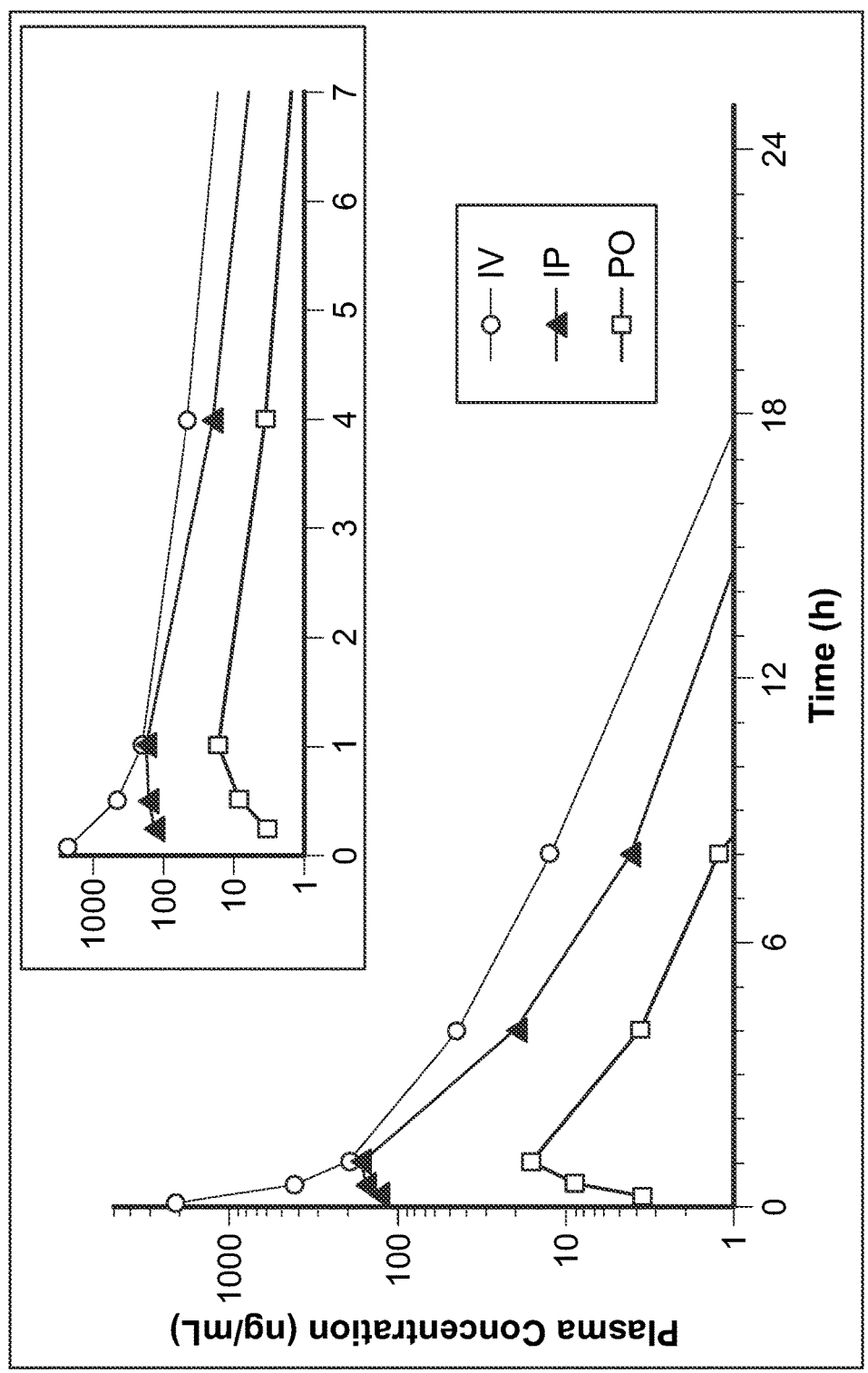
FIG. 15 depicts the average plasma concentration of DGMS-RARI in MCT-induced rats with time after injection with a 5 mg/kg dose of DGMS-RARI intravenously, intraperitoeally, and orally.

As shown in FIG. 15, when the MCT-induced rats were dosed with 5 mg/kg of DGMS-RARI intravenously, intraperitoeally, and orally, the average concentration of DGMS-RARI in the rat plasma decreased with time. Moreover, significant abnormalities in biochemical parameters and electrolytes were not observed.

Thus, the compounds disclosed herein were shown to prevent and reverse pulmonary arterial cell remodeling associated with pulmonary arterial hypertension.

Aspects of the Disclosure

Embodiment 1: A compound of Formula (II), or a pharmaceutically acceptable salt thereof:

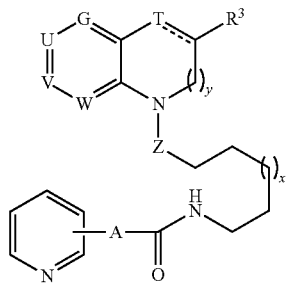

(II)

wherein:

$\rightleftharpoons$ is a single bond or a double bond;
each of x and y independently is 0, 1, or 2;

A is

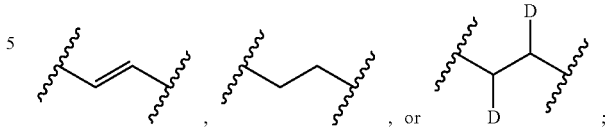

T is $CR^aR^b$ or $SiR^1R^2$, provided that when T is $SiR^1R^2$, then $\rightleftharpoons$ is a single bond;
each of G, U, V, and W independently is $CR^4$ or N, provided that at least three of G, U, V, and W are $CR^4$;
Z is $CH_2$ or $C=O$;
$R^a$ is H, $C_{1-4}$alkyl, or $CH_2CO_2R^5$;
$R^b$, when present, is H or $C_{1-4}$alkyl;
each of $R^1$ and $R^2$ independently is $C_{1-4}$alkyl or phenyl;
$R^3$ is H, $C_{1-4}$alkyl, or aryl;
each $R^4$ independently is H, halo, $C_{1-4}$alkyl, OH, $OC_{1-4}$alkyl, OBn, $O(C=O)(CH_2)_n(C=O)(CH_2CH_2O)_mC_{1-4}$alkyl, or $O(C=O)(CH_2)_n(C=O)(CH_2CH_2O)_mH$, or two adjacent $R^4$ groups are each $OC_{1-4}$alkyl, and together with the carbon atoms to which they are attached, form a five- or six-membered ring;
$R^5$ is H, $C_{1-4}$alkyl, $(CH_2CH_2O)_mC_{1-4}$alkyl, or $(CH_2CH_2O)_mH$;
n is 1-4; and
m is 1-10;
with the proviso that when y is 2, then the two carbon atoms adjacent to N can optionally be fused to a phenyl group, and the compound or salt thereof is not

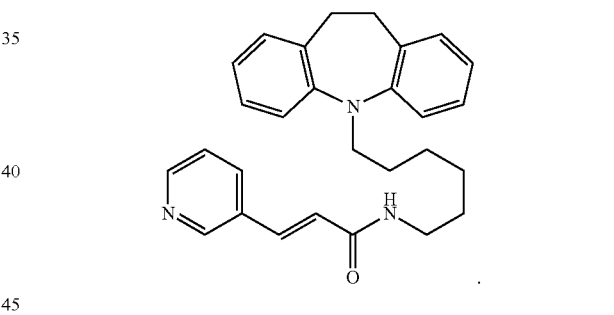

Embodiment 2: The compound or salt of embodiment 1 having a structure of Formula (II')

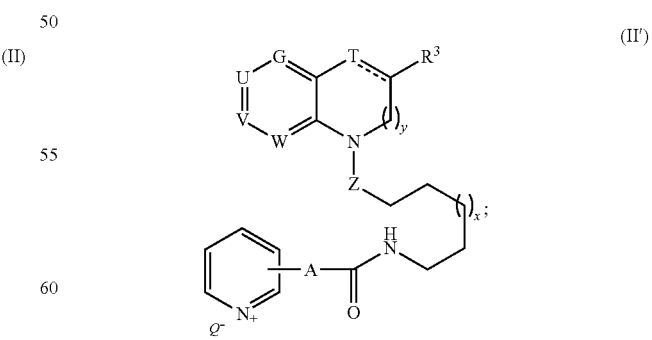

(II')

Embodiment 3: The compound or salt of embodiment 1, wherein x is 0.

Embodiment 4: The compound or salt of embodiment 1, wherein x is 1.

Embodiment 5: The compound or salt of embodiment 1, wherein x is 2.

Embodiment 6: The compound or salt of any one of embodiments 1-5, wherein y is 0.

Embodiment 7: The compound or salt of any one of embodiments 1-5, wherein y is 1.

Embodiment 8: The compound or salt of any one of embodiments 1-5, wherein y is 2.

Embodiment 9: The compound or salt of any one of embodiments 1-8, wherein A is

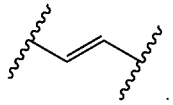 [SMILES: */C=C/*]

Embodiment 10: The compound or salt of any one of embodiments 1-8, wherein A is

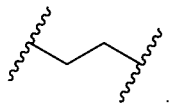

Embodiment 11: The compound or salt of any one of embodiments 1-8, wherein A is

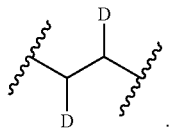 [SMILES: *C([2H])C(*)[2H]]

Embodiment 12: The compound or salt of any one of embodiments 1-11, wherein Z is $CH_2$.

Embodiment 13: The compound or salt of any one of embodiments 1-11, wherein Z is C=O.

Embodiment 14: The compound or salt of any one of embodiments 1-13, wherein each of G, U, V, and W is $CR^4$.

Embodiment 15: The compound or salt of any one of embodiments 1-13, wherein G is N.

Embodiment 16: The compound or salt of any one of embodiments 1-13, wherein U is N.

Embodiment 17: The compound or salt of any one of embodiments 1-13, wherein V is N.

Embodiment 18: The compound or salt of any one of embodiments 1-13, wherein W is N.

Embodiment 19: The compound or salt of any one of embodiments 1-18, wherein each $R^4$ group is H.

Embodiment 20: The compound or salt of any one of embodiments 1-13, wherein one $R^4$ group is halo, $C_{1-4}$alkyl, OH, $OC_{1-4}$alkyl, OBn, $O(C=O)(CH_2)_n(C=O)(CH_2CH_2O)_mC_{1-4}$alkyl, or $O(C=O)(CH_2)_n(C=O)(CH_2CH_2O)_mH$ and the other three $R^4$ groups are each H.

Embodiment 21: The compound or salt of embodiment 20, wherein one $R^4$ group is I, Br, Cl, F, Me, OH, OMe, $OCF_3$, OBn, or $O(C=O)(CH_2)_2(C=O)(CH_2CH_2O)_4Me$.

Embodiment 22: The compound or salt of any one of embodiments 1-13, wherein two $R^4$ groups are H and each of the other two $R^4$ groups is independently OH or $OC_{1-4}$alkyl.

Embodiment 23: The compound or salt of embodiment 22, wherein the two $R^4$ groups are attached to adjacent carbon atoms, each $R^4$ group is $OC_{1-4}$alkyl, and together with the carbon atoms to which they are attached, form a five- or six-membered ring.

Embodiment 24: The compound or salt of any one of embodiments 1-23, wherein $R^3$ is H.

Embodiment 25: The compound or salt of any one of embodiments 1-23, wherein $R^3$ is Me.

Embodiment 26: The compound or salt of any one of embodiments 1-23, wherein $R^3$ is Ph.

Embodiment 27: The compound or salt of any one embodiments 1-26, wherein T is $SiR^1R^2$ and === is a single bond.

Embodiment 28: The compound or salt of embodiments 1-27, wherein each of $R^1$ and $R^2$ independently is Me or Et.

Embodiment 29: The compound or salt of embodiment 28, wherein $R^1$ and $R^2$ are each Me or $R^1$ and $R^2$ are each Et.

Embodiment 30: The compound or salt of any one of embodiments 1-29, wherein T is $CR^aR^b$.

Embodiment 31: The compound or salt of embodiment 30, wherein === is a single bond.

Embodiment 32: The compound or salt of embodiment 31, wherein $R^a$ and $R^b$ are each H.

Embodiment 33: The compound or salt of embodiment 30, wherein === is a double bond.

Embodiment 34: The compound or salt of embodiment 33, wherein $R^a$ is H.

Embodiment 35: The compound or salt of embodiment 33, wherein $R^a$ is $CH_2CO_2R^5$.

Embodiment 36: The compound or salt, wherein $R^5$ is H, OMe, OEt, or $(CH_2CH_2O)_4Me$.

Embodiment 37: The compound or salt of embodiment 1, having a structure of Formula (III) or (III'):

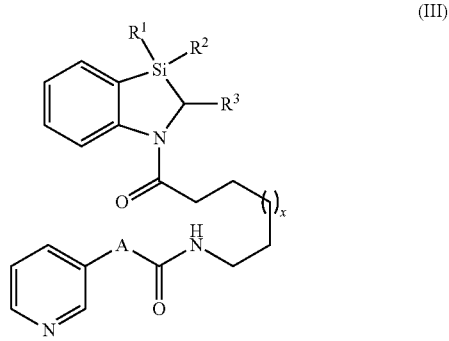

(III)

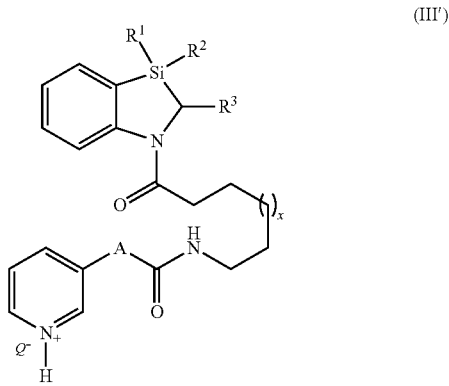

(III')

wherein Q is a counterion.

Embodiment 38: The compound or salt of embodiment 37, wherein x is 1; A is

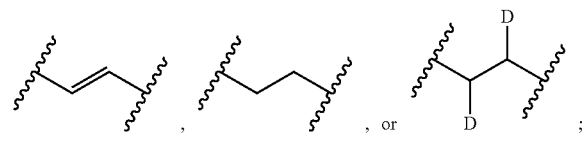, or 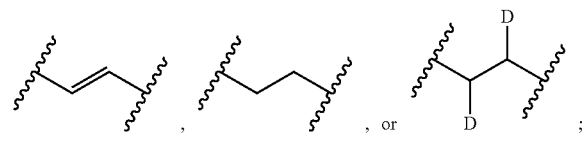;

each of $R^1$ and $R^2$ is Me or each of $R^1$ and $R^2$ is Et; $R^3$ is H or Me; and Q is Cl, OMs, or OTs.

Embodiment 39: The compound or salt of embodiment 1, having a structure of Formula (IV) or (IV'):

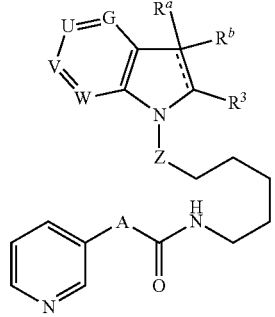 (IV)

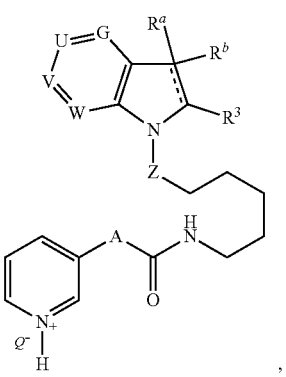 (IV')

wherein Q is a counterion.

Embodiment 40: The compound or salt of embodiment 39, wherein

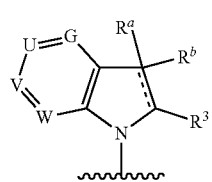

is selected from the group consisting of

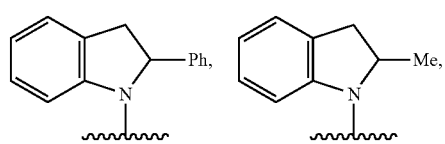

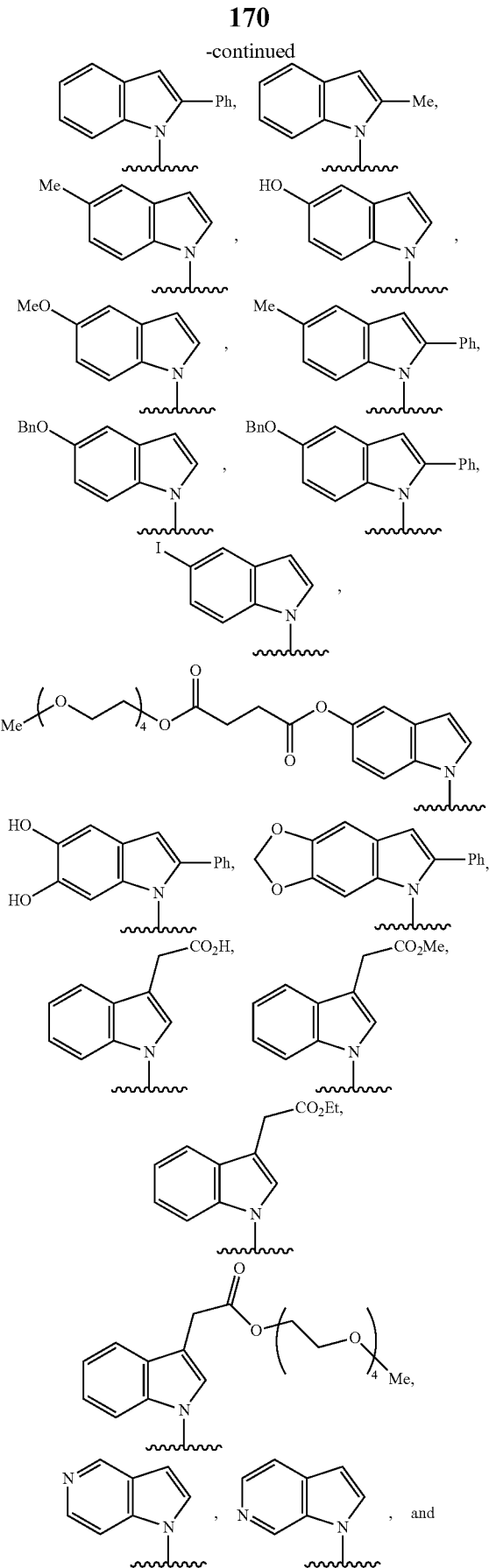

-continued

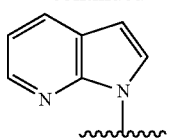

Embodiment 41: The compound or salt of embodiment 1, having a structure of Formula (V) or (V'):

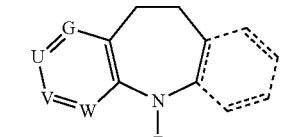
(V)

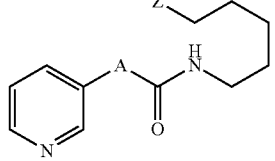
(V')

wherein

is present or absent and Q is a counterion.

Embodiment 42: The compound or salt of embodiment 1 selected from the group consisting of a compound listed in Table A, a compound listed in Table B, a compound listed in Table C, and a salt of any of the foregoing.

Embodiment 43: The compound or salt of embodiment 42 selected from a compound listed in Table A,

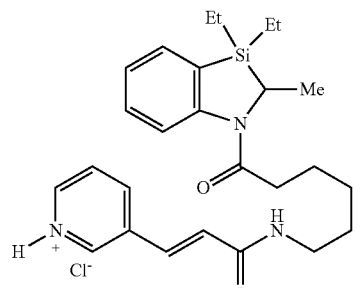

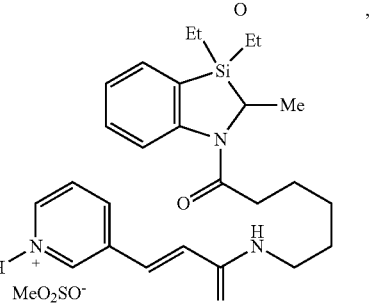
, and

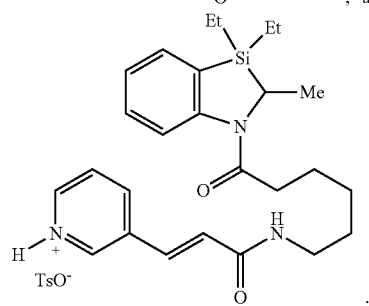

Embodiment 44: The compound or salt of embodiment 42 selected from

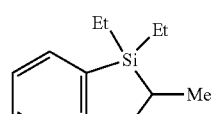

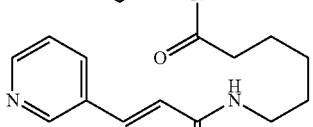
and

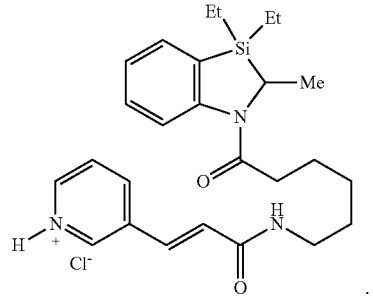

Embodiment 45: The compound or salt of embodiment 42 selected from a compound listed in Table B,

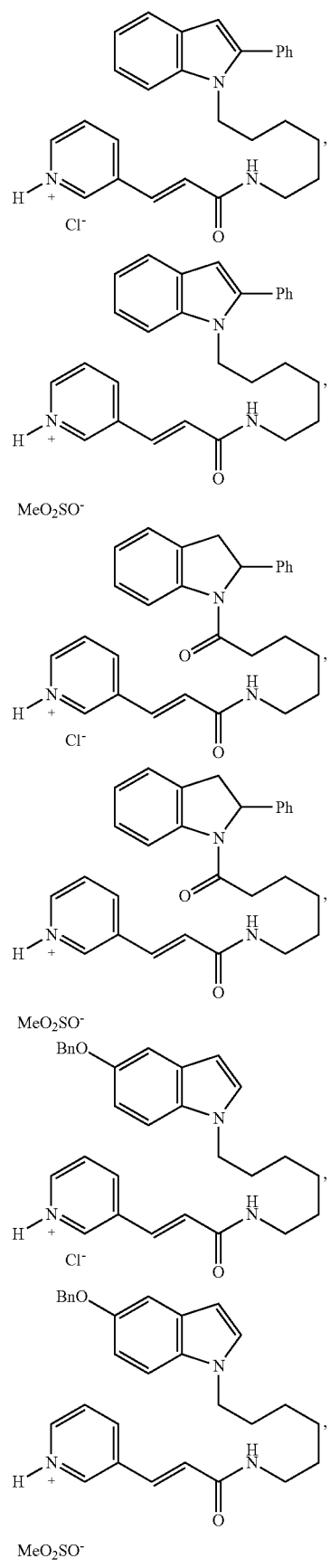
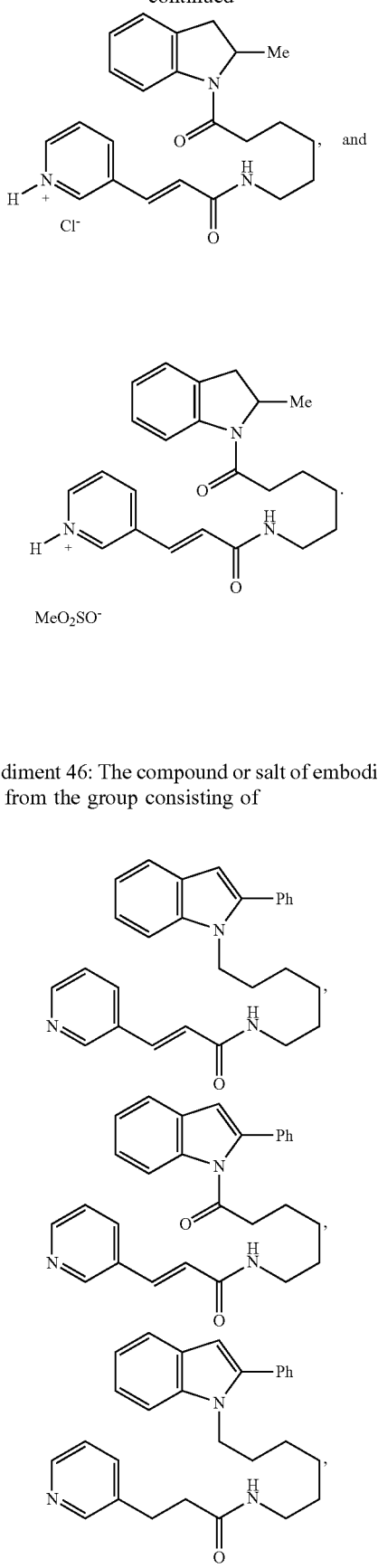
Embodiment 46: The compound or salt of embodiment 45 selected from the group consisting of -continued
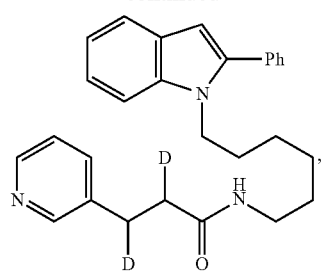
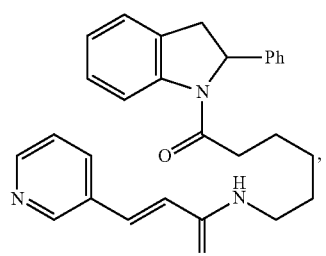
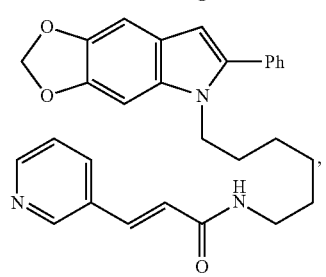
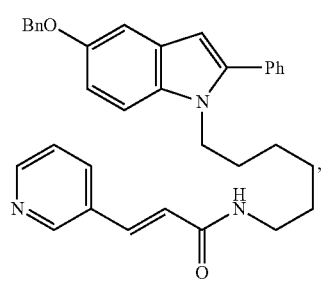
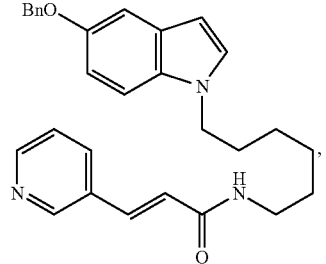
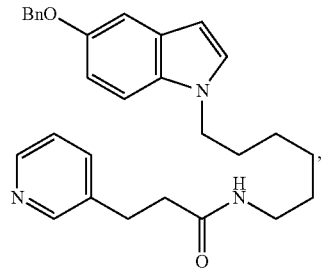
-continued
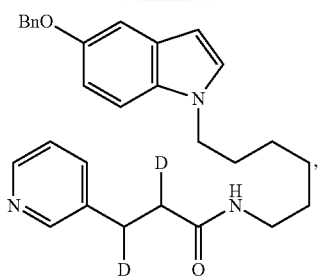
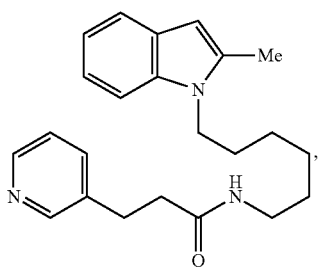
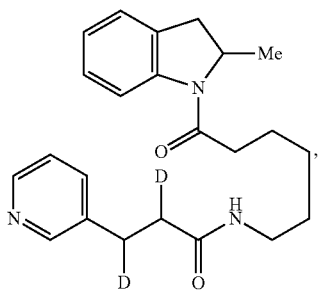
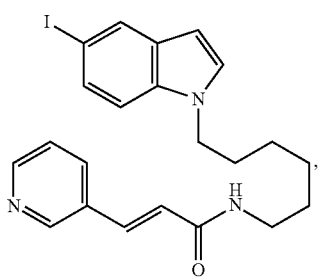
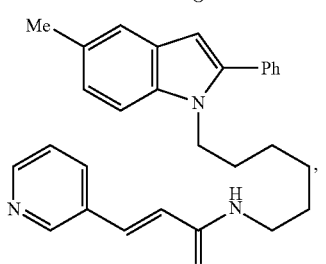
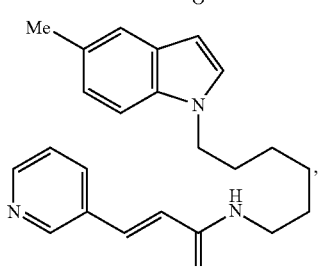

177
-continued
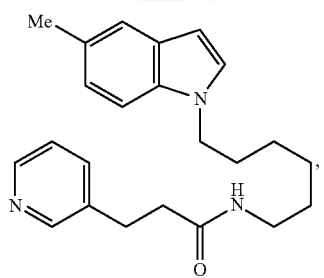
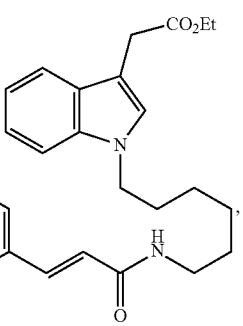
178
-continued
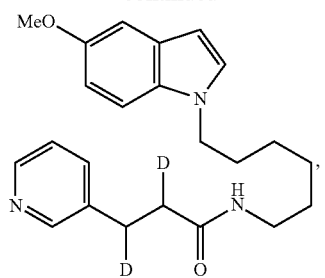
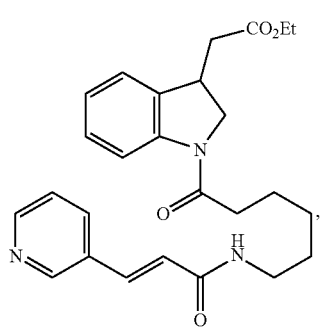
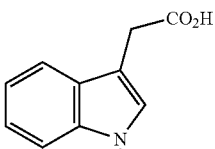
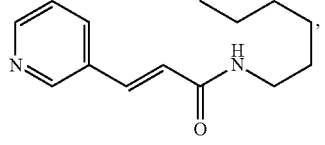
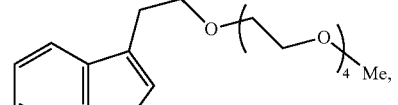
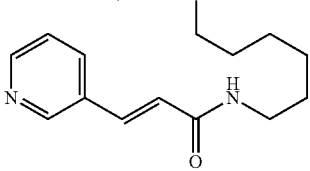

179
-continued
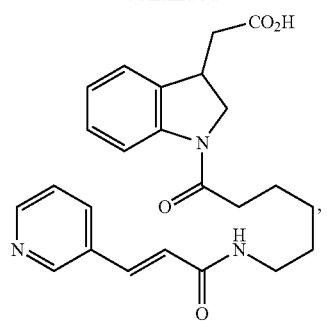
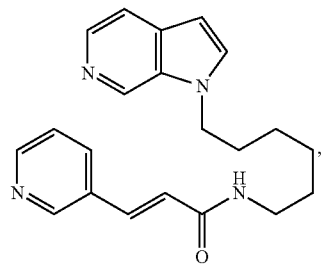
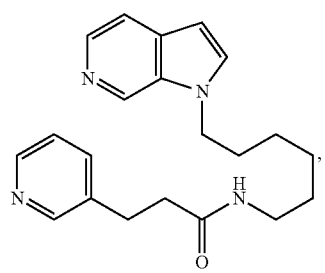
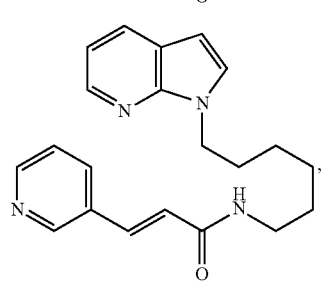
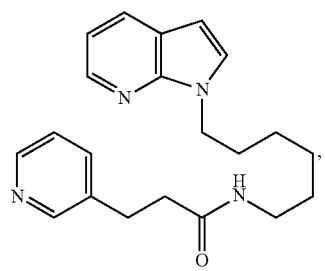
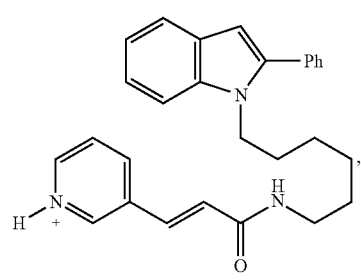
180
-continued
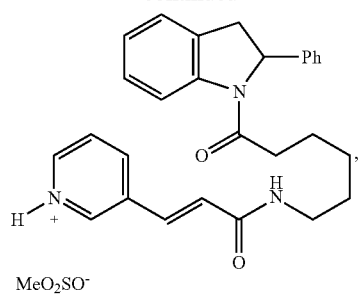
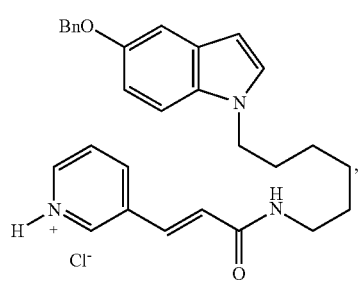
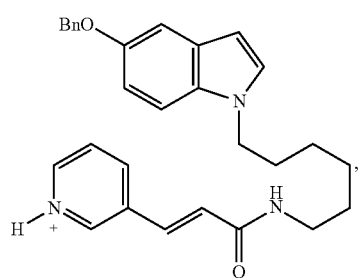
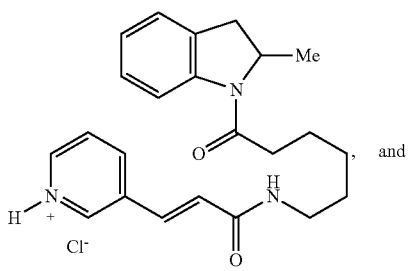, and Embodiment 47: The compound or salt of embodiment 45 selected form from

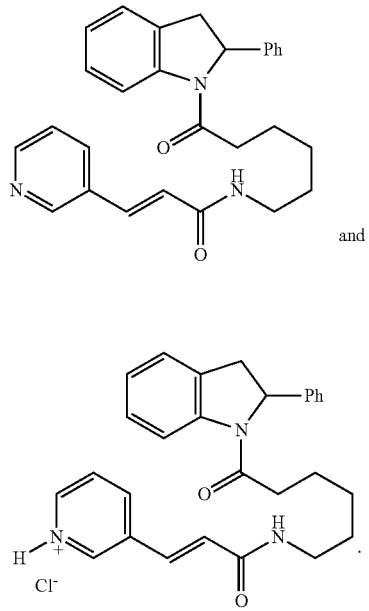 [SMILES: O=C(/C=C/c1cccnc1)NCCCCCC(=O)N1c2ccccc2CC1c1ccccc1 ; O=C(/C=C/c1ccc[nH+]c1)NCCCCCC(=O)N1c2ccccc2CC1c1ccccc1 ; [Cl-]]

and

Embodiment 48: The compound or salt of embodiment 42 selected from a compound listed in Table C.

Embodiment 49: A pharmaceutical composition comprising the compound or salt of any one of embodiments 1-48 and a pharmaceutically acceptable excipient.

Embodiment 50: A method of inhibiting nicotinamide phosphoribosyltransferase in a cell comprising contacting the cell with the compound or salt of any one of embodiments 1-48,

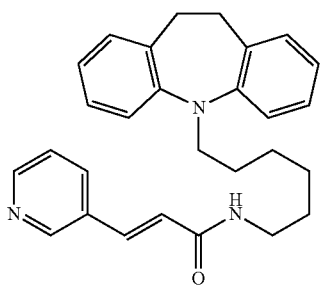 [SMILES: O=C(/C=C/c1cccnc1)NCCCCCCN1c2ccccc2CCc2ccccc21]

or a salt thereof, or the pharmaceutical composition of embodiment 49, in an amount effective to inhibit nicotinamide phosphoribosyltransferase.

Embodiment 51: The method of embodiment 50, wherein the contacting comprises administering the compound or composition to a subject.

Embodiment 52: The method of embodiment 51, wherein the subject suffers from pulmonary arterial hypertension.

Embodiment 53: A method of treating a subject having a disease or disorder wherein inhibition of nicotinamide phosphoribosyltransferase would provide a benefit comprising administering to the subject a therapeutically effective amount of a compound or salt of any one of embodiments 1-48,

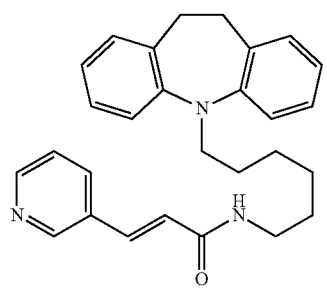 [SMILES: O=C(/C=C/c1cccnc1)NCCCCCCN1c2ccccc2CCc2ccccc21]

or a salt thereof, or the pharmaceutical composition of embodiment 49.

The method of embodiment 53, wherein the disease or disorder is pulmonary arterial hypertension.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step not specifically disclosed.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference.

We claim:
1. A compound of Formula (II):

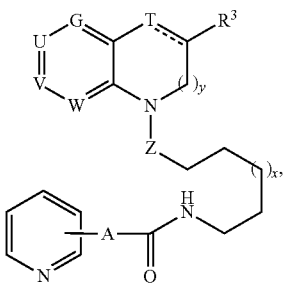
(II)

or a pharmaceutically acceptable salt thereof, wherein;
T is $CR^aR^b$;
each of G, U, V, and W independently is $CR^4$ or N, provided that at least three of G, U, V, and W are $CR^4$;
═ is a single bond or a double bond;
x is 0, 1, or 2;
y is 0 or 1;
A is

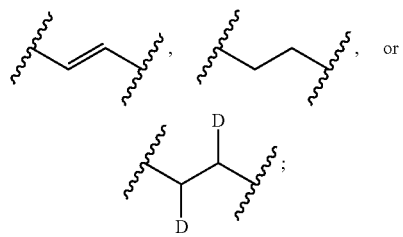

Z is C═O;
$R^a$ is H, $C_{1-4}$alkyl, or $CH_2CO_2R^5$;
$R^b$ is H, or $C_{1-4}$alkyl, or when ═ is a double bond then $R^b$ is absent;
$R^3$ is H, $C_{1-4}$alkyl, or aryl;
each $R^4$ independently is H, halo, $C_{1-4}$alkyl, OH, $OC_{1-4}$alkyl, OBn, $O(C═O)(CH_2)_n(C═O)O(CH_2CH_2O)_mC_{1-4}$alkyl, or $O(C═O)O(CH_2)_n(C═O)(CH_2CH_2O)_mH$;
$R^5$ is H, $C_{1-4}$alkyl, $(CH_2CH_2O)_mC_{1-4}$alkyl, or $(CH_2CH_2O)_mH$;
n is 1-4; and
m is 1-10.

2. The compound or salt of claim 1, having a structure of

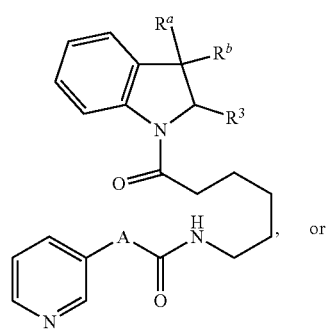
, or

-continued

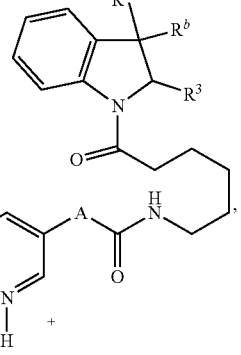

wherein
A is

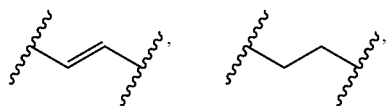
or

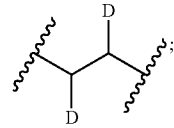
;

Q is a counterion;
$R^a$ is H, $C_{1-4}$ alkyl, or $CH_2CO_2R^5$;
$R^b$ is H;
$R^3$ is H, $C_{1-4}$ alkyl, or aryl.

3. The compound or salt of claim 2, wherein A is

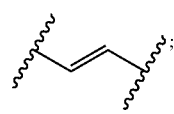
;

$R^a$ is H or $C_{1-4}$ alkyl;
and
$R^3$ is $C_{1-4}$ alkyl or phenyl.

4. The compound or salt of claim 3, wherein $R^3$ is Me or Ph.

5. The compound or salt of claim 1, wherein x is 1 and y is 0, and A is

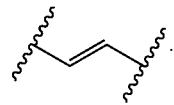 [SMILES: */C=C/*]
.

6. The compound or salt of claim 5, having a structure of

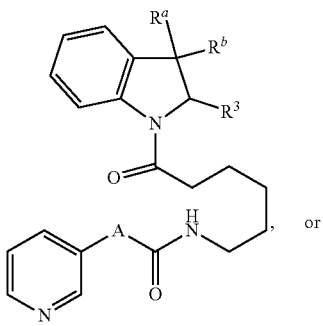, or

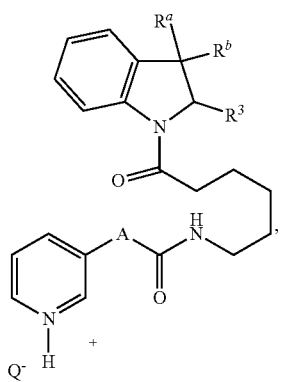

wherein
A is

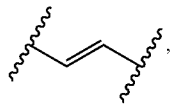,

Q is a counterion;
$R^a$ and $R^b$ are both H; and
$R^3$ is $CH_3$ or phenyl.

7. The compound or salt of claim 1, having a structure of Formula (IV):

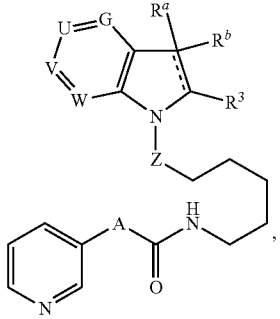

(IV)

wherein A is

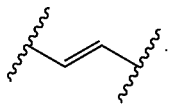 [SMILES: */C=C/*].

8. The compound or salt of claim 7, wherein $R^3$ is Me or Ph.

9. The compound or salt of claim 8, wherein each of G, U, V, and W is CH.

10. The compound or salt of claim 7, wherein $=$ is a single bond and each of $R^a$ and $R^b$ is H.

11. The compound or salt of claim 7, wherein

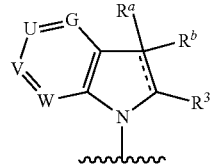

is selected from the group consisting of

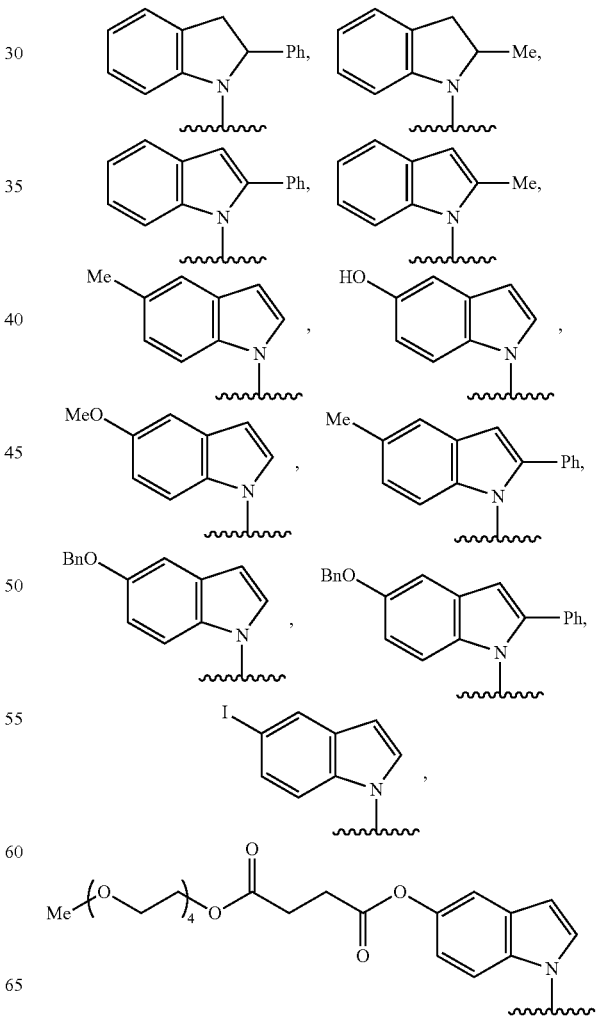

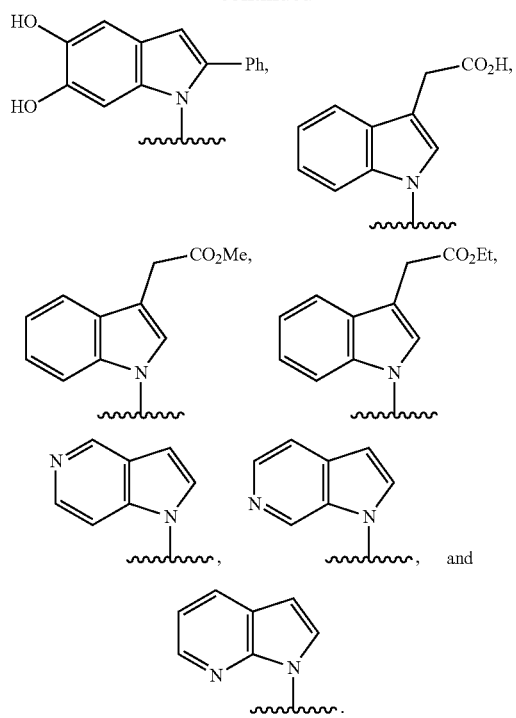
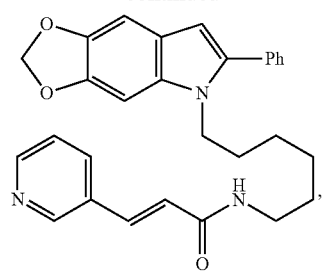
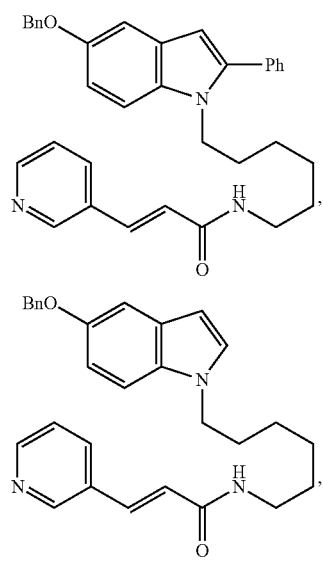
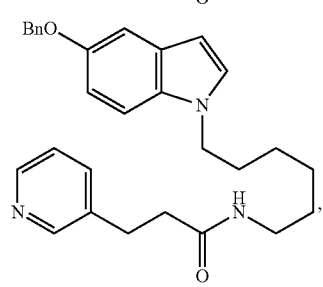
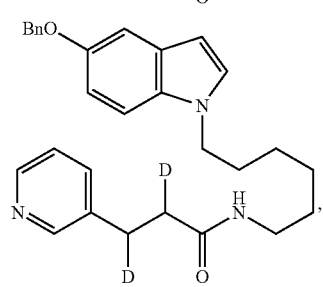
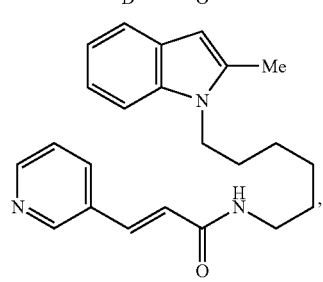
12. A compound or salt thereof, having a structure selected from the group consisting of:

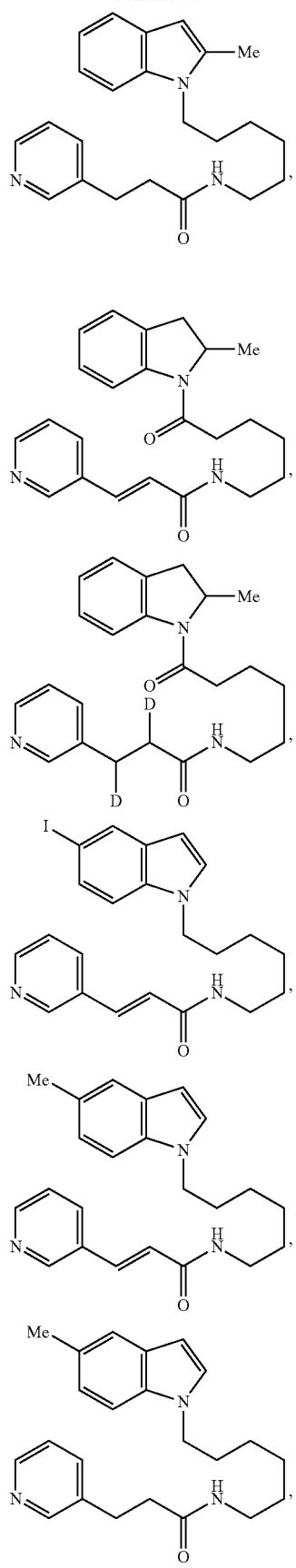
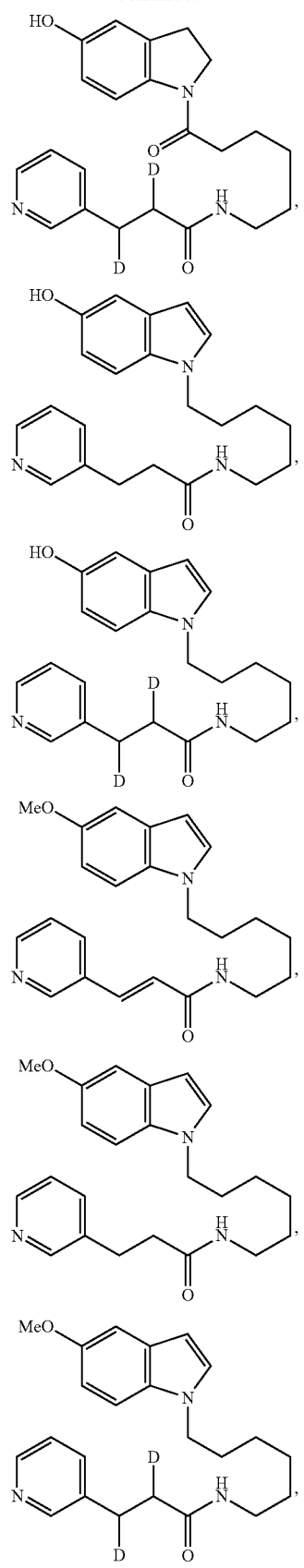

-continued
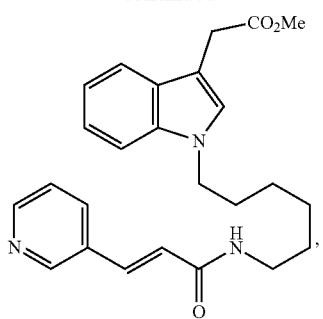
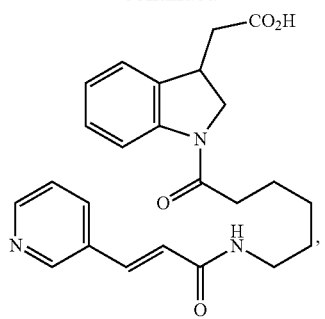
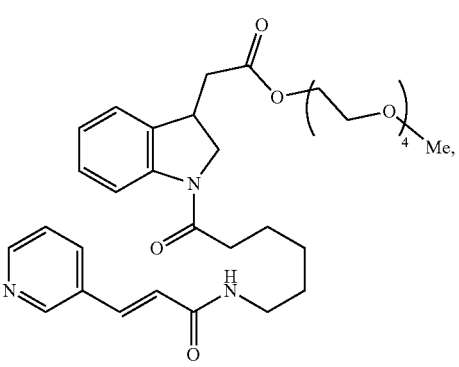
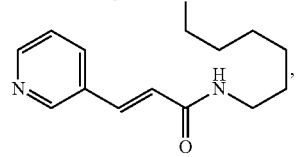
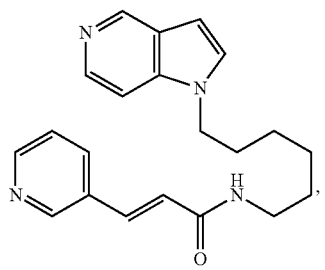
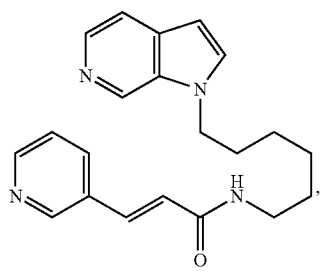

-continued
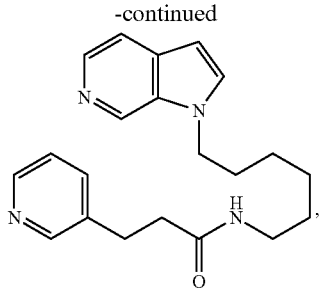
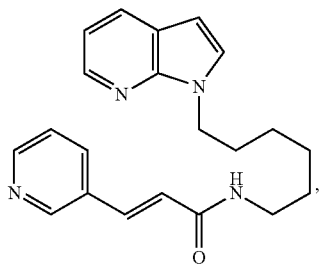
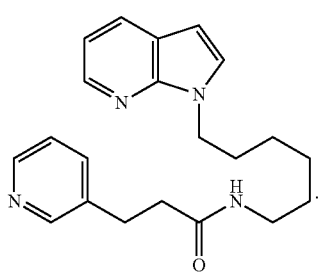
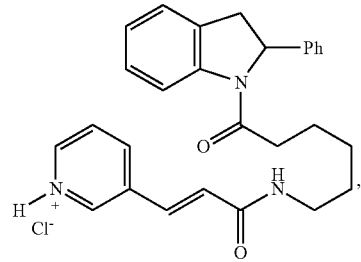
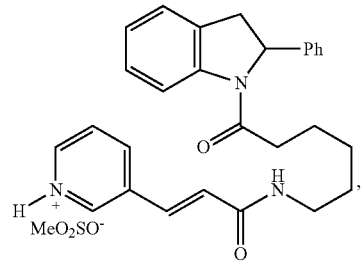
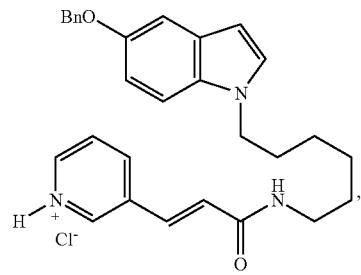
-continued
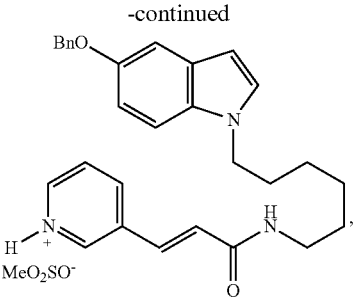
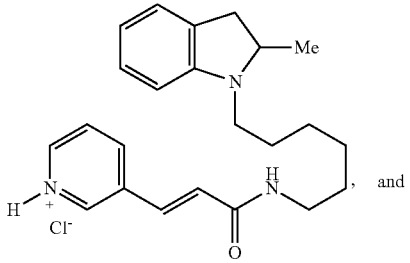, and
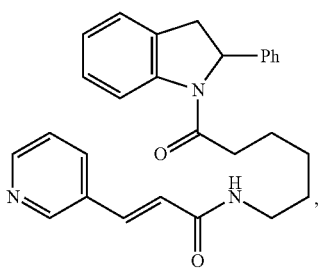 [SMILES: O=C(/C=C/c1cccnc1)NCCCCCC(=O)N1c2ccccc2CC1c1ccccc1].
13. The compound of claim 1 having the structure
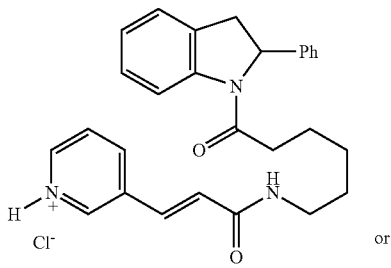
or a pharmaceutically acceptable salt thereof.
14. The compound or salt thereof of claim 13, having the structure
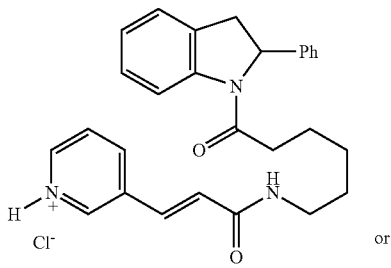 or

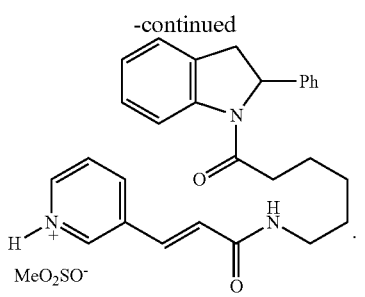
15. A method of treating a subject having pulmonary arterial hypertension comprising administering to the subject a therapeutically effective amount of the compound of claim 1 or claim 12.
* * * * *

UNITED STATES PATENT AND TRADEMARK OFFICE
CERTIFICATE OF CORRECTION

| | |
|---|---|
| PATENT NO. | : 11,584,766 B2 |
| APPLICATION NO. | : 16/967279 |
| DATED | : February 21, 2023 |
| INVENTOR(S) | : Tom G. Driver et al. |

It is certified that error appears in the above-identified patent and that said Letters Patent is hereby corrected as shown below:

On the Title Page

In Item (72), Inventor: Najing Su should be Naijing Su.

Signed and Sealed this
Tenth Day of September, 2024

Katherine Kelly Vidal
*Director of the United States Patent and Trademark Office*